(12) United States Patent
Donner

(10) Patent No.: US 10,292,720 B2
(45) Date of Patent: May 21, 2019

(54) METHODS OF FUSING A SACROILIAC JOINT

(71) Applicant: JCBD, LLC, Fort Collins, CO (US)

(72) Inventor: Edward Jeffrey Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 0 days.

(21) Appl. No.: 15/789,515

(22) Filed: Oct. 20, 2017

(65) Prior Publication Data

US 2018/0055521 A1     Mar. 1, 2018

Related U.S. Application Data

(63) Continuation of application No. 14/681,882, filed on Apr. 8, 2015, now Pat. No. 9,795,396, which is a
(Continued)

(51) Int. Cl.
*A61F 2/44*        (2006.01)
*A61B 17/17*      (2006.01)
(Continued)

(52) U.S. Cl.
CPC ...... *A61B 17/1739* (2013.01); *A61B 17/1626* (2013.01); *A61B 17/1757* (2013.01); *A61B 17/7055* (2013.01); *A61F 2/30988* (2013.01); *A61F 2/4455* (2013.01); *A61F 2/4611* (2013.01); *A61B 17/025* (2013.01); *A61B 17/7043* (2013.01); *A61B 17/8645* (2013.01);
(Continued)

(58) Field of Classification Search
CPC ....... A61B 17/7055; A61B 17/70; A61F 2/44; A61F 2/4455; A61F 2/447; A61F 2/46; A61F 2/4611; A61F 2002/30995
See application file for complete search history.

(56) References Cited

U.S. PATENT DOCUMENTS 5,334,205 A * 8/1994 Cain .................. A61B 17/1739
606/86 R
7,935,116 B2 5/2011 Michelson
(Continued)

OTHER PUBLICATIONS

China Office Action, CN201510622898.0, dated Feb. 1, 2018 (English translation).
(Continued)

*Primary Examiner* — Eduardo C Robert
*Assistant Examiner* — Michelle C Eckman
(74) *Attorney, Agent, or Firm* — Polsinelli PC; Joshua J. Pranckun; Samuel Wade Johnson

(57) ABSTRACT

A method of fusing a sacroiliac joint including: a) approaching a posterior aspect of a sacroiliac joint space with a joint implant including a body extending a length between a distal end and a proximal end; and b) delivering the joint implant into the sacroiliac joint space such that the joint implant passes through an access region defined between a posterior superior iliac spine and a posterior inferior iliac spine, the joint implant being oriented in the sacroiliac joint space such that a portion of the body of the joint implant is positioned within a joint plane of the sacroiliac joint space, and such that the distal end of the joint implant is positioned posteriorly of an anterior boundary of the sacroiliac joint space.

34 Claims, 91 Drawing Sheets

Related U.S. Application Data continuation of application No. 13/236,411, filed on Sep. 19, 2011, now Pat. No. 9,017,407, which is a continuation-in-part of application No. 12/998,712, filed as application No. PCT/US2011/000070 on Jan. 13, 2011, now Pat. No. 8,979,928.

(60) Provisional application No. 61/335,947, filed on Jan. 13, 2010.

(51) Int. Cl.

| | | |
|---|---|---|
| *A61F 2/30* | (2006.01) | |
| *A61B 17/70* | (2006.01) | |
| *A61B 17/16* | (2006.01) | |
| *A61F 2/46* | (2006.01) | |
| *A61B 17/02* | (2006.01) | |
| *A61B 17/86* | (2006.01) | |
| *A61B 17/00* | (2006.01) | |

(52) U.S. Cl.
CPC ........... *A61B 2017/0046* (2013.01); *A61F 2002/30163* (2013.01); *A61F 2002/30622* (2013.01); *A61F 2002/30995* (2013.01); *A61F 2002/4687* (2013.01); *A61F 2310/00017* (2013.01); *A61F 2310/00023* (2013.01); *A61F 2310/00179* (2013.01); *A61F 2310/00359* (2013.01)

(56) References Cited

U.S. PATENT DOCUMENTS

| | | | |
|---|---|---|---|
| 7,942,903 B2 | 5/2011 | Moskowitz et al. | |
| 8,414,648 B2* | 4/2013 | Reiley | A61B 17/1615 606/246 |
| 8,425,570 B2* | 4/2013 | Reiley | A61B 17/1615 128/898 |
| 8,444,693 B2* | 5/2013 | Reiley | A61B 17/1615 606/246 |
| 8,470,004 B2* | 6/2013 | Reiley | A61B 17/1615 606/246 |
| 8,882,818 B1* | 11/2014 | Vestgaarden | A61B 17/025 606/331 |
| 9,149,286 B1* | 10/2015 | Greenhalgh | A61B 17/1757 |
| 9,254,130 B2 | 2/2016 | Hollis | |
| 9,421,109 B2* | 8/2016 | Donner | A61B 17/68 |
| 9,452,065 B1* | 9/2016 | Lawson | A61F 2/4611 |
| 9,486,264 B2* | 11/2016 | Reiley | A61B 17/1659 |
| 9,622,783 B2* | 4/2017 | Reiley | A61B 17/1615 |
| 9,931,212 B1 | 4/2018 | Donner et al. | |
| 9,949,835 B2 | 4/2018 | Donner | |
| 10,034,676 B2* | 7/2018 | Donner | A61B 17/1739 |
| 10,058,430 B2 | 8/2018 | Donner et al. | |
| 10,064,727 B2 | 9/2018 | Donner et al. | |
| 10,064,728 B2 | 9/2018 | Donner et al. | |
| 2002/0103487 A1 | 8/2002 | Errico | |
| 2004/0193271 A1 | 9/2004 | Fraser | |
| 2005/0261775 A1 | 11/2005 | Baum | |
| 2006/0036251 A1* | 2/2006 | Reiley | A61B 17/1615 606/301 |
| 2006/0106376 A1* | 5/2006 | Godara | A61B 18/148 606/32 |
| 2007/0156241 A1* | 7/2007 | Reiley | A61B 17/1615 623/17.11 |
| 2007/0179610 A1 | 8/2007 | Biedermann | |
| 2007/0239278 A1 | 10/2007 | Heinz | |
| 2007/0270879 A1* | 11/2007 | Isaza | A61B 17/1739 606/104 |
| 2007/0299445 A1 | 12/2007 | Shadduck | |
| 2008/0021461 A1 | 1/2008 | Barker et al. | |
| 2008/0133016 A1 | 6/2008 | Heinz | |
| 2008/0140082 A1* | 6/2008 | Erdem | A61B 17/8805 606/92 |
| 2009/0099659 A1 | 4/2009 | Oh | |
| 2009/0204215 A1 | 8/2009 | McClintock | |
| 2009/0259261 A1* | 10/2009 | Reiley | A61F 2/4455 606/329 |
| 2010/0168798 A1 | 7/2010 | Clineff | |
| 2010/0168861 A1 | 7/2010 | Yundt | |
| 2010/0204796 A1 | 8/2010 | Bae | |
| 2010/0217086 A1 | 8/2010 | Deshmukh | |
| 2011/0087294 A1* | 4/2011 | Reiley | A61B 17/1659 606/279 |
| 2011/0087296 A1* | 4/2011 | Reiley | A61B 17/1659 606/303 |
| 2011/0098817 A1* | 4/2011 | Eckhardt | A61B 17/7055 623/17.11 |
| 2011/0160866 A1 | 6/2011 | Laurence | |
| 2011/0184519 A1* | 7/2011 | Trieu | A61B 17/7055 623/17.11 |
| 2011/0230968 A1 | 9/2011 | Perisic | |
| 2011/0238181 A1* | 9/2011 | Trieu | A61B 17/1735 623/17.11 |
| 2011/0264229 A1* | 10/2011 | Donner | A61F 2/30988 623/18.11 |
| 2012/0032808 A1 | 2/2012 | Cherubini | |
| 2012/0095560 A1* | 4/2012 | Donner | A61F 2/30988 623/17.11 |
| 2012/0191191 A1* | 7/2012 | Trieu | A61B 17/683 623/17.11 |
| 2012/0253406 A1 | 10/2012 | Bae | |
| 2013/0035724 A1 | 2/2013 | Fitzpatrick | |
| 2013/0053964 A1* | 2/2013 | Talwar | A61F 2/442 623/17.16 |
| 2013/0085535 A1* | 4/2013 | Greenhalgh | A61B 17/70 606/279 |
| 2013/0144343 A1* | 6/2013 | Arnett | A61B 17/70 606/279 |
| 2013/0144393 A1 | 6/2013 | Mutchler | |
| 2013/0173004 A1* | 7/2013 | Greenhalgh | A61F 2/4425 623/17.16 |
| 2013/0238093 A1* | 9/2013 | Mauldin | A61F 2/28 623/16.11 |
| 2013/0245763 A1* | 9/2013 | Mauldin | A61F 2/4455 623/17.11 |
| 2014/0031935 A1* | 1/2014 | Donner | A61F 2/4455 623/17.11 |
| 2014/0046380 A1* | 2/2014 | Asfora | A61B 17/1615 606/304 |
| 2014/0135850 A1* | 5/2014 | Parent | A61B 17/68 606/304 |
| 2014/0257411 A1* | 9/2014 | Rezach | A61B 17/7037 606/305 |
| 2014/0277460 A1* | 9/2014 | Schifano | A61F 2/4611 623/17.11 |
| 2014/0277463 A1* | 9/2014 | Yerby | A61F 2/32 623/17.11 |
| 2014/0288605 A1* | 9/2014 | Mesiwala | A61B 17/7055 606/279 |
| 2015/0094765 A1* | 4/2015 | Donner | A61B 17/1735 606/246 |
| 2015/0105828 A1* | 4/2015 | Reckling | A61B 17/1659 606/279 |
| 2015/0182268 A1* | 7/2015 | Donner | A61B 17/8066 606/281 |
| 2015/0250612 A1* | 9/2015 | Schifano | A61F 2/4611 623/17.16 |
| 2015/0342753 A1* | 12/2015 | Donner | A61B 17/1757 623/18.11 |
| 2016/0081809 A1* | 3/2016 | Schneider | A61B 17/84 623/17.11 |
| 2016/0081810 A1* | 3/2016 | Reiley | A61B 17/1604 623/17.11 |
| 2016/0128838 A1 | 5/2016 | Assell | |
| 2016/0157897 A1* | 6/2016 | Vaidya | A61B 17/7059 606/279 |
| 2016/0287171 A1* | 10/2016 | Sand | A61B 5/4851 |
| 2016/0302941 A1* | 10/2016 | Reiley | A61F 2/447 |
| 2016/0310188 A1* | 10/2016 | Marino | A61F 2/28 |

(56) References Cited

U.S. PATENT DOCUMENTS

| | | | |
|---|---|---|---|
| 2017/0007409 A1* | 1/2017 | Mauldin | A61B 17/0218 |
| 2017/0135733 A1 | 5/2017 | Donner et al. | |
| 2017/0164979 A1 | 6/2017 | Donner et al. | |
| 2017/0319240 A1 | 11/2017 | Donner et al. | |
| 2017/0325845 A1 | 11/2017 | Donner et al. | |
| 2017/0325846 A1 | 11/2017 | Donner et al. | |
| 2018/0035893 A1 | 2/2018 | Donner et al. | |
| 2018/0036017 A1 | 2/2018 | Donner et al. | |
| 2018/0085223 A1 | 3/2018 | Donner | |
| 2018/0092669 A1 | 4/2018 | Donner et al. | |
| 2018/0092748 A1 | 4/2018 | Donner et al. | |
| 2018/0104071 A1* | 4/2018 | Reckling | A61F 2/4603 |
| 2018/0271662 A1 | 9/2018 | Donner et al. | |
| 2018/0271663 A1 | 9/2018 | Donner et al. | |
| 2018/0318091 A1 | 11/2018 | Donner | |
| 2018/0325675 A1 | 11/2018 | Donner | |
| 2018/0325676 A1 | 11/2018 | Donner | |

OTHER PUBLICATIONS

China Office Action, CN201510622898.0, dated Sep. 1, 2017 (English translation).
Non-Final Office Action, U.S. Appl. No. 14/344,876, dated Jun. 2, 2017.
Non-Final Office Action, U.S. Appl. No. 14/660,784, dated Mar. 5, 2018.
Non-Final Office Action, U.S. Appl. No. 15/178,244, dated May 16, 2017.
Non-Final Office Action, U.S. Appl. No. 15/178,291, dated May 16, 2017.
Notice of Allowance, U.S. Appl. No. 14/514,221, dated Jun. 16, 2017.
Notice of Allowance, U.S. Appl. No. 14/723,384, dated Jun. 7, 2017.
Notice of Allowance, U.S. Appl. No. 15/061,524, dated Jul. 26, 2017.
Notice of Allowance, U.S. Appl. No. 15/178,244, dated Sep. 12, 2017.
Notice of Allowance, U.S. Appl. No. 15/178,291, dated Oct. 11, 2017.
Notice of Allowance, U.S. Appl. No. 15/828,556, dated Feb. 7, 2018.
Notice of Allowance, U.S. Appl. No. 15/828,677, dated Jan. 19, 2018.
Response to Non-Final Office Action, U.S. Appl. No. 14/344,876, dated Sep. 5, 2017.
Response to Non-Final Office Action, U.S. Appl. No. 15/178,244, dated Aug. 15, 2017.
Response to Non-Final Office Action, U.S. Appl. No. 15/178,291, dated Aug. 16, 2017.
Response to Restriction, U.S. Appl. No. 14/660,784, dated Nov. 28, 2017.
Restriction Requirement, U.S. Appl. No. 14/660,784, dated Sep. 28, 2017.
Corrected Notice of Allowability, U.S. Appl. No. 15/828,622, dated Nov. 19, 2018.
Final Office Action, U.S. Appl. No. 15/729,273, dated Nov. 20, 2018.
Non-Final Office Action, U.S. Appl. No. 15/993,277, dated Nov. 26, 2018.
Notice of Allowance, U.S. Appl. No. 14/660,784, dated Nov. 15, 2018.
Response to Non-Final Office Action, U.S. Appl. No. 15/418,633, dated Nov. 7, 2018.
Response to Non-Final Office Action, U.S. Appl. No. 15/662,045, dated Nov. 12, 2018.
Amendment Under 1.312, U.S. Appl. No. 15/992,987, dated Sep. 26, 2018.
Amendment Under 1.312, U.S. Appl. No. 15/993,170, dated Sep. 26, 2018.
Amendment Under 1.312, U.S. Appl. No. 15/828,622, dated Oct. 26, 2018.
Australian Examination Report, AU2016204937, dated May 21, 2018.
Canadian Office Action, CA2849095, dated May 28, 2018.
Corrected Notice of Allowability, U.S. Appl. No. 15/992,987, dated Oct. 9, 2018.
Corrected Notice of Allowability, U.S. Appl. No. 15/993,170, dated Oct. 9, 2018.
European Examination Report, EP12799773.2, dated Jun. 4, 2018.
Final Office Action, U.S. Appl. No. 14/344,876, dated Apr. 13, 2018.
Final Office Action, U.S. Appl. No. 14/660,784, dated Jul. 20, 2018.
Non-Final Office Action, U.S. Appl. No. 15/216,472, dated Sep. 25, 2018.
Non-Final Office Action, U.S. Appl. No. 15/385,446, dated Jul. 24, 2018.
Non-Final Office Action, U.S. Appl. No. 15/418,633, dated Aug. 7, 2018.
Non-Final Office Action, U.S. Appl. No. 15/662,045, dated Aug. 10, 2018.
Non-Final Office Action, U.S. Appl. No. 15/664,862, dated Oct. 3, 2018.
Non-Final Office Action, U.S. Appl. No. 15/729,273, dated May 2, 2018.
Notice of Allowance, U.S. Appl. No. 14/344,876, dated May 18, 2018.
Notice of Allowance, U.S. Appl. No. 15/828,622, dated Aug. 9, 2018.
Notice of Allowance, U.S. Appl. No. 15/910,753, dated May 21, 2018.
Notice of Allowance, U.S. Appl. No. 15/912,216, dated Jun. 20, 2018.
Notice of Allowance, U.S. Appl. No. 15/912,260, dated May 10, 2018.
Notice of Allowance, U.S. Appl. No. 15/992,987, dated Aug. 16, 2018.
Notice of Allowance, U.S. Appl. No. 15/993,170, dated Aug. 8, 2018.
Preliminary Amendment, U.S. Appl. No. 15/831,589, dated Jul. 27, 2018.
Response to Final Office Action, U.S. Appl. No. 14/344,876, dated Apr. 27, 2018.
Response to Final Office Action, U.S. Appl. No. 14/660,784, dated Oct. 22, 2018.
Response to Non-Final Office Action, U.S. Appl. No. 14/660,784, dated Jun. 4, 2018.
Response to Non-Final Office Action, U.S. Appl. No. 15/385,446, dated Oct. 24, 2018.
Response to Non-Final Office Action, U.S. Appl. No. 15/729,273, dated Aug. 1, 2018.
Response to Restriction, U.S. Appl. No. 15/216,472, dated Jun. 4, 2018.
Restriction Requirement, U.S. Appl. No. 15/216,472, dated Apr. 2, 2018.
Restriction Requirement, U.S. Appl. No. 15/664,608, dated Oct. 5, 2018.

* cited by examiner

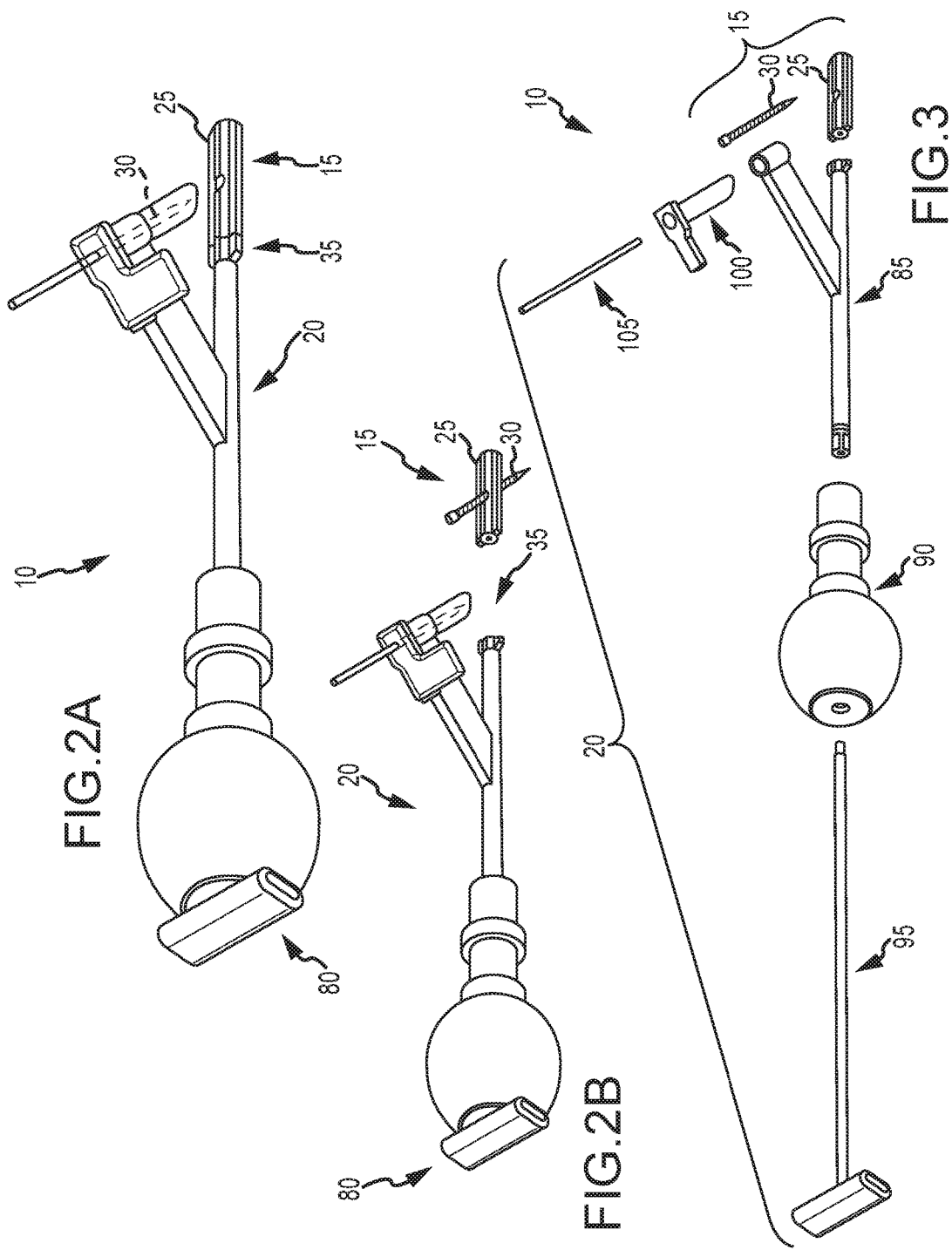

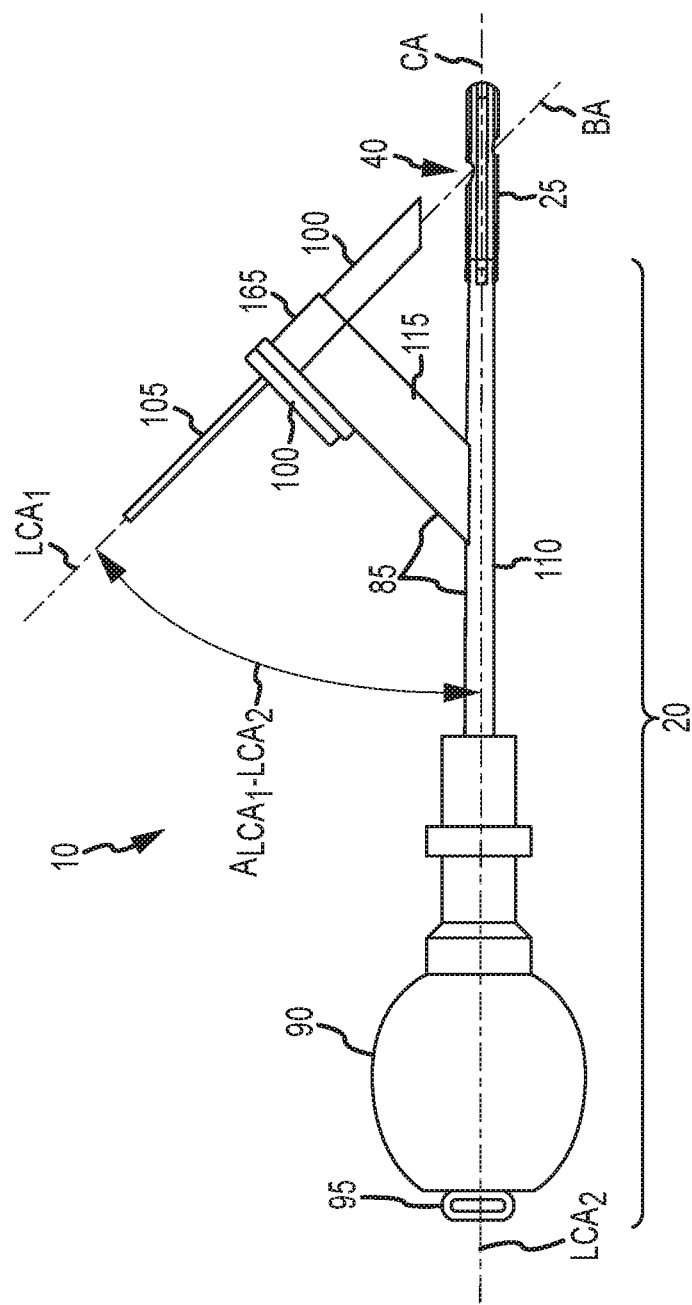

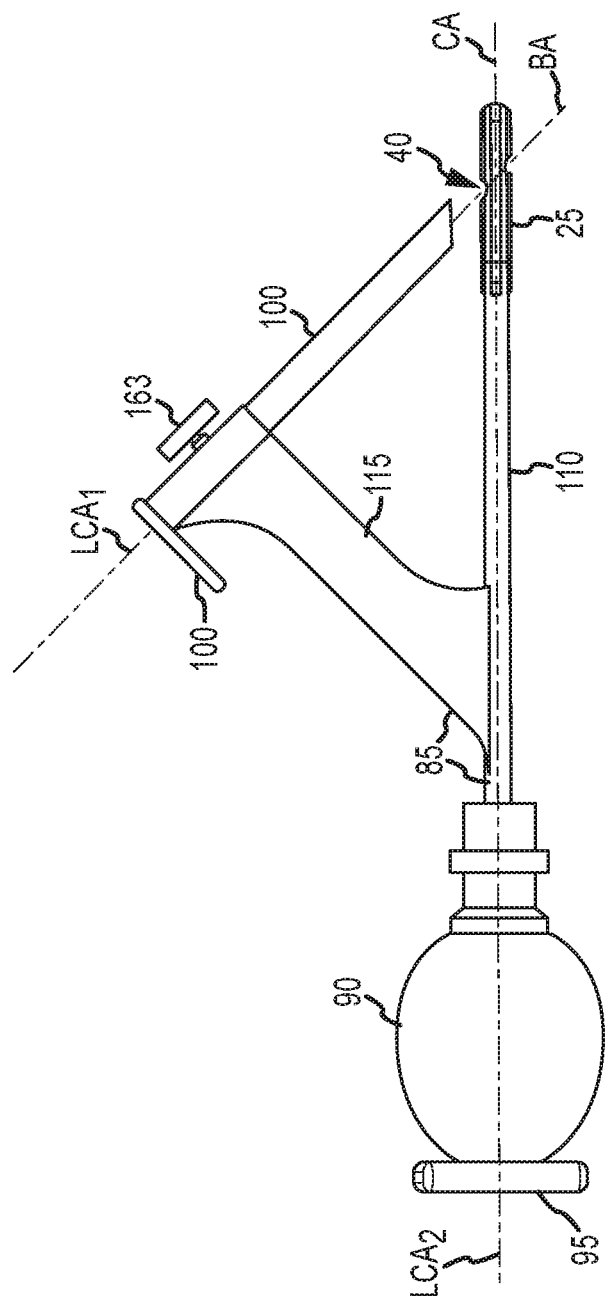

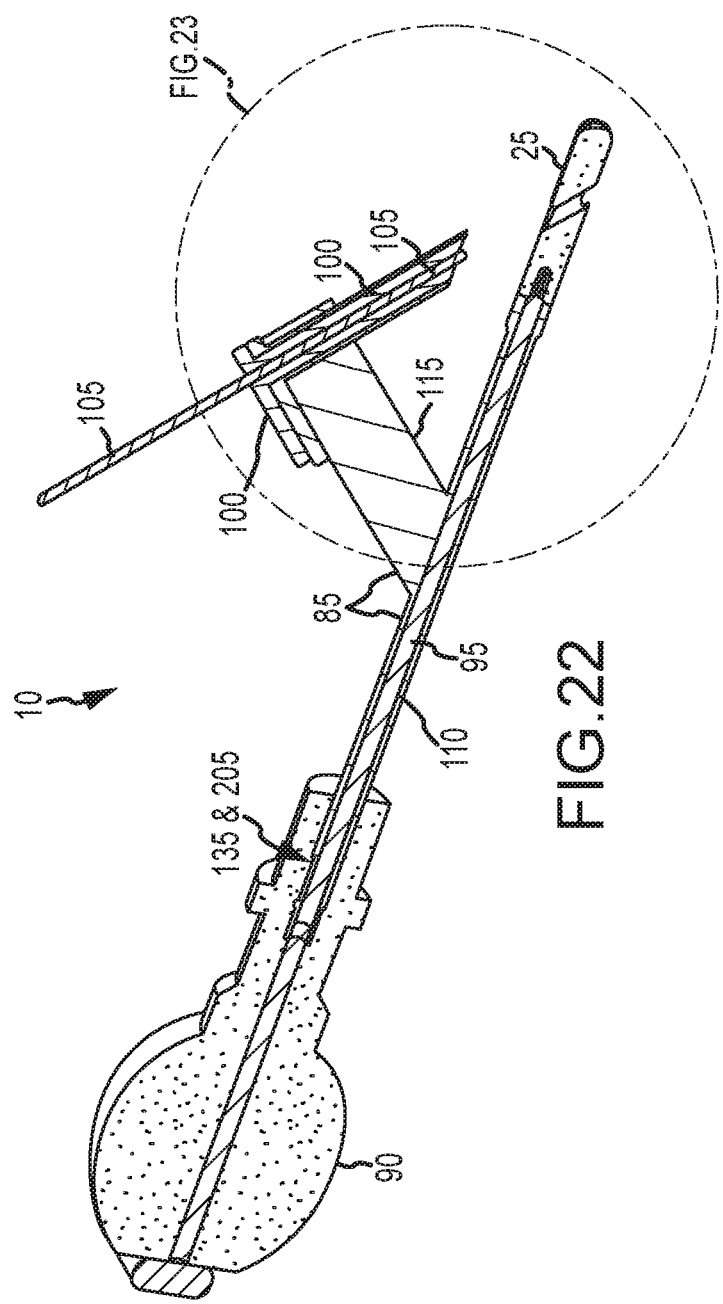

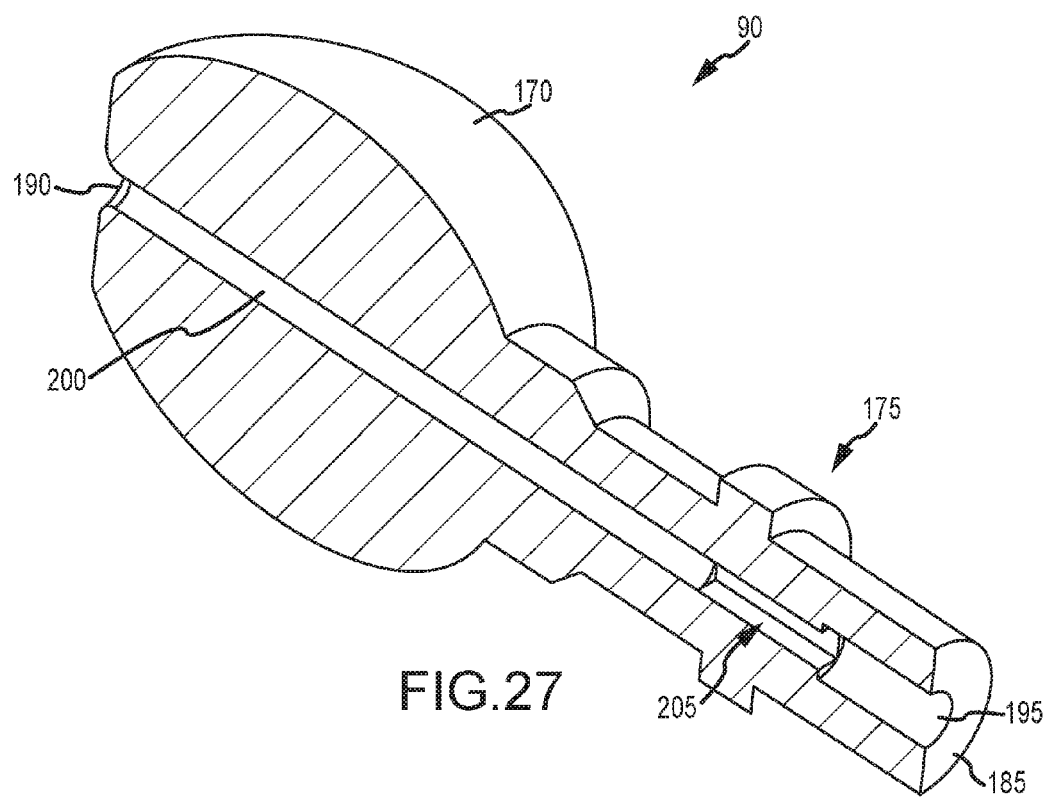

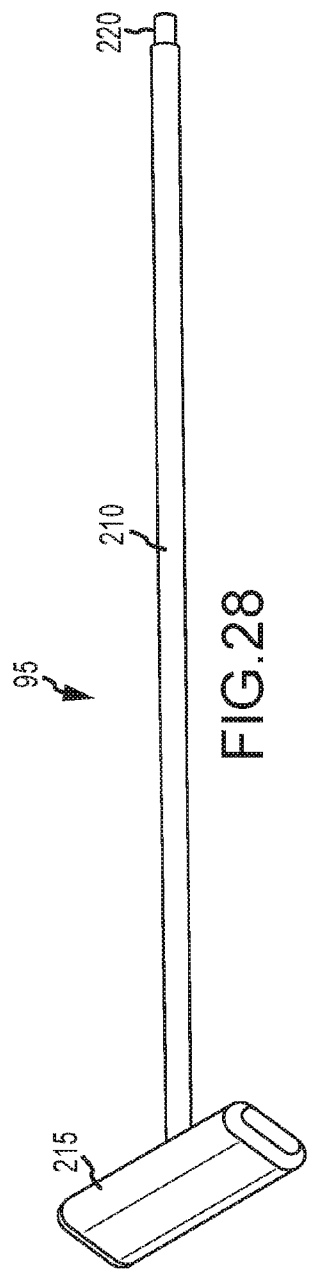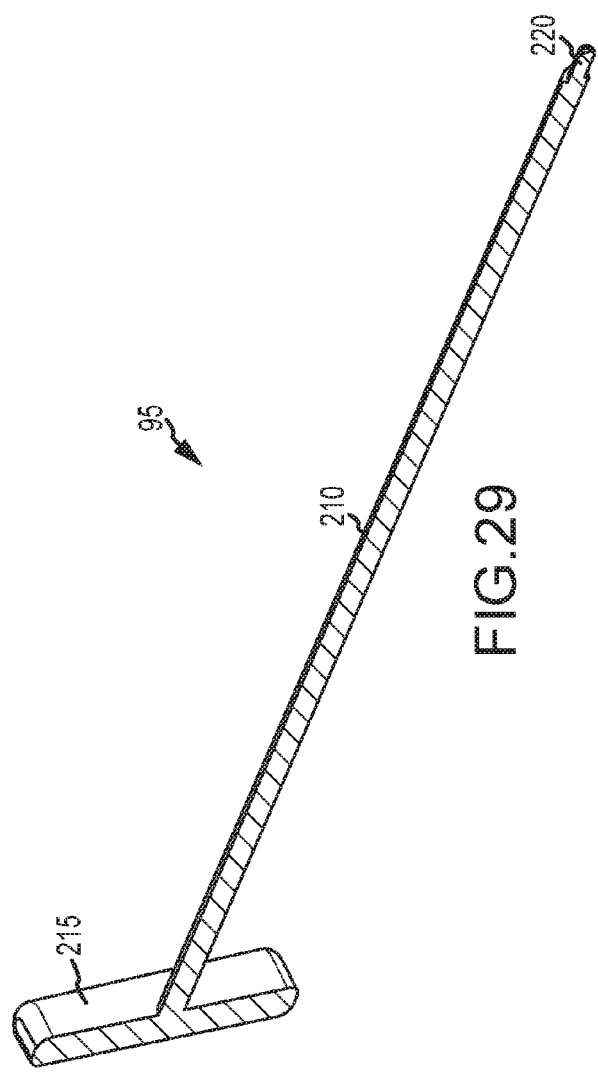

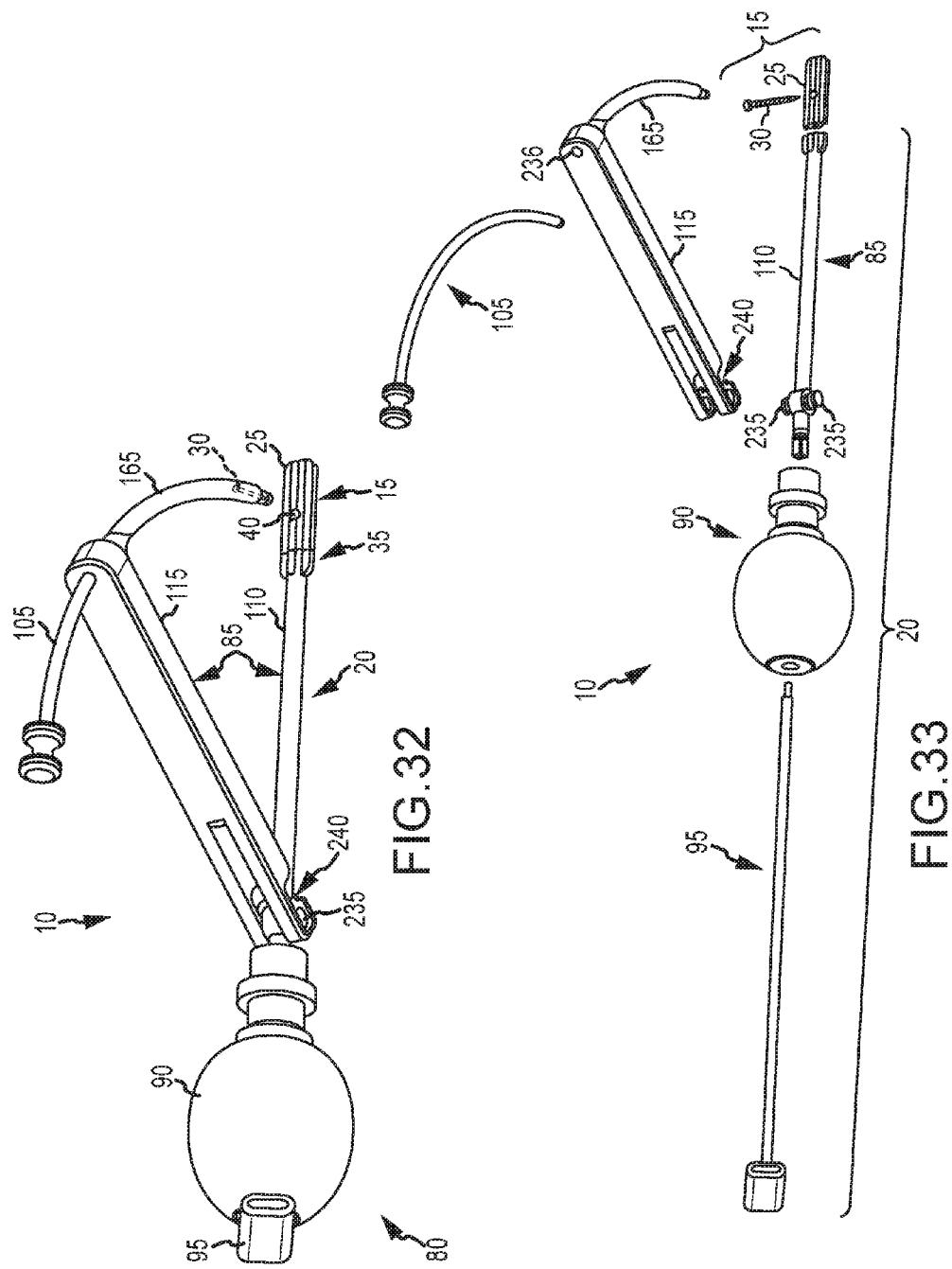

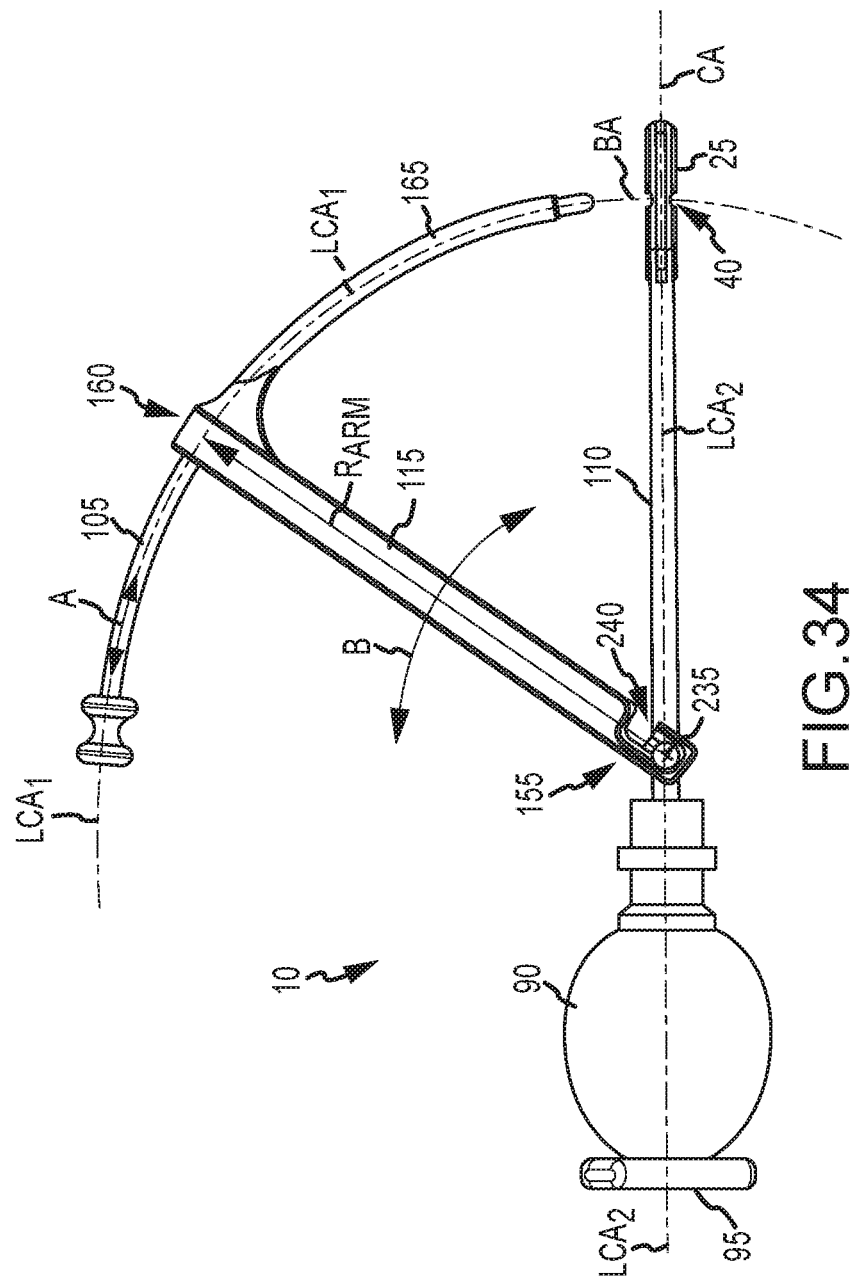

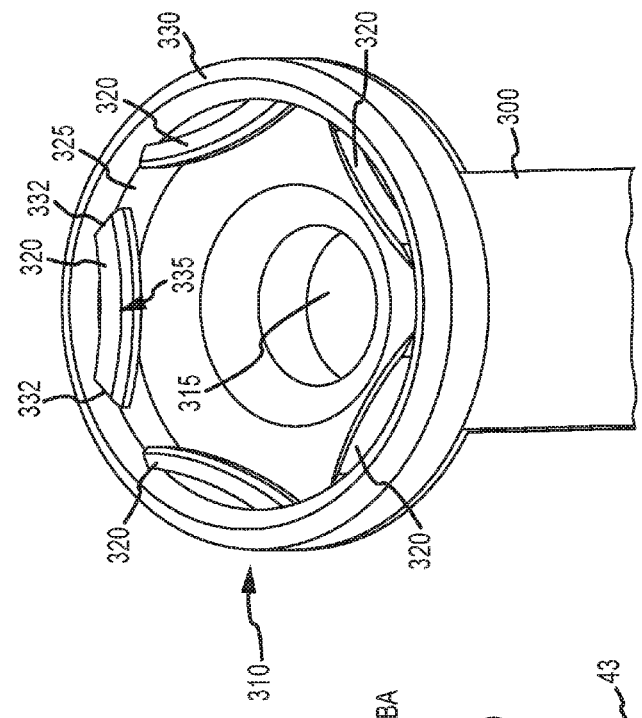

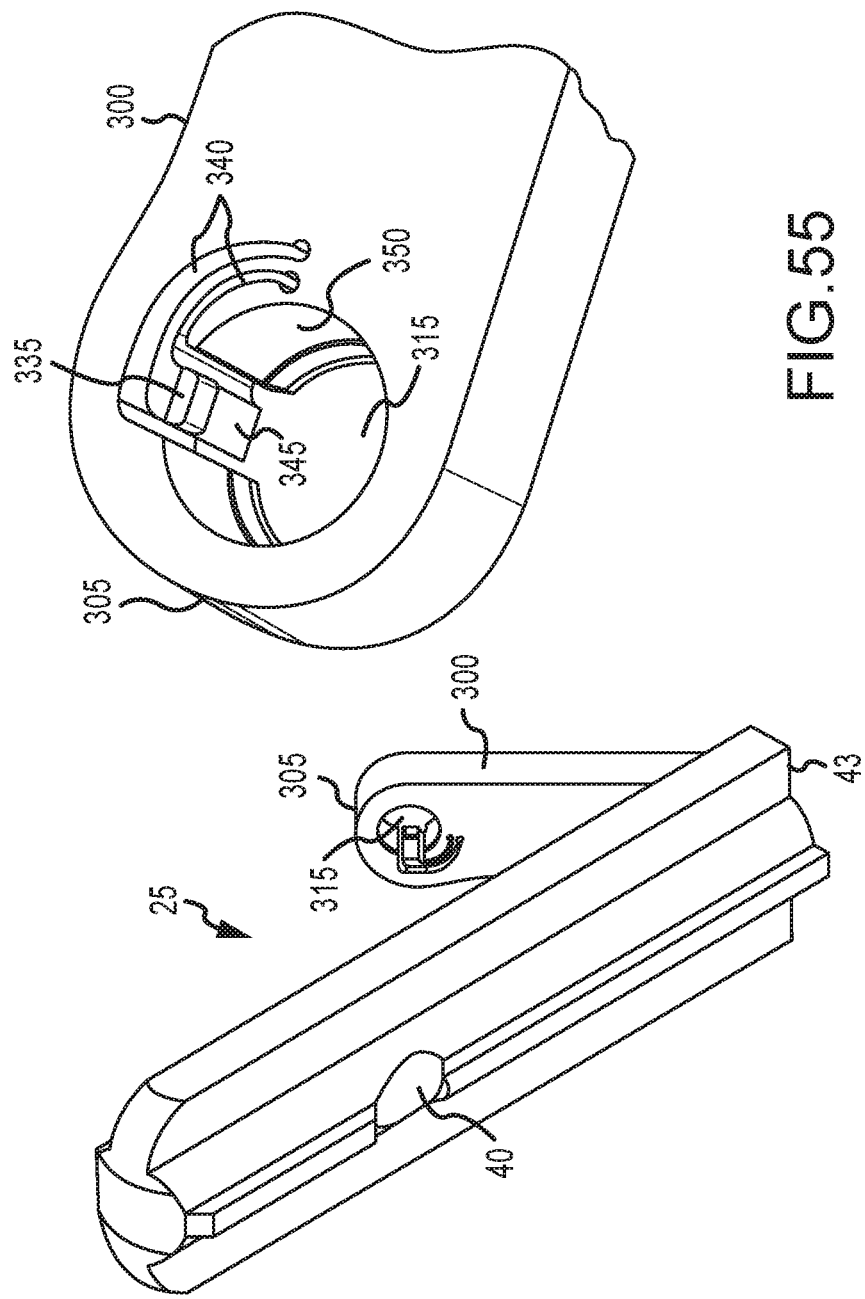

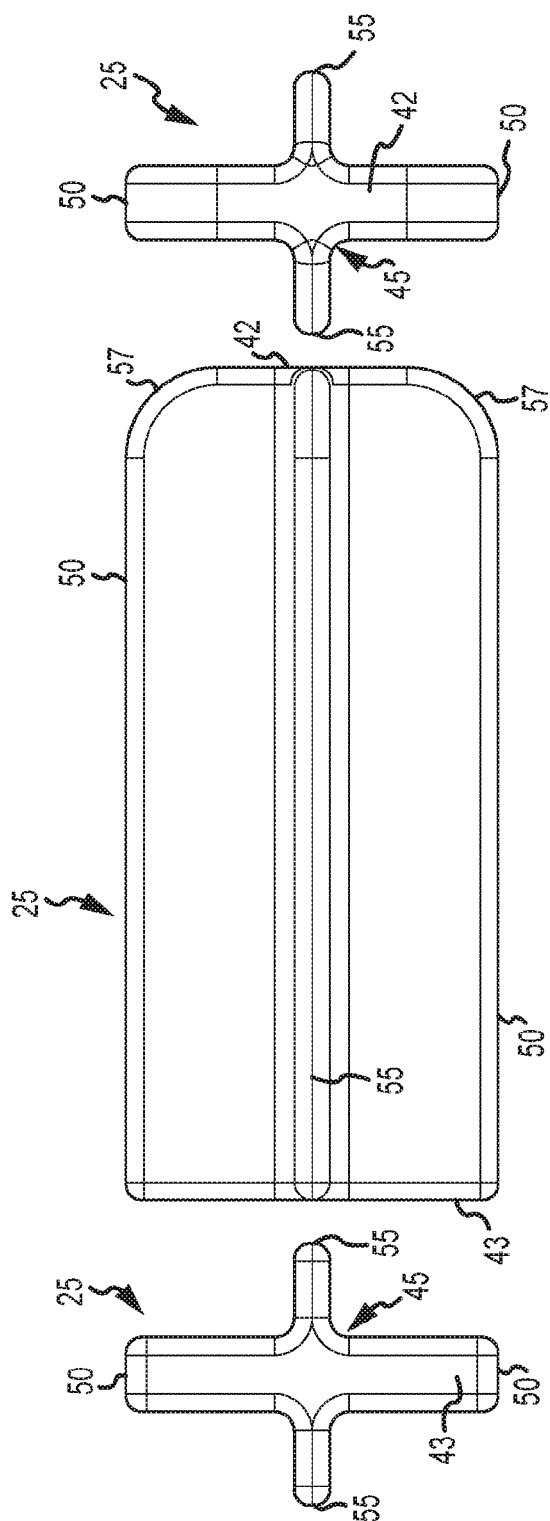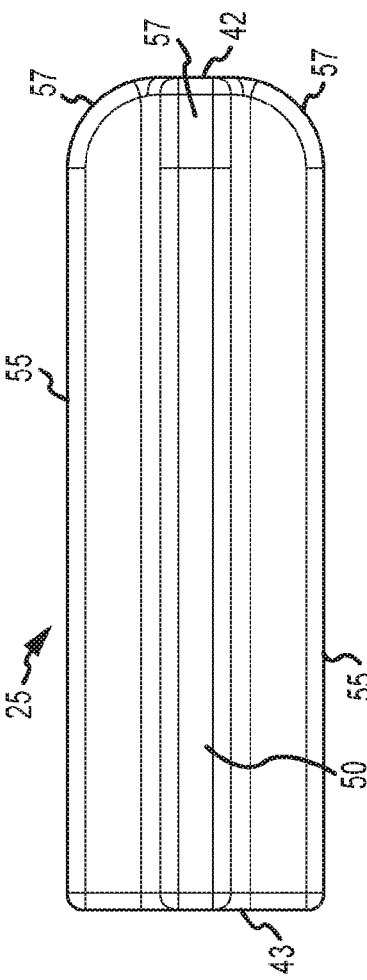

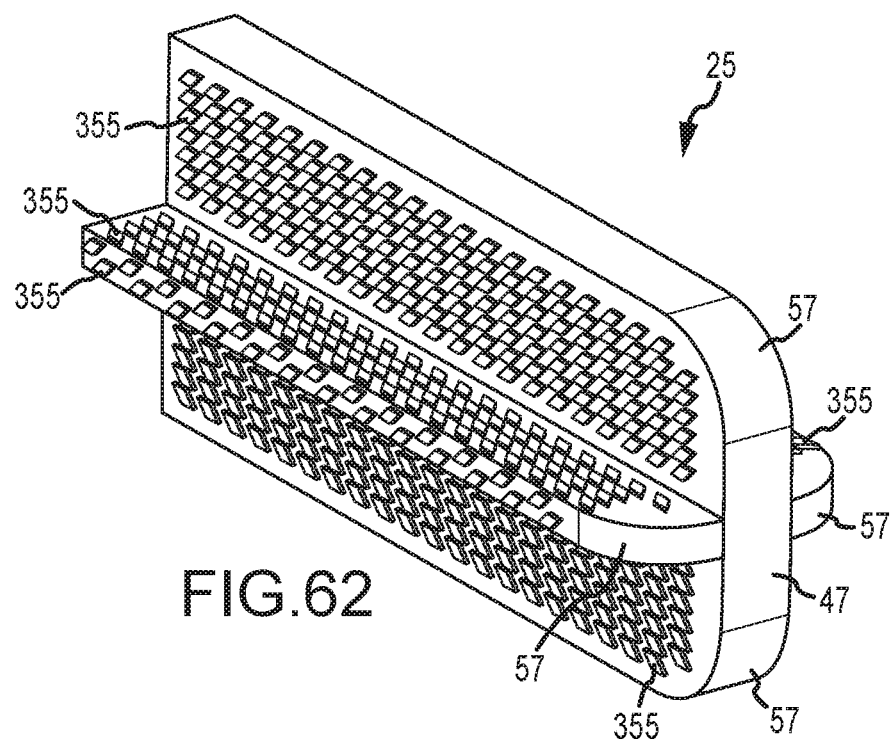
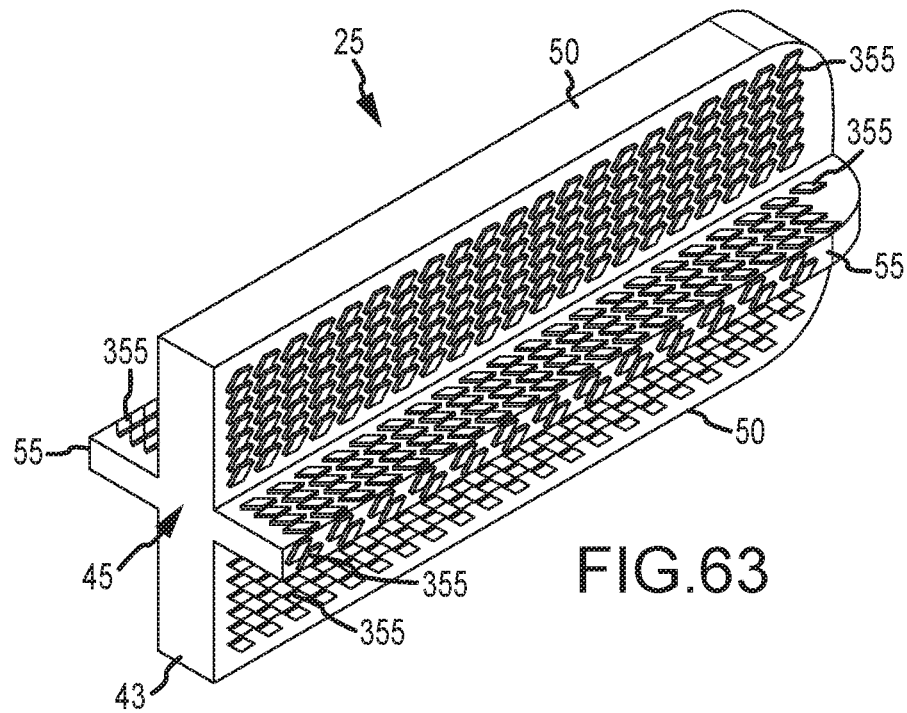

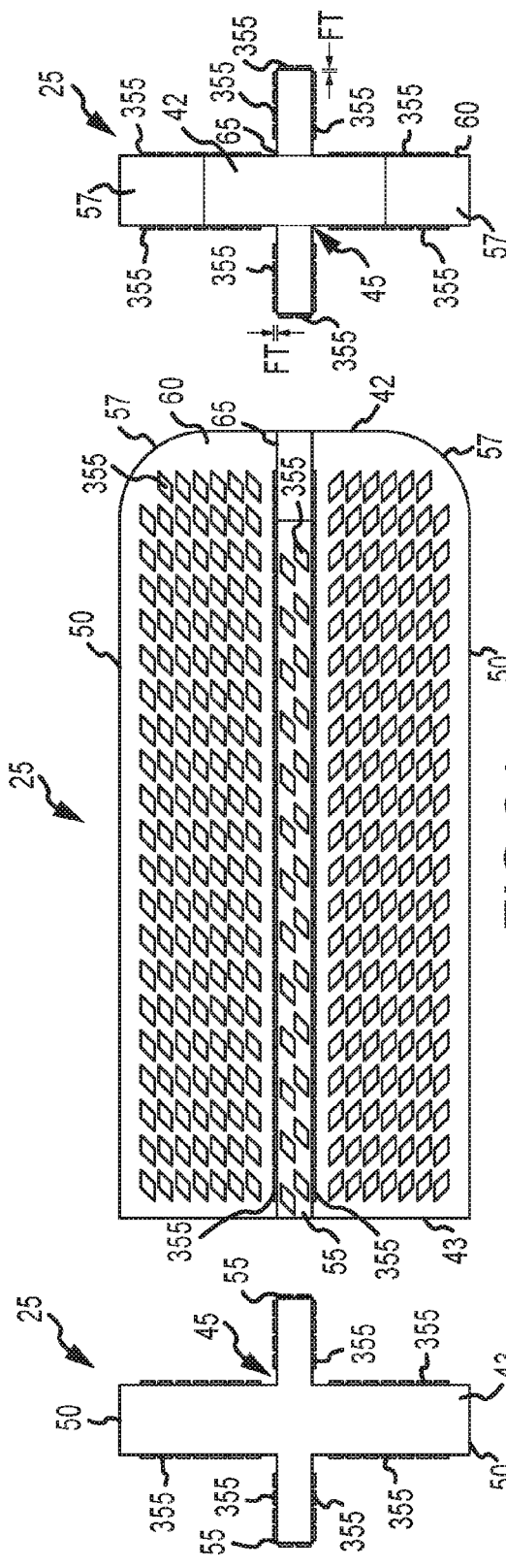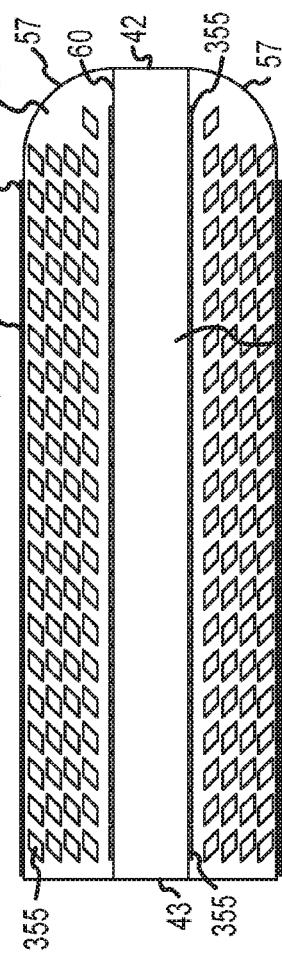

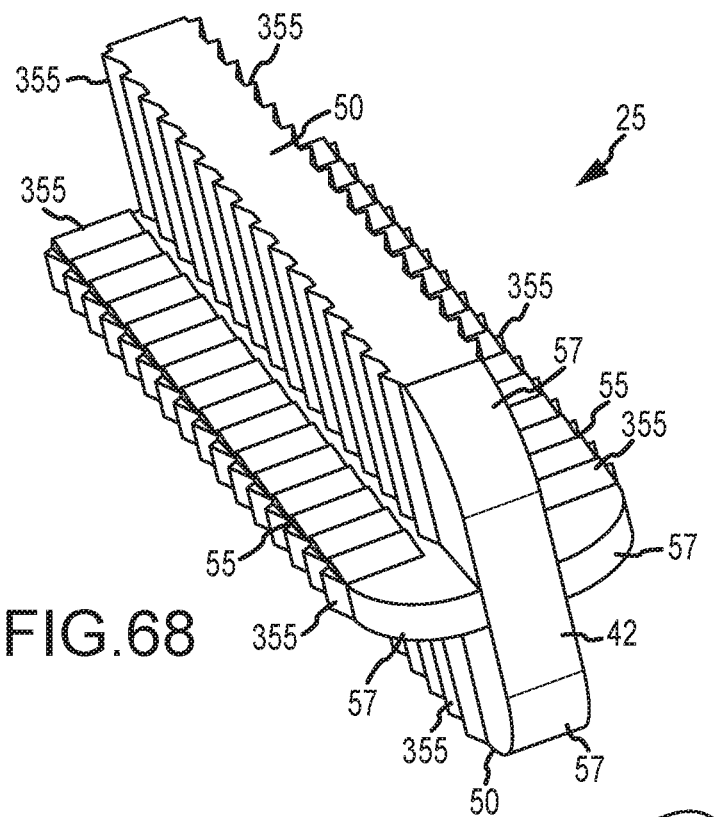
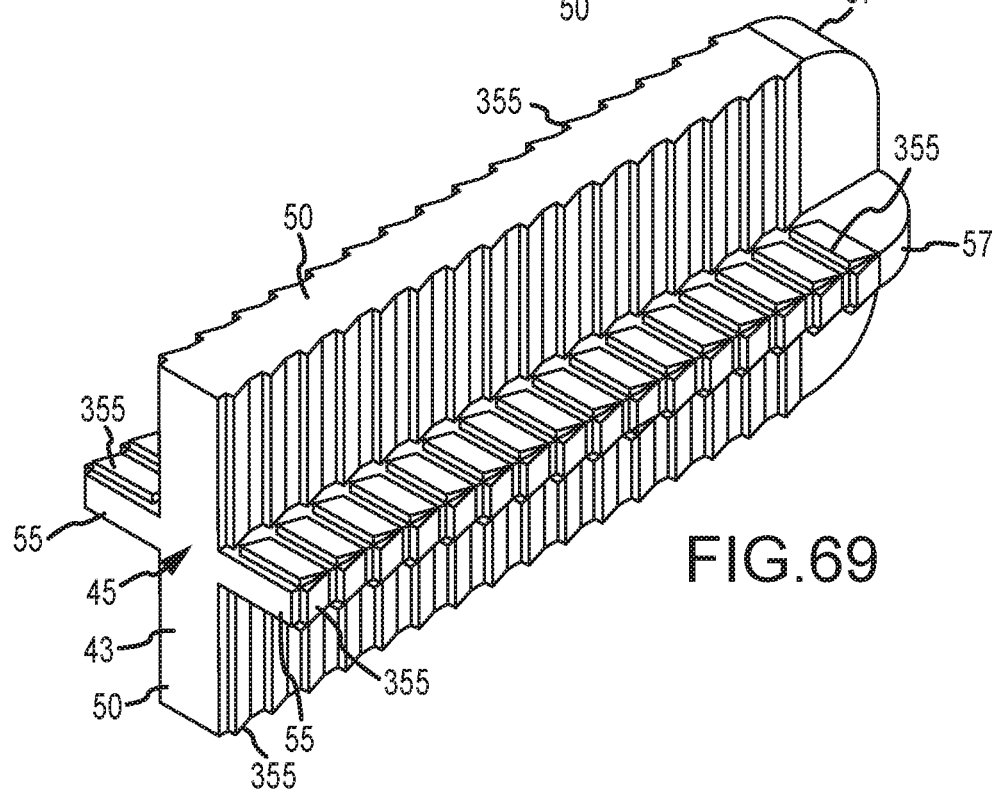

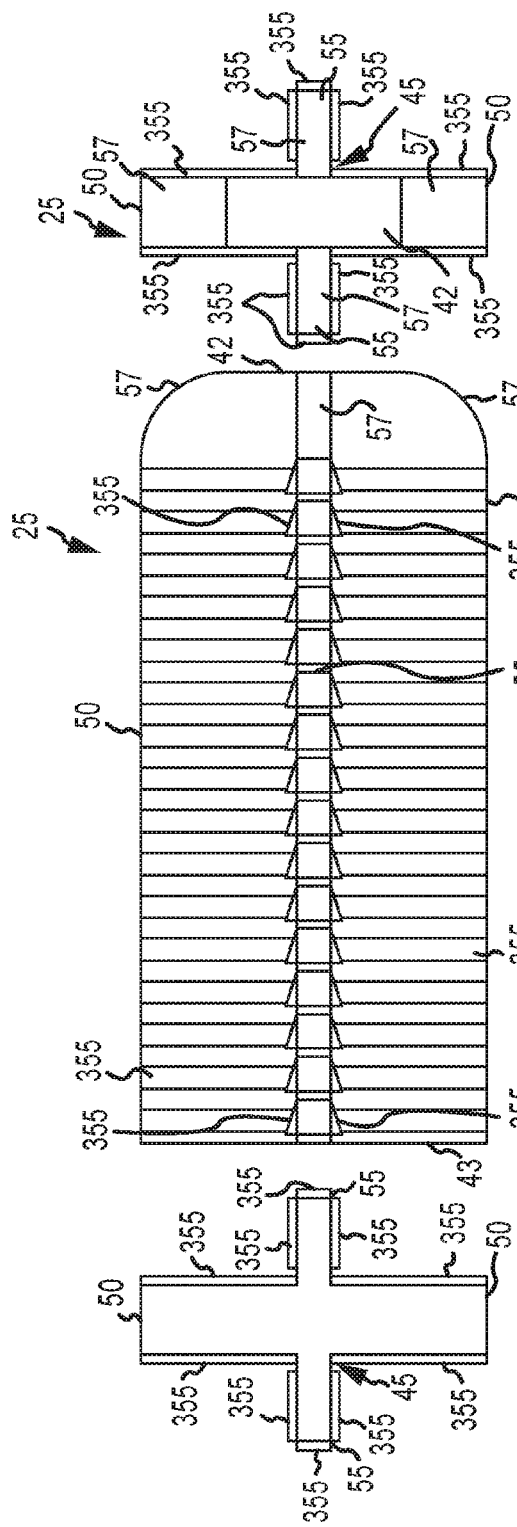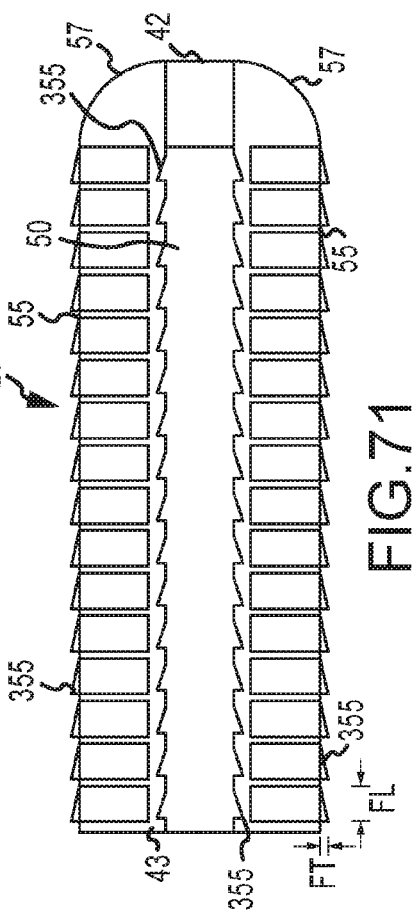

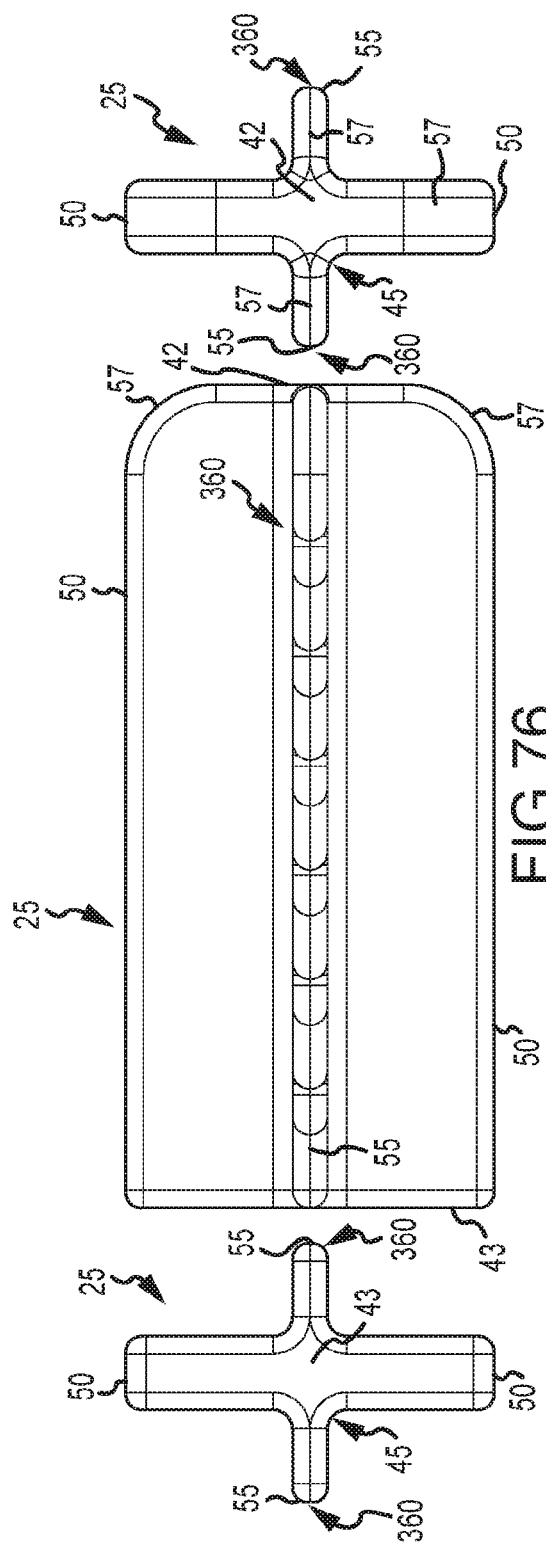

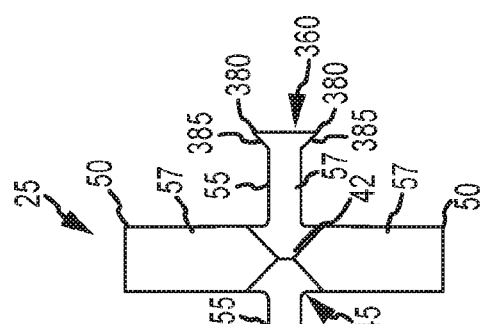
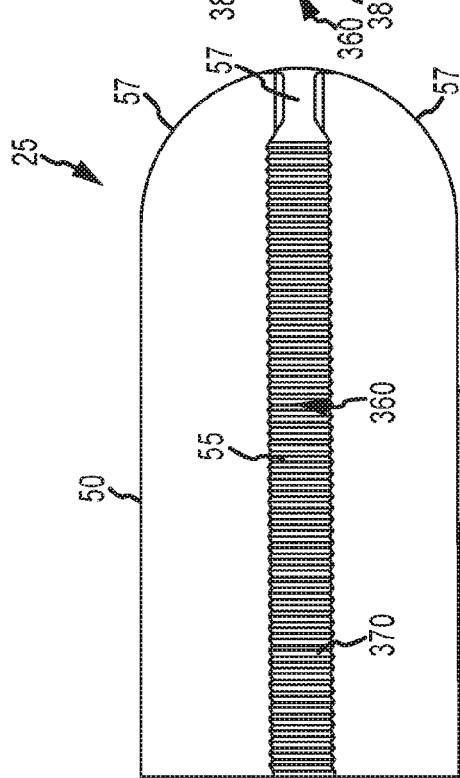
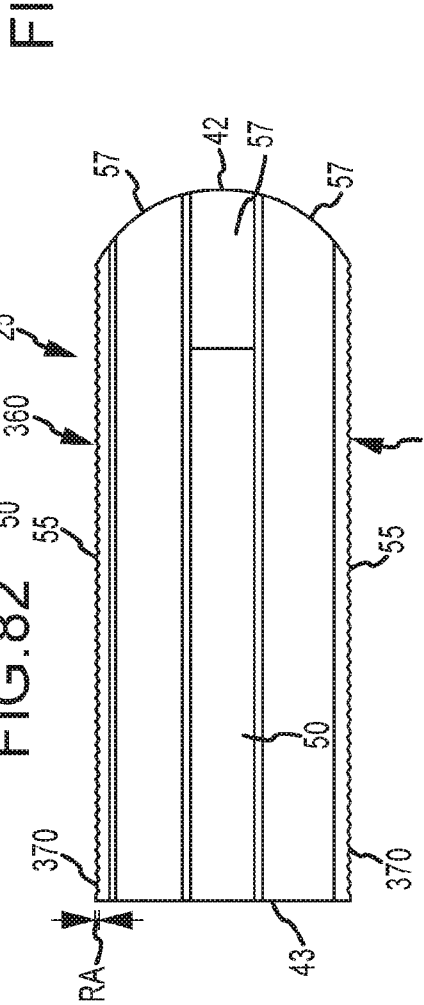
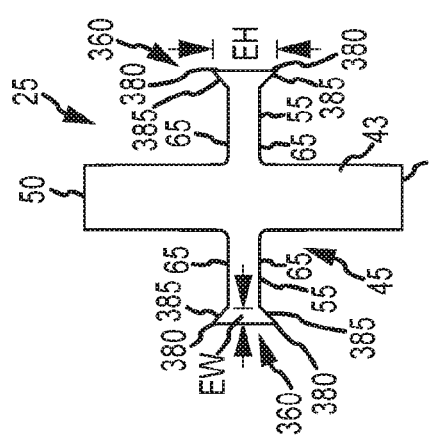

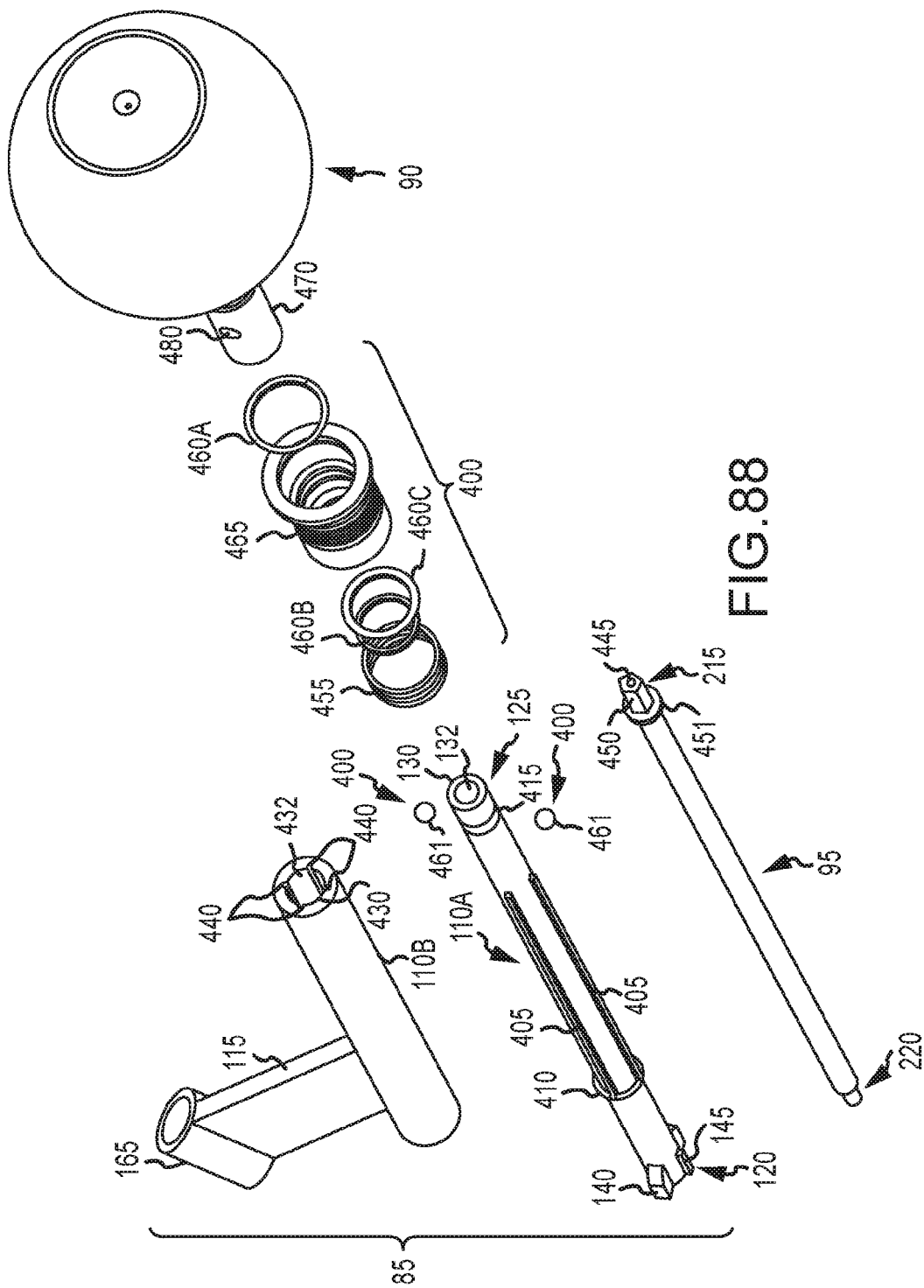

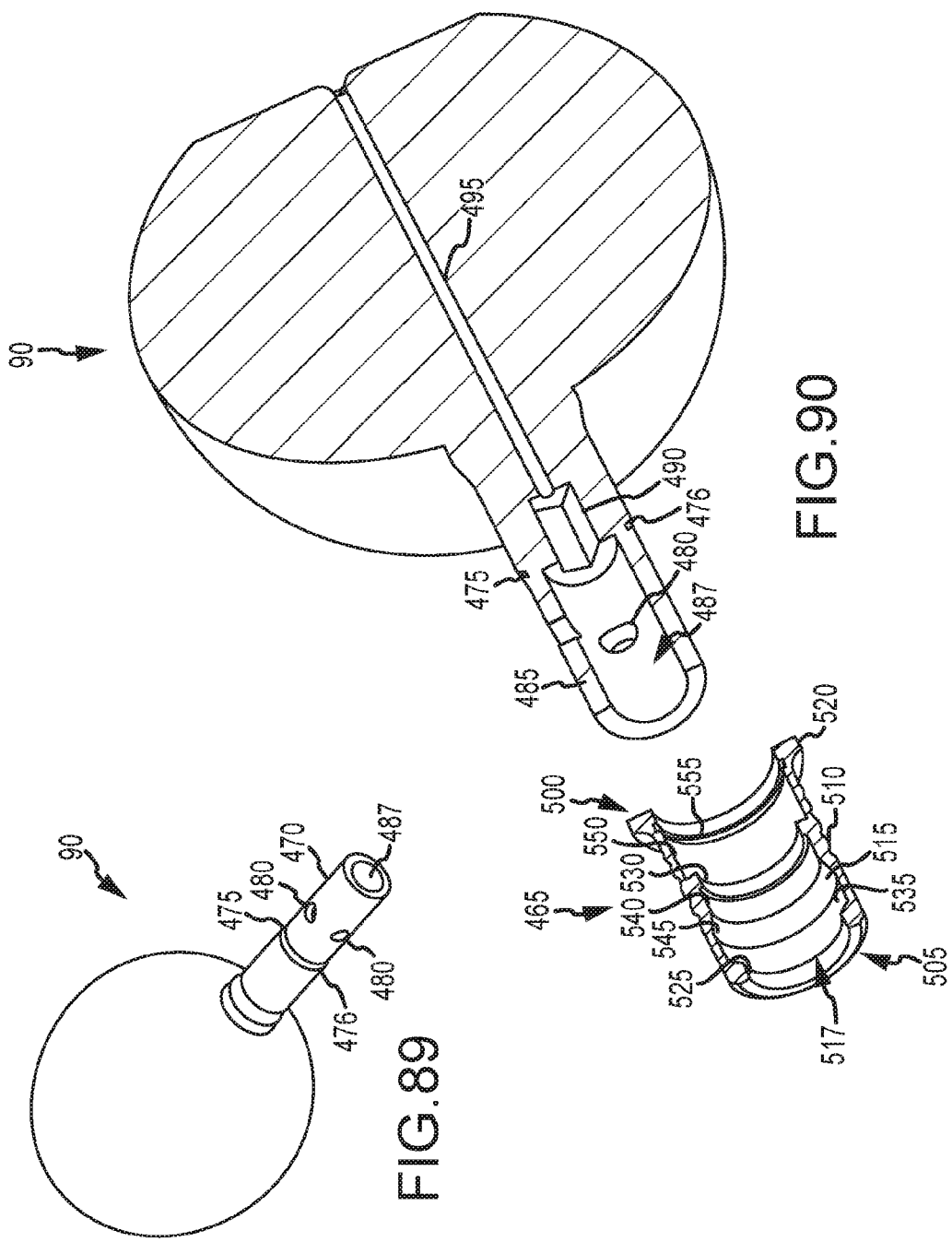

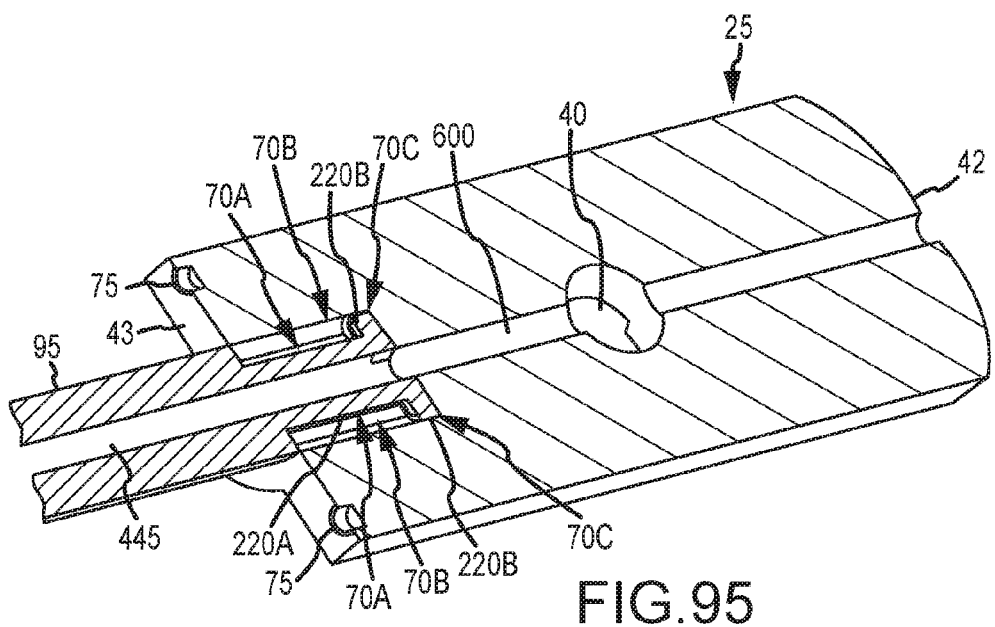

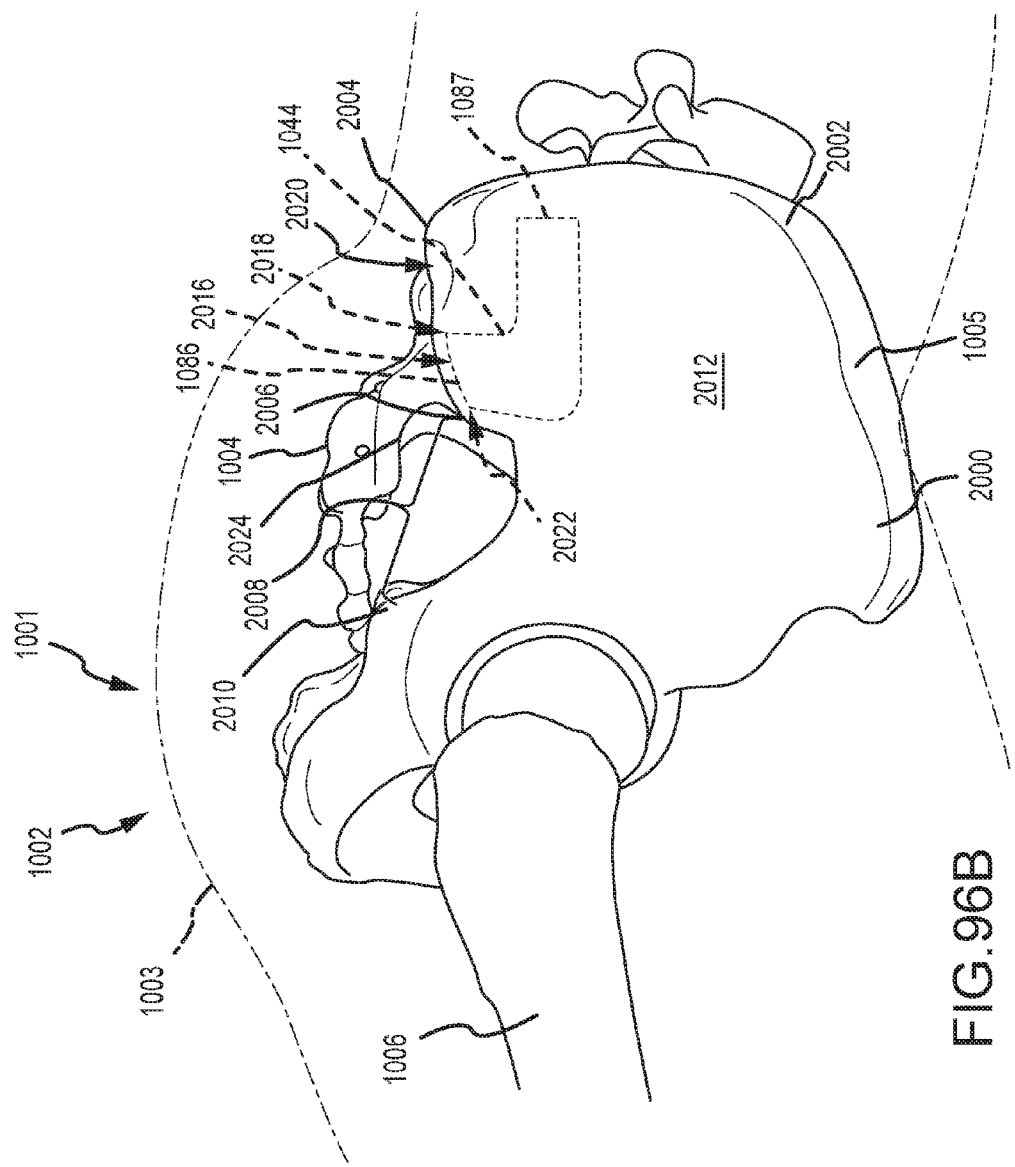

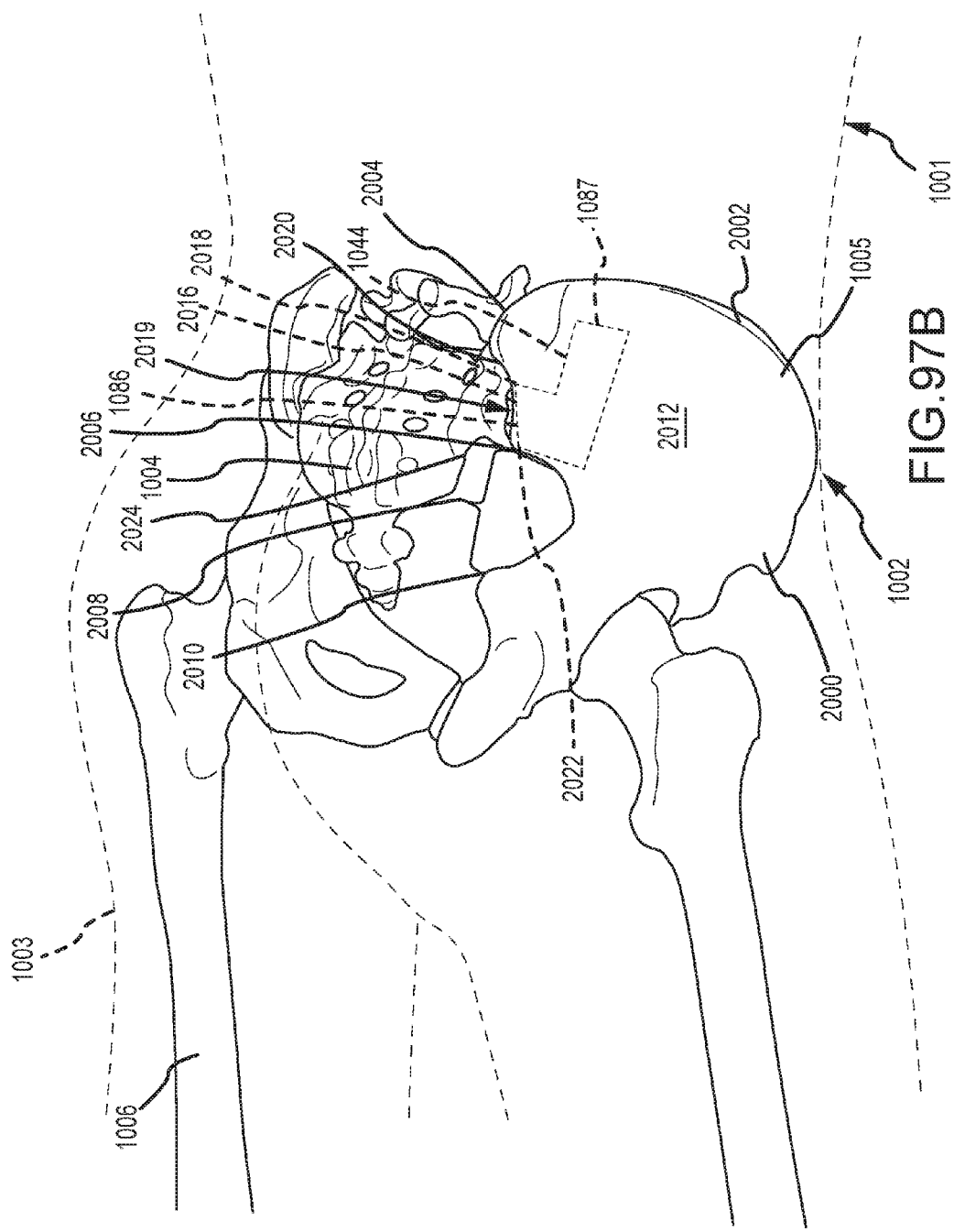

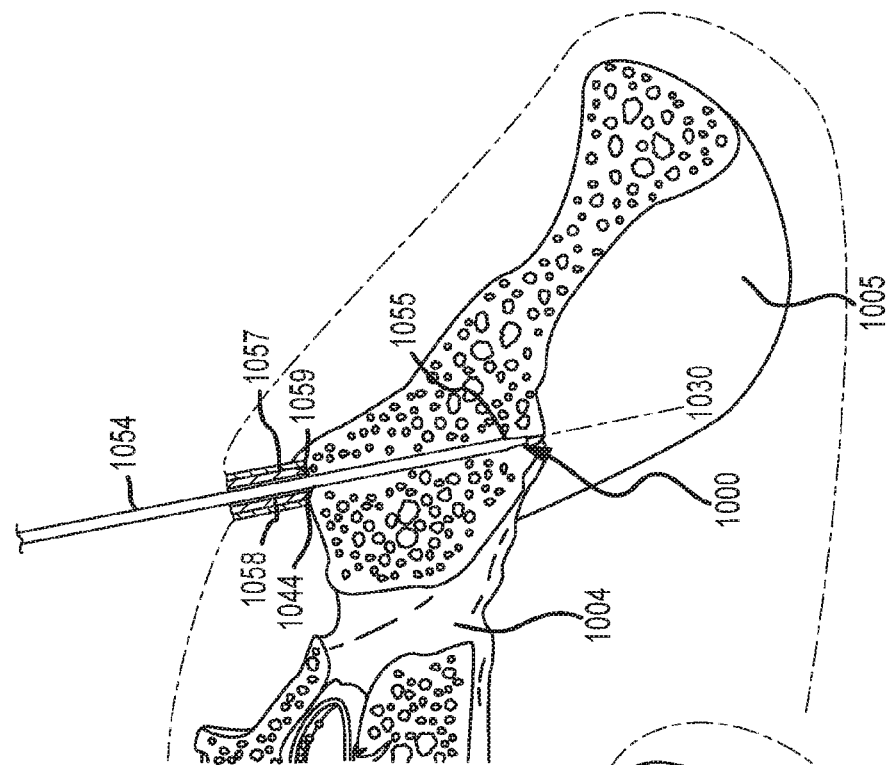
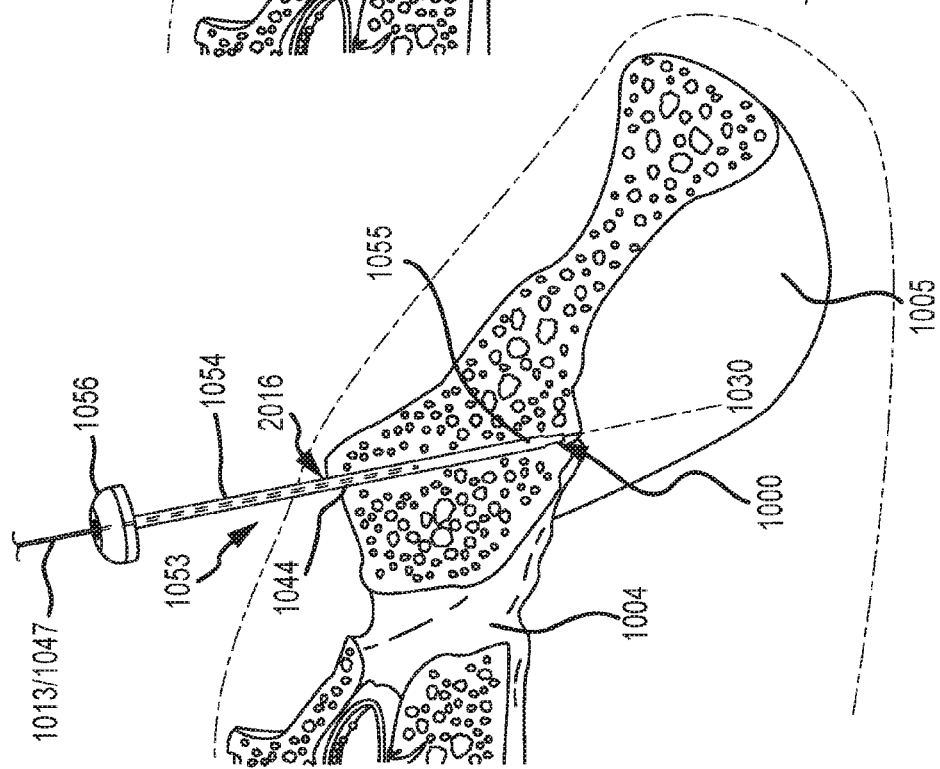

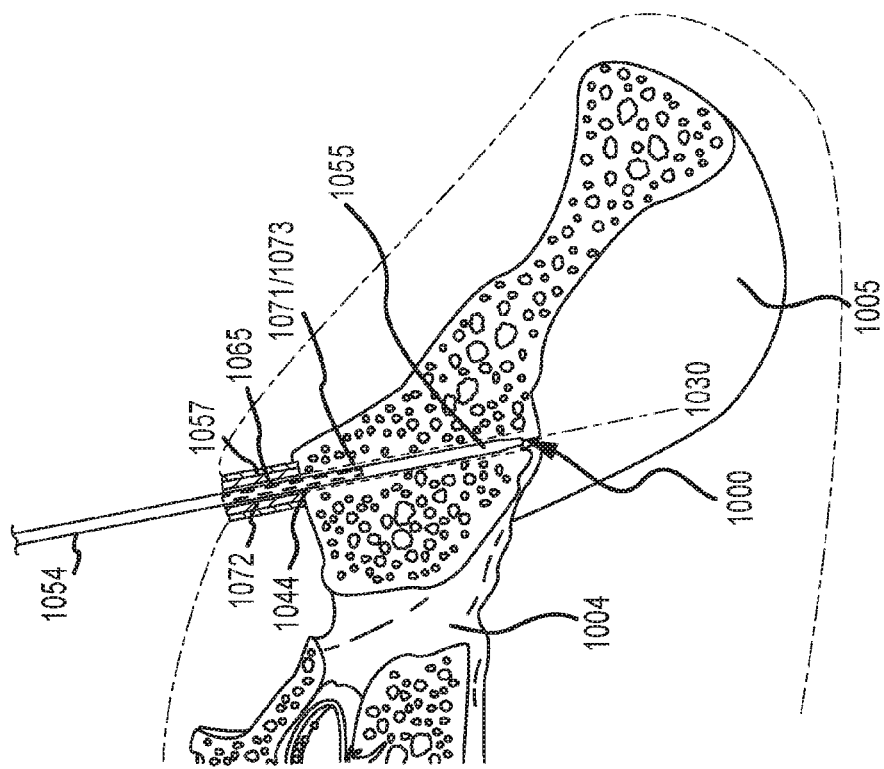
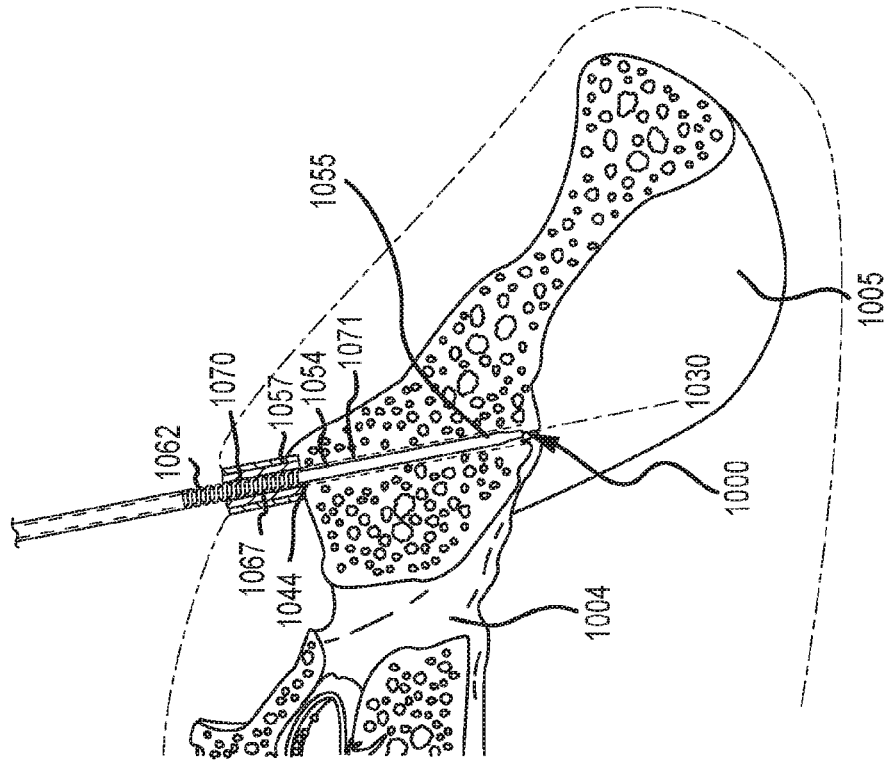

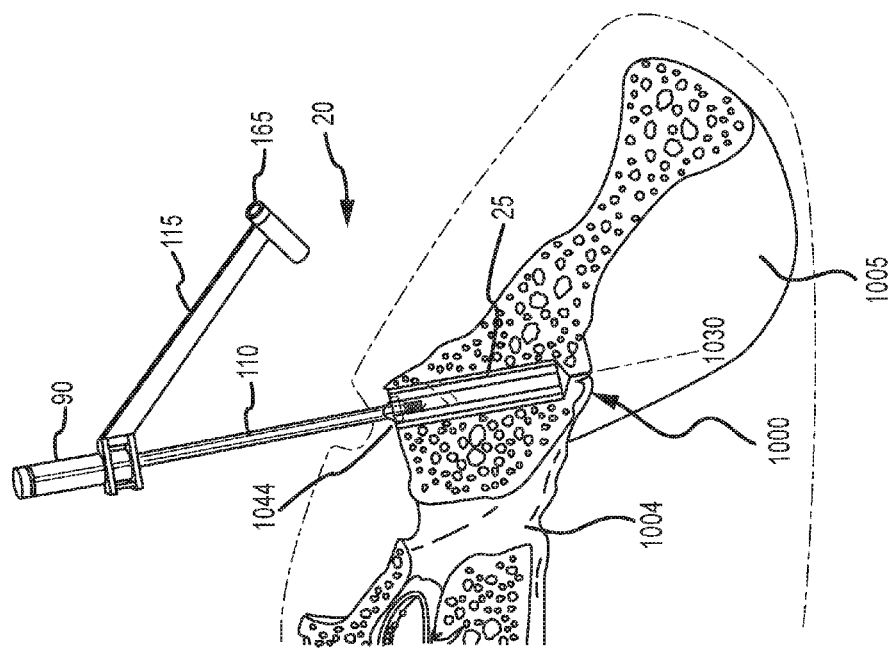
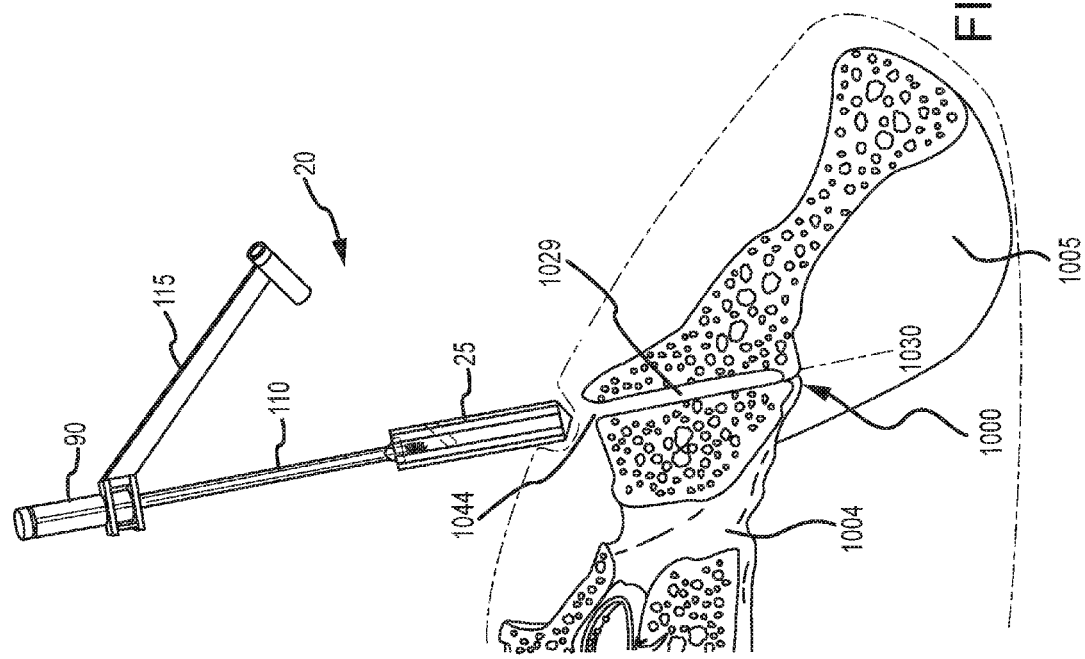

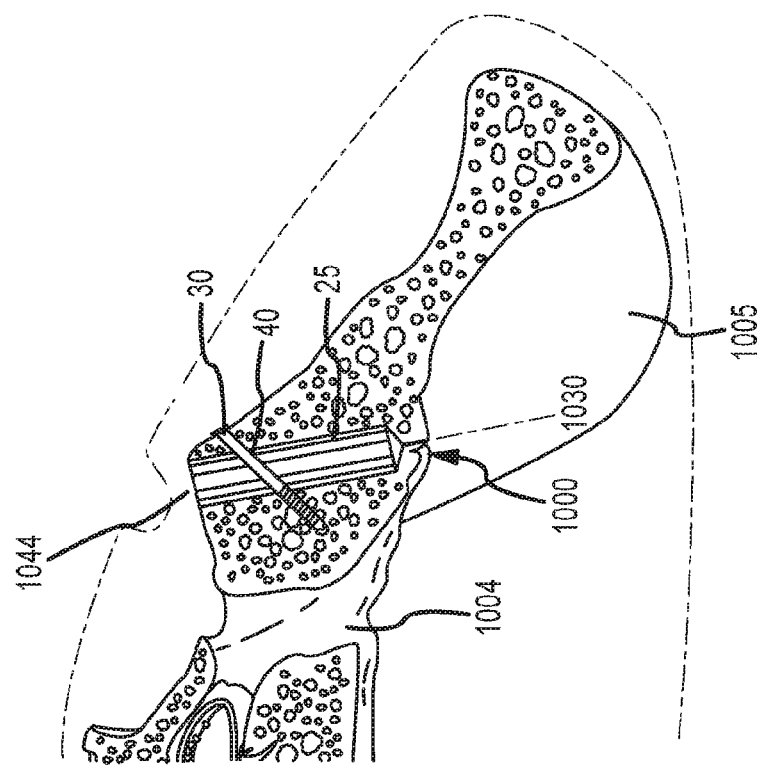
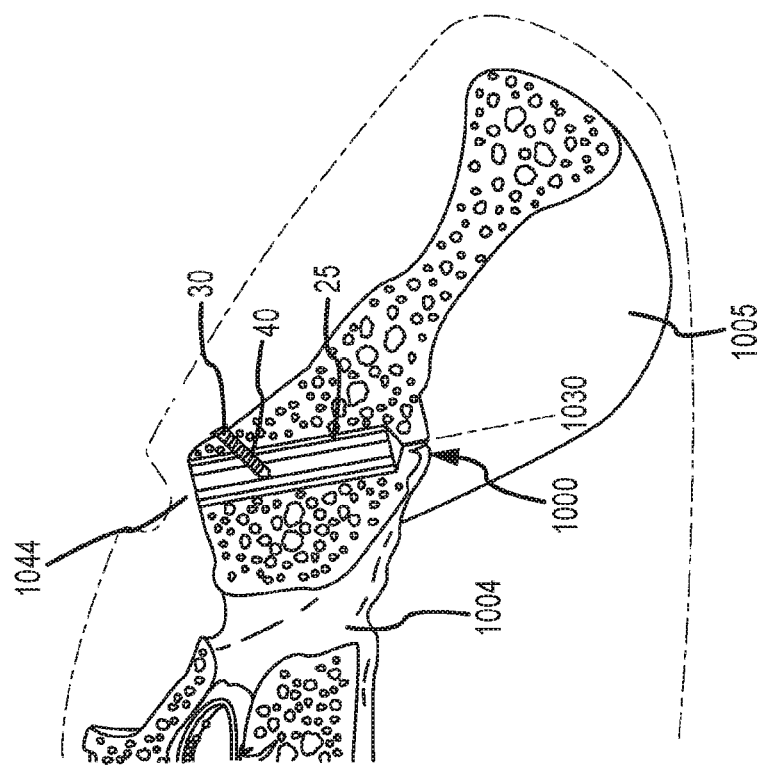

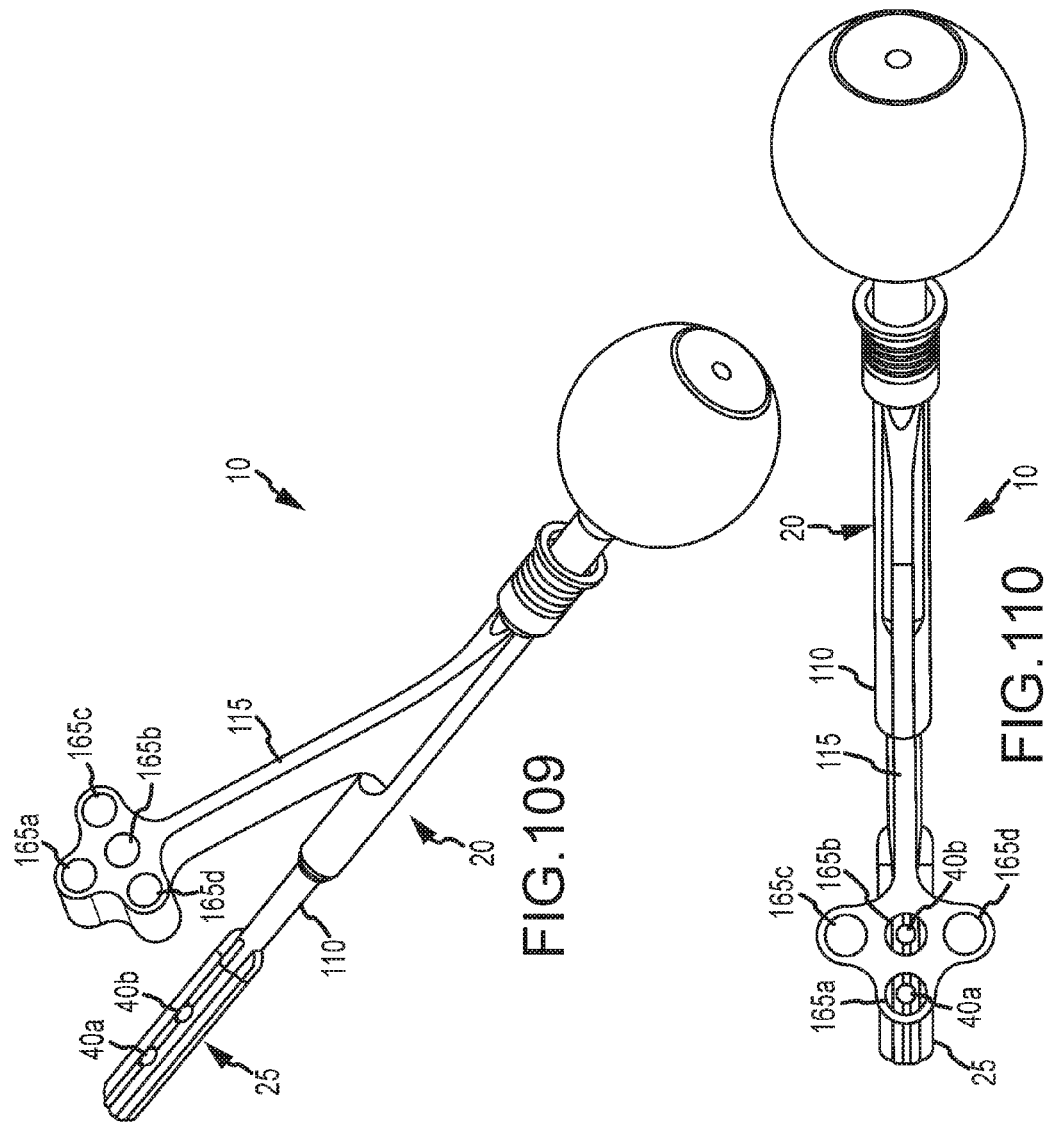

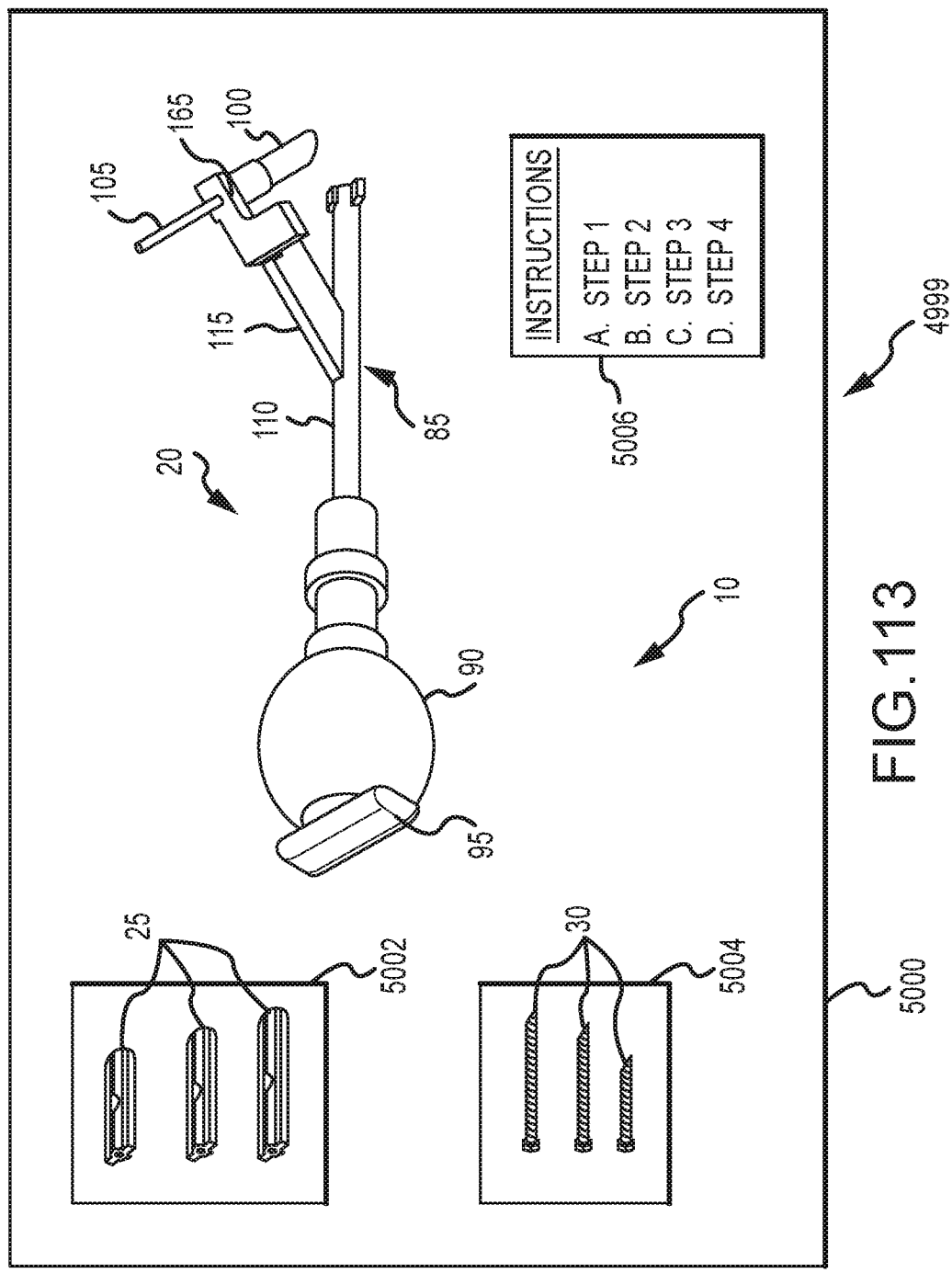

METHODS OF FUSING A SACROILIAC JOINT

CROSS REFERENCE TO RELATED APPLICATIONS

The present application is a continuation application of U.S. patent application Ser. No. 14/681,882 filed Apr. 8, 2015, which application is a continuation application of U.S. patent application Ser. No. 13/236,411 filed Sep. 19, 2011, now U.S. Pat. No. 9,017,407, which application is a continuation-in-part application of U.S. patent application Ser. No. 12/998,712 ("the '712 application"), which was filed May 23, 2011, now U.S. Pat. No. 8,979,928. The '712 application is the National Stage of International Patent Cooperation Treaty Patent Application PCT/US2011/000070 (the 'PCT application"), which was filed Jan. 13, 2011. The PCT application claims the benefit of U.S. Provisional Patent Application 61/335,947, which was filed Jan. 13, 2010. All of the aforementioned applications are hereby incorporated by reference in their entireties into the present application.

FIELD OF THE INVENTION

Aspects of the present invention relate to medical apparatus and methods. More specifically, the present invention relates to devices and methods for fusing a sacroiliac joint.

BACKGROUND OF THE INVENTION

The sacroiliac joint is the joint between the sacrum and the ilium of the pelvis, which are joined by ligaments. In humans, the sacrum supports the spine and is supported in turn by an ilium on each side. The sacroiliac joint is a synovial joint with articular cartilage and irregular elevations and depressions that produce interlocking of the two bones.

Pain associated with the sacroiliac joint can be caused by traumatic fracture dislocation of the pelvis, degenerative arthritis, sacroiliitis an inflammation or degenerative condition of the sacroiliac joint, osteitis condensans ilii, or other degenerative conditions of the sacroiliac joint. Currently, sacroiliac joint fusion is most commonly advocated as a surgical treatment for these conditions. Fusion of the sacroiliac joint can be accomplished by several different conventional methods encompassing an anterior approach, a posterior approach, and a lateral approach with or without percutaneous screw or other type implant fixation. However, while each of these methods has been utilized for fixation and fusion of the sacroiliac joint over the past several decades, substantial problems with respect to the fixation and fusion of the sacroiliac joint remain unresolved.

A significant problem with certain conventional methods for fixation and fusion of the sacroiliac joint including the anterior approach, posterior approach, or lateral approach may be that the surgeon has to make a substantial incision in the skin and tissues for direct access to the sacroiliac joint involved. These invasive approaches allow the sacroiliac joint to be seen and touched directly by the surgeon. Often referred to as an "open surgery", these procedures have the attendant disadvantages of requiring general anesthesia and can involve increased operative time, hospitalization, pain, and recovery time due to the extensive soft tissue damage resulting from the open surgery.

A danger to open surgery using the anterior approach can be damage to the L5 nerve root, which lies approximately two centimeters medial to the sacroiliac joint or damage to the major blood vessels. Additionally, these procedures typically involve fixation of the sacroiliac joint (immobilization of the articular surfaces of the sacroiliac joint in relation to one another) by placement of one or more screws or one or more trans-sacroiliac implants (as shown by the non-limiting example of FIG. 1) or by placement of implants into the S1 pedicle and iliac bone.

Use of trans-sacroiliac and S1 pedicle-iliac bone implants can also involve the risk of damage to the lumbosacral neurovascular elements. Damage to the lumbosacral neurovascular elements as well as delayed union or non-union of the sacroiliac joint by use of these procedures may require revision surgery to remove all or a portion of the implants or repeat surgery as to these complications.

Another significant problem with conventional procedures utilizing minimally invasive small opening procedures can be that the procedures are technically difficult, requiring biplanar fluoroscopy of the articular surfaces of the sacroiliac joint and extensive surgical training and experience. Despite the level of surgical training and experience, there is a substantial incidence of damage to the lumbosacral neurovascular elements. Additionally, sacral anomalies can further lead to mal-placement of implants leading to damage of surrounding structures. Additionally, these procedures are often performed without fusion of the sacroiliac joint, which does not remove the degenerative joint surface and thereby does not address the degenerative condition of the sacroiliac joint, which may lead to continued or recurrent sacroiliac joint pain.

Another significant problem with conventional procedures can be the utilization of multiple trans-sacroiliac elongate implants, which do not include a threaded surface. This approach requires the creation of trans-sacroiliac bores in the pelvis and nearby sacral foramen, which can be of relatively large dimension and which are subsequently broached with instruments, which can result in bone being impacted into the pelvis and neuroforamen.

The creation of the trans-sacroiliac bores and subsequent broaching of the bores requires a guide pin, which may be inadvertently advanced into the pelvis or sacral foramen, resulting in damage to other structures. Additionally, producing the trans-sacroiliac bores, broaching, or placement of the elongate implants may result in damage to the lumbosacral neurovascular elements, as above discussed. Additionally, there may be no actual fusion of the articular portion of the sacroiliac joint, which may result in continued or recurrent pain requiring additional surgery.

Another substantial problem with conventional procedures can be that placement of posterior extra-articular distracting fusion implants and bone grafts may be inadequate with respect to removal of the articular surface or preparation of cortical bone, the implant structure and fixation of the sacroiliac joint. The conventional procedures may not remove sufficient amounts of the articular surfaces or cortical surfaces of the sacroiliac joint to relieve pain in the sacroiliac joint. The conventional implant structures may have insufficient or avoid engagement with the articular surfaces or cortical bone of the sacroiliac joint for adequate fixation or fusion. The failure to sufficiently stabilize and fuse the sacroiliac joint with the conventional implant structures and methods may result in a failure to relieve the condition of sacroiliac joint being treated. Additionally, conventional methods of driving apart a sacrum and ilium may lead to mal-alignment of the sacroiliac joint and increased pain.

The inventive sacroiliac fusion system described herein addresses the problems associated with conventional methods and apparatuses used in fixation and fusion of the sacroiliac joint.

BRIEF SUMMARY OF THE INVENTION

One implementation of the present disclosure may take the form of a sacroiliac joint fusion system including a joint implant, an anchor element and a delivery tool. The joint implant includes a distal end, a proximal end, a body extending between the proximal and distal ends, and a first bore extending non-parallel to a longitudinal axis of the body. The anchor element includes a distal end and a proximal end and is configured to be received in the first bore. The delivery tool includes an implant arm and an anchor arm. The implant arm includes a proximal end and a distal end. The distal end of the implant arm is configured to releasably couple to the proximal end of the joint implant such that a longitudinal axis of the implant arm is substantially at least one of coaxial or parallel with the longitudinal axis of the body of the joint implant. The anchor arm includes a proximal end and a distal end. The distal end of the anchor arm is configured to engage the proximal end of the anchor element. The anchor arm is operably coupled to the implant arm in an arrangement such that the longitudinal axis of the anchor element is generally coaxially aligned with a longitudinal axis of the first bore when the distal end of the implant arm is releasably coupled with the proximal end of the joint implant and the distal end of the anchor arm is engaged with the proximal end of the anchor element. The arrangement is fixed and nonadjustable.

Another implementation of the present disclosure may take the form of a sacroiliac joint fusion system including a joint implant, an anchor element and a delivery tool. The joint implant includes a distal end, a proximal end, a body extending between the proximal and distal ends, and a first bore extending non-parallel to a longitudinal axis of the body. The anchor element includes a distal end and a proximal end and is configured to be received in the first bore. The delivery tool includes an implant arm and an anchor arm. The implant arm includes a proximal end and a distal end. The distal end of the implant arm is configured to releasably couple to the proximal end of the joint implant such that a longitudinal axis of the implant arm is substantially at least one of coaxial or parallel with the longitudinal axis of the body of the joint implant. The anchor arm includes a proximal end and a distal end. The distal end of the anchor arm includes a guide. The anchor arm is pivotally coupled to the implant arm and configured such that a center of the guide moves along an arc that extends through generally the center of the first bore of the implant when the distal end of the implant arm is releasably coupled with the proximal end of the joint implant. The anchor arm is configured to deliver the anchor element to the first bore.

Yet another implementation of the present disclosure may take the form of a sacroiliac joint fusion system including a joint implant and a tool. In one embodiment, the joint implant includes a longitudinal axis and a first bore extending non-parallel to the longitudinal axis. The anchor element is configured to be received in the first bore. The delivery tool includes an implant arm and an anchor arm. The implant arm is configured to releasably couple to the joint implant. The anchor arm is coupled to the implant arm and configured to deliver the anchor element to the first bore. The final manufactured configuration of the tool and final manufactured configuration of the joint implant are such that, when the system is assembled such that the implant arm is releasably coupled to the joint implant, a delivery arrangement automatically exists such that the anchor arm is correctly oriented to deliver the anchor element to the first bore.

Another implementation of the present disclosure may take the form of a method of sacroiliac joint fusion. In one embodiment, the method includes: a) approaching a sacroiliac joint space with a joint implant comprising at least first and second planar members radially extending generally coplanar with each other from opposite sides of a body of the joint implant; b) delivering the joint implant into a sacroiliac joint space, the joint implant being oriented in the sacroiliac joint space such that the first and second planar members are generally coplanar with a joint plane of the sacroiliac joint space; and c) causing an anchor element to be driven generally transverse to the joint plane through bone material defining at least a portion of the sacroiliac joint space and into a bore of the joint implant that extends generally transverse to the body of the joint implant.

Yet another implementation of the present disclosure may take the form of a medical kit for the fusion of a sacroiliac joint including a caudal access region and a joint plane. In one embodiment, the kit includes: a) a delivery tool comprising an implant arm and an anchor arm coupled to the implant arm; b) a joint implant comprising a bore defined therein that extends generally transverse to a longitudinal length of the joint implant; and c) an anchor element configured to be received in the bore of the joint implant. The bore of the implant, the implant, the implant arm and the anchor arm have an as-manufactured configuration that allows the anchor arm to properly align the anchor element to be received in the bore of the implant when the implant is coupled to the implant arm.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 2A is an isometric view of a first embodiment of a system for fusing a sacroiliac joint.

FIG. 2B is the same view as FIG. 2A, except the delivery tool and implant assembly are decoupled from each other.

FIG. 3 is the same view as FIG. 2A, except the system is exploded to better illustrate its components.

FIG. 21A is a side elevation of the system wherein the tool is attached to the implant assembly for delivery of the implant assembly to the sacroiliac joint.

FIG. 21C is the same view of FIG. 21A, except illustrating a version of the same embodiment wherein the anchor arm is more proximally located along the implant arm.

FIG. 22 is the same view as FIG. 21A, except shown as a longitudinal cross section.

FIG. 27 is a cross sectional distal isometric view of the handle.

FIG. 28 is an isometric view of the implant retainer.

FIG. 29 is a longitudinal cross sectional isometric view of the implant retainer.

FIG. 32 is an isometric view of a second embodiment of a system for fusing a sacroiliac joint.

FIG. 33 is the same view as FIG. 32, except the system is exploded to better illustrate its components.

FIG. 34 is a side elevation of the system embodiment of FIG. 32.

FIGS. 51-52 are, respectively, isometric and side elevation views of an implant having an anchor member receiving arm.

FIG. 53 is an enlarged view of the disk-shaped seat of the implant arm of FIG. 51.

FIG. 54 is an isometric view of an implant with another type of anchor member locking mechanism.

FIG. 55 is an enlarged view of the free end of the anchor member locking mechanism of FIG. 54.

FIGS. 56-61 are, respectively, front isometric, rear isometric, side elevation, plan, front elevation, and rear elevation views of another embodiment of the implant.

FIGS. 62-67 are, respectively, front isometric, rear isometric, side elevation, plan, front elevation, and rear elevation views of yet another embodiment of the implant.

FIGS. 68-73 are, respectively, front isometric, rear isometric, side elevation, plan, front elevation, and rear elevation views of still another embodiment of the implant.

FIGS. 74-79 are, respectively, front isometric, rear isometric, side elevation, plan, front elevation, and rear elevation views of yet another embodiment of the implant.

FIGS. 80-85 are, respectively, front isometric, rear isometric, side elevation, plan, front elevation, and rear elevation views of still yet another embodiment of the implant.

FIGS. 87-88 are generally opposite isometric views of the delivery tool in an exploded state.

FIG. 89 is an isometric view of the handle.

FIG. 90 is an exploded isometric view of the retaining collar and handle shown in longitudinal cross section.

FIG. 95 is the same view as FIG. 93, except with the retainer received in the hole.

FIG. 96B is an enlarged view of the hip region of FIG. 96A.

FIG. 97B is an enlarged view of the hip region of FIG. 97A.

FIG. 109 is an isometric view of the system wherein the tool is attached to the implant for delivery of the implant to the sacroiliac joint.

FIG. 110 is a view of the system wherein the implant and anchor arm are shown in plan view.

FIG. 113 is a plan view of a medical kit containing the components of the system, namely, the delivery tool, multiple implants of different sizes, and multiple anchor members of different sizes, wherein the system components are sealed within one or more sterile packages and provided with instructions for using the system.

DETAILED DESCRIPTION

Figure 1:
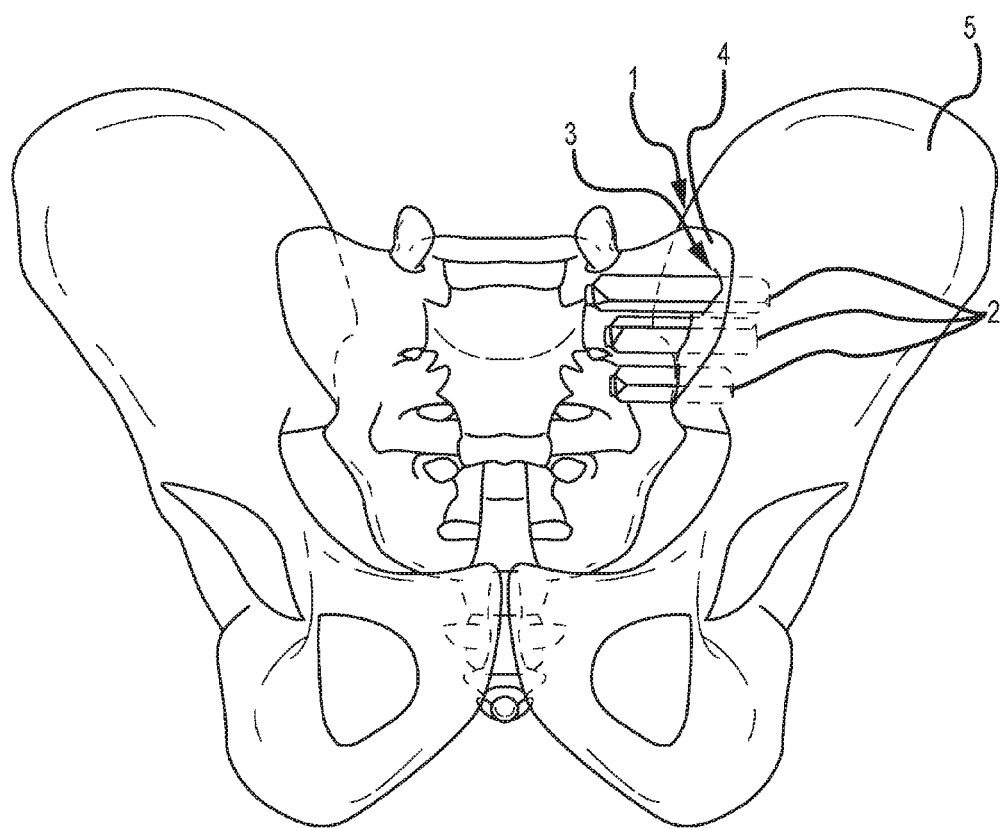
FIG. 1 is an anterior view of the pelvic region and a conventional method and device for stabilizing the sacroiliac joint.

Implementations of the present disclosure involve a system 10 for fusing a sacroiliac joint. The system 10 includes a delivery tool 20 and an implant assembly 15 for delivery to a sacroiliac joint via the delivery tool 20. The implant assembly 15, which includes an implant 25 and anchor 30, is configured to fuse a sacroiliac joint once implanted at the joint. The tool 20 is configured such that the anchor 30 can be quickly, accurately and reliably delivered to a bore 40 of an implant 25 supported off of the tool distal end in a sacroiliac joint.

To begin a detailed discussion of a first embodiment of the system 10, reference is made to FIGS. 2A-3. FIG. 2A is an isometric view of the system 10. FIG. 2B is the same view as FIG. 2A, except an implant assembly 15 of the system 10 is separated from a delivery tool 20 of the system 10. FIG. 3 is the same view as FIG. 2A, except the system 10 is shown exploded to better illustrate the components of the system 10.

As can be understood from FIGS. 2A and 2B, the system 10 includes a delivery tool 20 and an implant assembly 15 for implanting at the sacroiliac joint via the delivery tool 20, the implant assembly 15 being for fusing the sacroiliac joint. As indicated in FIG. 3, the implant assembly 15 includes an implant 25 and an anchor element 30 (e.g., a bone screw or other elongated body). As discussed below in greater detail, during the implantation of the implant assembly 15 at the sacroiliac joint, the implant 25 and anchor element 30 are supported by a distal end 35 of the delivery tool 20, as illustrated in FIG. 2A. The delivery tool 20 is used to deliver the implant 25 into the sacroiliac joint space. The delivery tool 20 is then used to cause the anchor element 30 to extend through the ilium, sacrum and implant 25 generally transverse to the sacroiliac joint and implant 25. The delivery tool 20 is then decoupled from the implanted implant assembly 15, as can be understood from FIG. 2B.

Figure 4:
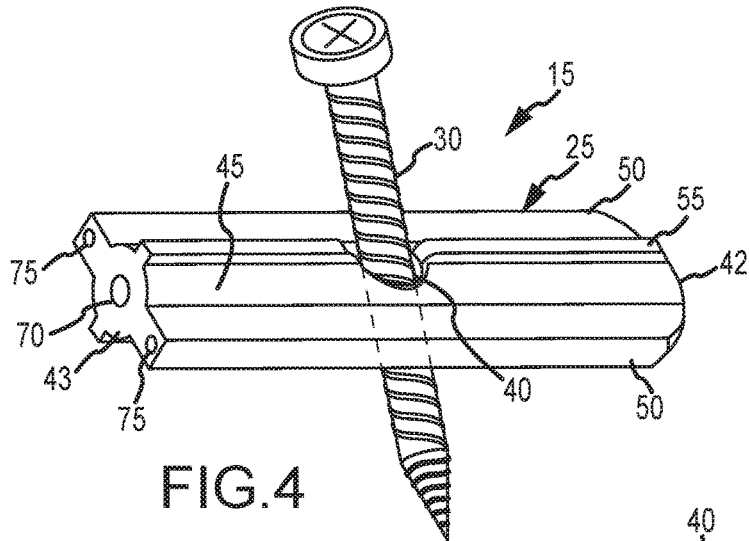
FIG. 4 is a top-side isometric view of the implant assembly.
Figure 5:
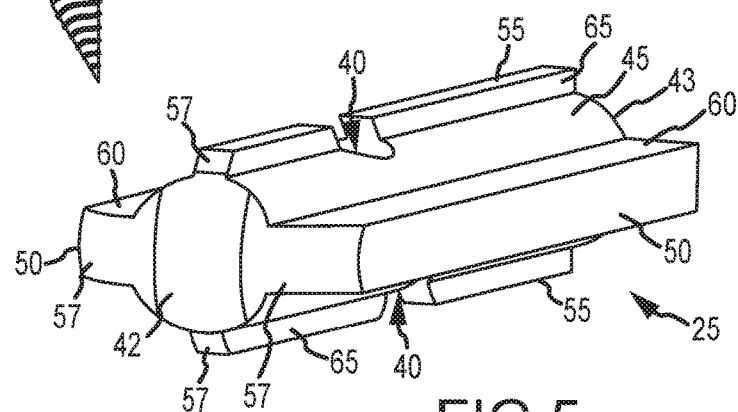
FIG. 5 is a distal end isometric view of the implant of the implant assembly of FIG. 4.

To begin a detailed discussion of components of an embodiment of the implant assembly 15, reference is made to FIG. 4, which is a side isometric view of the implant assembly 15. As shown in FIG. 4, the implant assembly 15 includes an implant 25 and an anchor element 30. The anchor element 30 may be in the form of an elongated body such as, for example, a nail, rod, pin, threaded screw, expanding body, etc. The anchor element 30 is configured to be received in a bore 40 defined through the implant 25. The bore 40 extends through the implant 25 and is sized such that the anchor element 30 can at least extend into or through the implant 25 as illustrated in FIG. 4.

Figure 12:
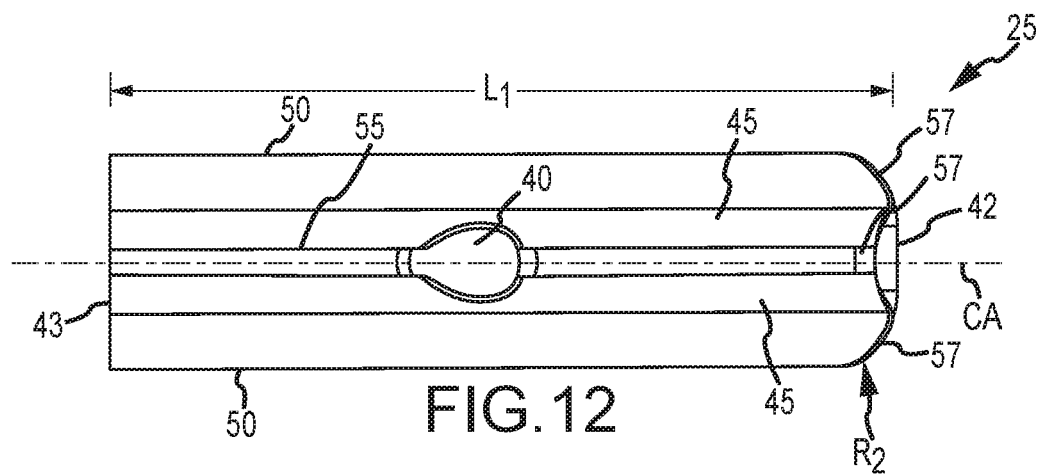
FIGS. 12 and 13 are opposite plan views of the implant.
Figure 13:
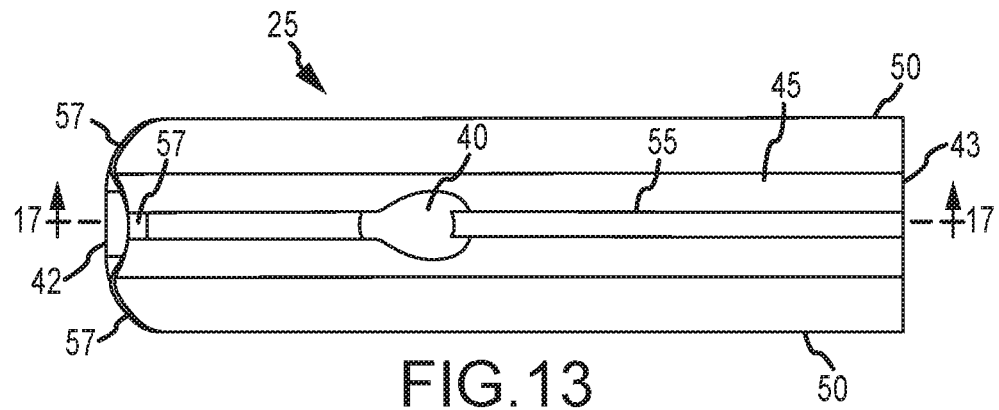
Figure 16:
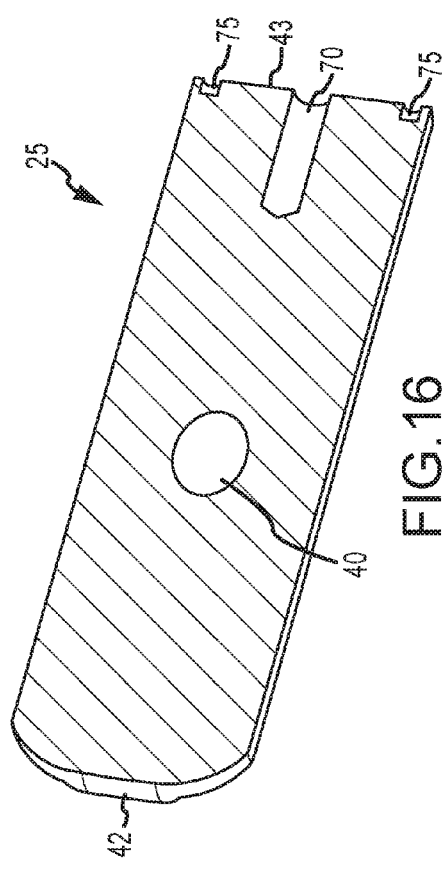
FIG. 16 is an isometric longitudinal cross section of the implant as taken along section line 16-16 of FIG. 11.
Figure 17:
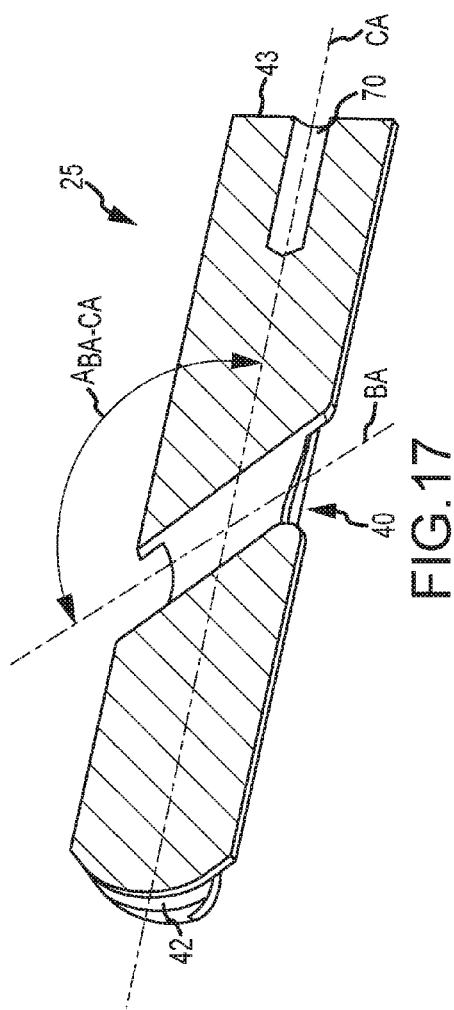
FIG. 17 is an isometric longitudinal cross section of the implant as taken along section line 17-17 of FIG. 13.

For a detailed discussion of the implant 25, reference is made to FIGS. 5-17. FIGS. 5-9 are various isometric views of the implant 25. FIGS. 12 and 13 are opposite plan views of the implant 25, and FIGS. 10, 11, 14 and 15 are various elevation views of the implant. FIGS. 16 and 17 are isometric longitudinal cross sections of the implant 25 as taken along corresponding section lines in FIGS. 11 and 13, respectively.

As shown in FIGS. 5-15, in one embodiment, the implant 25 includes a distal or leading end 42, a proximal or trailing end 43, a longitudinally extending body 45, a bore 40 extending through the body, and keels, fins or planar members 50, 55 that radially extend outwardly away from the body 45. In one embodiment, the radially extending planar members 50, 55 may be grouped into pairs of planar members 50, 55 that are generally coplanar with each other. For example, planar members 50 that are opposite the body 45 from each other generally exist in the same plane. More specifically, as best understood from FIGS. 14 and 15, the planar faces 60 of a first planar member 50 are generally coplanar with the planar faces 60 of a second planar member 50 opposite the body 45 from the first planar member 50. Likewise, the planar faces 65 of a third planar member 55 are generally coplanar with the planar faces 65 of a fourth planar member 55 opposite the body 45 from the third planar member 50.

Figure 14:
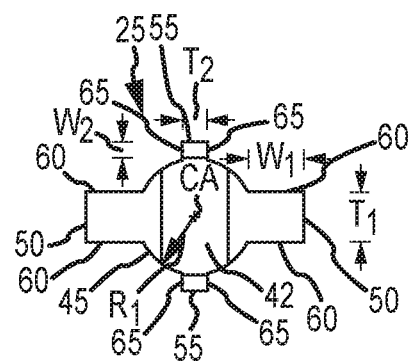
FIG. 14 is a distal end elevation of the implant.
Figure 15:
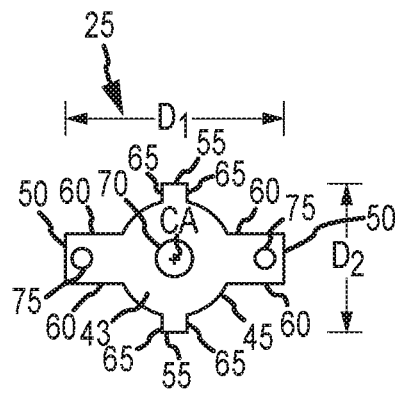
FIG. 15 is a proximal end elevation of the implant.

As best understood from FIGS. 14 and 15, one set of planar members 50 (i.e., the large planar members 50) may extend radially a greater distance $D_1$ than the distance $D_2$ extended radially by the other set of planar members 55 (i.e., the small planar members 55). Also, the width $W_1$ of a large planar member 50 from its outer edge to its intersection with the body 45 may be greater than the width $W_2$ of a small planar member 55 from its outer edge to its intersection with the body 45. Also, the thickness $T_1$ of the large planar members 50 may be greater than the thickness $T_2$ of the small planar members 55. Thus, one set of planar members 50 may be both wider and thicker than the other set of planar members 55. In other words, one set of planar members 50 may be larger than the other set of planar members 55.

In one embodiment, the distance $D_1$ spanned by the large planar members 50 is between approximately 5 mm and approximately 30 mm, with one embodiment having a distance $D_1$ of approximately 20 mm, and the distance $D_2$ spanned by the small planar members 55 is between approximately 5 mm and approximately 20 mm, with one embodiment having a distance $D_2$ of approximately 14 mm. The width $W_1$ of a large planar member 50 is between approximately 2.5 mm and approximately 15 mm, with one embodiment having a width $W_1$ of approximately 5 mm, and the width $W_2$ of a small planar member 55 is between approximately 1 mm and approximately 10 mm, with one embodiment having a width $W_2$ of approximately 3 mm. The thickness $T_1$ of a large planar member 50 is between approximately 2 mm and approximately 20 mm, with one embodiment having a thickness $T_1$ of approximately 4 mm, and the thickness $T_2$ of a small planar member 55 is between approximately 1 mm and approximately 10 mm, with one embodiment having a thickness $T_2$ of approximately 2 mm.

As indicated in FIGS. 5-15, the first set of planar members 50 are generally perpendicular with the second set of planar members 55. Since the sets of planar members 50, 55 are perpendicular to each other, in one embodiment, the intersection of the planar members 50, 55 at a central longitudinal axis of the implant 25 may form the body 45 of the implant 25. In other embodiments, and as illustrated in FIGS. 5-14, the body 45 may be of a distinct shape so as to have, for example, a cylindrical or other configuration. In one embodiment, as indicated in FIG. 14, the cylindrical body 45 has a radius $R_1$ of between approximately 1 mm and approximately 20 mm, with one embodiment having a radius $R_1$ of approximately 10 mm.

As illustrated in FIG. 12, in one embodiment, the implant 25 has a length $L_1$ of between approximately 5 mm and approximately 70 mm, with one embodiment having a length $L_1$ of approximately 45 mm.

As indicated in FIGS. 5 and 9-14, the implant distal end 42 may have a bullnose or otherwise rounded configuration, wherein the rounded configuration extends outward away from the distal extremity of the body 45 and along the distal or leading edges of the planar members 50, 55. Thus, as can be understood from FIGS. 5 and 9-13, the leading or distal edges 57 of the planar members 50, 55 may be rounded in the radially extending length of the lead or distal edges and/or in a direction transverse to the radially extending length of the lead or distal edges. In one embodiment, the leading edges 57 of the planar members 50, 55 each have a radius $R_2$ of between approximately 1 mm and approximately 15 mm, with one embodiment having a radius $R_2$ of approximately 10 mm. In one embodiment, the leading end 42 of the implant body 45 and the leading edges 57 of the planar members 50, 55 have a generally conical point configuration.

As indicated in FIGS. 6-8, 10-13, and 15, the implant proximal end 43 has a generally planar face that is generally perpendicular to a longitudinal center axis CA of the implant 25. A center attachment bore 70 and two lateral attachment bores 75 on opposite sides of the center bore 70 are defined in the implant proximal end 43. The center bore 70 is centered about the longitudinal center axis CA, and the lateral attachment bores 75 are near outer ends of the long planar members 50, generally centered in the thickness of the larger planar members 50. Alternatively, in particular embodiments, the implant proximal end 43 can be configured to have a face similarly configured to the implant distal end 42 (i.e. rounded, bullet nosed, etc.) to allow for a simplified removal of implant 25 during a revision surgery.

As indicated in FIGS. 16 and 17, the center bore 70 may be a blind hole in that it only has a single opening. Alternatively, the center bore 70 may be configured as a hole that communicates between the implant proximal end 43 and implant bore 40. A center bore so configured may be able to receive a fastener to permit interference with the anchor member 30 extending through the bore 40 after implantation to resist migration of said anchor member.

As illustrated in FIG. 16, the lateral bores 75 are also blind holes and can be configured to not extend nearly as far into the body 45 as the center hole 70 and can be configured to be not nearly as great in diameter as the center hole 70. In one embodiment, the center attachment bore 70 has a diameter of between approximately 2 mm and approximately 10 mm, with one embodiment having a diameter of approximately 5 mm. In one embodiment, the lateral attachment bores 75 can each have a diameter of between approximately 0.5 mm and approximately 3 mm, with one embodiment having a diameter of approximately 1.5 mm.

As can be understood from FIG. 17, the implant bore 40, which is configured to receive the anchor member 30, has a longitudinal center axis BA that is generally transverse to the longitudinal center axis CA of the implant 25. In one embodiment, the implant bore longitudinal center axis BA forms an angle $A_{BA-CA}$ with the implant longitudinal center axis CA. For example, the angle $A_{BA-CA}$ may be between approximately 15 degrees and approximately 135 degrees, with one embodiment being approximately 45 degrees.

As shown in FIGS. 4-17, the bore 40 is generally located within a plane with which the small radial planar members 55 are located. That the bore 40 is located in the same plane as occupied by the small radial planar members 55 is also the case where the bore 40 angularly deviates from being perpendicular with the longitudinal axis of the implant body 45.

In one embodiment, the implant 25 may be machined, molded, formed, or otherwise manufactured from stainless steel, titanium, ceramic, polymer, composite, bone or other biocompatible materials. The anchor member 30 may be machined, molded, formed or otherwise manufactured from similar biocompatible materials.

Figure 118A:
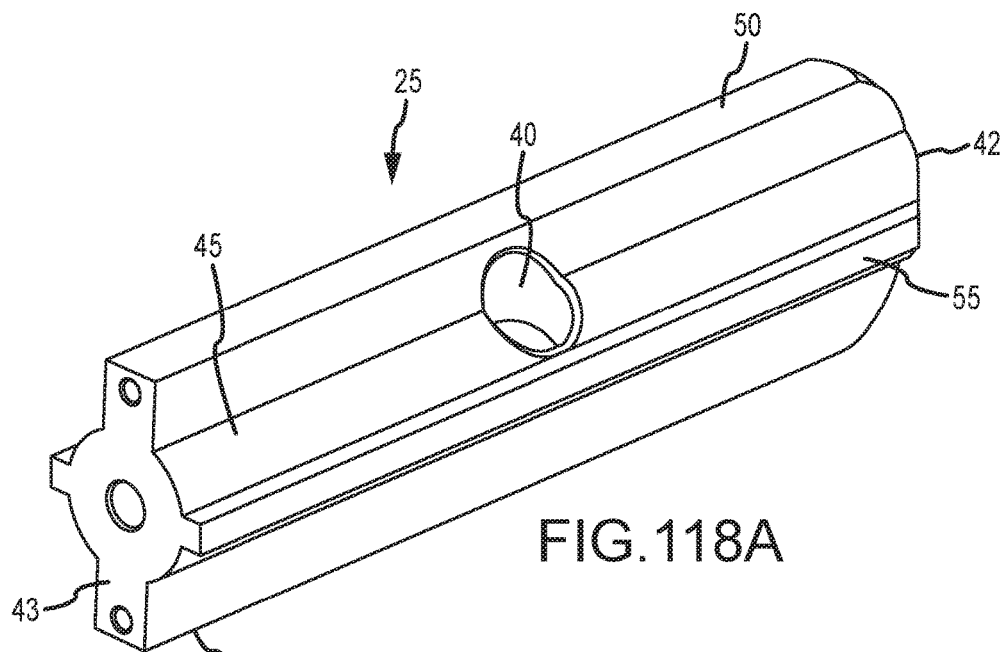
FIGS. 118A-118C, which are, respectively, isometric and opposite plan views of an implant with a side-to-side deviated bore.
Figure 118B:
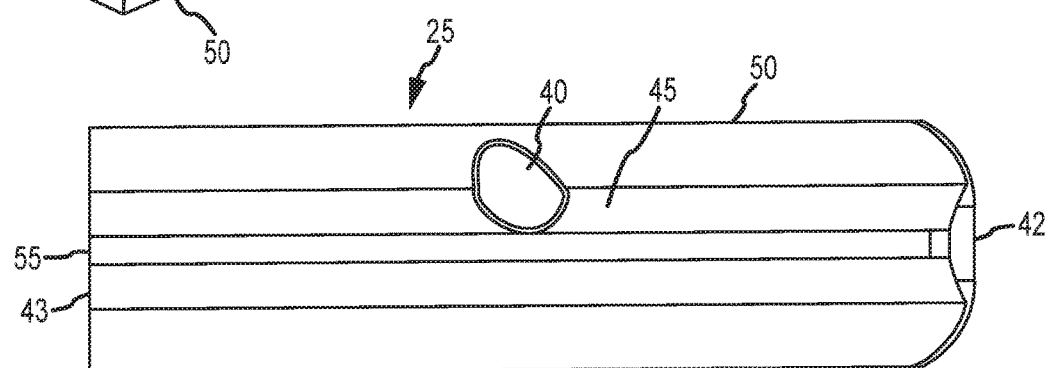
Figure 118C:
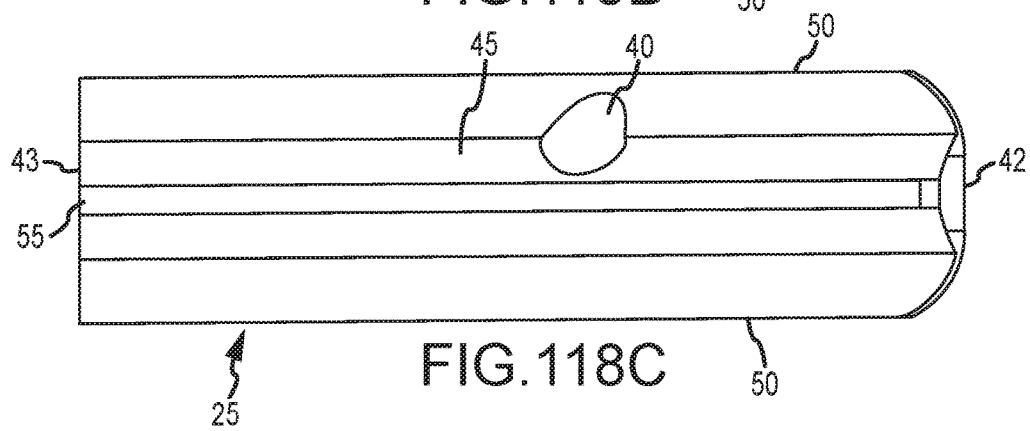

In some embodiments, the implant 25 may be substantially as described above with respect to FIGS. 4-17, except the bore 40 of the implant 25 may be angled side-to-side relative to the longitudinal axis of the implant body 45 such that the bore 40 is not contained in the plane occupied by the small radial planar members 55. For example, as shown in FIGS. 118A-118C, which are, respectively, isometric and opposite plan views of an implant 25 with such a side-to-side deviated bore 40, the bore daylights in the body 45 and large radial planar members 50. In doing so, the bore 40 deviates side-to-side from the plane in which the small planar members 55 are located. Since the bore daylights in the body 45 and large planar members 50, the bore 40 of FIGS. 118A-118C differs from that of FIGS. 4-17, wherein the bore 40 daylights in the small radial members 55.

Just like delivery tool 20 of FIG. 2A has an as-manufactured configuration that allows the anchor arm 115 to deliver the anchor element 30 to the bore 40 of the implant 25 of FIGS. 4-17 without necessitating modification of the delivery tool 20 configuration subsequent to the tool 20 leaving its manufacturing facility, a delivery tool 20 can be configured to similarly interact with the bore 40 of the implant 25 of FIGS. 118A-118C.

In some embodiments, the implant 25 may be substantially as described above with respect to FIGS. 4-17, except the implant 25 may further include an anchor member receiving arm 300. For example, as shown in FIGS. 51-52, which are, respectively, isometric and side elevation views of an implant 25 having an anchor member receiving arm 300, the arm 300 may be generally cantilevered off of the proximal end 43 of the implant 25. The arm 300 includes a free end 305 with a disk-shaped seat 310 having a center hole 315 with a center axis that is coaxially aligned with the center axis BA of the bore 40. As illustrated in FIG. 53, which is an enlarged view of the disk-shaped seat 310, the disk-shaped seat 310 has a plurality of arcuate members 320 distributed along an inner circumferential boundary 325 of a rim 330 of the disk-shaped seat 310. There may be five or more or less arcuate members 320 distributed generally evenly about the inner circumferential surface 325 of the rim 330.

In one embodiment, each arcuate member 320 has ends 332 that intersect the inner circumferential surface 325 of the rim 330, with a center point 335 of the arcuate member 320 that is offset or spaced apart from inner circumferential surface 325 of the rim 330. Thus, in one embodiment, the arcuate members 320 may be deflectable so as to allow the head of the anchor member 30 to pass between the center points 335 of the members 330 as the head of the anchor member 30 is seated in the seat 310. As a result, the arcuate members 320 can act against the head of the anchor member 30 to prevent the anchor member from working its way out of the bore 40 and opening 315 of the implant 25, thereby serving as an anchor member locking mechanism.

Other arms 300 may have an anchor member locking mechanism with a different configuration. For example, as illustrated in FIG. 54, which is an isometric view of an implant 25 with another type of anchor member locking mechanism, the arm 300 may be generally cantilevered off of the proximal end 43 of the implant 25. The arm 300 includes a free end 305 with a center hole 315 with a center axis that is coaxially aligned with the center axis BA of the bore 40. As illustrated in FIG. 55, which is an enlarged view of the free end 305, the hole 315 has a cantilevered abutment arm 335 defined in the body of the arm 300 via a series of parallel arcuate slots 340.

In one embodiment, a face 345 of the abutment arm 335 is deflectable and biased radially inward of the inner circumferential surface 350 of the hole 315 such that when the anchor member 30 is extended through the hole 315, the face 345 abuts against the anchor member to prevent the anchor member from working its way out of the bore 40 and opening 315 of the implant 25, thereby serving as an anchor member locking mechanism.

While in the implant embodiment discussed with respect to FIGS. 4-17 may have a cylindrical body 45 at which the planar members 50, 55 intersect, in other embodiments the body 45 of the implant 25 may simply be the region 45 of the implant 25 where the planar members 50, 55 intersect. For example, as shown in FIGS. 56-61, which are, respectively, front isometric, rear isometric, side elevation, plan, front elevation, and rear elevation views of an implant 25, the body 45 of the implant 25 is simply the region 45 of the implant 25 where the planar members 50, 55 intersect. Although not shown in FIGS. 56-61, in one embodiment, the implant 25 has the bore 40 and holes 70, 75 substantially as depicted and discussed with respect to the implant of FIGS. 4-17. Also, the rest of the features of the implant 25 of FIGS. 56-61 are substantially as discussed with respect to the implant 25 of FIGS. 4-17, a main difference being the lack of the cylindrical body 45 and the edges of adjacent intersecting surfaces of the implant 25 of FIGS. 56-61 being rounded or arcuate as opposed to sharp or well-defined edges, as is the case between adjacent intersecting surfaces of the implant embodiment of FIGS. 4-17.

Depending on the embodiment, the implant 25 may have surface features or texture designed to prevent migration of the implant once implanted in the joint space. For example, as shown in FIGS. 62-67, which are, respectively, front isometric, rear isometric, side elevation, plan, front elevation, and rear elevation views of an implant 25 with antimigration surface features 355, the body 45 of the implant 25 is simply the region 45 of the implant 25 where the planar members 50, 55 intersect. Although not shown in FIGS. 62-67, in one embodiment, the implant 25 has the bore 40 and holes 70, 75 substantially as depicted and discussed with respect to the implant of FIGS. 4-17. Also, the rest of the features of the implant 25 of FIGS. 62-67 are substantially as discussed with respect to the implant 25 of FIGS. 56-61, a main difference being the edges of adjacent intersecting surfaces the implant 25 of FIGS. 56-61 being sharp or well defined edges as opposed to round or arcuate edges, as is the case between adjacent intersecting surfaces of the implant embodiment of FIGS. 56-61.

As to particular embodiments as shown in FIGS. 56-61, and in other embodiments as disclosed throughout, the implants described herein can be configured to be used as trials during certain steps of the procedure to determine appropriate implant sizes and to allow a physician, who is presented with a kit containing the delivery system 20 and multiple sizes of the implant 20, to evaluate particular embodiments of an implant as described herein that would be best suited to a particular patient, application or implant receiving space.

As shown in FIGS. 62-67, the anti-migration features 355 are generally evenly distributed along the planar surfaces 60, 65 of the planar members 50, 55 in a rows and columns arrangement. The anti-migration features 355 are generally similarly distributed along the planar surfaces of the edges of the planar members 55. The anti-migration features 355 may be in the form of trapezoids, squares, rectangles, etc. As indicated in FIG. 66, the anti-migration features 355 may have a rectangular cross sectional elevation with a thickness FT of between approximately 0.2 mm and approximately 5 mm, with one embodiment having a thickness FT of approximately 1 mm.

As another example, as shown in FIGS. 68-73, which are, respectively, front isometric, rear isometric, side elevation, plan, front elevation, and rear elevation views of an implant 25 with another type of anti-migration surface features 355, the body 45 of the implant 25 is simply the region 45 of the implant 25 where the planar members 50, 55 intersect. Although not shown in FIGS. 68-73, in one embodiment, the implant 25 has the bore 40 and holes 70, 75 substantially as depicted and discussed with respect to the implant of FIGS. 4-17. Also, the rest of the features of the implant 25 of FIGS. 68-73 are substantially as discussed with respect to the implant 25 of FIGS. 62-67, including the sharp or well defined edges between adjacent intersecting surfaces of the implant 25.

As shown in FIGS. 68-73, the anti-migration features 355 are in the form of unidirectional serrated teeth or ridges 355, wherein the ridges 355 have a triangular cross sectional elevation best understood from FIGS. 70 and 71, wherein the rearward or trailing end of the features 355 are the truncated or vertical end of the triangle cross sectional elevation, and the front or leading end of the features 355 are the point end of the triangle cross sectional elevation. As indicated in FIG. 71, the anti-migration features 355 with the triangular cross sectional elevations have a thickness FT of between approximately 0.2 mm and approximately 5 mm, with one embodiment having a thickness FT of approximately 1 mm, and a length FL of between approximately 0.5 mm and approximately 15 mm, with one embodiment having a thickness FT of approximately 2.5 mm. The triangular ridges 355 are generally evenly distributed along the planar surfaces 60, 65 of the planar members 50, 55 in ridges that run transverse to the length of the implant 25. The anti-migration features 355 are generally similarly distributed along the planar surfaces of the edges of the planar members 55.

In continuing reference to FIGS. 68-73, although the anti-migration features 355 are depicted in the form of unidirectional serrated teeth or ridges 355 on each of the textured surfaces of the implant, the invention is not so limited and, as to particular embodiments, can be configured to have said features 355 arranged in multiple directions, unidirectional, or a combination of multiple direction on some surfaces of the implant and unidirectional on other surfaces of the implant. Accordingly, the features 355 can be so arranged on the various surfaces of the implant so as to prevent undesired migration in particular directions due to the forces present at the sacroiliac joint 1000.

Depending on the embodiment, the implant 25 may have an edge configuration of the planar members 55 designed to prevent migration of the implant once implanted in the joint space. For example, as shown in FIGS. 74-79 which are, respectively, front isometric, rear isometric, side elevation, plan, front elevation, and rear elevation views of an implant 25 with anti-migration edges or ends 360, the body 45 of the implant 25 is simply the region 45 of the implant 25 where the planar members 50, 55 intersect. Although not shown in FIGS. 74-79, in one embodiment, the implant 25 has the bore 40 and holes 70, 75 substantially as depicted and discussed with respect to the implant of FIGS. 4-17. Also, the rest of the features of the implant 25 of FIGS. 74-79 are substantially as discussed with respect to the implant 25 of FIGS. 56-61, with the exception of the anti-migration edges 360 of the implant embodiment of FIGS. 74-79.

As shown in FIGS. 74-79, the anti-migration edges 360 of the planar members 55 are in the form of notches 365 generally evenly distributed along longitudinally extending free edges or ends of the planar members 55. As indicated in FIG. 77, the notches 365 may have parallel sides 370 inwardly terminating as an arcuate end 375. The orientation of each notch 365 may be such that the center line NL of the notch 365 forms an angle NA with the center axis CA of the implant 25 that is between approximately 90 degrees and approximately 15 degrees, with one embodiment having an angle NA of approximately 45 degrees. As indicated in FIG. 77, each notch 365 may have a length LN between the extreme point on the arcuate end 375 and the outer edge boundary of the notch of between approximately 0.2 mm and approximately 10 mm, with one embodiment having a length LN of approximately 3 mm. Each notch 365 may have a width WN of between approximately 0.5 mm and approximately 20 mm, with one embodiment having a width WN of approximately 2 mm.

As another example, as shown in FIGS. 80-85, which are, respectively, front isometric, rear isometric, side elevation, plan, front elevation, and rear elevation views of an implant 25 with another type of anti-migration edges or ends 360, the body 45 of the implant 25 is simply the region 45 of the implant 25 where the planar members 50, 55 intersect. Although not shown in FIGS. 80-85, in one embodiment, the implant 25 has the bore 40 and holes 70, 75 substantially as depicted and discussed with respect to the implant of FIGS. 4-17. Also, with the exception of its anti-migration edges 360 and its more arcuate distal or leading end 42, the rest of the features of the implant 25 of FIGS. 80-85 are substantially as discussed with respect to the implant 25 of FIGS. 62-67, including the sharp or well defined edges between adjacent intersecting surfaces of the implant 25.

As shown in FIGS. 80-85, the anti-migration edges 360 are flared longitudinally extending free edges or ends of the planar members 55. The edges 360 include a series of ridges 370 that are generally evenly distributed along the length of the edges 360 and oriented transverse to the length of the edges 360.

As indicated in FIG. 83, the ridges 370 have triangular cross sectional elevations with an overall height RA of between approximately 0.2 mm and approximately 8 mm, with one embodiment having a width RA of approximately 1 mm. As illustrated in FIG. 85, the flared longitudinally extending free edges or ends of the planar members 55 have rim edges 380 defining the top and bottom edges of the anti-migration edges 360 of the planar members 55, wherein the rim edges 380 have slopes 385 transitioning between the planar surfaces 65 of the planar members 55 and the rim edges 380.

The edges 360 have a height EH between the edges 380 of between approximately 0.5 mm and approximately 15 mm, with one embodiment having a height EH of approximately 4 mm. The width EW of the flared edge 360 from the beginning of the sloped transition 385 to the face of the edge 360 is between approximately 0.2 mm and approximately 9 mm, with one embodiment having a width EW of approximately 1 mm.

In particular embodiments, the implants with features as described above with respect to FIGS. 62-83 can alternatively be configured to function as a broach or other surgical site preparation tool that can assist in the removal of certain tissues, for example, cartilage or bone, during certain steps of a procedure.

To begin a detailed discussion of components of an embodiment of the delivery tool 20, reference is again made to FIGS. 2A-3. As shown in FIG. 2A, the delivery tool 20 includes a distal end 35 and a proximal end 80. The distal end 35 supports the implant assembly 15 components 25, 30, and the proximal end 80 is configured to be grasped and manipulated to facilitate the implantation of the implant assembly 15 in the sacroiliac joint.

Figure 18:
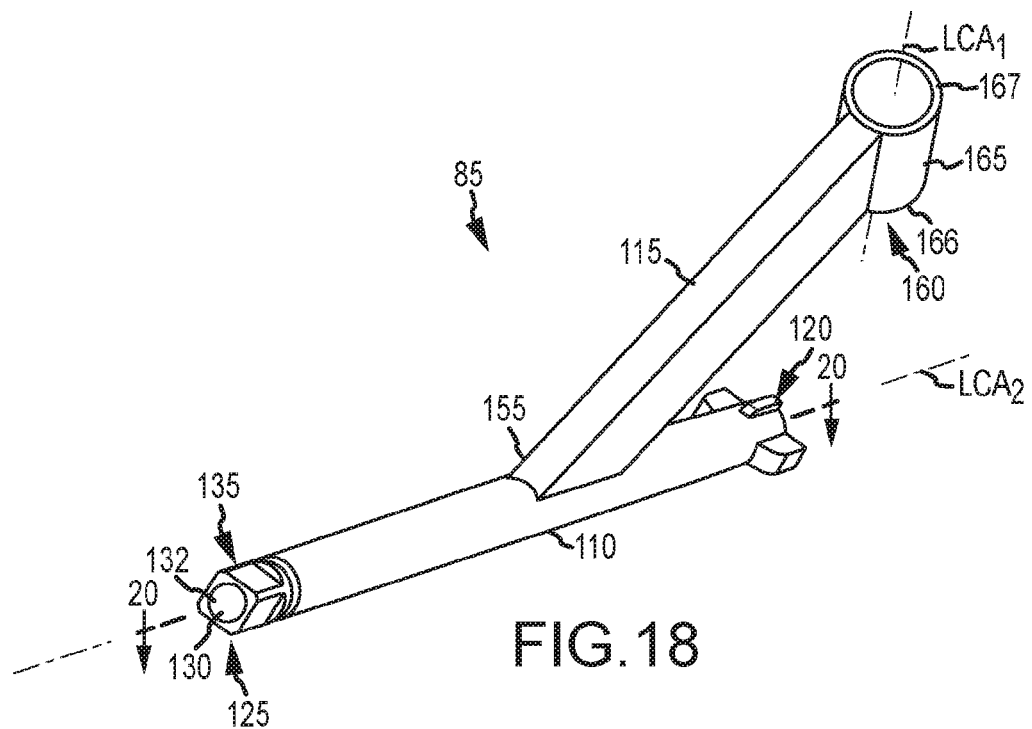
FIG. 18 is a proximal isometric view of the arm assembly.

As illustrated in FIG. 3, the delivery tool 20 further includes an arm assembly 85, a handle 90, an implant retainer 95, a sleeve 100 and a trocar or guidewire 105. As shown in FIG. 18, which is a proximal isometric view of the arm assembly 85, the arm assembly 85 includes an implant arm 110 and an anchor arm 115 supported off of the implant arm 110. The implant arm 110 includes a distal end 120, a proximal end 125 and a proximal cylindrical opening 130 of a cylindrical bore 132. The proximal end 125 includes a squared outer surface configuration 135 that facilitates a mechanical engagement arrangement with the handle 90 such as the mechanical arrangement that exists between a wrench and nut.

Figure 19:
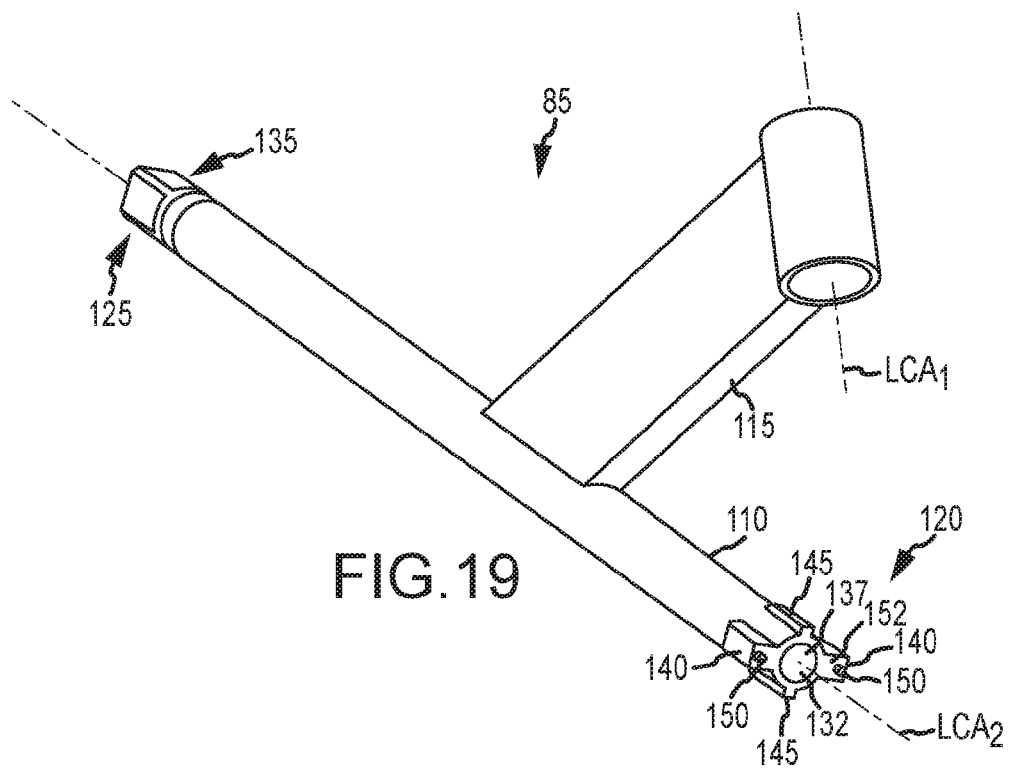
FIG. 19 is a distal isometric view of the arm assembly 85.
Figure 20:
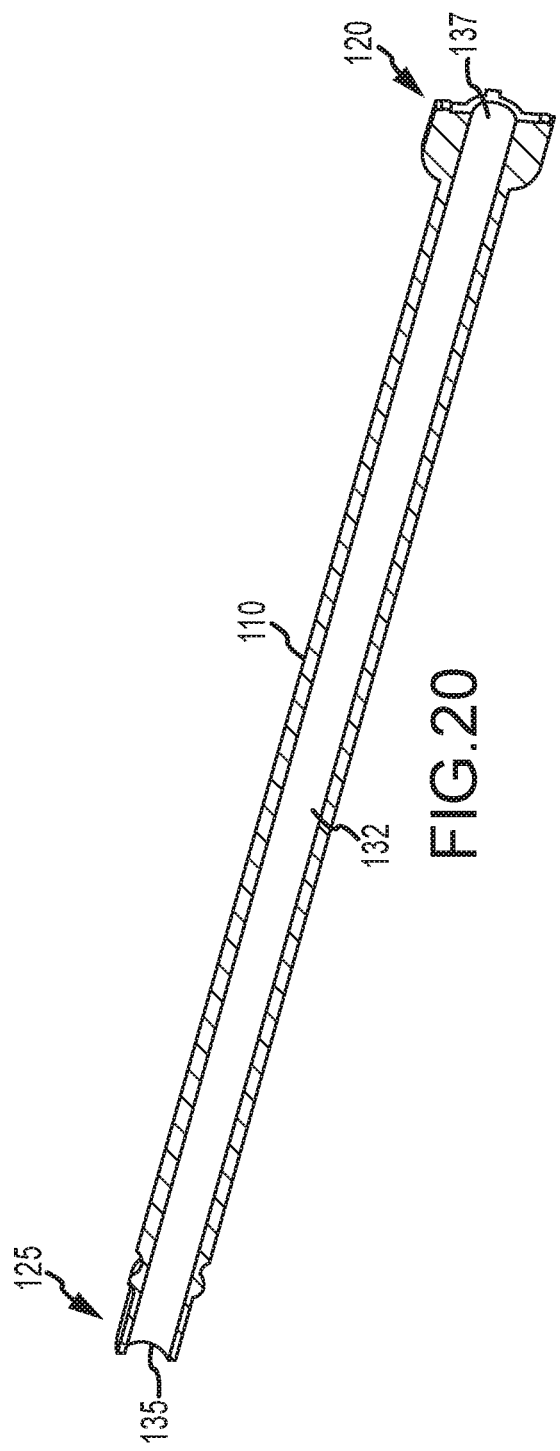
FIG. 20 is a longitudinal cross section of the implant arm as taken along section line 20-20 in FIG. 18.

As shown in FIG. 19, which is a distal isometric view of the arm assembly 85, the distal end 120 includes cylindrical opening 137 of a cylindrical bore 132, large planar members, keels, or fins 140 and small planar members, keels, or fins 145, pins 150, and a planar extreme distal face 152. As depicted in FIG. 20, which is a longitudinal cross section of the implant arm 110 as taken along section line 20-20 in FIG. 18, the cylindrical bore 132 extends the full length of the implant arm 110 between the proximal opening 135 and the distal opening 137.

Figure 23:
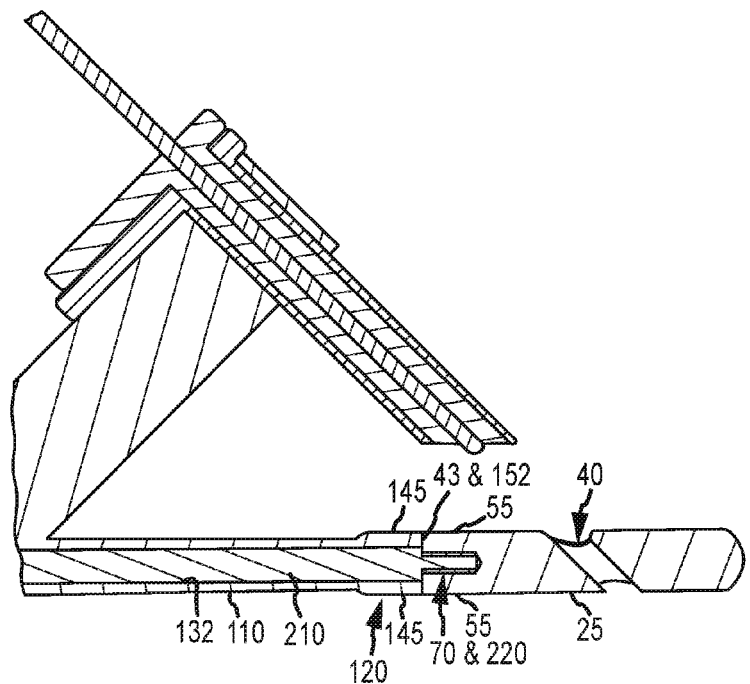
FIG. 23 is an enlarged view of the distal region of the system circled in FIG. 22.
Figure 24:
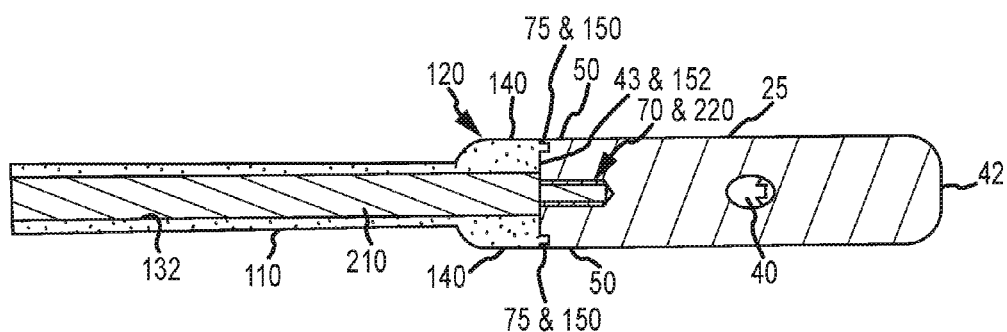
FIG. 24 is an enlarged cross sectional plan view taken in a plane 90 degrees from the section plane of FIG. 23.

For a detailed discussion of the interaction between the features of the implant arm distal end 120 and the proximal end 43 of the implant 25, reference is now made to FIGS. 2A and 21A and 22-24. FIG. 21A is a side elevation of the system 10 wherein the tool 20 is attached to the implant assembly 15 for delivery of the implant assembly 15 to the sacroiliac joint. FIG. 22 is the same view as FIG. 21A, except shown as a longitudinal cross section. FIG. 23 is an enlarged view of the distal region of the system 10 circled in FIG. 22. FIG. 24 is an enlarged cross sectional plan view taken in a plane 90 degrees from the section plane of FIG. 23.

As can be understood from FIGS. 2A and 21A and 22-24, when the system 10 is assembled for the delivery of the implant assembly 15 to the sacroiliac joint, the proximal end 43 of the implant 25 (see FIG. 6) is supported off of the implant arm distal end 120 (see FIG. 19). As can be understood from a comparison of FIGS. 6 and 19 and more clearly depicted in FIGS. 23 and 24, the cylindrical body 45, and planar members 50, 55 of the implant 25 and the cylindrical implant arm 110 and planar members 140, 145 of the implant arm 110 respectively correspond with respect to both shape and size such that when the implant 25 is supported off of the implant arm distal end 120 as depicted in FIGS. 2A and 21A and 22-24, the respective outer surfaces of the implant 25 and implant arm distal end 120 transition smoothly moving from the implant 25 to the implant arm distal end 120, and vice versa. Also, as shown in FIGS. 23 and 24, when the system 10 is assembled for the delivery of the implant assembly 15 to the sacroiliac joint, the planar extreme proximal face 43 of the implant 25 abuts against the planar extreme distal face 152 of the implant arm distal end 120, the pins 150 being received in a recessed fashion in the lateral bores 75. The pins 150 being received in the lateral bores 75 prevents the implant 25 from pivoting relative to the implant arm 110. The pins 150 can be configured to have a rectangular, circular or any other cross section and the corresponding lateral bores 75 can also be configured to have corresponding shapes in cross section.

Alternatively, in order to further restrict undesirable movement between components of a system 10, namely between that of a delivery tool 20 and an implant 25, the distal face 152 of the implant arm distal end 120 can be configured to rap around, and can also be recessed into or grappled to, the exterior surface of the elongate body 45, or planar members 50, or 55 of the implant 25 a distance DE, from about 0.2 mm to about 20 mm (e.g., 10 mm), in the direction of implant distal end 42. According to particular embodiments, a recess can extend a distance DA from said exterior surfaces in the general direction of implant longitudinal axis CA, from about 0.25 mm to 5 mm (e.g., 1.25 mm). In a non-limiting example of a particular embodiment, the distal face 152 of the implant arm distal end 120 can be further configured to wrap completely or only a portion of the periphery of an implant by occupying only a portion, CAR, as defined by a number of degrees around implant longitudinal axis CA, from about 1 degree to about 180 degrees (e.g., 30 degrees). In particular embodiments, said features can be configured to be located in the area between the planar members 50 and 55.

As shown in FIGS. 18 and 19, the anchor arm 115 is supported off of the implant arm 110 at an angle and includes a proximal end 155 and a distal end 160 distally terminating in a sleeve or collar 165 having a longitudinal center axis $LCA_1$ that is generally transverse to the longitudinal axis of the anchor arm 115. Collar 165 has a length of between approximately 10 mm and approximately 60 mm (e.g., 20 mm) disposed between collar ends 166 and 167 configured to permit and maintain accurate alignment of the first sleeve 100 along $LCA_1$ during the course of the procedure. The anchor arm proximal end 155 intersects the implant arm 110 at a location between the proximal and distal ends of the implant arm.

As indicated in FIGS. 18 and 19, the implant arm 110 also includes a longitudinal center axis $LCA_2$. As shown in FIG. 21A, when the system 10 is assembled such that the implant 25 is mounted on the distal end of the implant arm 110, the longitudinal center axis CA of the implant 25 is coaxially aligned with the longitudinal center axis $LCA_2$ of the implant arm 110, and the longitudinal center axis BA of the implant bore 40 is coaxially aligned with the longitudinal center axis $LCA_1$ of the anchor arm collar 165. Thus, the longitudinal center axis CA of the implant 25 and the longitudinal center axis $LCA_2$ of the implant arm 110 exist on a first common longitudinally extending axis, and the longitudinal center axis BA of the implant bore 40 and the longitudinal center axis $LCA_1$ of the anchor arm collar 165 exist on a second common longitudinally extending axis.

In one embodiment, the longitudinal center axis $LCA_1$ of the anchor arm collar 165 forms an angle $A_{LCA1\text{-}LCA2}$ with the longitudinal center axis $LCA_2$ of the implant arm 110. For example, the angle $A_{LCA1\text{-}LCA2}$ may be between approximately 15 degrees and approximately 135 degrees, with one embodiment being approximately 45 degrees.

As can be understood from FIG. 21A, when the system 10 is assembled such that the implant 25 is mounted on the distal end of the implant arm 110, the longitudinal center axis $LCA_2$ of the implant arm 110 is coaxial with the longitudinal center axis CA of the implant 25 and the longitudinal center axis of the handle 90. Thus, the line of action for the insertion of the implant 25 into the sacroiliac joint is coaxial with the longitudinal center axes of the implant 25, implant arm 110 and handle 90.

As can be understood from the preceding discussion, in one embodiment, when the system 10 is assembled such that the implant 25 is mounted on the distal end of the implant arm 110, the angle $A_{BA\text{-}CA}$ may be substantially the same as the angle $A_{LCA1\text{-}LCA2}$. Also, the longitudinal center axis BA of the implant bore 40 is coaxially aligned with the longitudinal center axis $LCA_1$ of the anchor arm collar 165. Thus, as will be described in detail below, the anchor arm collar 165 is oriented so as to guide drills and other tools in creating a channel through tissue and bone leading to the implant bore 40 when the implant 25 is positioned in the sacroiliac joint while the implant 25 is still attached to the distal end of the implant arm 110, as shown in FIG. 21. Additionally, the anchor arm collar 165 is oriented so as to guide the anchor member 30 into the implant bore 40 when the implant 25 is positioned in the sacroiliac joint while the implant 25 is still attached to the distal end of the implant arm 110, as shown in FIG. 21A.

As can be understood from FIG. 21A, in one embodiment, the above-described coaxial and angular relationships are rigidly maintained due to the anchor arm 115 and its collar 165 being in a fixed, non-adjustable configuration, and the interconnection between the proximal end of the anchor arm 115 and the implant arm 110 being a fixed, non-adjustable configuration at least with respect to the angle $A_{LCA1\text{-}LCA2}$ between the longitudinal center axis $LCA_1$ of the anchor arm collar 165 and the longitudinal center axis $LCA_2$ of the implant arm 110. Thus, in one embodiment, the delivery tool 20 comes from the manufacture to the physician in a fixed, non-adjustable configuration having the coaxial and angular relationships articulated above with respect to FIG. 21A.

Figure 21B:
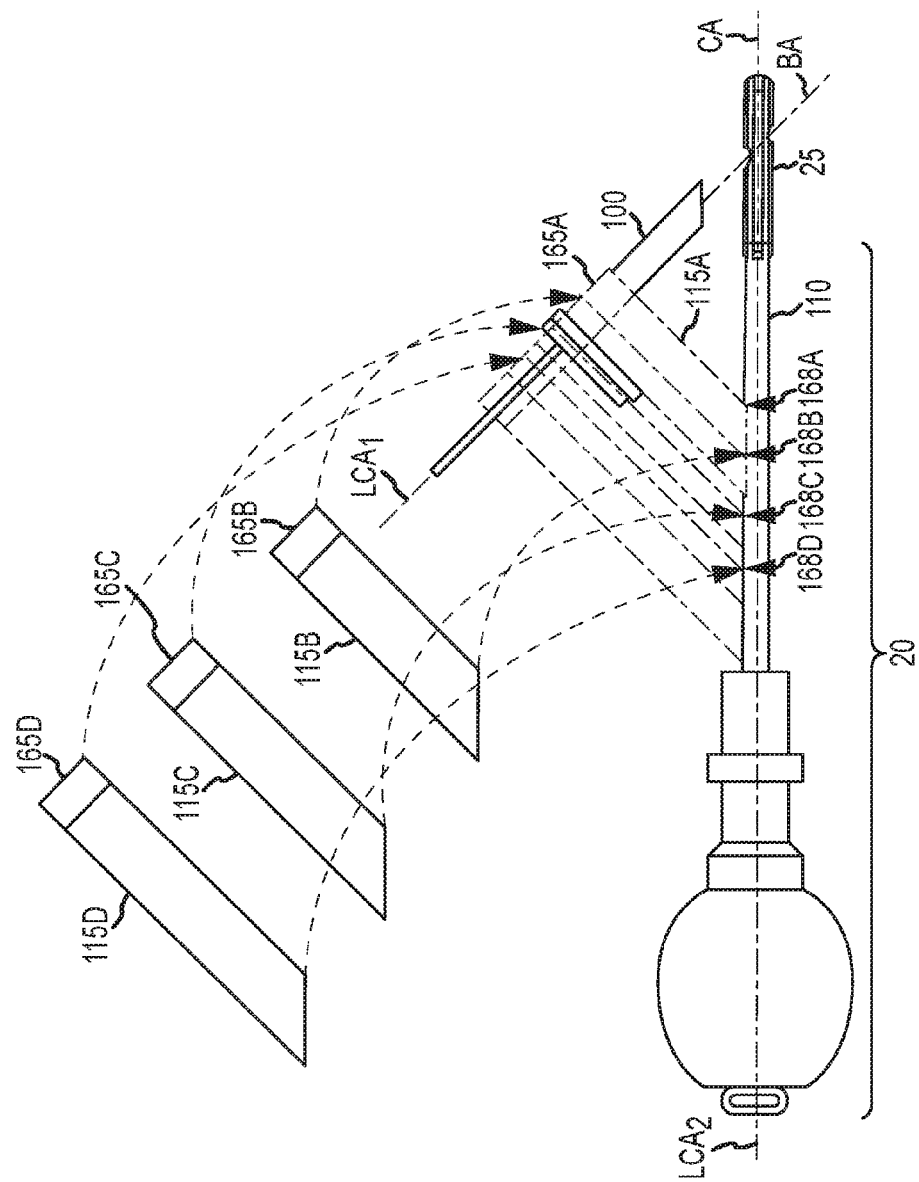
FIG. 21B is the same view as FIG. 21A, except illustrating a series of interchangeable anchor arms that may be coupled to the implant arm to adjust the tool for the patient, but maintain the angular relationship between the components of system that allows the anchor member to be delivered into the implant bore without adjustment to the delivery tool.

FIG. 21B is the same view as FIG. 21A, except of another embodiment of the delivery tool 20 wherein the tool 20 includes multiple anchor arms 115A-115D that can be coupled to specific respective locations 168A-168D on the implant arm 110 to account for different patient sizes, yet still maintain the coaxial and angular relationships set out above. As shown in FIG. 21B, the delivery tool 20 may include two or more, for example, four, anchor arms 115A-115D, each anchor arm having a different overall length. Despite having different overall lengths, because each anchor arm 115A-115D is configured to couple to a specific respective location 168A-168D on the implant arm 110, the longitudinal center axis $LCA_1$ of each anchor arm collar 165A-165D is still coaxially aligned with the longitudinal center axis BA of the implant bore 40 when each anchor arm is mounted at its correct respective location 168A-168D on the implant arm 110. Thus, although the embodiment depicted in FIG. 21B is adjustable with respect to patient size via the interchangeable anchor arms 115A-115D, the above-described coaxial and angular relationships are rigidly maintained due to the anchor arms 115A-115D and their collars 165 being in a fixed, non-adjustable configuration, and the interconnection between the proximal end of the anchor arms 115A-115D and the implant arm 110 being a fixed, non-adjustable configuration at least with respect to the angle $A_{LCA1\text{-}LCA2}$ between the longitudinal center axis $LCA_1$ of the anchor arm collar 165 and the longitudinal center axis $LCA_2$ of the implant arm 110. Thus, although the embodiment depicted in FIG. 21B is adjustable with respect to the patient size via the interchangeable anchor arms 115A-115D, the delivery tool 20 comes from the manufacture to the physician in a fixed, non-adjustable configuration with respect to the coaxial and angular relationships articulated above with respect to FIG. 21A.

Although not shown in FIG. 21B, in some embodiments, multiple sleeves 100 may be provided with the system 10. For example, the system 10 may include four anchor arms 165A-165D of different lengths, and the system may also include four sleeves 100 of different lengths, each sleeve 100 being configured for use with a specific anchor arm. For example, since anchor arm 165D is the longest anchor arm, its corresponding sleeve 100 may be the longest of the sleeves. Similarly, since anchor arm 165A is the shortest anchor arm, its corresponding sleeve 100 may be the shortest of the sleeves.

Because of the multiple interchangeable anchor arms 165A-165D that are each configured for attachment to a specific respective location 168A-168D on the implant arm 110, the delivery tool 20 may be adjusted to accommodate patients of different sizes and still maintain the angular relationships between the components of system 10 that allows the anchor member 30 to be delivered into the implant bore 40 without any further adjustment to the delivery tool. Because the angular relationships are rigidly maintained between the arms 110, 115, the collar 165, and the implant bore 40 despite the anchor arms 115A-115B being interchangeable, the anchoring of the implant 25 in the sacroiliac joint via the anchor member 30 may be achieved quickly and safely. In other words, because the tool does not need to be adjusted with respect to angular relationships, the surgery is simplified, reduced in duration, and reduces the risk of the anchor member 30 being driven through a nerve, artery or vein.

In some embodiments, the system 10 may be provided with two or more tools 20, each tool having a configuration for a specific size of patient. For example, the tool 20 depicted in FIG. 21A may be provided for smaller patients in that there is reduced distance between the anchor arm collar 165 and the implant 25. As depicted in FIG. 21C, which is the same view of FIG. 21A, except illustrating a version of the same tool 20 configured to accommodate larger patients, the distance between anchor arm collar 165 and implant 25 is greater due to the anchor arm 165 being more proximally located on the implant arm 110 as compared to the configuration depicted in FIG. 21A. It should be noted that, although the version depicted in FIG. 21C is configured to accommodate larger patients, the coaxial and angular relationships discussed above with respect to FIG. 21A are the same for the version depicted in FIG. 21C. For the version depicted in FIG. 21C, the sleeve 100 is substantially elongated as compared to the sleeve 100 of FIG. 21A. Depending on the size of the patient, the physician may select or be provided with one of the tool configurations shown in FIG. 21A or 21C.

Additionally, the sleeve 100 of FIG. 21C can be prevented from undesired migration within the anchor arm collar 165 during a procedure by utilizing a locking mechanism 163 in close proximity to the collar 165. As a non-limiting example, a locking mechanism can be configured as a fastener 163, which, in certain embodiments, can be threaded and rotatably advanced into the collar 165 to cause a greater amount of friction upon the sleeve 100.

Figure 25:
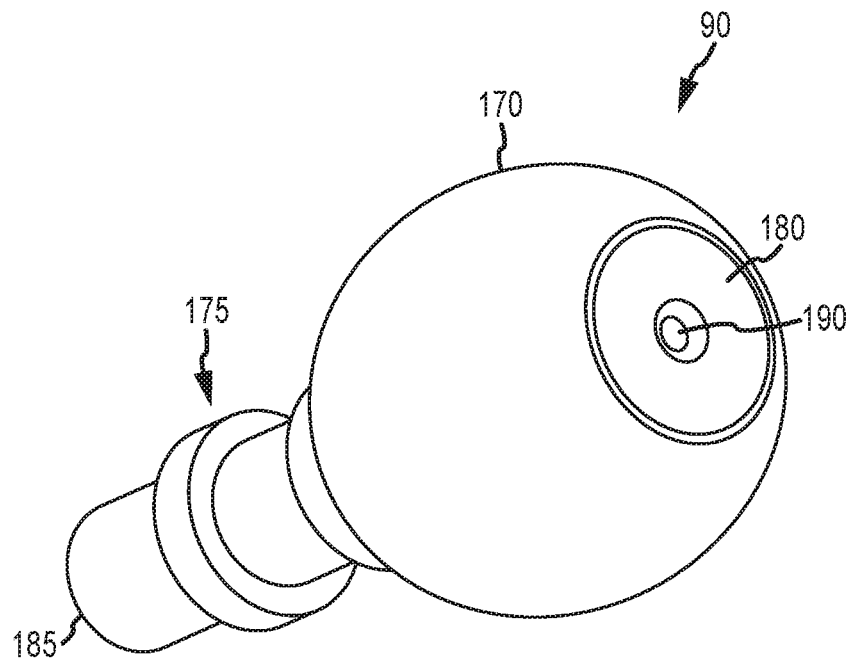
FIG. 25 is a proximal isometric view of the handle.
Figure 26:
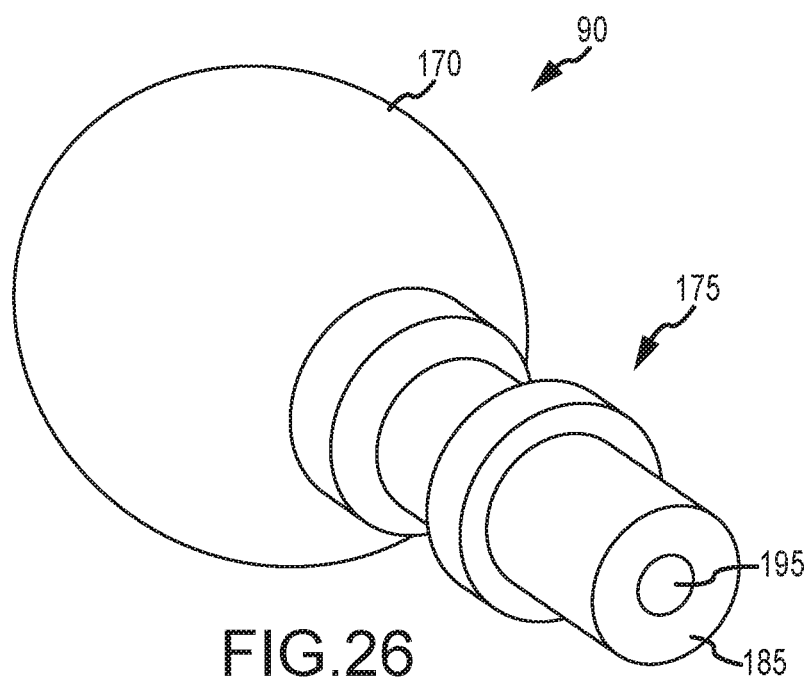
FIG. 26 is a distal isometric view of the handle.

As shown in FIGS. 25-27, which are various isometric views of the handle 90, the handle 90 includes a gripping portion 170, a neck portion 175, a proximal end 180, a distal end 185, a proximal opening 190, a distal opening 195 and a bore 200 extending longitudinally through the handle 90 between the openings 190, 195. The proximal opening 190 is defined in the proximal end 180, which forms the extreme proximal portion of the gripping portion 170. The distal opening 195 is defined in the distal end 185, which forms the extreme distal portion of the neck portion 175. The neck portion 175 has multiple regions having different diameters, thereby forming a collared configuration. The gripping portion 170 may have a generally spherical or oval hemispheric shape.

As shown in FIG. 27, a squared inner surface configuration 205 is defined in a segment of the bore 195 located in the neck portion 175, the rest of the bore 195 having a cylindrical configuration. Thus, as can be understood from FIGS. 1, 21A and 22, when the implant arm distal end 125 is received in the handle bore 200, the squared inner surface configuration 205 facilitates a mechanical engagement arrangement with the squared outer surface configuration 135 of the implant arm distal end 125. As a result, grasping the handle so as to cause the handle to pivot about its longitudinal center axis causes the implant arm to similarly pivot about its longitudinal center axis, which is generally coaxial with the longitudinal center axis of the handle. The fit between the squared surface configurations 135, 205 may be such as to form an interference fit, thereby preventing the handle from being pulled off of the implant arm distal end without the intentional application of substantial separating force.

Figure 6:
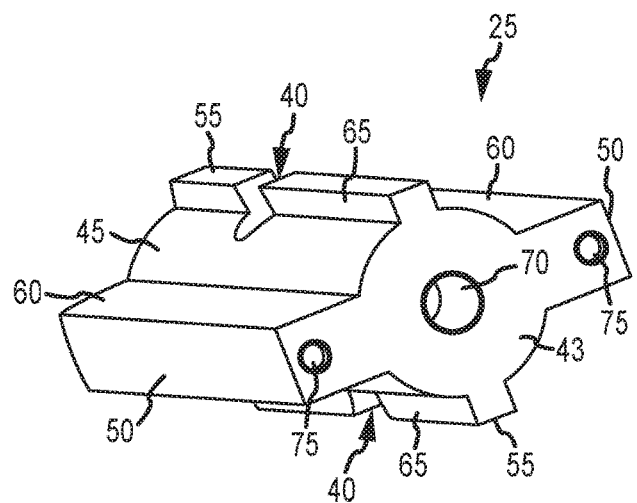
FIG. 6 is a proximal end isometric view of the implant.

As illustrated in FIGS. 28 and 29, which are full isometric and longitudinal cross sectional isometric views of the implant retainer 95, the implant retainer 95 includes a longitudinal cylindrical member 210, T-handle 215 on a proximal end of the longitudinal cylindrical member 210, and an implant engagement feature 220 on a distal end the longitudinal cylindrical member 210. As can be understood from FIGS. 2A and 21A and 22-24, when the system 10 is assembled for the delivery of the implant assembly 15 to the sacroiliac joint, the longitudinal cylindrical member 210 extending through the handle bore 200 (see FIG. 27) and implant arm bore 132 (FIG. 20) such that a distal side of the T-handle 215 abuts or nearly abuts with the handle proximal face or end 180 (FIG. 25) and the implant engagement feature 220 is received in the implant center bore 70 (FIG. 6). In one embodiment, the implant engagement feature 220 is in the form of a threaded shaft for engaging complementary threads in the center bore 70, thereby securing the implant proximal face against the implant arm distal face and the pins in the lateral bores, as depicted in FIGS. 22-24. In other embodiments, the implant engagement feature 220 and the center bore 70 are configured so as to form an interference fit between the two such that an intentional separating force is required to remove the implant engagement feature from within the center bore and allow the release of the implant from the distal end of the implant arm, as indicated in FIG. 2B.

Figure 30A:
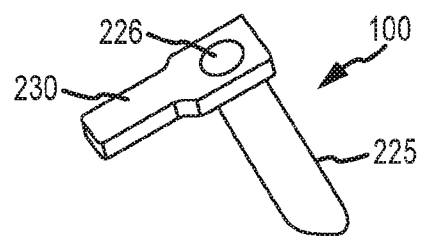
FIG. 30A is an isometric view of the sleeve.
Figure 30B:
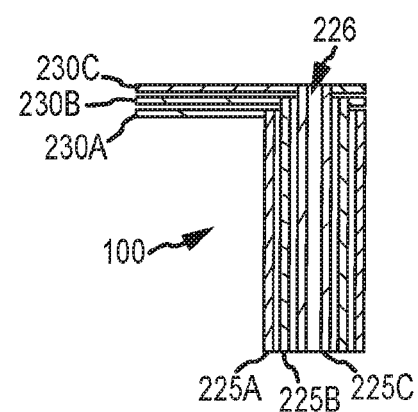
FIG. 30B is a longitudinal cross section of an embodiment of the sleeve having multiple sleeve portions.

FIG. 30A is an isometric view of a sleeve 100 that is configured to be received in the anchor arm collar 165, as can be understood from FIGS. 2A, 21A, and 22-23. The sleeve 100 may have a tubular portion 225 that extends from a plate 230 and defines a lumen 226 extending the length of the tubular portion 225. As indicated in FIG. 30B, which is a longitudinal cross section of one embodiment of the sleeve 100, the sleeve 100 is formed of multiple sleeve portions 100A-100C nested together such that the tubular portions 225A-225B are concentrically arranged and the plates 230A-230B are stacked. As each sleeve portion 100A-100C has a tubular portion 225A-225B with a different diameter, the sleeve portions 100A-100C can be employed as needed to dilate an incision opening or guide different diameter guidewires, trocars, drills, etc. in the direction of the implant bore 40.

Figure 31:
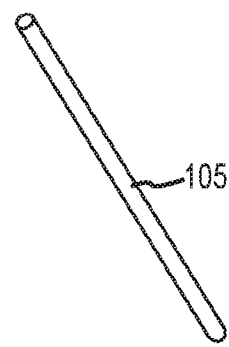
FIG. 31 is an isometric view of a trocar, guidewire, drill, screwdriver, etc. for insertion through the lumen of the sleeve.

FIG. 31 is an isometric view of a trocar, guidewire, drill, screwdriver, etc. that may be inserted through the lumen 226 of the tubular portion 225 in gaining access to, or driving the anchor member 30 into, the implant bore 40 when the implant 25 is positioned in the sacroiliac joint via the distal end of the implant arm 110.

To begin a detailed discussion of a second embodiment of the system 10, reference is made to FIGS. 32-33. FIG. 32 is an isometric view of the system 10, and FIG. 33 is the same view as FIG. 32, except the system 10 is shown exploded to better illustrate the components of the system 10.

As can be understood from FIGS. 32 and 33, the system 10 includes a delivery tool 20 and an implant assembly 15 for implanting at the sacroiliac joint via the delivery tool 20, the implant assembly 15 being for fusing the sacroiliac joint. As indicated in FIG. 33, the implant assembly 15 includes an implant 25 and an anchor element 30 (e.g., a bone screw or other elongated body). In one embodiment, the implant assembly 15 is the same as that described above with respect to FIGS. 4-17. As discussed below in greater detail, during the implantation of the implant assembly 15 at the sacroiliac joint, the implant 25 and anchor element 30 are supported by a distal end 35 of the delivery tool 20, as illustrated in FIG. 32. The delivery tool 20 is used to deliver the implant 25 into the sacroiliac joint space. The delivery tool 20 is then used to cause the anchor element 30 to extend through the ilium, sacrum and implant 25 generally transverse to the sacroiliac joint and implant 25. The delivery tool 20 is then decoupled from the implanted implant assembly 15.

As shown in FIG. 32, the delivery tool 20 includes a distal end 35 and a proximal end 80. The distal end 35 supports the implant assembly 15 components 25, 30, and the proximal end 80 is configured to be grasped and manipulated to facilitate the implantation of the implant assembly 15 in the sacroiliac joint.

As illustrated in FIG. 33, the delivery tool 20 further includes an arm assembly 85, a handle 90, an implant retainer 95, and a trocar or guidewire 105. As shown in FIG. 33 and also in FIG. 34, which is a side elevation of the system 10, the arm assembly 85 includes an implant arm 110 and an anchor arm 115.

Figure 35:
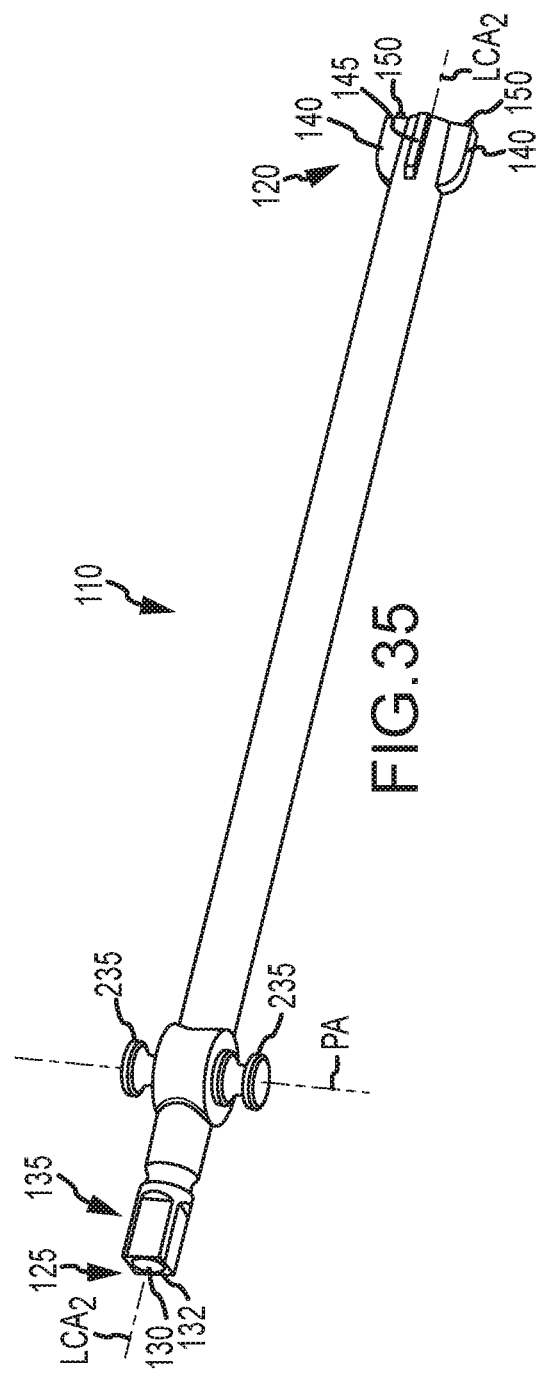
As shown in FIG. 35 is a proximal isometric view of the implant arm of the embodiment of FIG. 32.

As shown in FIG. 35, which is a proximal isometric view of the implant arm 110, the implant arm 110 includes a distal end 120, a proximal end 125 and a proximal cylindrical opening 130 of a cylindrical bore 132. The proximal end 125 includes a squared outer surface configuration 135 that facilitates a mechanical engagement arrangement with the handle 90 such as the mechanical arrangement that exists between a wrench and nut. As the handle 90 is the same as described above with respect to FIGS. 25-27, the handle 90 receives and mechanically interlocks with the distal region of the implant arm 110 as described above with respect to FIG. 22.

As with the implant arm 110 discussed above with respect to FIG. 19 and as can be understood from FIG. 34, the distal end 120 of the implant arm 110 includes a cylindrical opening 137 (see FIG. 19) of a cylindrical bore 132, large planar members, keels, or fins 140 and small planar members, keels, or fins 145, pins 150, and a planar extreme distal face 152 (see FIG. 19). Just as explained with respect to FIG. 20 above, the cylindrical bore 132 of the embodiment depicted in FIG. 34 extends the full length of the implant arm 110 between the proximal opening 135 and the distal opening 137.

As the retaining member 95 of the embodiment of FIG. 33 is the same as described above with respect to FIGS. 28-29, the retainer member 95 extends through the handle 90 and implant arm 110 to mechanically interlock with the implant center bore 70 as described above with respect to FIGS. 22-24. Also, the configuration of the distal end 120 of the implant arm 110 of FIG. 35 is the same as the configuration of the distal end 120 of the implant arm 110 of FIG. 19. Accordingly, the distal end 120 of the implant arm 110 of FIG. 35 interacts with the proximal end of the implant 25 as describe above with respect to FIGS. 22-24.

As indicated in FIG. 35, the implant arm 110 includes pivot pins 235 on opposite sides of the implant arm 110, the pivot pins 235 having a pivot axis PA that is perpendicular to the plane in which the implant bore 40 passes through the implant 25. In other words, the pivot axis PA is perpendicular to the longitudinal center axis $LCA_2$ of the implant arm 110 and contained within the same plane as the longitudinal center axis $LCA_2$ of the implant arm 110. The pivot pins 235 are located on the implant arm 110 near the distal end of the handle 90.

Figure 36:
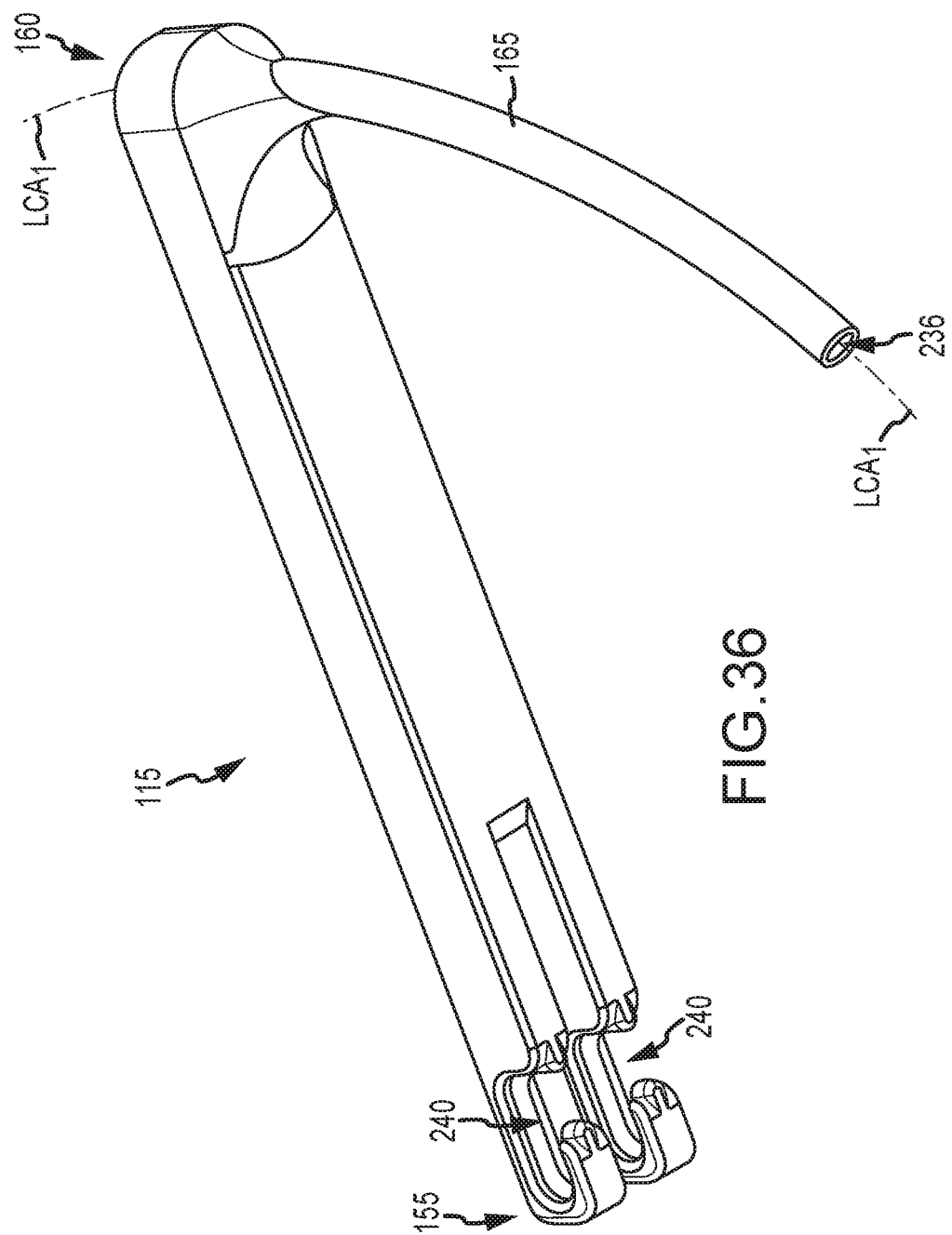
FIG. 36 is an isometric view of the anchor arm.

As illustrated in FIG. 36, which is an isometric view of the anchor arm 115, the anchor arm 115 includes a proximal end 155 and a distal end 160 distally terminating in a sleeve or collar 165 that is arcuate and substantially extended as compared to the collar 165 of the embodiment depicted in FIG. 18. The arcuate and extended collar 165 has an arcuate longitudinal center axis $LCA_1$ that is generally transverse to the longitudinal axis of the anchor arm 115. A lumen 236 extends the length of the collar 165 to daylight in openings at both ends of the collar 165.

As shown in FIG. 36, the anchor arm proximal end 155 includes notches 240, which, as can be understood from FIGS. 32 and 34, receive the respective pivot pins 235. As a result, the anchor arm 115 is pivotally supported off of the implant arm 110 via the notches 240 at the anchor arm proximal end 155 pivotally receiving the pivot pins 235 of the implant arm 110.

As can be understood from FIGS. 32-34, an arcuate member 105 can be inserted in the lumen 236 of the arcuate extended collar 165. The curvature of the arcuate member 105 matches the curvature of the lumen 236 of the arcuate collar 165. The arcuate member 105 may be a trocar, guidewire, drill, screwdriver, etc. that may be inserted through the lumen 236 of the collar 165 in gaining access to, or driving the anchor member 30 into, the implant bore 40 when the implant 25 is positioned in the sacroiliac joint via the distal end of the implant arm 110. As indicated by the arrow A in FIG. 34, the arcuate member 105 is slideably displaceable through the arcuate length of the collar 165. Also, as indicated by arrow B, the anchor arm 110 is pivotal about the pivot pins 235.

As indicated in FIG. 35, the implant arm 110 includes a longitudinal center axis $LCA_2$. As shown in FIG. 34, when the system 10 is assembled such that the implant 25 is mounted on the distal end of the implant arm 110, the longitudinal center axis CA of the implant 25 is coaxially aligned with the longitudinal center axis $LCA_2$ of the implant arm 110, and the longitudinal center axis BA of the implant bore 40 is coaxially aligned with the longitudinal center axis $LCA_1$ of the anchor arm collar 165. In other words, in the context of the embodiment of FIG. 34, the arcuate longitudinal center axis $LCA_1$ extends to be coaxially aligned with the longitudinal center axis BA of the implant bore 40. In one embodiment, as indicated in FIG. 34, the longitudinal center axis $LCA_1$ of the anchor arm collar 165 has an arm radius $R_{ARM}$ that extends into coaxial alignment with the longitudinal center axis BA of the implant bore 40. For example, the arm radius $R_{ARM}$ may be between approximately 50 mm and approximately 300 mm, with one embodiment being approximately 160 mm.

As can be understood from FIG. 34, when the system 10 is assembled such that the implant 25 is mounted on the distal end of the implant arm 110, the longitudinal center axis $LCA_2$ of the implant arm 110 is coaxial with the longitudinal center axis CA of the implant 25 and the longitudinal center axis of the handle 90. Thus, the line of action for the insertion of the implant 25 into the sacroiliac joint is coaxial with the longitudinal center axes of the implant 25, implant arm 110 and handle 90. Thus, as will be described in detail below, the anchor arm collar 165 is oriented so as to guide drills and other tools in creating a channel through tissue and bone leading to the implant bore 40 when the implant 25 is positioned in the sacroiliac joint while the implant 25 is still attached to the distal end of the implant arm 110, as shown in FIG. 34. Additionally, the anchor arm collar 165 is oriented so as to guide the anchor member 30 into the implant bore 40 when the implant 25 is positioned in the sacroiliac joint while the implant 25 is still attached to the distal end of the implant arm 110, as shown in FIG. 32.

Because the tool embodiment depicted in FIG. 32 has an anchor arm 115 that is pivotally supported off of the implant arm 110 and the anchor arm collar 165 is arcuate and slideably receives an arcuate trocar, etc. 105, the tool 20 is able to account for different patient sizes, yet still maintain the coaxial and angular relationships set out above. In other words, regardless of whether the anchor arm 115 is pivoted so as to move the anchor arm distal end 160 closer to or further away from the implant bore 40 to accommodate a smaller or larger patient, the trocar 105 can be withdrawn from or extended towards the implant bore 40 as needed to deliver the anchor 30 to the implant bore 40, the trocar 105 being maintained in the necessary coaxial alignment of the longitudinal axis $LCA_1$ of the collar 165 with the longitudinal axis BA of the implant bore 40.

Because the angular relationships are rigidly maintained between the trocar 105 and the implant bore 40 despite the anchor arm 115 being pivotal relative to the implant arm, the anchoring of the implant 25 in the sacroiliac joint via the anchor member 30 may be achieved quickly and safely. In other words, because the tool does not need to be adjusted with respect to angular relationships, the surgery is simplified, reduced in duration, and reduces the risk of the anchor member 30 being driven through a nerve, artery or vein.

Figure 37:
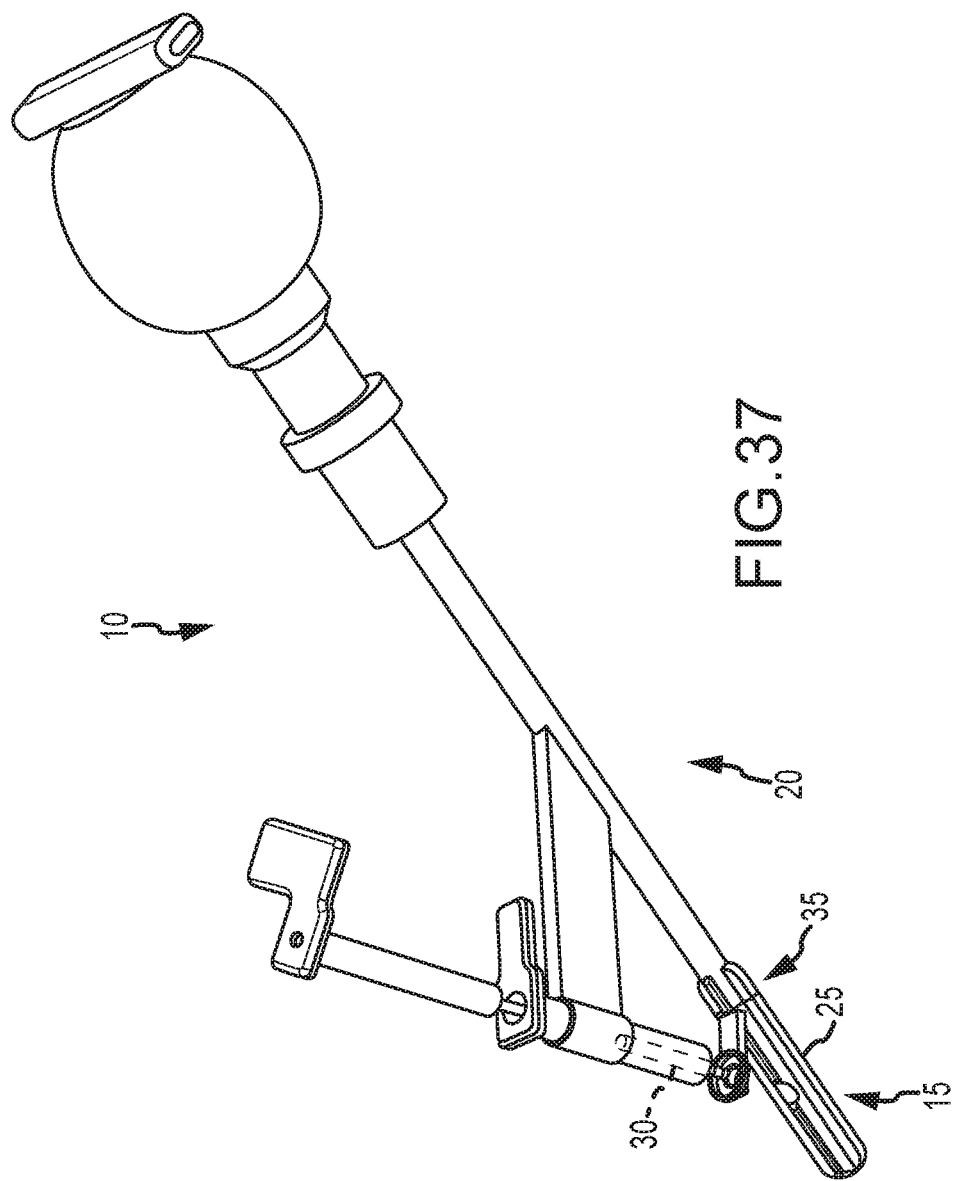
FIGS. 37 and 38 are different isometric views of a third embodiment of the system.
Figure 38:
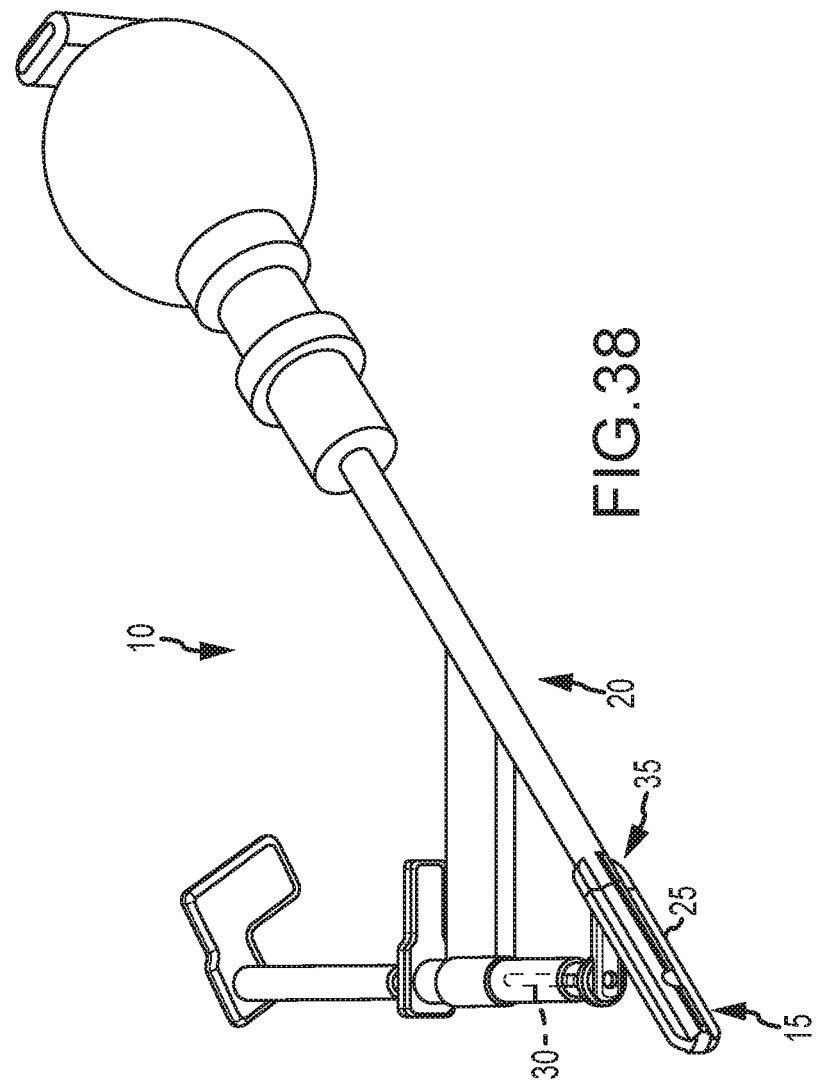
Figure 39:
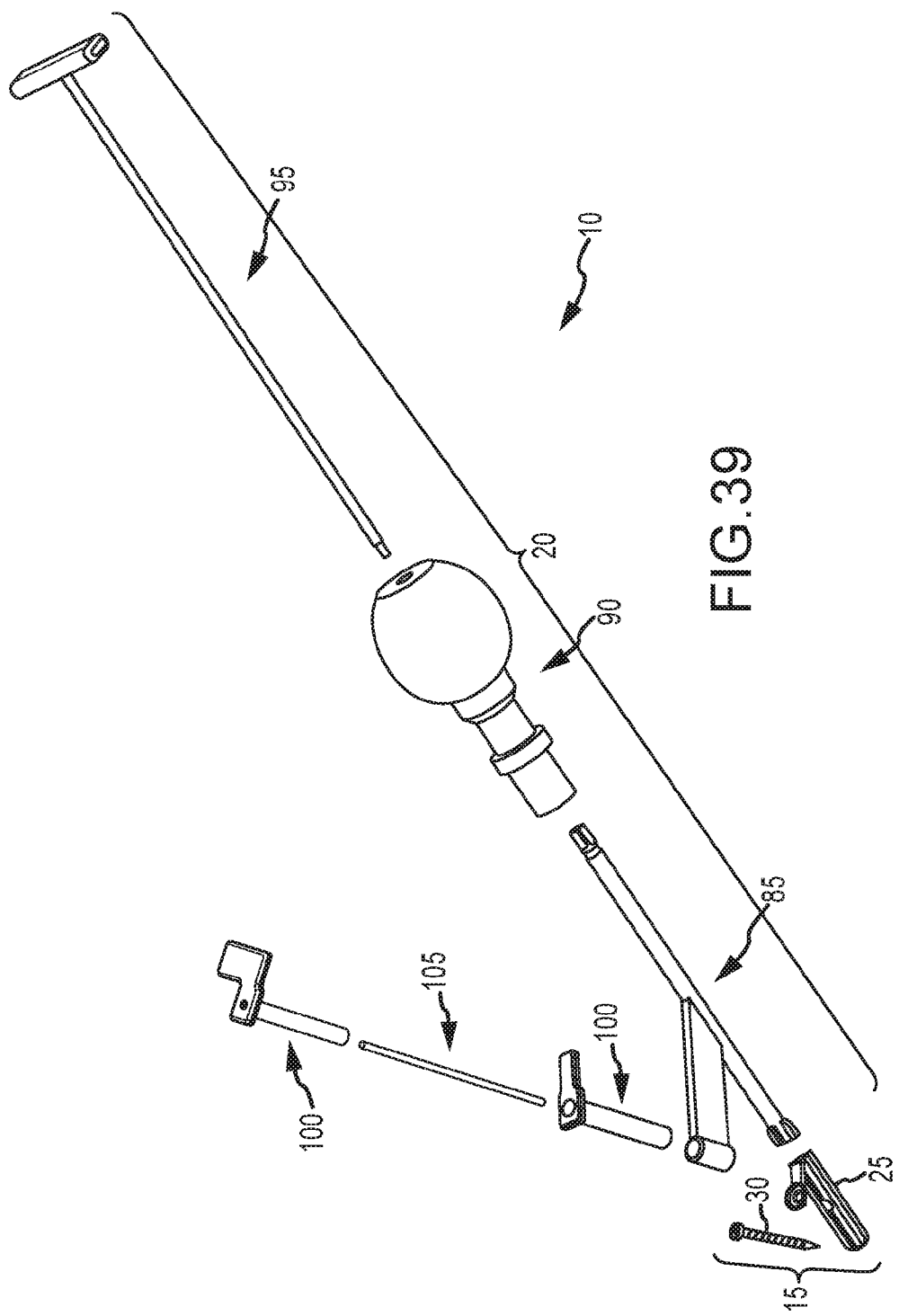
FIG. 39 is the same view as FIG. 37, except the system is shown exploded to better illustrate the components of the system.
Figure 40:
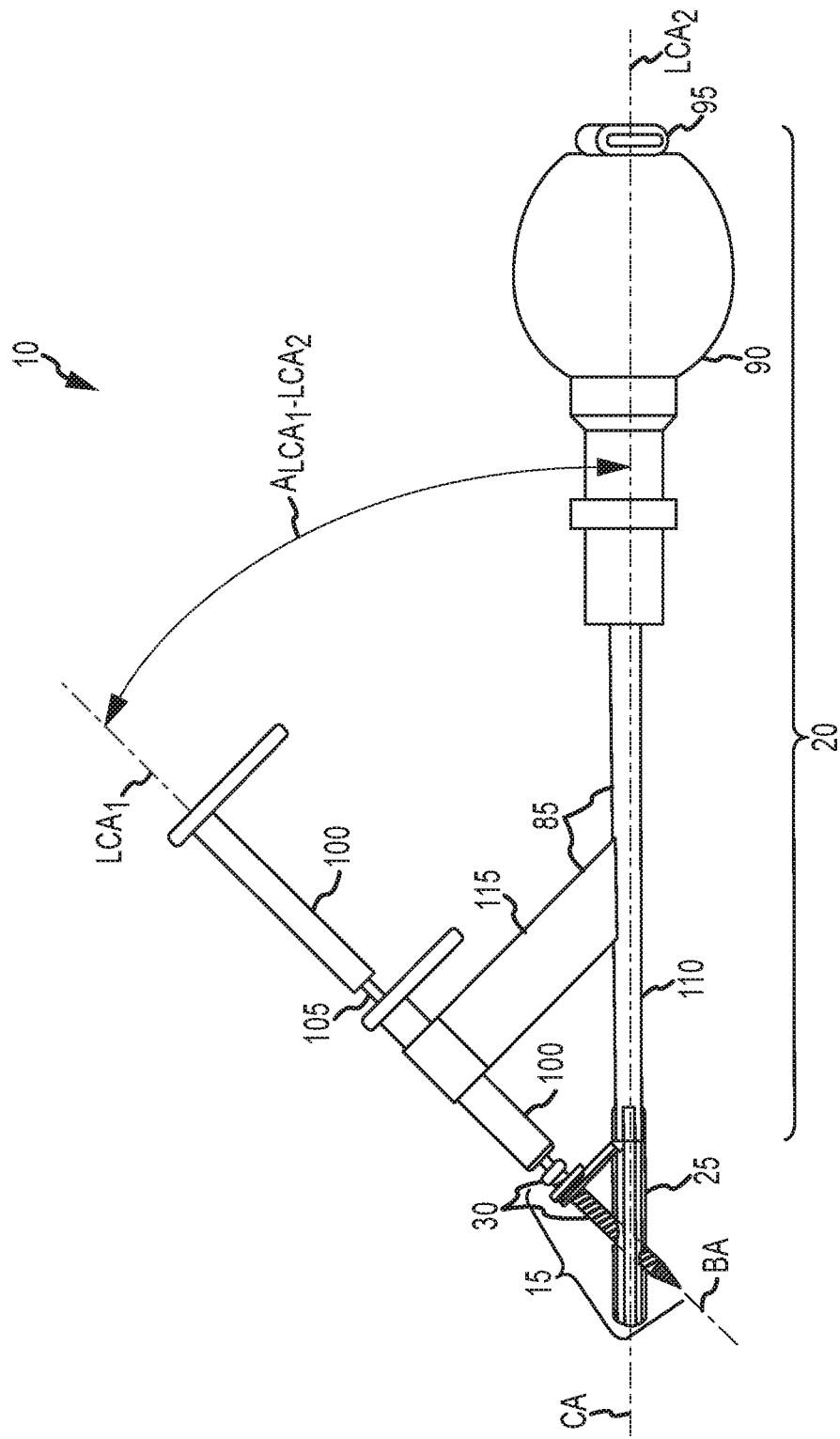
FIG. 40 is a side elevation of the system of FIG. 37, wherein the tool is attached to the implant assembly for delivery of the implant assembly to the sacroiliac joint.
Figure 41:
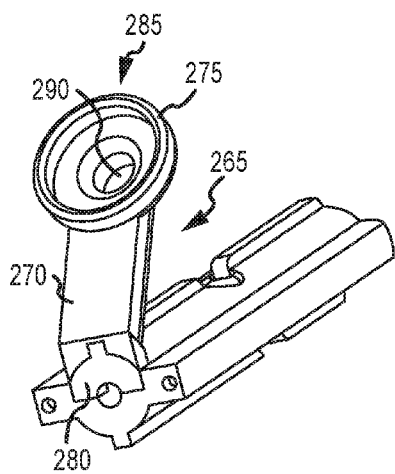
FIGS. 41-44 are various isometric views of the implant of the third embodiment of the system.
Figure 42:
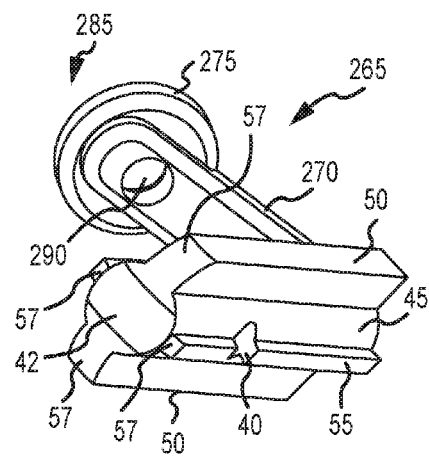
Figure 43:
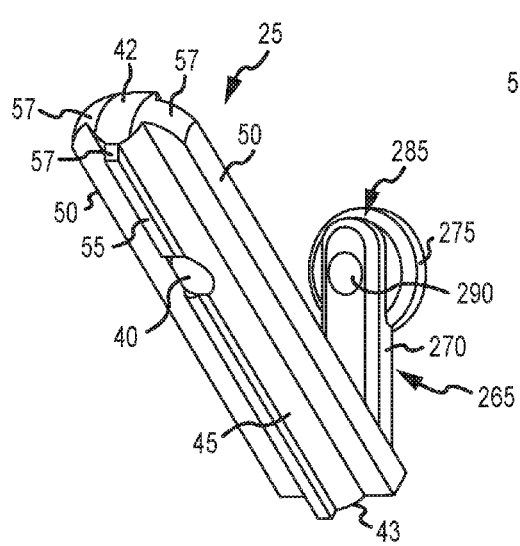
Figure 44:
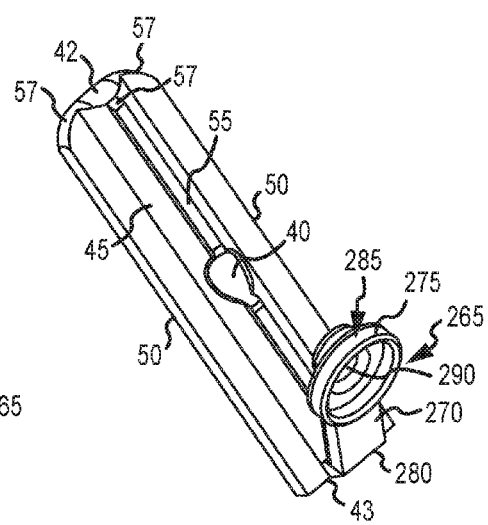

To begin a detailed discussion of a third embodiment of the system 10, reference is made to FIGS. 37-40. FIGS. 37 and 38 are different isometric views of the system 10. FIG. 39 is the same view as FIG. 37, except the system 10 is shown exploded to better illustrate the components of the system 10. FIG. 40 is a side elevation of the system wherein the tool is attached to the implant assembly for delivery of the implant assembly to the sacroiliac joint.

As can be understood from FIGS. 37-40, the system 10 includes a delivery tool 20 and an implant assembly 15 for implanting at the sacroiliac joint via the delivery tool 20, the implant assembly 15 being for fusing the sacroiliac joint. As indicated in FIG. 39, the implant assembly 15 includes an implant 25 and an anchor element 30 (e.g., a bone screw or other elongated body).

As can be understood from a comparison of FIGS. 2A-3 to FIGS. 37-40, the delivery tool 20 of FIGS. 2A-3 is the same as the delivery tool 20 of FIGS. 37-40. Thus, for a complete description of the delivery tool 20 of FIGS. 37-40 and its components, namely, the arm assembly 85, handle 90, implant retainer 95, a trocar or guidewire 105, and multiple nested sleeves 100, refer back to the corresponding discussion given above with respect to FIGS. 2A-3 and 18-31.

Figure 45:
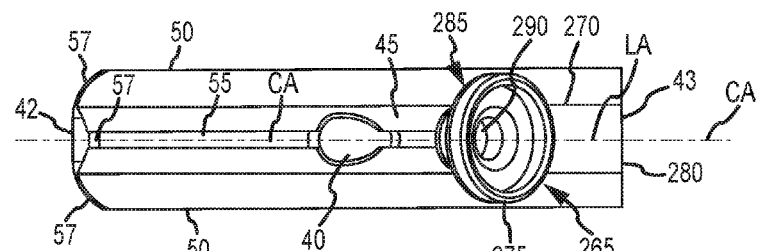
FIGS. 45-46 are opposite plan views of the implant.
Figure 46:
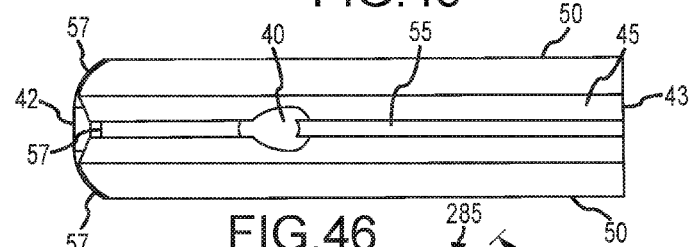
Figure 49:
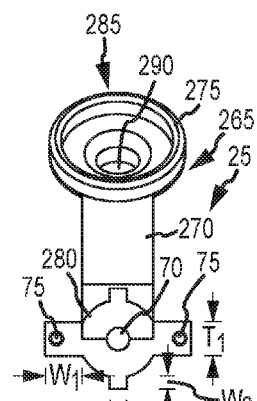
FIGS. 47-50 are various elevation views of the implant.

As indicated in FIGS. 37-40, the system 10 includes an implant assembly 15 with an implant 25 similar the implant 25 discussed above with respect to FIGS. 4-18, except the implant 25 of FIGS. 37-40 also includes a guide arm 265. To begin a detailed discussion of components of the embodiment of the implant 25 of FIGS. 37-40, reference is made to FIGS. 41-50. FIGS. 41-44 are various isometric views of the implant 25. FIGS. 45-46 are opposite plan views of the implant 25, and FIGS. 47-50 are various elevation views of the implant.

A comparison of FIGS. 41-50 to FIGS. 5-18 reveals that the two implant embodiments are the same, except the implant embodiment of FIGS. 41-50 has a guide arm 265. Thus, for a complete description of the features of the implant 25 other than the guide arm 265, which is discussed below, refer back to the corresponding discussion given above with respect to FIGS. 5-18.

As shown in FIGS. 41-45 and 46-50, the guide arm 265 includes a longitudinally extending member 270 and a guide portion 275. The guide arm 265 is cantilevered off of a side of the implant near the proximal or trailing end 43 of the implant 25. Thus, the guide arm 265 includes an attached end 280, which is attached to, or extends from, the implant proximal end 43, and a free end 285, which defines the guide portion 275.

Figure 48:
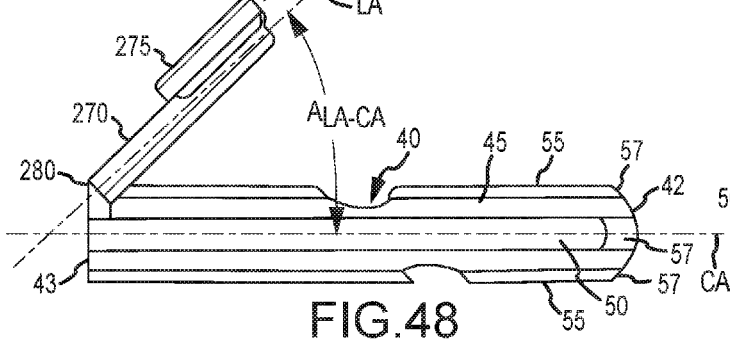
Figure 50:
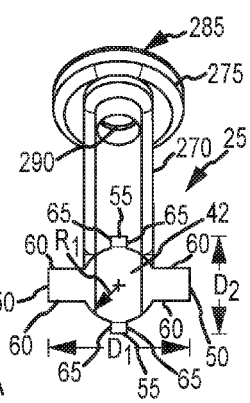
Figure 56:
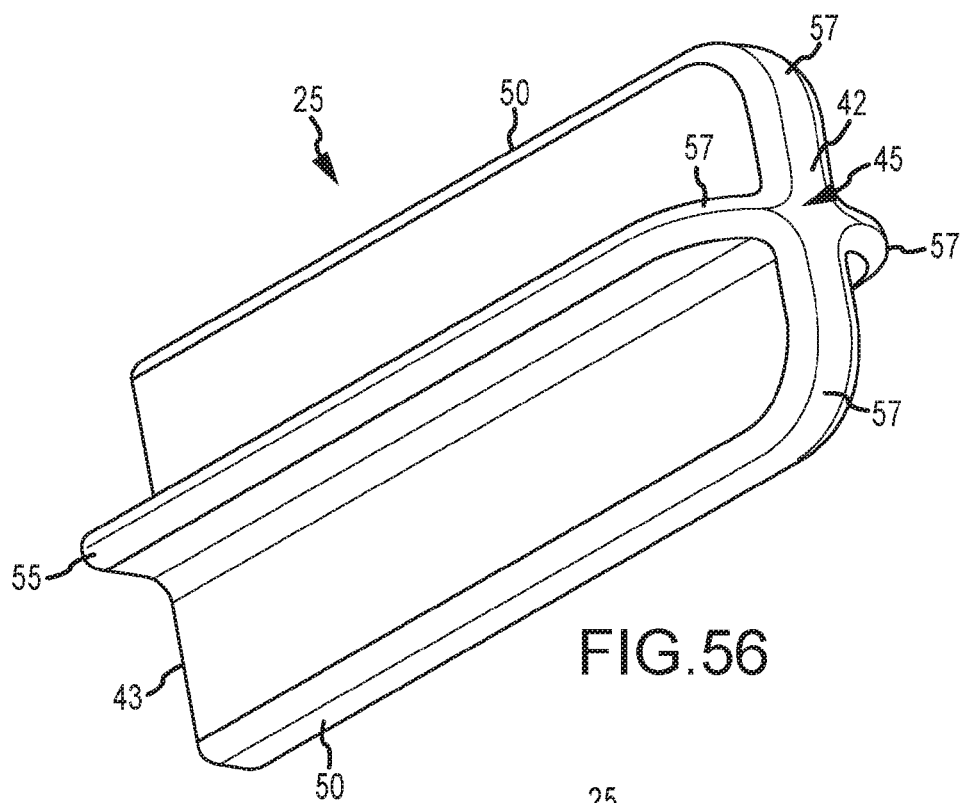
Figure 57:
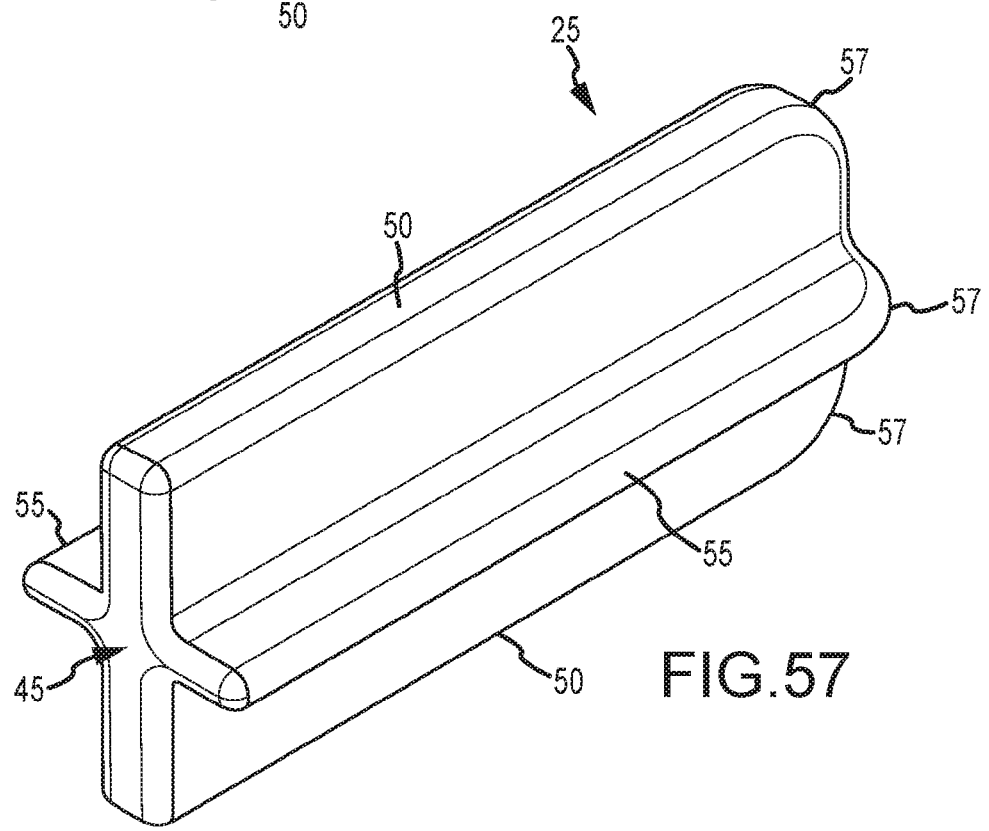
Figure 74:
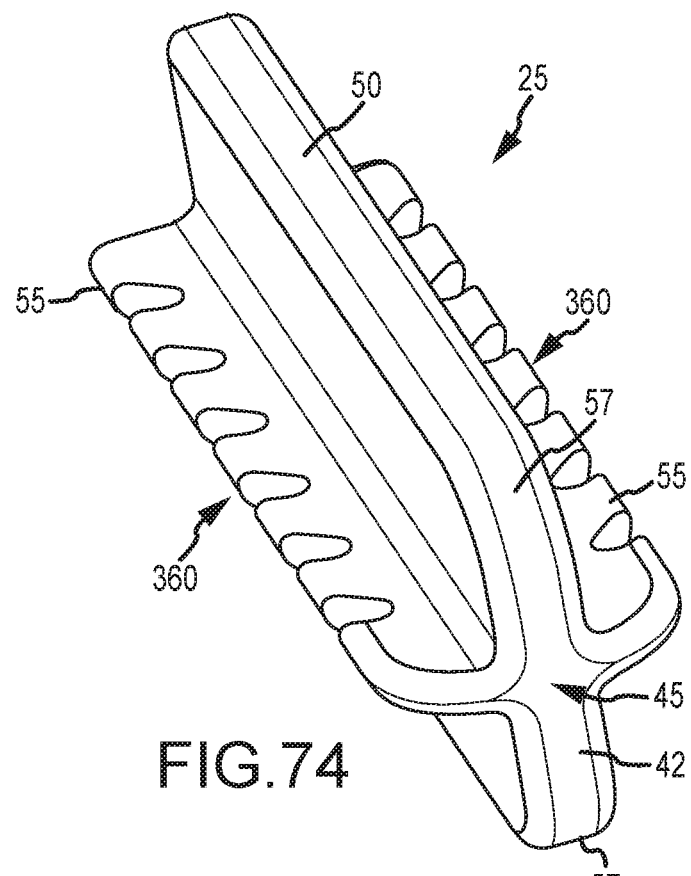
Figure 75:
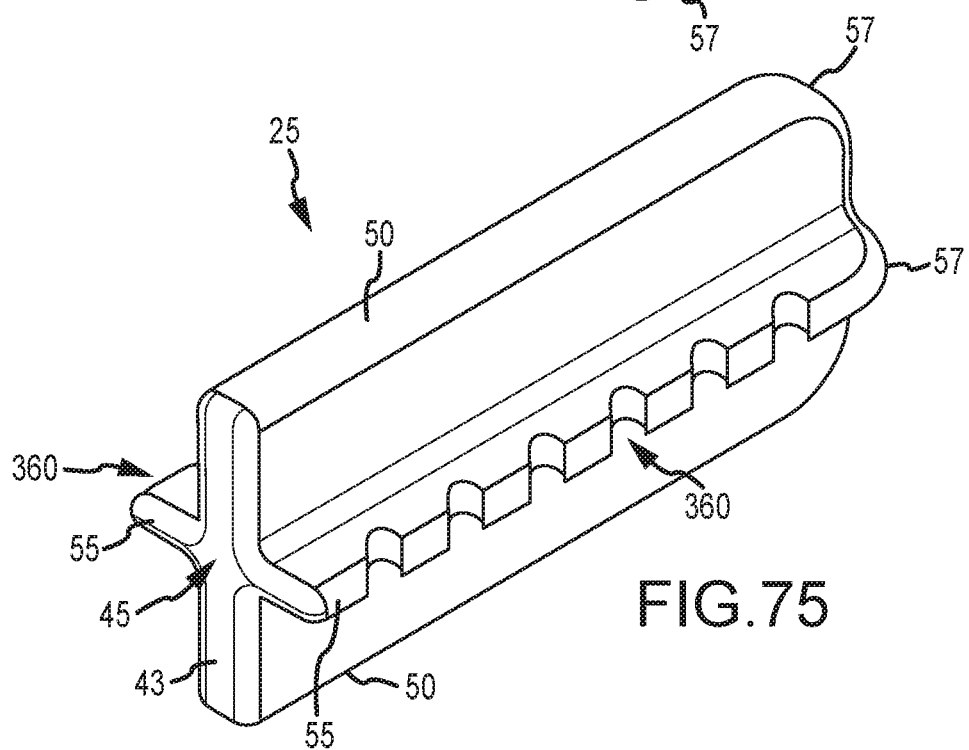
Figure 80:
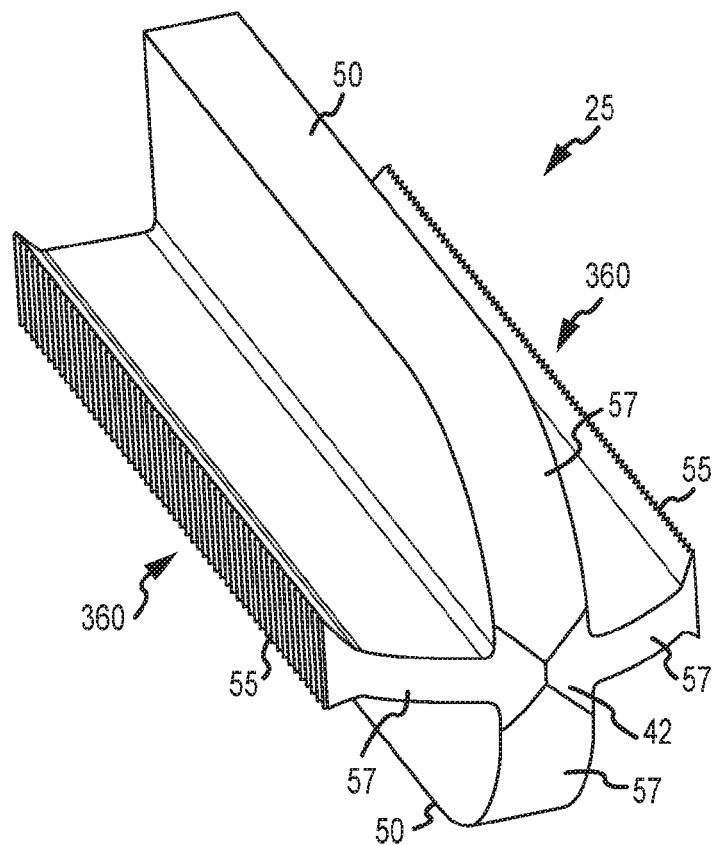
Figure 81:
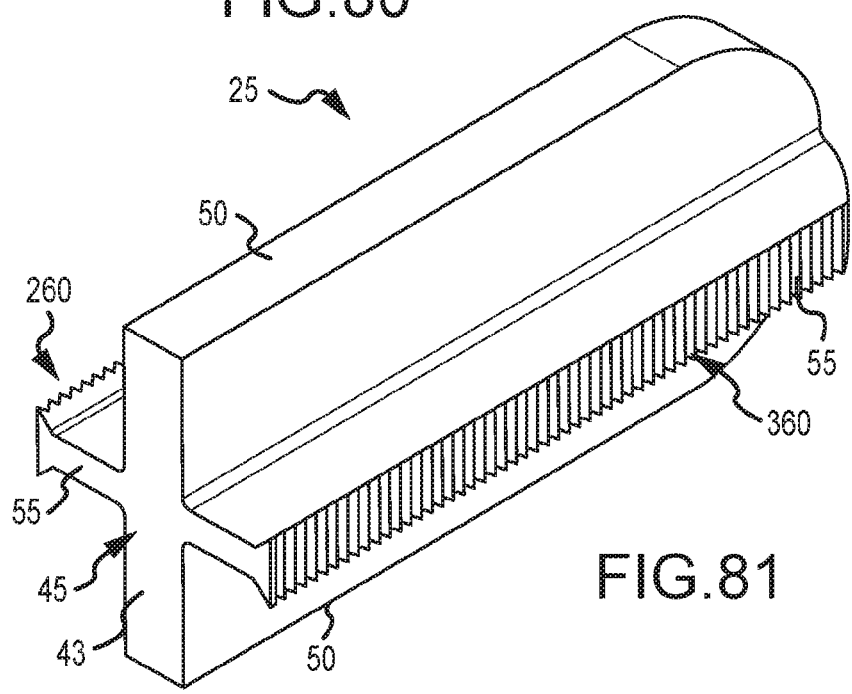

The longitudinally extending member 270 may be in the form of a planar member or other shaped member. As illustrated in FIG. 45, the longitudinal axis LA of the member 270 is generally coplanar with the longitudinal axis CA of the implant body 45. However, as indicated in FIG. 48, the longitudinal axis LA of the member 270 forms an angle $A_{LA\text{-}CA}$ with the longitudinal axis CA of the implant body 45. For example, the angle $A_{LA\text{-}CA}$ may be between approximately 5 degrees and approximately 60 degrees, with one embodiment being approximately 40 degrees.

Figure 47:
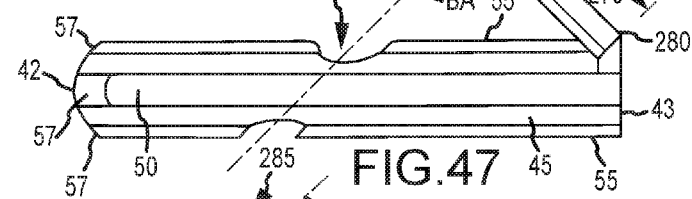

As illustrated in FIGS. 41-45 and 47-50, the guide portion 275 is in the form of a collar defining a central hole 290. As indicated in FIG. 47, the member 270 has an overall length AD from its intersection with the rest of the implant to the tip of the free end 285 of between approximately 5 mm and approximately 60 mm, with one embodiment being approximately 20 mm. Also, the center axis GA of the hole 290 is coaxially aligned with the center axis BA of the bore 40. The overall length AE from the intersection of the member 270 with the rest of the implant to the center axis GA is between approximately 2 mm and approximately 58 mm, with one embodiment being approximately 17 mm.

Since the center axis GA of the hole 290 is coaxially aligned with the center axis BA of the bore 40, when the system 10 is assembled such that the implant 25 is mounted on the distal end of the implant arm 110 with the longitudinal center axis $LCA_2$ of the implant arm 110 coaxial with the longitudinal center axis CA of the implant 25, the respective longitudinal axes $LCA_1$, BA and GA of the anchor arm collar 165, the bore 40 and the guide hole 290 are coaxially aligned, as can be understood from FIG. 40. Thus, when the implant body 45 is located in the sacroiliac joint and the guide collar 275 of the implant 25 is located near or against bone adjacent to the sacroiliac joint, the anchor member 30 may be accurately driven through the guide hole 290, through the bone and through the implant bore 40 to anchor the implant at the sacroiliac joint in such a manner to allow the implant to fuse the joint.

In one embodiment, the implant 25 may be machined, molded, formed, or otherwise manufactured from stainless steel, titanium, ceramic, polymer, composite or other biocompatible materials. The anchor member 30 may be machined, molded, formed or otherwise manufactured from similar biocompatible materials.

For the delivery tools 20 depicted in FIGS. 2A, 21A, 21C, 32, 37, and 40, the handle 90 and arm assembly 85 are coupled together so as to not allow rotational movement relative to each other, and the implant retainer 95 is rotationally displaceable within the handle 90 and arm assembly 85. In other embodiments of the tool 20, the handle 90 and implant retainer 95 are coupled together so as to rotate as a unit relative to the arm assembly 85. An example of such an embodiment is illustrated in FIG. 86, which is an isometric view of the delivery tool 20.

Figure 86:
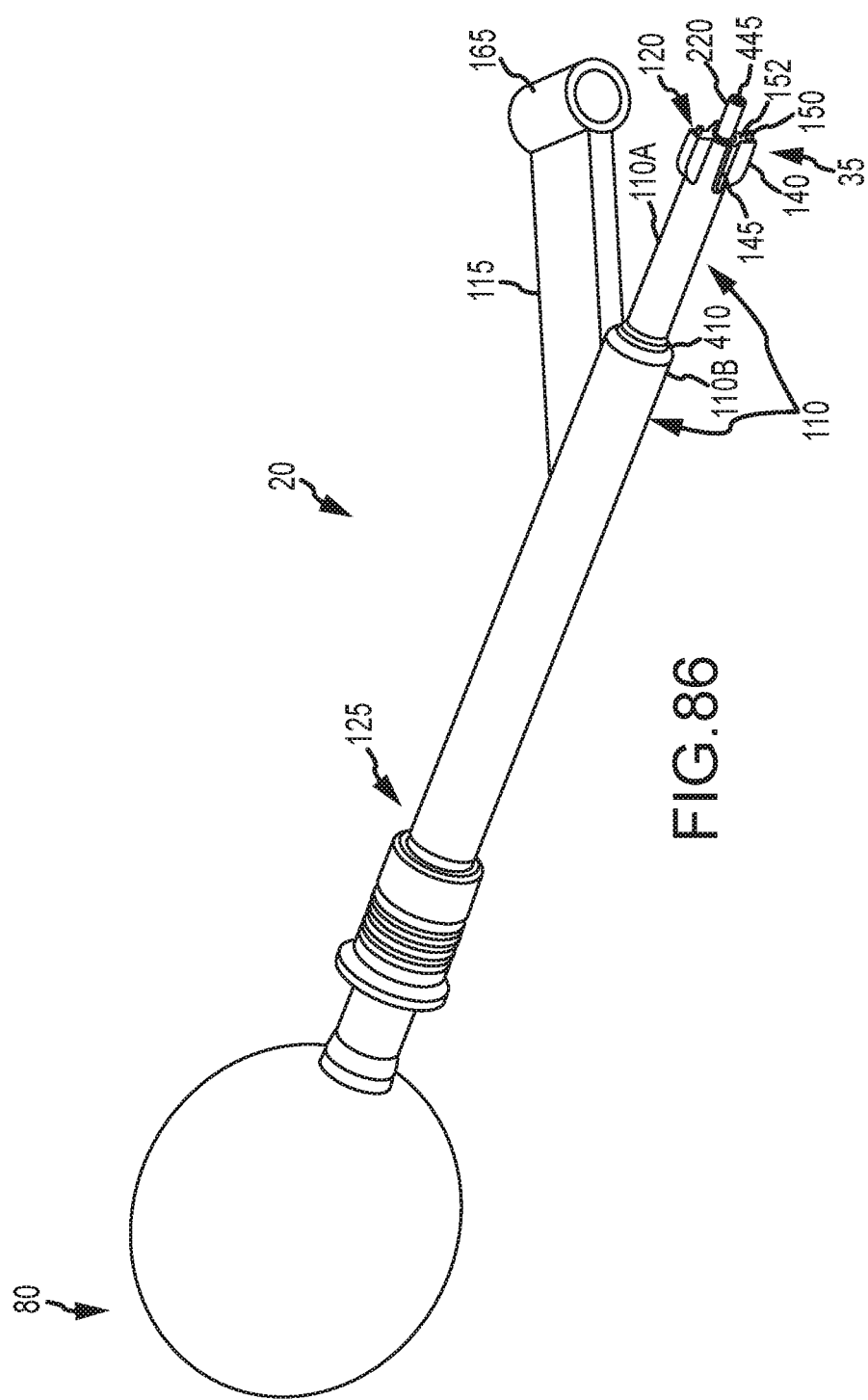
FIG. 86 is an isometric view of the delivery tool.
Figure 87:
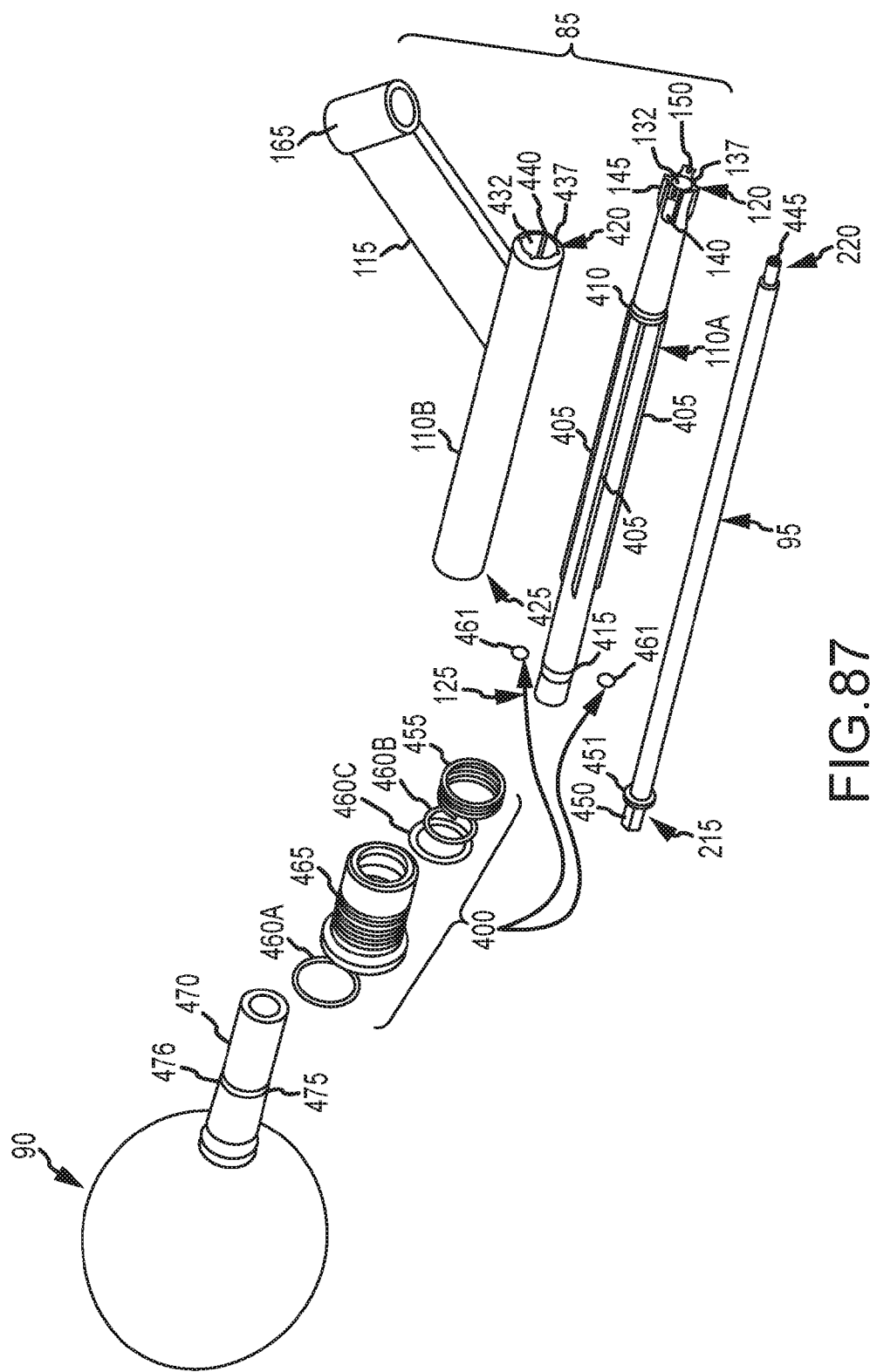

As shown in FIG. 86, the delivery tool 20 includes a distal end 35 and a proximal end 80. As shown in FIGS. 87-88, which are generally opposite isometric views of the delivery tool 20 in an exploded state, the tool 20 further includes an arm assembly 85, a handle 90, an implant retainer 95, and a collar assembly 400. The tool 20 may also include a sleeve 100 and a trocar or guidewire 105 as discussed above with respect to the embodiment of FIG. 3.

As can be understood from FIGS. 86-88, the arm assembly 85 includes an implant arm 110 and an anchor arm 115 supported off of the implant arm 110. The implant arm 110 has a two-piece construction of an inner sleeve 110A and an outer sleeve 110B. The implant arm inner sleeve 110A includes a distal end 120, a proximal end 125, a proximal cylindrical opening 130 of a cylindrical bore 132, and a distal cylindrical opening 137 of the bore 132. The cylindrical bore 132 extends the full length of the implant arm inner portion 110A between the proximal opening 135 and the distal opening 137. Longitudinally extending raised ribs 405 are radially distributed about the outer circumferential surface of the implant arm inner portion 110A. The longitudinal ribs 405 distally terminate by intersecting a raised circumferential ring 410 on the outer circumferential surface of the inner implant arm portion 110A. A groove 415 is circumferentially extends about the outer circumference of the implant arms inner portion 110A. The distal end 120 of the implant arm inner portion 110A also includes large planar members, keels, or fins 140 and small planar members, keels, or fins 145, pins 150, and a planar extreme distal face 152 similar to that discussed above with respect to the embodiment of FIG. 2A.

As illustrated in FIGS. 87-88, the implant arm outer portion 110B includes a distal end 420, a proximal end 425, a proximal cylindrical opening 430 of a cylindrical bore 432, and a distal cylindrical opening 437 of the bore 432. The cylindrical bore 432 extends the full length of the implant arm outer portion 110B between the proximal opening 435 and the distal opening 437. Longitudinally extending grooves 440 are radially distributed about the inner circumferential surface of the bore 432 in an arrangement that matches the longitudinal raised ribs 405 of the implant arm inner portion 110A such that the ribs 405 are received in the grooves 440 in a mated arrangement when the inner portion 110A is received in the bore 432 of the outer portion 110B. The anchor arm 115 extends off the implant arm outer portion 110B at an angle as described above with respect to the previously discussed embodiments. The anchor arm 115 terminates at its free end in a collar 165 similar to those already discussed above.

As shown in FIGS. 87 and 88, the implant retainer 95 includes a proximal end 215, a distal end 220, and a lumen 445 extending the full length of the implant retainer 95. The proximal end 215 includes a squared, pentagonal or hexagonal outer surface configuration 450 that facilitates a mechanical engagement arrangement with the handle 90 such as the mechanical arrangement that exists between a wrench and nut. A ring 451 radial extends from the retainer 95 at the distal edge of the squared, pentagonal or hexagonal configuration 450. The distal end 220 may be threaded or otherwise configured to engage a proximal end of anyone of the implants 25 disclosed herein.

As illustrated in FIGS. 87 and 88, the collar assembly 400 includes a helical spring 455, rings 460A and 460B, washer 460C, retainer balls 461, and a retaining collar 465. As shown in FIG. 89, which is an isometric view of the handle 90, a cylindrical neck portion 470 of the handle 90 includes a shoulder 476 which slopes down to a circumferential groove 475 and a pair of holes 480 defined in the outer circumferential surface of the neck 470.

As indicated in FIG. 90, which is an exploded isometric view of the retaining collar 465 and handle 90 shown in longitudinal cross section, the holes 480 extend through the cylindrical wall 485 that defines the neck 470 and a cylindrical void 487 within the neck. A squared, pentagonal or hexagonal inner surface configuration 490 is defined in the handle 90 distal the cylindrical void 487 to receive in a mating arrangement the complementarily shaped outer configuration 450 of the proximal end of the implant retainer 95. A lumen 495 extends from a proximal end of the handle to open into the squared, pentagonal or hexagonal inner surface configuration 490.

As shown in FIG. 90, the retaining collar 465 includes a proximal end 500, a distal end 505, an outer circumferential surface 510 and an inner circumferential surface 515 that defines the hollow interior of the collar 517. The outer circumferential surface 510 extends radially outward to form a rim 520 near the proximal end 500. The inner circumferential surface 515 has a stepped and ramped configuration. Specifically, working distal to proximal, the inner circumferential surface 515 includes a proximal inner ring 525 separated from an intermediate inner ring 530 by a proximal large diameter region 535 separated from a small diameter region 540 by a ramped surface 545. Proximal the intermediate inner ring 530 is another large diameter region 550 bordered on its proximal boundary by a groove 555.

Figure 91:
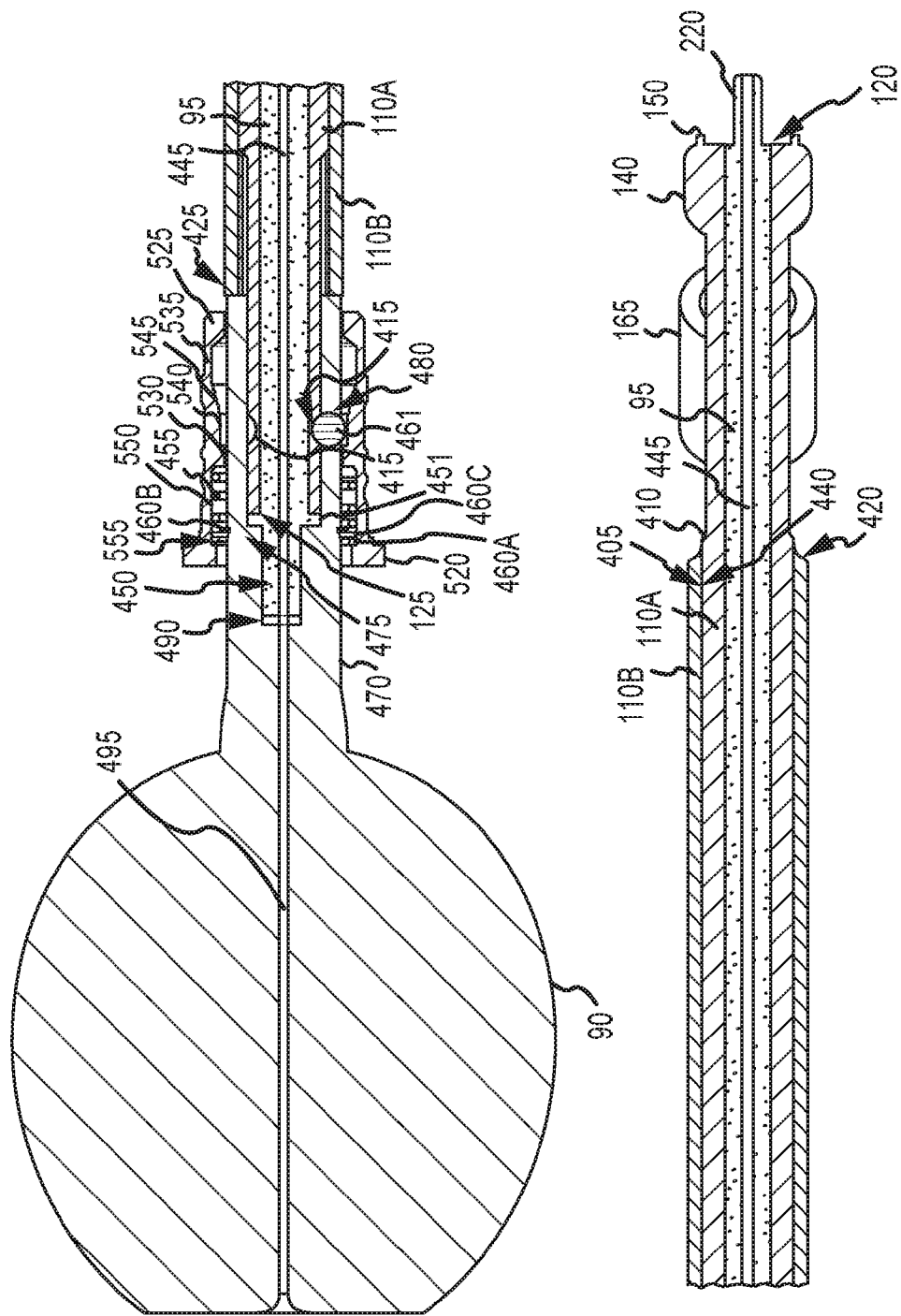
FIG. 91 is a longitudinal cross section of the delivery tool 20 when assembled as shown in FIG. 86.

As can be understood from FIG. 91, which is a longitudinal cross section of the delivery tool 20 when assembled as shown in FIG. 86, the implant arm inner portion 110A is received in the implant arm outer portion 110B such that the ribs 405 are matingly received in the corresponding slots 440 and the ring 410 abuts against the distal end 420 of the outer portion 110B. The implant retainer 95 extends through the inner portion 110A such that the distal end 220 of the implant retainer distally extends from the distal end 120 of the inner portion 110A and the ring 451 abuts against the proximal end 125 of the inner portion 110A. The proximal ends of the inner portion 110A and retainer 95 are received in the volume 487 (see FIG. 90) of the neck 470, the squared, pentagonal, or hexagonal portion 450 of the retainer 95 matingly received in the complementarily shaped volume 490 of the neck such that the ring 451 abuts against the step in the neck between the volume 490 of the neck and the rest of the volume of the neck distal thereto. The distal end of the neck 470 abuts against the proximal end 425 of the outer portion 110B.

As illustrated in FIG. 91, a first lock ring 460A is received in the groove 555 in the collar 465. A second lock ring 460B is received in the circumferential groove 475. A washer 460C is received on the neck 470 and abuts shoulder 476, which prevents washer 460C from advancing proximally beyond shoulder 476, and washer 460C is held in place distally by second lock ring 460B. Helical spring 455 circumferentially extends about the neck 470 between the washer 460C and the intermediate inner ring 530 of the collar 465. Thus, the spring biases the collar 465 distally on the neck 470. First lock ring 460A prevents collar 465 from distal disengagement from neck 470; the ring 460A, due to the forces exerted by a compressed spring 455 abuts washer 460C under normal conditions until manipulation by a medical person acting to move collar 465 proximally which in turn moves first lock ring 460A proximally thereby creating a further distance between first lock ring 460A and washer 460C.

As depicted in FIG. 91, neck holes 480 can be configured to have a sufficient diameter to allow the retaining balls 461 to enter from the opening nearest the outer circumferential surface of the neck 470 and to be seated within holes 480, the configuration further allowing a portion of the retaining balls 461 to extend into the cylindrical void 487 such to allow sufficient engagement with groove 415 as further described below. The neck holes 480 can be further configured, as depicted in FIG. 91, to have a slight reduction in their diameter, the reduction of diameter occupying a small portion of the holes 480 nearest the cylindrical void 487, thereby allowing for a configuration between neck 470, neck holes 480 and retaining balls 461 such that the retaining balls 461 are resistant to completely entering cylindrical void 487 after the removal of inner portion of the implant retainer 95 and implant arm inner portion 110A. The balls 461 are each held in their respective holes 480 in the neck 470 by the balls 461 being trapped between the neck holes 480 and inner circumferential surface of the collar 465. Therefore, when the collar 465 is biased distally on the neck, the balls 461 are inwardly forced by the reduced diameter region 540 to lock into the groove 415 of the inner portion 110A, retaining the proximal end of the anchor arm 110 in the handle/collar assembly. When the collar 465 is pulled proximally by a medical person using the tool 20, the balls 461 are exposed to the large diameter region 535, allowing the balls 461 sufficient play to radially outwardly move in the holes 480 to allow the balls to escape the groove 415, thereby allowing the proximal end of the anchor arm 110 to be removed from the handle/collar assembly.

As shown in FIG. 91, the lumens 495 and 445 are aligned to make one continuous lumen through the assembled tool 20. Thus, the tool 20 can be fed over a guidewire, stylet, needle or etc., or such implements can be fed through the lumen. Also, a bone paste, in situ curable biocompatible material, or similar material can be fed through the lumen to an implant 25 positioned in the joint via the tool.

As can be understood from FIGS. 86-91, the collar assembly 400 retains the proximal end of the implant arm 110 in the neck of the handle 90. The collar assembly 400 can be displaced proximally on the neck of the handle 90 to allow the proximal end of the implant arm 110 to be removed from the neck of the handle. When the implant arm 110 is coupled to the handle 90, the portions 110A and 110B of the implant arm 110 are locked together and prevented from displacing relative to each other, but the handle 90 and retainer 95 can be caused to rotate as a unit relative to the implant arm 110 to cause the distal end 220 of the retainer 95 engage or disengage the implant 25 as desired. Accordingly, the configuration allows for the removal of a handle 90 during the course of a procedure while allowing the retainer 95 to maintain engagement with implant 25 as desired.

Additionally, as a non-limiting example, according to particular embodiments, a reversible locking ratcheting mechanism can be employed to prevent undesired rotation of the handle and other components which could loosen the connection between implant 25 and retainer 95.

Figure 92:
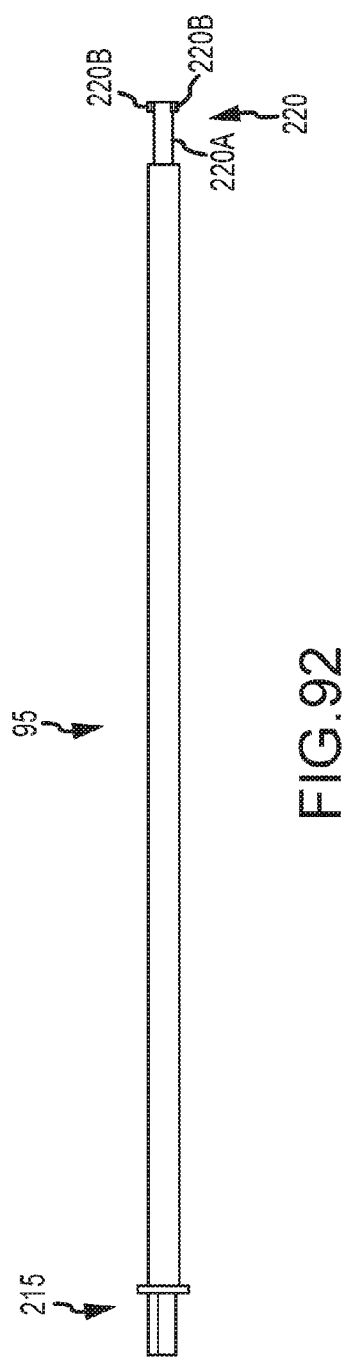
FIG. 92 is a side view of an implant retainer similar to that described with respect to FIGS. 86-91, except having a modified distal end.

As illustrated in FIG. 92, which is a side view of an implant retainer 95 similar to that described with respect to FIGS. 86-91, except having a modified distal end 220. Specifically, the embodiment of FIG. 92 has T-shaped distal end 220. In one embodiment, the T-shaped distal end 220 includes a cylindrical center portion 220A and ears or tabs 220B oppositely positioned on the center portion 220A from each other.

Figure 93:
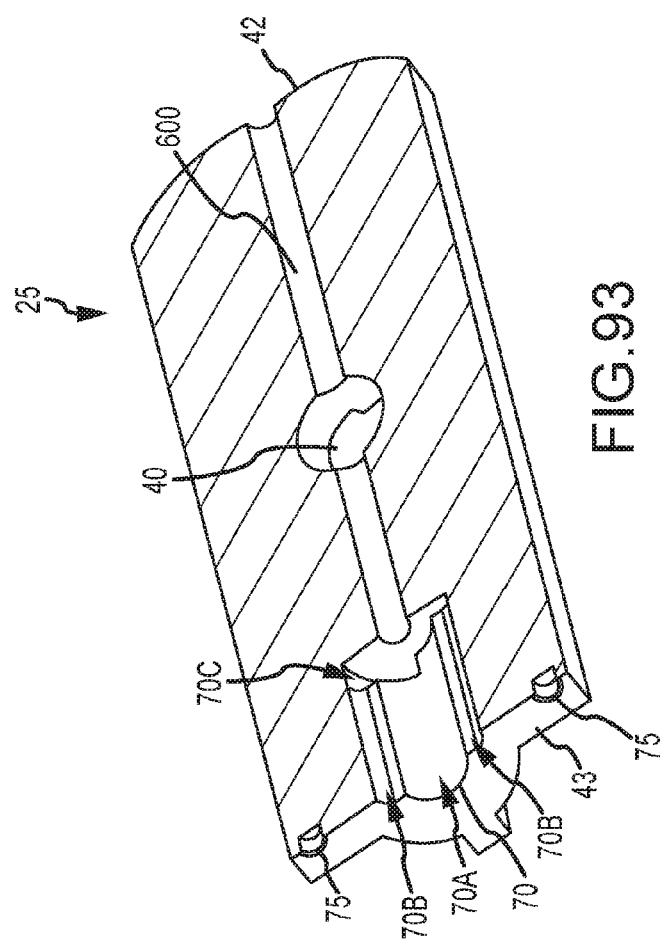
FIGS. 93-94 are, respectively, longitudinal and transverse cross sectional views of an implant with an engagement hole configured to complementarily engage with the T-shaped distal end of the retainer of FIG. 92.
Figure 94:
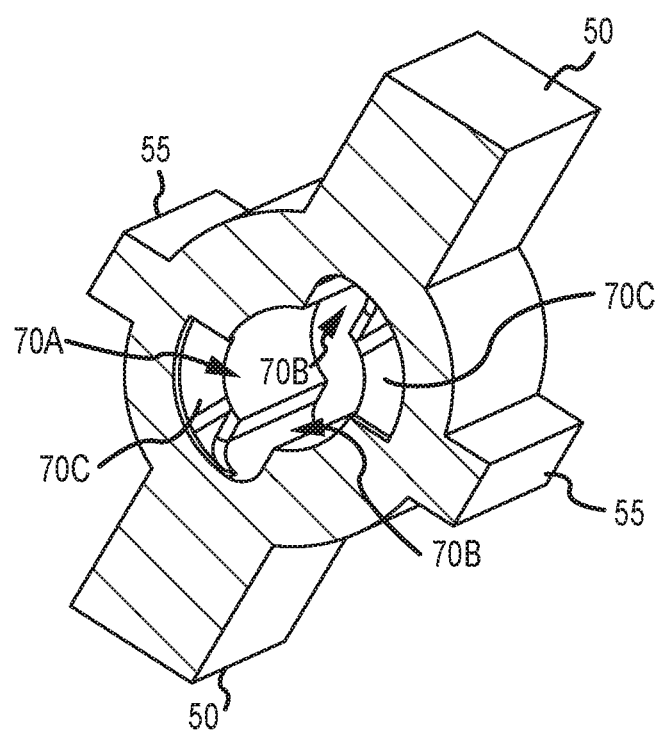

FIGS. 93-94 are, respectively, longitudinal and transverse cross sectional views of an implant 25 with an engagement hole 70 configured to complementarily engage with the T-shaped distal end 220 of the retainer 95 of FIG. 92. As illustrated in FIGS. 93-94, the hole 70 includes a cylindrical longitudinally extending center portion 70A with longitudinally extending grooves 70B located oppositely from each other. Inner radially extending grooves 70C intersect the distal ends of the grooves 70B.

As shown in FIG. 95, which is the same view as FIG. 93, except with the retainer 95 received in the hole 70, the cylindrical retainer portion 220A is received in the cylindrical hole portion 70A, and the retainer tab portions 220B are received in the hole grooves 70B. Once the distal end 220 of the retainer 95 is sufficiently received in the hole 70 such that the retainer tab portions 220B are aligned with the associated radially extending grooves 70C as illustrated in FIG. 95, the retainer 95 can be rotated within the hole 70 to cause the tab portions 220B to move into the radially extending grooves 70C, thereby locking the distal end 220 of the retainer 95 in the hole 70 of the implant 25. Grooves 70C can be configured such as to form an interference fit, thereby preventing retainer 95 from being separated from the implant 25 without the intentional application of substantial rotational separating force. Reversing the rotation of the retainer can cause the tab portions 220B to exit the radial grooves 70C, thereby unlocking the retainer distal end from the implant hole. Alternatively, according to particular embodiments, as a non-limiting example, radially extending grooves 70C can be configured to have at least one ramped surface, which upon rotation of retainer 95 into the grooves 70C, urges the distal end 220 a distance further in the direction of distal end 42 of implant 25 thereby creating increased friction between ring 45 of retainer 95 and proximal end 125 of 110A thereby preventing undesirable reverse rotation of the retainer without the intentional application of substantial rotational separating force, which otherwise could lead to an unlocking of the retainer distal end from the implant hole.

As illustrated in FIG. 93, in one embodiment, the implant 25 may include a lumen 600 extending the length of the implant through the anchor hole 40 and the retainer engagement hole 70. Such a lumen 600 may serve to receive a guidewire or stylet there through. Such a lumen 600 may serve to receive an injection of bone paste material, or other biocompatible material.

To begin a detailed discussion of a fourth embodiment of the system 10, reference is made to FIGS. 109 and 110. FIG. 109 is an isometric view of the system 10 wherein the tool 20 is attached to the implant 25 for delivery of the implant to the sacroiliac joint. FIG. 110 is a view of the system 10 wherein the implant 25 and anchor arm 115 are shown in plan view.

As can be understood from FIGS. 109-110, the system 10 includes a delivery tool 20 and an implant 25 for implanting at the sacroiliac joint via the delivery tool 20, the implant 25 being for fusing the sacroiliac joint. As can be understood from a comparison of FIGS. 109 and 86, the tool embodiment of FIG. 109 is substantially similar to the tool embodiment of FIG. 86, except the tool embodiment of FIG. 109 has an anchor arm 115 that distally ends in multiple anchor collars 165a-165d.

Figure 7:
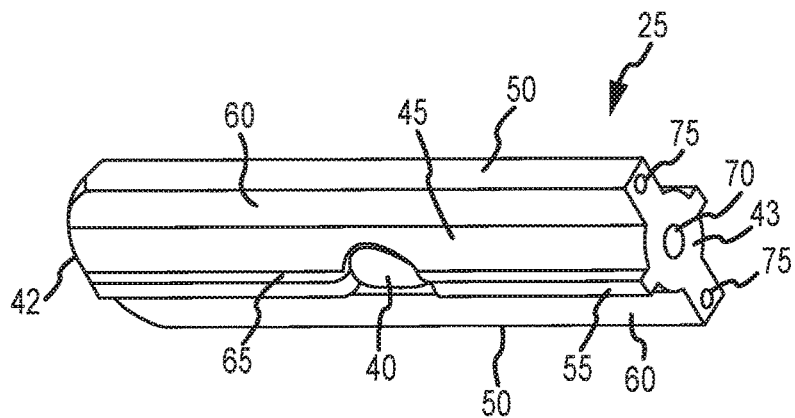
FIG. 7 is a bottom-side isometric view of the implant assembly.
Figure 8:
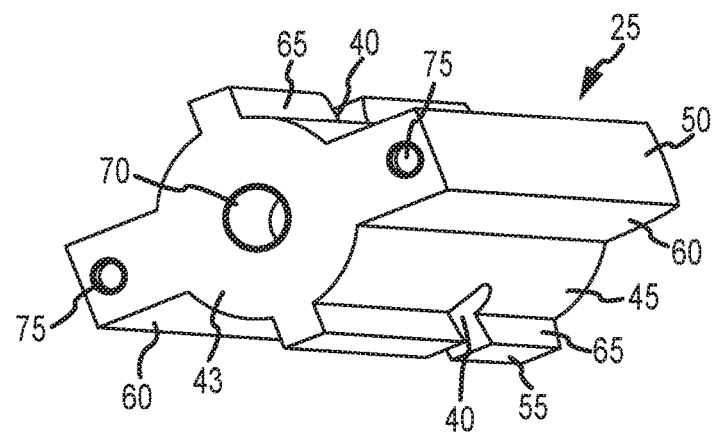
FIG. 8 is another proximal end isometric view of the implant.
Figure 9:
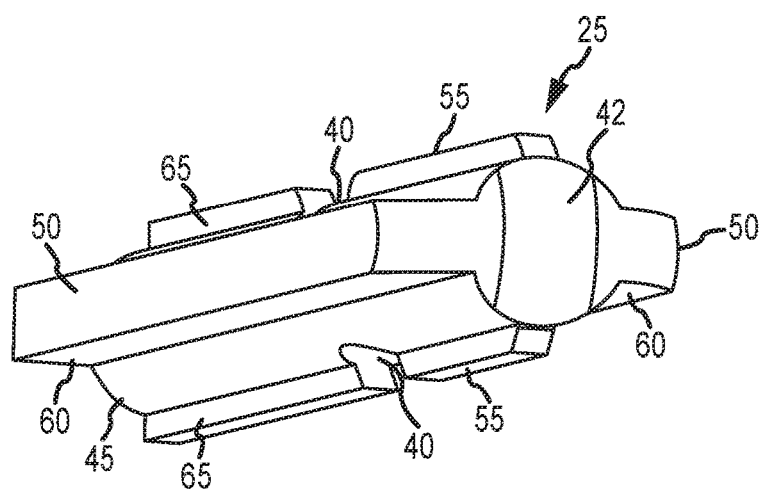
FIG. 9 is another distal end isometric view of the implant.
Figure 10:
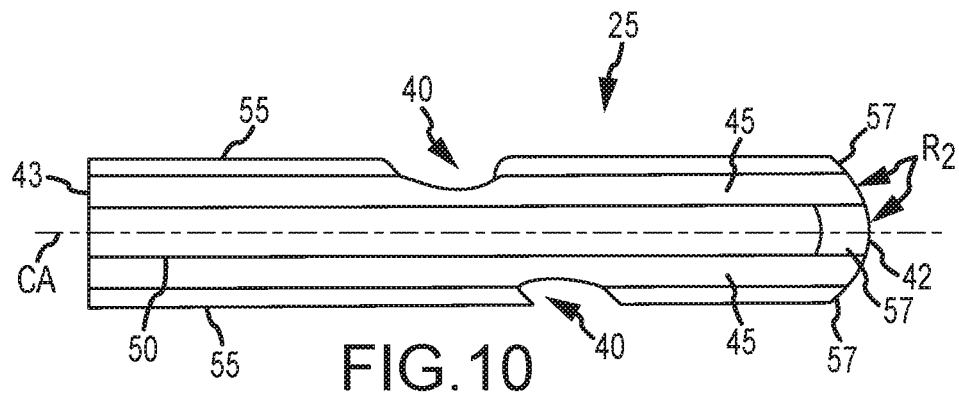
FIGS. 10 and 11 are opposite side elevation views of the implant.
Figure 11:
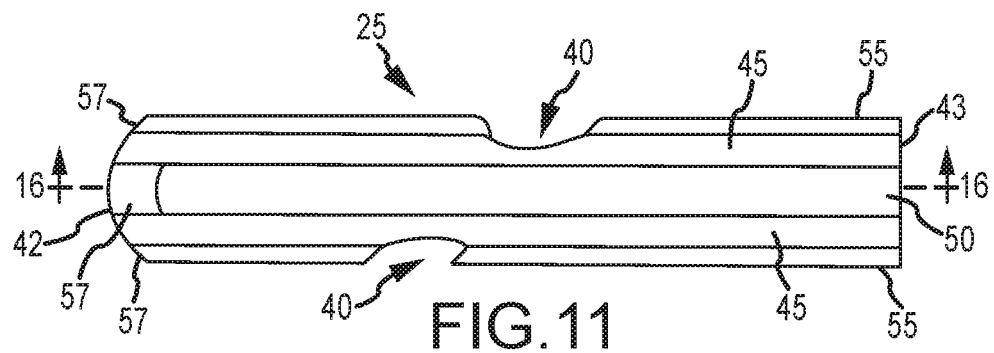

As can be understood from a comparison of FIGS. 109 and 7, the implant embodiment of FIG. 109 is substantially similar to the implant embodiment of FIG. 7, except the implant embodiment of FIG. 109 has multiple bores 40a-40b.

As illustrated in FIGS. 109-110, the anchor collars 165 may include two linearly aligned center collars 165a and 165b, and a lateral anchor collar 165c and 165d may be located on either side of the most proximal center collar 165b. As indicated in FIG. 110, the two center collars 165a and 165b may be axially aligned with the respective bores 40a and 40b of the implant 25 when the implant 25 is supported off of the distal end of the implant arm 110 of the tool 20. As a result, an anchor member 30 (see, for example, FIG. 4) may be delivered into each of the bores 40a and 40b via the respective anchor collars 165a and 165b. The lateral anchor collars 165c and 165d may be employed to deliver yet additional anchor members 30 to additional anchor member receiving features (e.g., bores, etc.) existing on, or extending from the sides of, the implant 25, where such additional anchor member receiving features are present on the implant 25. Alternatively, lateral collars 165c and 165d can be configured to deliver additional anchor members 30 into the bone of the ilium and sacrum while not passing through a bore 40 (i.e., preconfigured to place anchor members 30 immediately adjacent the longitudinal side edges of the implant 25.

Figure 96A:
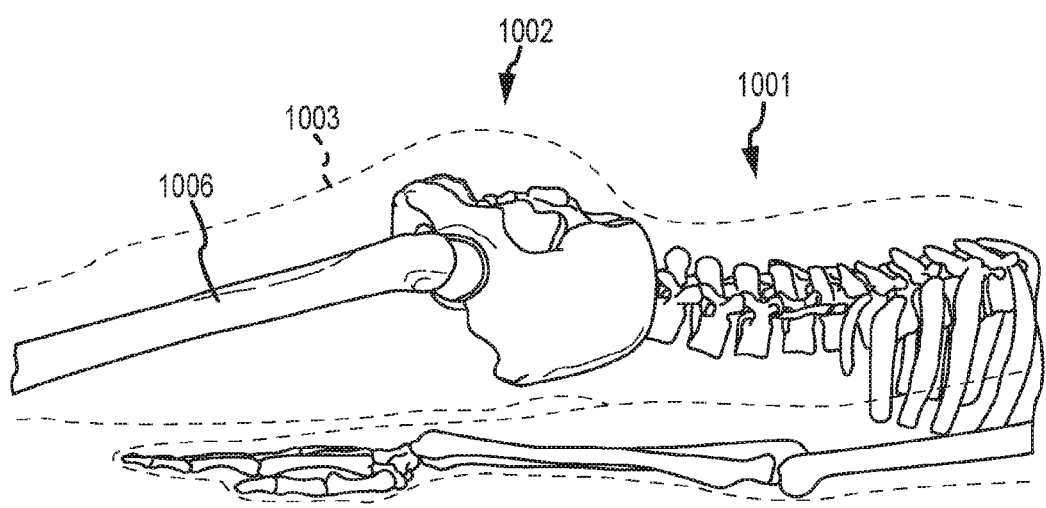
FIG. 96A is a right lateral side view of a hip region of a patient lying prone, wherein the soft tissue surrounding the skeletal structure of the patient is shown in dashed lines.

To begin a discussion regarding the methodology associated with employing any of the above-described delivery tools 20 in implanting any of the above-described implants 25 in the sacroiliac joint 1000 of a patient 1001, reference is first made to FIGS. 96A-98B to identify the bone landmarks adjacent, and defining, the sacroiliac joint 1000. FIG. 96A is a right lateral side view of a hip region 1002 of a patient 1001 lying prone, wherein the soft tissue 1003 surrounding the skeletal structure 1006 of the patient 1001 is shown in dashed lines. FIG. 96B is an enlarged view of the hip region 1002 of FIG. 96A. As illustrated in FIGS. 96A and 96B, a lateral view of the patient's hip region 1002 reveals certain features of the ilium 1005, including the anterior superior iliac spine 2000, the iliac crest 2002, the posterior superior iliac spine 2004, the posterior inferior iliac spine 2006, the greater sciatic notch 2008 extending from the posterior inferior iliac spine 2006 to the ischial spine 2010, and the tubercle of iliac crest 2012. The sacroiliac joint articular region 1044 is shown in dashed lines. A posterior inferior access region 2016 of the sacroiliac joint articular region 1044 has a superior end 2018 on the sacroiliac joint line 2019 that is between approximately 0 mm and approximately 40 mm inferior the posterior inferior overhang 2020 of the posterior superior iliac spine 2004. The posterior inferior access region 2016 of the sacroiliac joint articular region 1044 has an inferior end 2022 on the sacroiliac joint line that is at approximately the intersection of the posterior inferior iliac spine 2006 with the lateral anterior curved boundary 2024 of the sacrum 1004. In other words, the posterior inferior access region 2016 of the sacroiliac joint articular region 1044 has an inferior end 2022 on the sacroiliac joint line that is at approximately the superior beginning of the greater sciatic notch 2008.

Figure 97A:
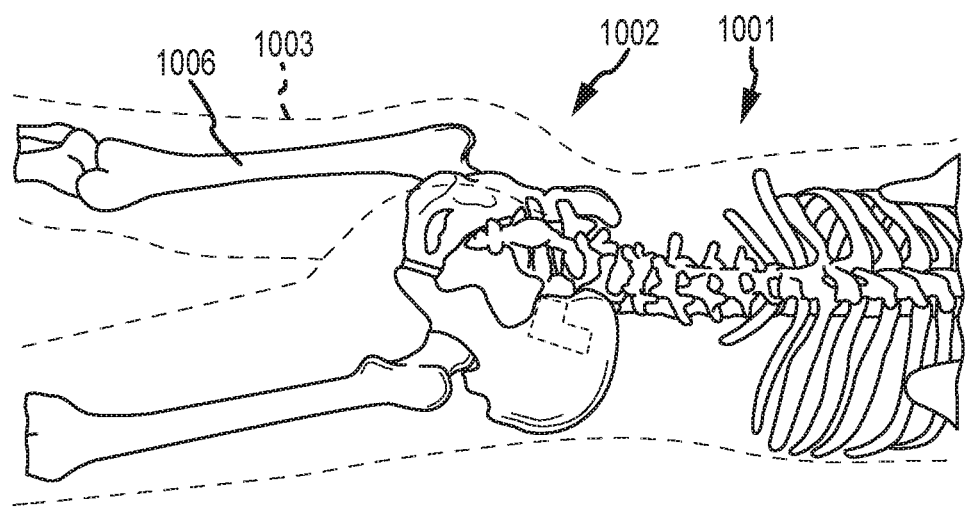
FIG. 97A is a lateral-posterior view of the hip region of the patient of FIG. 96A, wherein the patient is lying prone and the soft tissue surrounding the skeletal structure of the patient is shown in dashed lines.

FIG. 97A is a lateral-posterior view of the hip region 1002 of the patient 1001 of FIG. 96A, wherein the patient 1001 is lying prone and the soft tissue 1003 surrounding the skeletal structure 1006 of the patient 1001 is shown in dashed lines. FIG. 97B is an enlarged view of the hip region 1002 of FIG. 97A. As shown in FIGS. 97A and 97B, a lateral-posterior view of the patient's hip region 1002 reveals the same features of the sacrum 1004 and ilium 1005 as discussed above with respect to FIGS. 96A and 96B, except from another vantage point. The vantage point provided via FIGS. 97A and 97B provides further understanding regarding the posterior inferior access region 2016 of the sacroiliac joint articular region 1044 and superior end 2018 and inferior end 2022 of the posterior inferior access region 2016 relative to nearby anatomical features, such as, for example, the posterior inferior overhang 2020 of the posterior superior iliac spine 2004, the intersection of the posterior inferior iliac spine 2006 with the lateral anterior curved boundary 2024 of the sacrum 1004, and the superior beginning of the greater sciatic notch 2008.

Figure 98A:
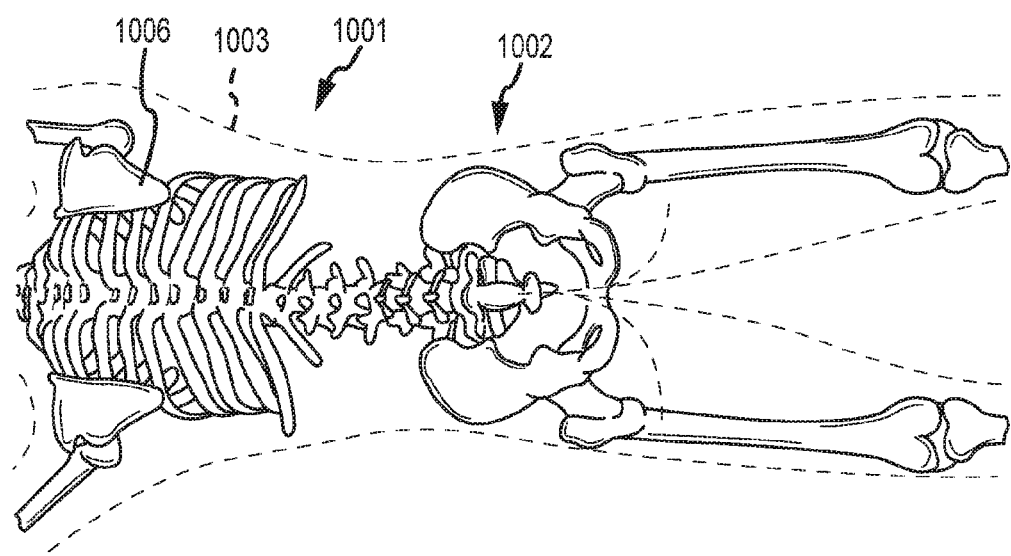
FIG. 98A is a posterior view of the hip region of the patient of FIG. 96A, wherein the patient is lying prone and the soft tissue surrounding the skeletal structure of the patient is shown in dashed lines.
Figure 98B:
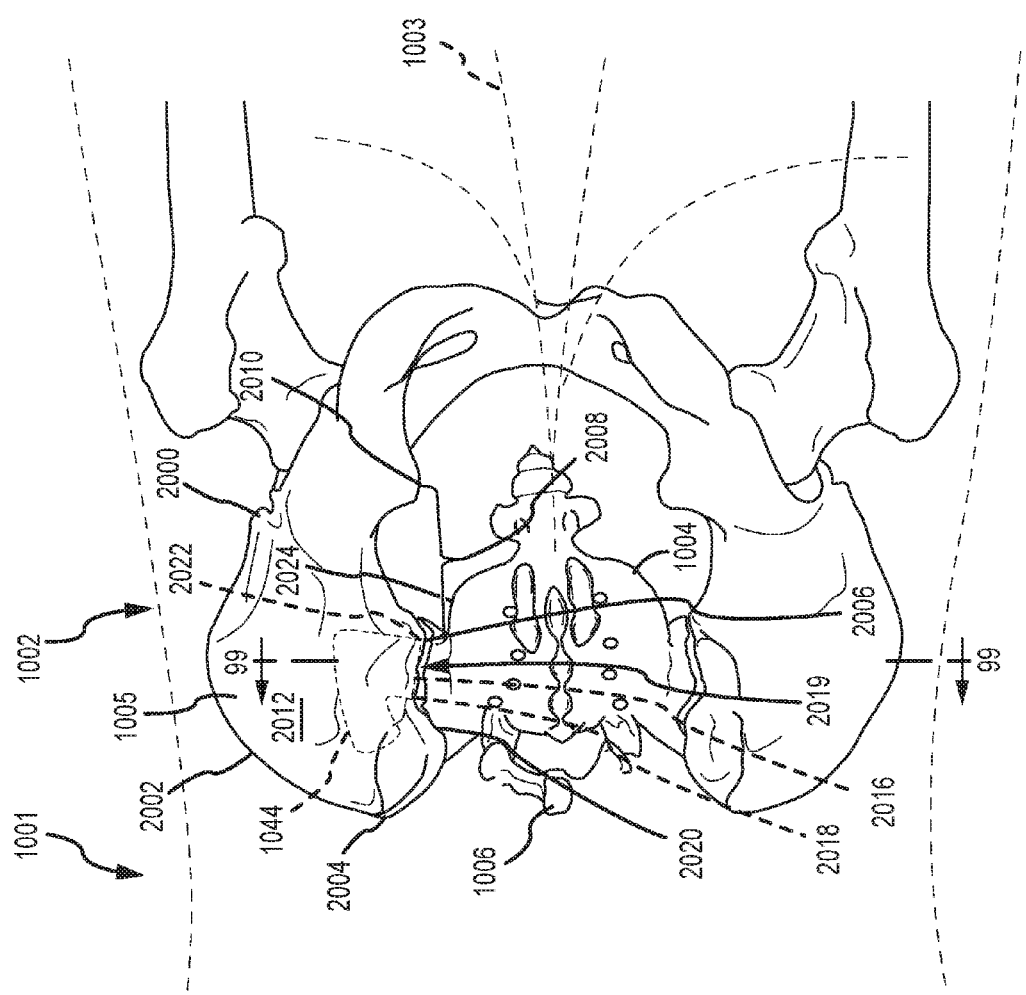
FIG. 98B is an enlarged view of the hip region of FIG. 98A.

FIG. 98A is a posterior view of the hip region 1002 of the patient 1001 of FIG. 96A, wherein the patient 1001 is lying prone and the soft tissue 1003 surrounding the skeletal structure 1006 of the patient 1001 is shown in dashed lines. FIG. 98B is an enlarged view of the hip region 1002 of FIG. 98A. As shown in FIGS. 98A and 98B, a posterior view of the patient's hip region 1002 reveals the same features of the sacrum 1004 and ilium 1005 as discussed above with respect to FIGS. 96A and 96B, except from yet another vantage point. The vantage point provided via FIGS. 98A and 98B provides yet further understanding regarding the posterior inferior access region 2016 of the sacroiliac joint articular region 1044 and superior end 2018 and inferior end 2022 of the posterior inferior access region 2016 relative to nearby anatomical features, such as, for example, the posterior inferior overhang 2020 of the posterior superior iliac spine 2004, the intersection of the posterior inferior iliac spine 2006 with the lateral anterior curved boundary 2024 of the sacrum 1004, and the superior beginning of the greater sciatic notch 2008.

Now that the relevant anatomical landmarks have been identified with respect to FIGS. 96A-98B, the methodology associated with employing any of the above-described delivery tools 20 in implanting any of the above-described implants 25 in the sacroiliac joint 1000 of a patient 1001 can be discussed. In doing so, reference will be made to FIGS. 99A-99P, which are each a step in the methodology and illustrated as the same transverse cross section taken in along a plane extending medial-lateral and anterior posterior along section line 99-99 in FIG. 98B. In this cross section, articular surfaces 1016 are covered by a thick layer of articular cartilage with a joint space existing between them, the FIGS. 99A-99P are simplified for illustrative purposes and do not show these features to scale. Now referring primarily to FIG. 99A, an embodiment of the method can include the step of placing a patient under sedation prone on a translucent operating table (or other suitable surface). The sacroiliac joint 1000 can be locally anesthetized to allow for injecting a radiographic contrast 1046 (as a non-limiting example, Isoview 300 radiographic contrast) under fluoroscopic guidance into the inferior aspect of the sacroiliac joint 1000 to outline the articular surfaces 1016 of the sacroiliac joint 1000) defined between the sacrum 1004 and ilium 1005, the sacroiliac joint 1000 having an interarticular region 1044. Injection of the radiographic contrast 1046 within the sacroiliac joint 1000 can be accomplished utilizing a tubular member 1047)(such as a syringe needle) having first tubular member end 1048 which can be advanced between the articulating surfaces 1016 of the sacroiliac joint 1000 and having a second tubular member end 1049 which removably couples to a hub 1050. The hub 1050 can be configured to removably couple to a syringe barrel 1051 (or other device to contain and deliver an amount of radiographic contrast 1046). In the example of a syringe barrel 1051, the syringe barrel 1051 can have an internal volume capable of receiving an amount of the radiographic contrast 1046 sufficient for outlining the articular surfaces 1016 of the sacroiliac joint 1000, for example, under lateral fluoroscopy. A plunger 1052 can be slidingly received within the barrel 1051 to deliver the radiographic contrast 1046 through the tubular member 1047 into the sacroiliac joint 1000. The tubular member 1047 can have a gauge in the range of about 16 gauge and about 20 gauge and can further be incrementally marked on the external surface to allow determination of the depth at which the first needle end 1048 has advanced within the sacroiliac joint 1000. As the first needle end 1048 advances into the sacroiliac joint 1000 the radiographic dye 1046 can be delivered from within the syringe barrel 1051 into the sacroiliac joint 1000 to allow visualization of the sacroiliac joint 1000 and location of the tubular needle 1047 within the sacroiliac joint 1000.

Now referring primarily to FIG. 99B, once the first tubular member end 1048 has been sufficiently advanced into the sacroiliac joint 1000 and the articular surfaces 1016 of the sacroiliac joint 1000 have been sufficiently visualized, the hub 1050 can be removed from the tubular member 1047 leaving the tubular member 1047 fixed within the sacroiliac joint 1000 as a initial guide for tools subsequently used to locate or place the sacroiliac joint implant 25 non-transversely between the articulating surfaces 1016 of the sacroiliac joint 1000 (e.g., locate the implant 25 non-transversely to the joint plane 1030 generally defined by the articulating surfaces 1016 of the interarticular region 1044 of the sacroiliac joint 1000) or in removal of a portion of the sacroiliac joint 1000 within the region defined by the articular surfaces 1016 to generate an implant receiving space 1029 (see FIG. 99H). Alternately, one or more guide pins 1013 can be inserted along substantially the same path of the tubular member 1047 for fixed engagement within the sacroiliac joint 1000 and used in subsequent steps as a guide(s).

Figure 99B:
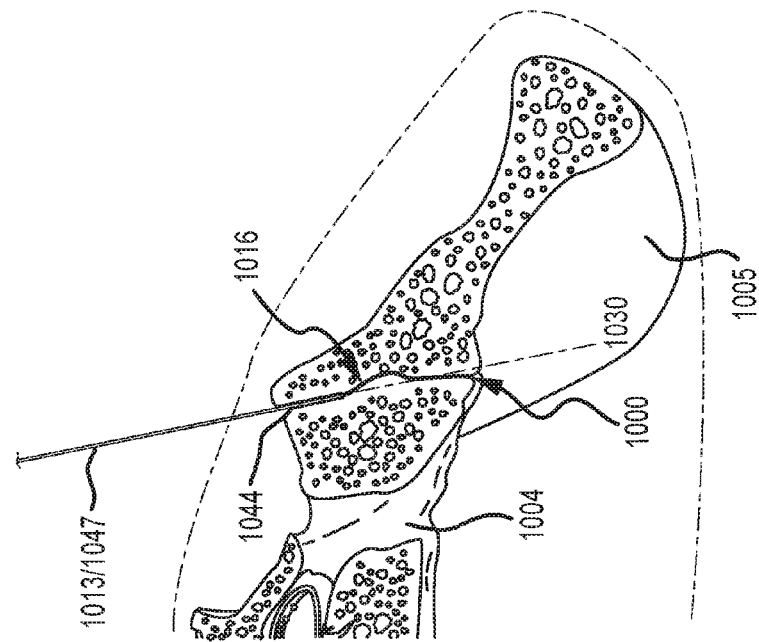
FIGS. 99A-99Q are each a step in the methodology and illustrated as the same transverse cross section taken along a plane extending medial-lateral and anterior posterior along section line 99-99 in FIG. 98B.
Figure 99A:
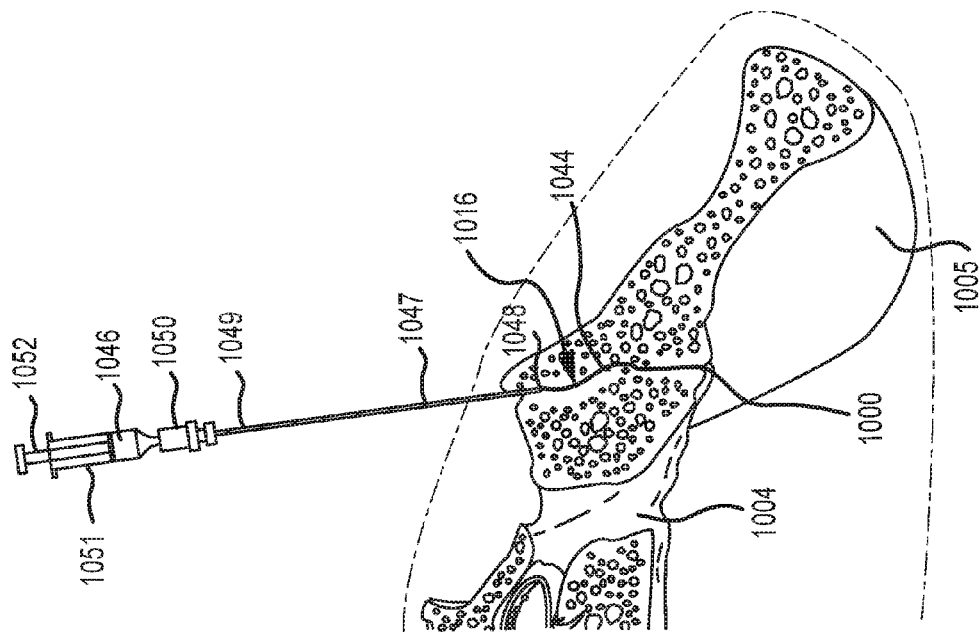
Figure 99H:
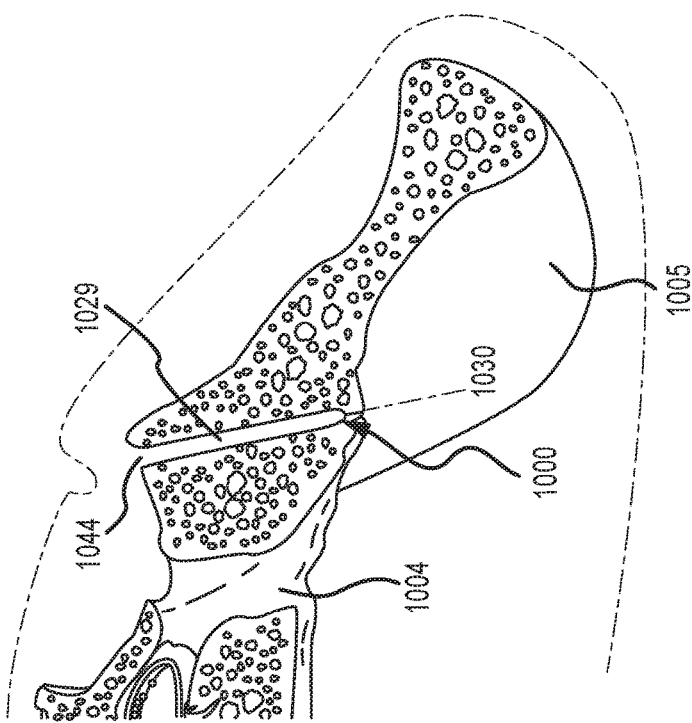

Now referring primarily to FIG. 99C, a small incision 1053 can be made in the skin at the posterior superior (or as to certain embodiments inferior) aspect of the sacroiliac joint 1000, extending proximal and distal to the tubular member 1047 along the line of the sacroiliac joint 1000 to provide a passage to access the interarticular space between the articulating surfaces 1016 (see FIG. 99B) of the sacroiliac joint 1000. More specifically, as can be understood from FIGS. 96A-98B, in one embodiment, the small incision 1053 can be made along the joint line 2019 of the sacroiliac joint 1000 in the tissue covering the posterior inferior access region 2016 of the sacroiliac joint articular region 1044. A cannulated probe 1054 can be slidingly engaged with the tubular member 1047 (or guide pin 1013) extending outwardly from the sacroiliac joint 1000 (while the sacroiliac joint may be shown in the figures as being substantially linear for illustrative purposes, it is to be understood that the normal irregular features of the sacroiliac joint have not been removed). The cannulated probe 1054 can have a probe body 1054 of generally cylindrical shape terminating in a spatulate tip 1055 at the end advanced into the sacroiliac joint 1000. A removable cannulated probe handle 1056 couples to the opposed end of the probe body 1054. The spatulate tip 1055 can be guided along the tubular needle 1047 or guide wire 1013 into the posterior portion of the sacroiliac joint 1000 and advanced to the anterior portion of the sacroiliac joint 1000 under lateral fluoroscopic visualization. The cannulated probe handle 1056 can then be removed providing the generally cylindrical probe body 1054 extending outwardly from the sacroiliac joint 1000 through the incision 1053 made in the skin.

Alternatively, probe 1054 can be used to guide, advance or place a needle, guide wire or other instrument up to, near, or into the joint.

Additionally, in particular embodiments, probe handle 1056 or the opposed end of the probe body 1054, or both, can be configured to have an interference fit or a luer lock hub to communicate with a syringe barrel 1051 in order to advance contrast, in situ curable biocompatible materials, stem cells, or etc through the cannulated probe 1054 or cannulated probe handle 1056.

Now referring primarily to FIG. 99D, a passage from the incision 1053 (see FIG. 99C) to the sacroiliac joint 1000 can be generated by inserting a cannula 1057 into the incision. A soft tissue dilator 1058 having a blunt end 1059 can be advanced over the probe body 1054, or a plurality of soft tissue dilators of increasing size, until the blunt end 1059 of the soft tissue dilator 1058 and the corresponding cannula end contact the posterior aspect of the sacroiliac joint 1000. More specifically, as can be understood from FIGS. 96A-98B, in one embodiment, the ends of the dilator 1058 and cannula 1057 contact the joint line 2019 of the sacroiliac joint 1000 at the posterior inferior access region 2016 of the sacroiliac joint articular region 1044. The soft tissue dilator 1058 can be removed from within the cannula 1057. The external surface of the cannula 1057 can be sufficiently engaged with the surrounding tissue to avoid having the tissue locate with in the hollow inside of the cannula 1057. A non-limiting embodiment of the cannula 1057 provides a tubular body having substantially parallel opposed side walls which terminate in a radius at both ends (lozenge shape) into which a plurality of different jigs can be inserted. Alternatively, as a non-limiting example, according to particular embodiments, cannula 1057 and corresponding dilators 1058 and alignment jigs 1060 can be configured to have tubular bodies with an elliptical or circular cross section.

Figure 100A:
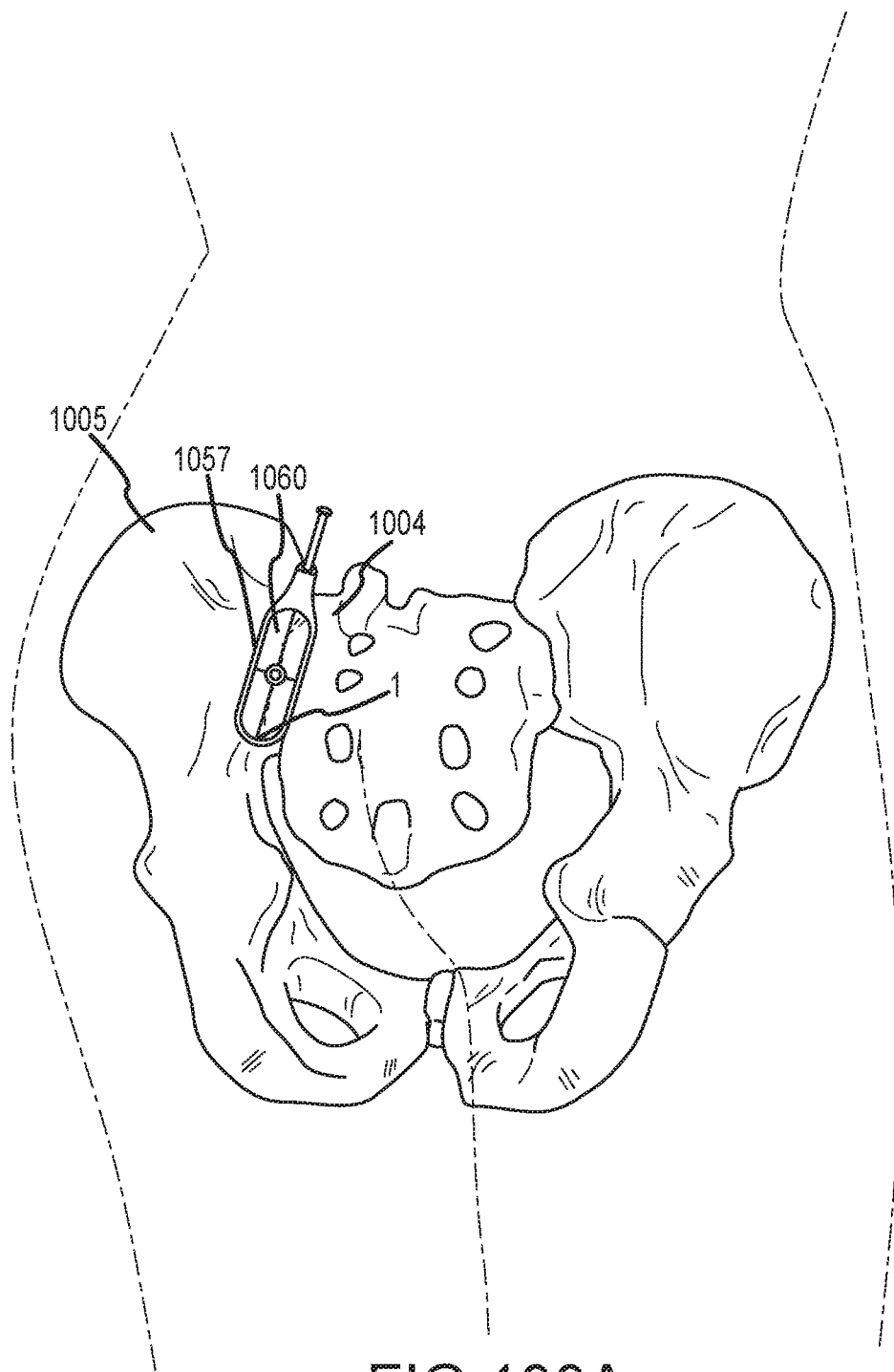
FIG. 100A is a posterior-lateral view of the hip region of the patient, illustrating the placement of a cannula alignment jig.
Figure 100B:
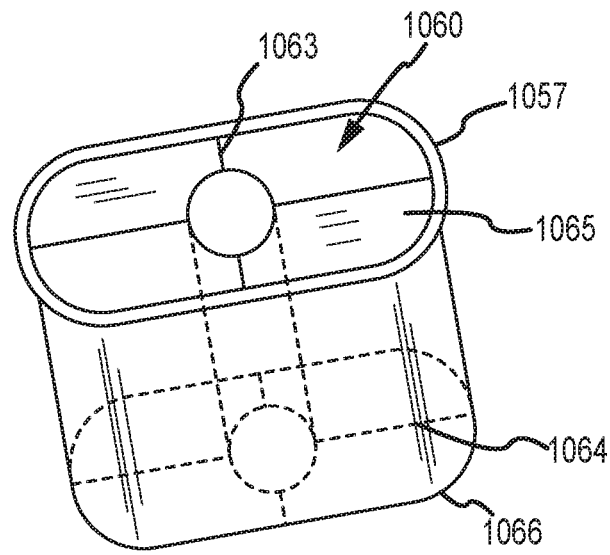
FIGS. 100B-100C are different isometric views of the cannula alignment jig.
Figure 100C:
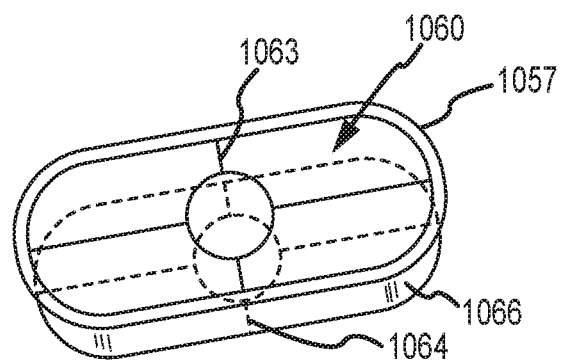

Now referring primarily to FIGS. 100A-100C, a cannula alignment jig 1060 can be advanced over the probe body 1054 (or guide pins 1013) and received within the cannula 1057. Substantially, identical cross hairs 1063, 1064 can be disposed on the upper jig surface 1065 and the lower jig surface 1066. Alignment of the cross hairs 1063, 1064 under x-ray with the sacroiliac joint 1000 can confirm that the cannula 1057 has proper orientation in relation to the paired articular surfaces 1016 of the sacroiliac joint 1000. The cannula 1057 properly oriented with the paired articular surfaces 1016 can then be disposed in fixed relation to the sacroiliac joint by placement of fasteners through the cannula 1057 into the sacrum 1004 or the ilium 1005.

Figure 101A:
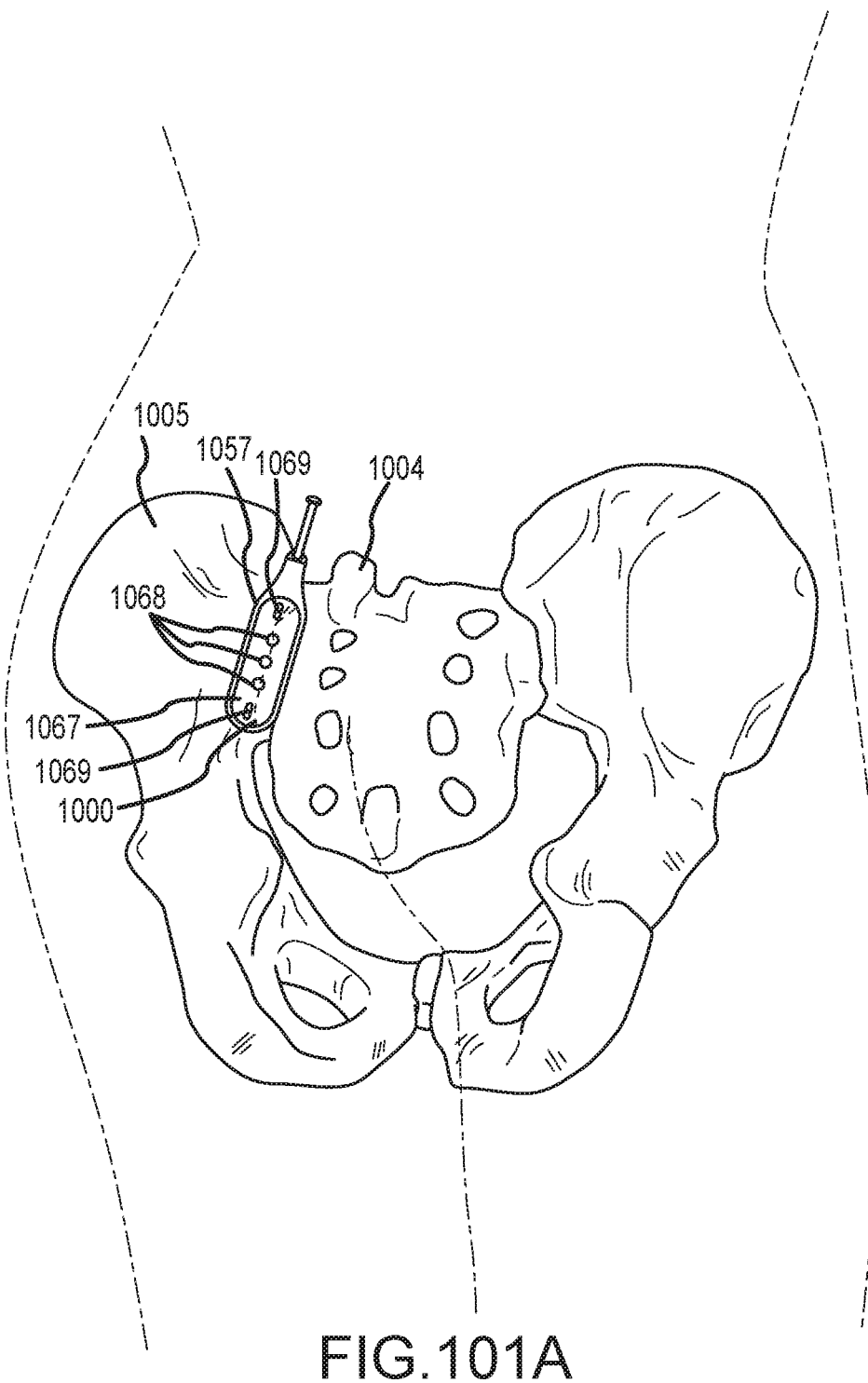
FIG. 101A is a posterior-lateral view of the hip region of the patient, illustrating the placement of a drill jig.
Figure 101B:
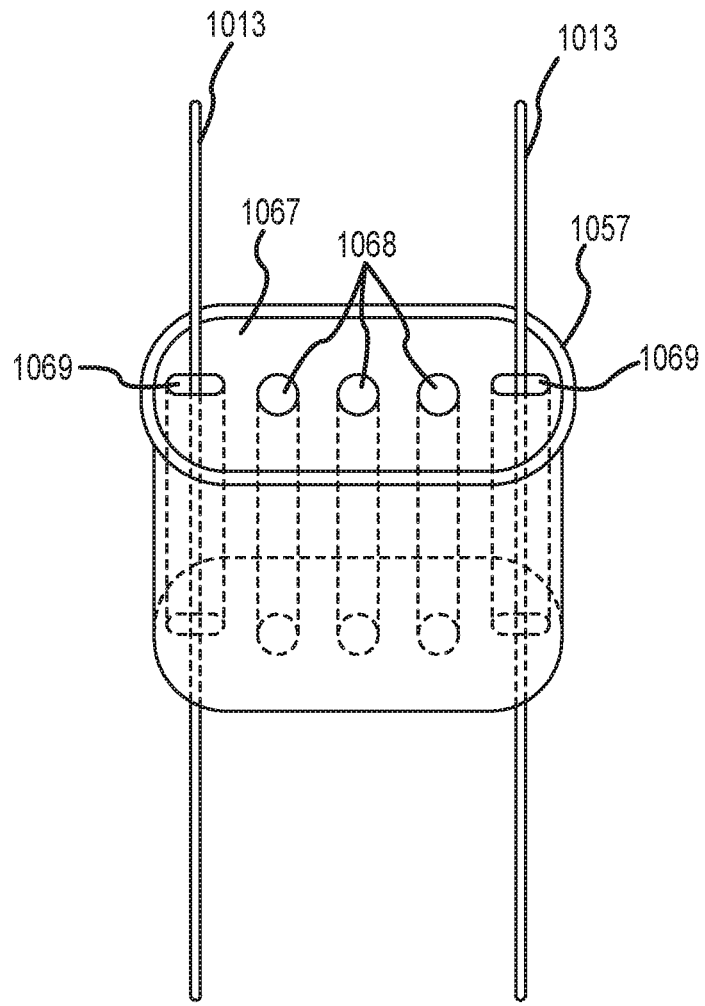
FIG. 101B is an isometric view of the drill jig.
Figure 102A:
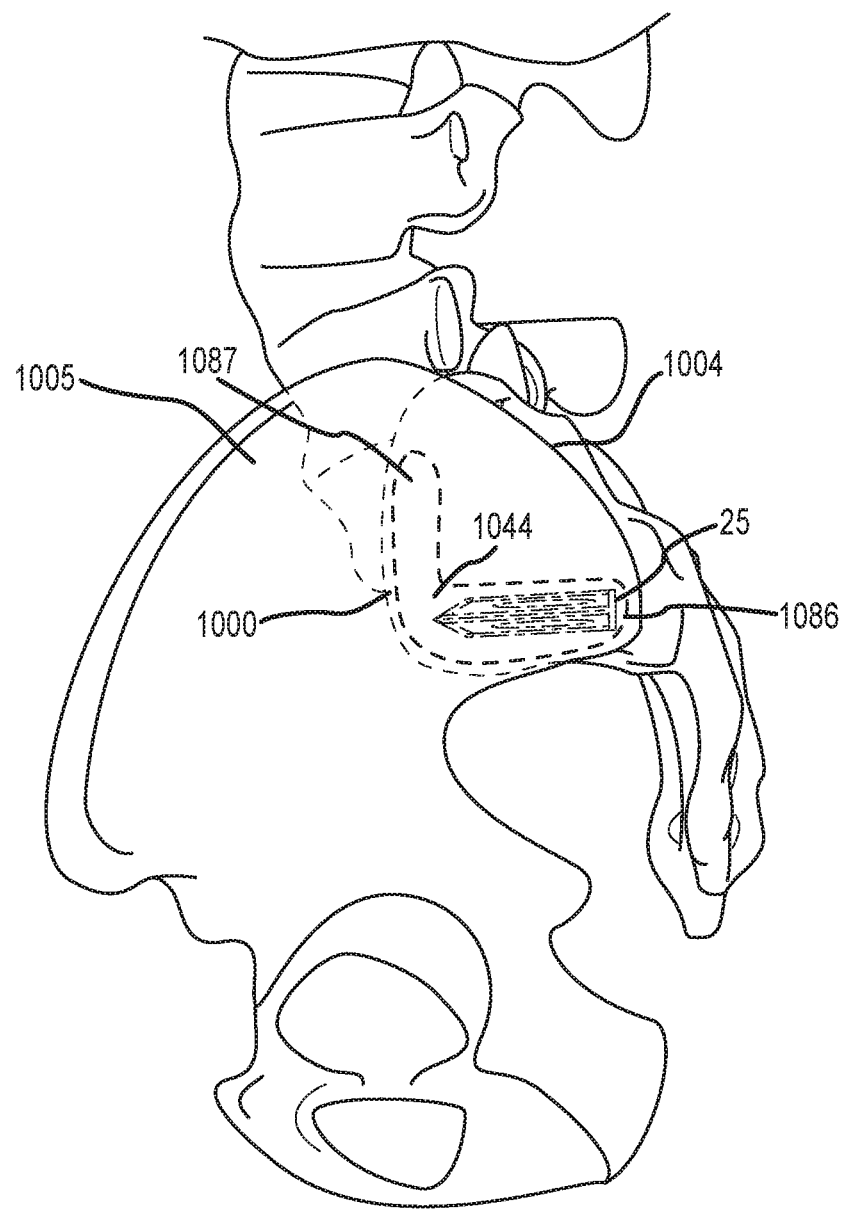
FIG. 102A is a lateral view of the hip region of the patient, illustrating the implant implanted in the caudal region of the sacroiliac join space.
Figure 102B:
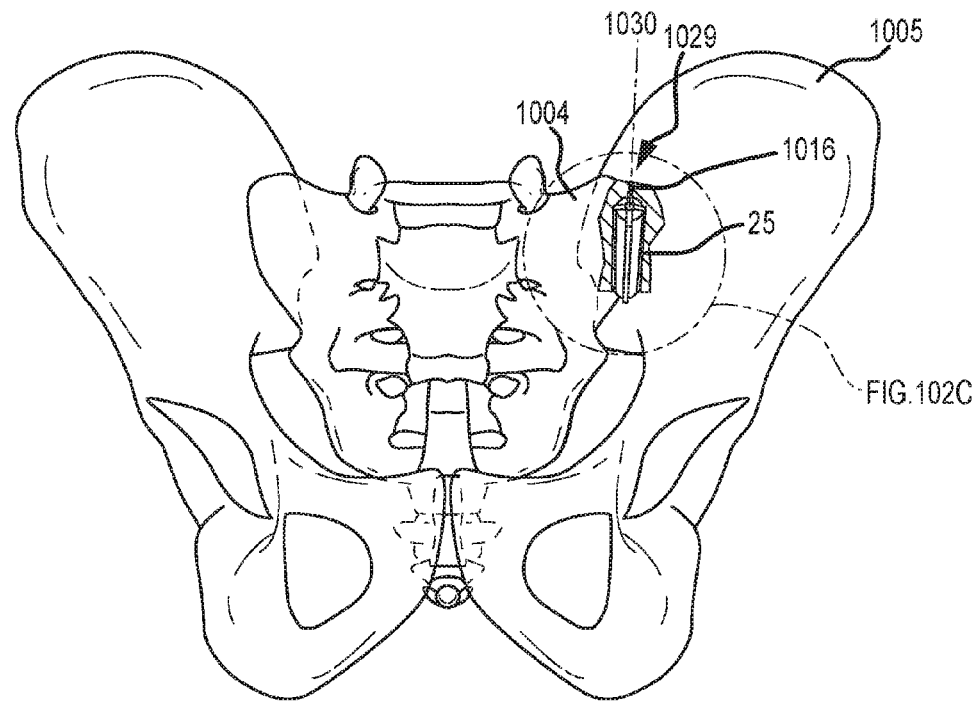
FIG. 102B is an anterior view of the hip region of the patient, illustrating the implant implanted in the caudal region of the sacroiliac join space.
Figure 102C:
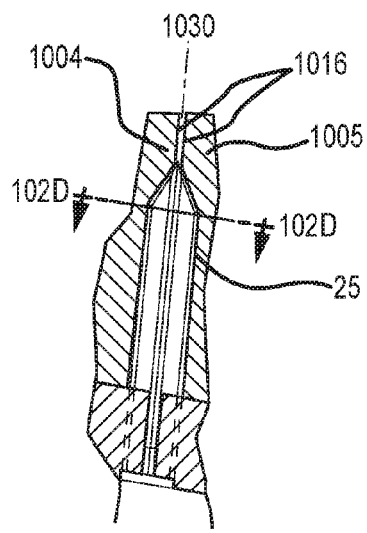
FIG. 102C is an enlarged view of the implant taken along the plane of the sacroiliac joint.
Figure 102D:
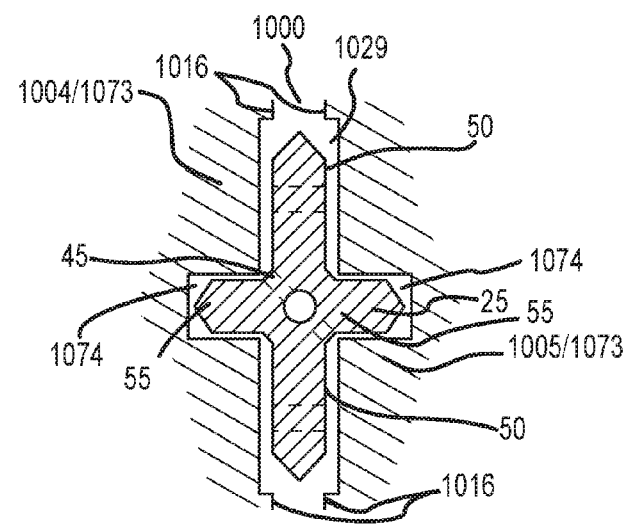
FIG. 102D is a transverse cross section of the implant and joint plane taken along section line 102D-102D of FIG. 102C.

Now referring to FIGS. 101A and 101B, a first drill jig 1067 can be advanced over the probe body 1054 (or guide pins 1013) and received within the cannula 1057. The probe body 1054 (or guide pins 1013) extending outwardly from the sacroiliac joint 1000 passes through a drill guide hole 1068 of the first drill jig 1067 (or a plurality of guide pins 1013 can extend through a corresponding plurality of guide pin holes 1069). The drill guide hole 1068 can take the form of a circular hole as shown in the Figures, a slot, or other configuration to restrict the movement of the drill bit 1062 (see FIG. 99E) within the drill jig 1060 and provide a guide for a drill bit 1062 in relation to the sacroiliac joint 1000. Guide pin holes 1069 can receive guide pins which can be positioned between the articular surfaces 1016 of the sacroiliac joint 1000 to demarcate the zone of desired treatment or safe working zones while using, for example, lateral fluoroscopy. As a non-limiting example, a first guide pin 1013 can be advanced through a first guide pin hole 1069, or alternatively a guide pin 1013 is first inserted into the sacroiliac joint 1000 and subsequently a guide jig 1067 is advanced over the guide pin 1013, the first guide pin 1013 can enter near inferior end 2022 of the posterior inferior access region 2016 of the sacroiliac joint articular region 1044 via the sacroiliac joint line 2019 to border a portion of the greater sciatic notch 2008 thereby allowing a medical person, computer guided surgical system, or other observer to more easily highlight under x-ray a border which should not be crossed during the procedure due to the presence of nerve and other structures. Similarly, a second guide pin 1013 can be placed in another guide pin hole 1069 to demarcate a second limit to a desired zone of treatment, or safe working zone. For example, a second guide pin 1013 can enter near the superior end 2018 of the posterior inferior access region 2016 of the sacroiliac joint articular region 1044 via the sacroiliac joint line 2019 to be positioned to border an area of the sacroiliac joint 1000 such as a transition zone between the extraarticular 3007 (see FIG. 106B) and the interarticular region 1044 which, for example, has been highlighted by contrast material as above described.

Now referring to FIG. 99E, a cannulated drill bit 1070 can be advanced over the probe body 1054 and within a drill guide hole 1068 (see FIGS. 101A and 101B) of the first drill jig 1067. The cannulated drill bit 1070 under fluoroscopic guidance can be advanced into the interarticular region 1044 between the articulating surfaces 1016 of the sacroiliac joint 1000 to produce a first bore 1071 (shown in broken line) to a determined depth. As to certain embodiments of the method, an amount of articular cartilage or other tissues from between the articular surfaces 1016 of the sacroiliac joint 1000 can be removed sufficient to allow embodiments of the sacroiliac joint implant 25 to be implanted in replacement of the removed articular cartilage or tissue. Because the method removes the degenerative articular cartilage or tissue between the articular surfaces 1016 of the sacroiliac joint 1000, the articular surfaces 1016 of the sacroiliac joint 1000 can remain intact or substantially intact allowing the sacroiliac joint implant 25 to be non-transversely located between the articular surfaces 1016 of the sacroiliac joint 1000. Understandably, other instruments can be utilized separately or in combination with a cannulated drill bit 1062 for the removal of articular cartilage or tissue between articular surfaces 1016 such as: box chisels, side cutting router bits, burs, flexible burs and bits, hole saws, curettes, lasers (such as $CO_2$, Neodymium/YAG (yttrium-aluminumgarnet), argon, and ruby), electrosurgical equipment employing electromagnetic energy (the cutting electrode can be a fine micro-needle, a lancet, a knife, a wire or band loop, a snare, an energized scalpel, or the like) where the energy transmitted can be either monopolar or bipolar and operate with high frequency currents, for example, in the range of about 300 kHz and about 1000 kHz whether as pure sinusoidal current waveform where the "crest factor" can be constant at about 1.4 for every sinus waveform, and a voltage peak of approximately 300 V to enable a "pure" cutting effect with the smallest possible coagulation effect or as amplitude modulated current waveforms where the crest factor varies between 1.5 and 8, with decreasing crest factors providing less of a coagulation effect. Electrosurgical waveforms may be set to promote two types of tissue effects, namely coagulation (temperature rises within cells, which then dehydrate and shrink) or cut (heating of cellular water occurs so rapidly that cells burst). The proportion of cells coagulated to those cut can be varied, resulting in a "blended" or "mixed" effect. Additionally, a fully rectified current, or a partially rectified current, or a fulguration current where a greater amount or lateral heat is produced can be employed to find the articular surfaces of the joint and aid in advancing a probe or guide wire into a position in between the articulating surfaces. These currents can effectively degrade the cartilage and allow advance into the joint without grossly penetrating much beyond the cartilage.

Now referring to FIG. 99F, as to certain embodiments of the invention, the first drill jig 1067 can be removed from within the cannula 1057 and a second drill jig 1072 can be advanced over the probe body 1054 and received within the cannula 1057; however, the invention is not limited to any particular number of drill jigs and as to certain embodiments of the method the first drill jig 1067 can include all the required drill guide hole(s) 1068 (or slots or other configurations of the drill guide) and as to other embodiments of the method a plurality of drill jigs can be utilized in serial order to provide all the drill guide holes 1068. As to the particular embodiment of the invention shown by the Figures, the first drill jig 1067 can provide one or more additional drill guide holes 1068 which guide in relation to the first bore 1071 a second or more cannulated drills 1062 of the same or different configuration to be inserted within and advanced into the sacroiliac joint 1000 to produce a second bore 1073 (generally shown in broken line as 1071/1073) or a plurality of bores within the sacroiliac joint 1000 spaced apart in predetermined pattern to allow removal of sufficient articular cartilage 1016 or other tissue from the interarticular space of sacroiliac joint 1000 for placement of embodiments of the sacroiliac joint implant 25 within the region defined by and between the paired articular surfaces 1016 of the sacroiliac joint 1000. As to certain methods of the invention, the first drill jig 1067 or the second drill jig 1072 or a plurality of drill jigs can be utilized in serial order to remove a portion of the sacroiliac joint 1000 for generation of an implant receiving space 1029 (see, for example, FIG. 99H). As these embodiments of the method, articular cartilage or other tissues and sufficient subchondral bone can be removed from between the articular surfaces 1016 of the sacroiliac joint 1000 sufficient to allow placement of certain embodiments of the sacroiliac joint implant 25 and one or more radial member receiving channels 1074 can be cut into at least one of the articular surfaces 1016 of said sacroiliac joint 1000 sufficient to receive other embodiments of the sacroiliac implant 25. The one or more radial member receiving channels 1074 can be cut a depth into the subchondral, cortical bone or cancellous bone of the sacrum 1004 or ilium 1005.

Figure 99G:
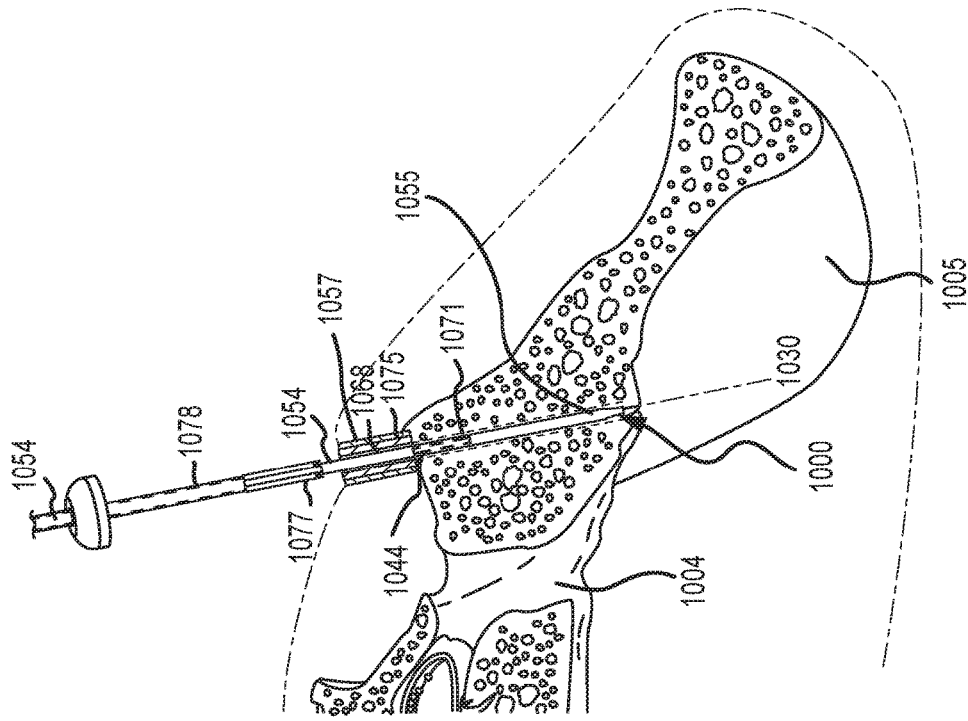

Now referring primarily to FIG. 99G, in a subsequent step, the last in the serial presentation of drill jigs 1067, 1072 can be removed from within the cannula 1057 and a broach jig 1075 can be advanced over the probe body 1054 to locate within the cannula 1057. The broach jig 1075 can include a broach guide hole 1076 which receives a first broach end 1077 of a cannulated broach 1078 advanced over the probe body 1054. The first broach end 1077 can have a configuration which can be advanced into the sacroiliac joint 1000. As to certain embodiments of the method, the first broach end 1077 can be adapted to remove an amount of articular cartilage and other tissue from between the articular surfaces 1016 within the articular region 1044 of the sacroiliac joint 1000 for non-transverse placement of a sacroiliac joint implant 25 having an elongate body 45, or having an elongate body 45 and a first radial member 50, or an elongate body 45 having a first and second radial members 50 between the articular surfaces 1016 of the sacroiliac joint 1000. As to other embodiments of the method, the cannulated broach 1078 can remove a sufficient portion of the sacroiliac joint 1000 to generate an implant receiving space 1029 to receive embodiments of the sacroiliac joint implant 25 having an elongate body 45, an elongate body 45 and at least one radial member 50 adapted for non-transverse placement between the articular surfaces 1016 or at least one radial member 55 adapted to extend into the bone of the sacrum 1004 or the ilium 1005.

As a non-limiting example, FIG. 99G shows a broach 1078 configured to remove a portion of the sacroiliac joint 1000 to produce a implant receiving space 1029 (shown in FIG. 99H) to receive embodiments of the sacroiliac joint implant 25 having an elongate body 45 to which a first radial member 50 and a second radial member 50 extend along the longitudinal axis CA of the elongate body 45 in substantially opposed relation adapted to locate between the articular surfaces 1016 of the sacroiliac joint 1000 and further having a third radial member 55 and a fourth radial member 55 which extend along the longitudinal axis CA of the elongate body 45 in substantially opposed relation adapted to correspondingly extend correspondingly into the bone of the sacrum 1004 and the ilium 1005.

Now referring primarily to FIGS. 102A-102D, the implant receiving space 1029 and the sacroiliac joint implant 25 can be configured having related dimension relations such that placement of the sacroiliac joint implant 25 within the implant receiving space 1029 disposes the sacrum 1004 and the ilium 1005 in substantially immobilized relation and substantially avoids alteration of the positional relation of the sacrum 1004 and the ilium 1005 from the normal condition, or avoids driving together or driving apart the sacrum 1004 from the ilium 1005 outside of or substantially outside of the normal positional relation. An intention in selecting configurations of the sacroiliac joint implant 25 and the implant receiving space 1029 being immobilization of the sacrum 1004 in relation to the ilium 1005 while maintaining the sacroiliac joint 1000 in substantially normal or substantially normal positional relation, or returning the sacroiliac joint 1000 to a substantially normal positional relation to correct a degenerative condition of the sacroiliac joint 1000.

As a non-limiting example, configurations of an implant receiving space 1029 allow embodiments of the sacroiliac joint implant 25 to be placed non-transversely between the caudal portion 1086 of the articular surfaces 1016 of the sacroiliac joint 1000. While certain embodiments of the sacroiliac joint implant 25 may only provide an elongate body 45 which locates within a correspondingly configured implant receiving space 1029 to engage at least a portion of the bone of the ilium 1005 or sacrum 1004, the invention is not so limited, and can further include at least a first radial member or a first and a second radial member at least a portion of the external surface of the first radial member 50 engaging a portion of the bone 1073 of the sacrum 1004 and the ilium 1005. As to those embodiments of the sacroiliac joint implant 25 which have a third radial member 55 and a fourth radial member 55, the implant receiving space 1029 can further include one or more radial member receiving channels 1074, which correspondingly allow the third and fourth radial members 55, 55 to extend into the bone 1073 of the sacrum 1004 or the ilium 1005 (whether subchondral, cortical, cancellous, or the like), or impact of the sacroiliac joint implant 25 into the implant receiving space 1029 without the radial member receiving channels 1074 can forcibly urge the radial members 55, 55 into the bone 1073 of the sacrum 1004 and the ilium 1005. An anchor member 30 (such as treaded members) can be inserted through the bore 40 in the implant 25 and into the sacrum 1004 and ilium 1005 to fix the location of the fixation fusion implant 25 within the implant receiving space 1029.

While the preceding discussion is given in the context of the implant 25 being implanted non-transversely in the caudal portion 1086 of the sacroiliac joint 1000, in other embodiments, the implant 25 may be implanted in other locations within the sacroiliac joint. For example, as disclosed in U.S. patent application Ser. No. 12/998,712, which is incorporated herein by reference, in some embodiments, the implant 25 may be implanted non-transversely in the cranial portion 1087 (see FIG. 102A) of the sacroiliac joint 1000 by the similar procedures or steps as above described with the incision and generation of the passage to the superior articular portion of the sacroiliac joint 1000. The implant may also be implanted in the sacroiliac joint in such a manner so as to extend between the cranial and caudal portions, as also disclosed in U.S. patent application Ser. No. 12/998,712.

Figure 103A:
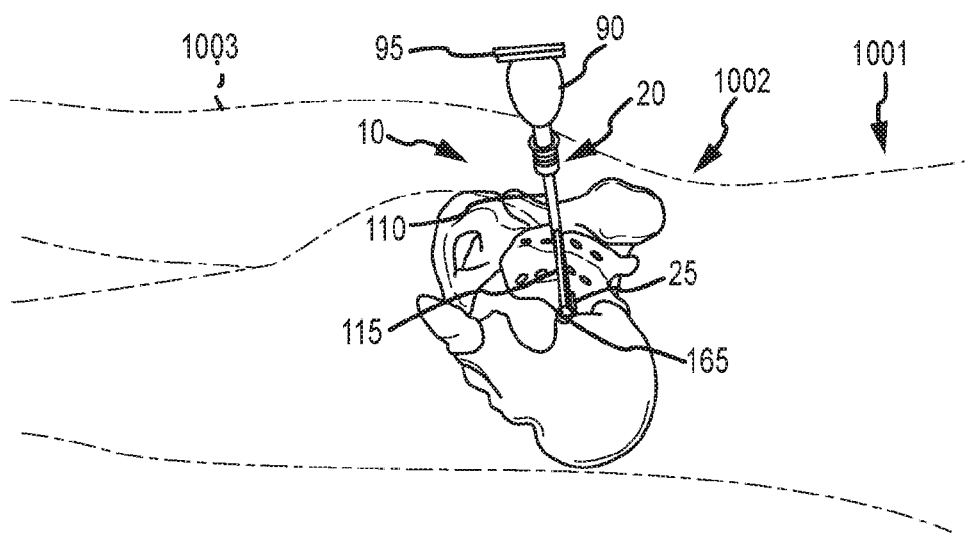
FIG. 103A is generally the same view as FIG. 97A, except illustrating the delivery tool being used to deliver the implant to the sacroiliac joint space.
Figure 103B:
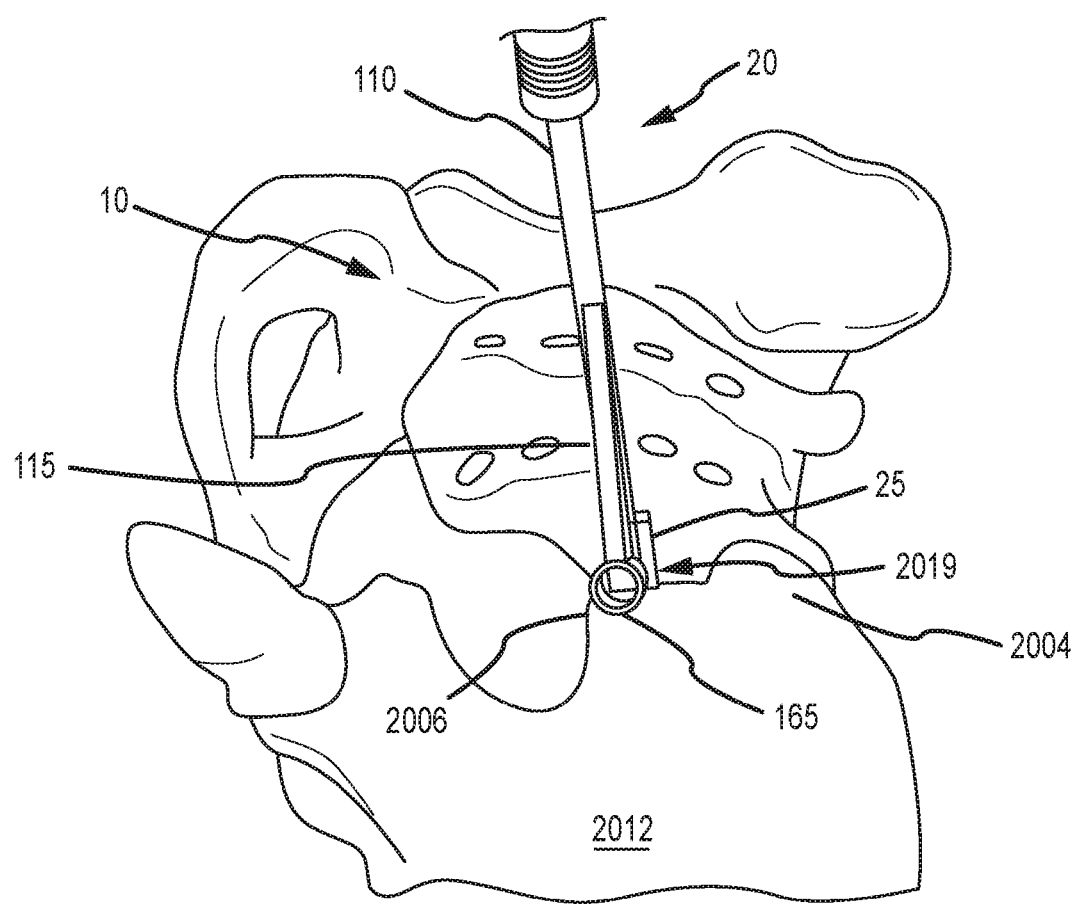
FIG. 103B is an enlarged view of the hip region of FIG. 103A.
Figure 104:
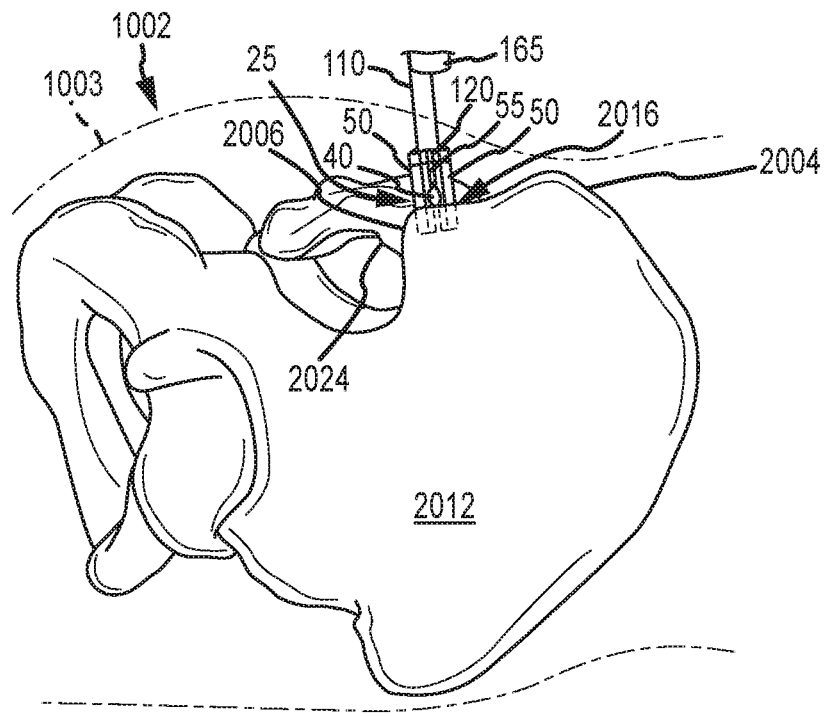
FIG. 104 is generally the same enlarged view as FIG. 96B, except illustrating the delivery tool being used to deliver the implant to the sacroiliac joint space.

To begin a discussion of employing the delivery tool 20 to implant the implant 25 in the sacroiliac joint 1000 once the implant receiving space 1029 has been created, reference is made to FIGS. 99I, 103A, 103B and 104. FIG. 103A is generally the same view as FIG. 97A, and FIG. 103B is an enlarged view of the hip region of FIG. 103A. FIG. 104 is generally the same enlarged view as FIG. 96B. As shown in FIGS. FIGS. 99I, 103A, 103B and 104, once the implant receiving space 1029 has been created as discussed above with respect to FIGS. 99A-99H, the implant 25 can be supported off of the distal end 120 of the implant arm 110 of the delivery tool 20 and positioned such that the distal end 42 of the implant 25 begins to enter the sacroiliac joint articular region 1044 via the posterior inferior access region 2016, which is described in detail above with respect to FIGS. 96A-98B. As can be understood from FIGS. 103A-104, in entering the sacroiliac joint space, the implant 25 is oriented such that its wide planar members 50 are oriented generally parallel to, and aligned with, the sacroiliac joint line 2019 (i.e., the wide planar members 50 are generally located within the joint plane 1030), and the implant's narrow planar members 55 are generally transverse to the joint plane 1030 (see, e.g., FIGS. 102C and 102D). The longitudinal axis $LCA_2$ of the implant arm 110 of the delivery tool 20 has a generally anterior trajectory that is located within the joint plane 1030. Alternatively, according to particular embodiments, as a non-limiting example, the longitudinal axis $LCA_2$ of the implant arm 110 of the delivery tool 20 can have a trajectory which can be defined as being generally lateral or, in particular embodiments, generally posterior. In some embodiments, when the implant 25 is being delivered into the joint space, the implant arm 110 can be said to be at least one of generally superior or cephald the sciatic notch.

Figure 105:
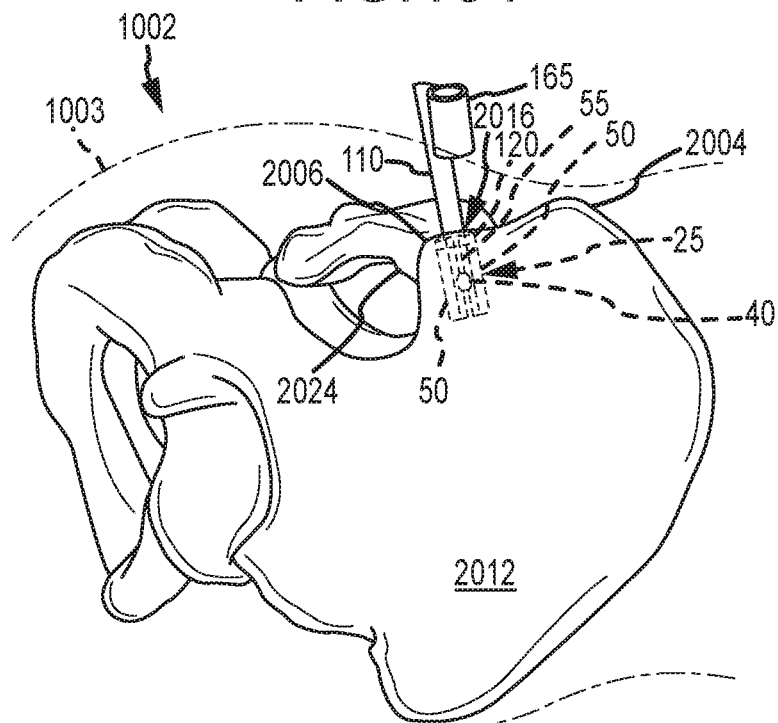
FIG. 105 is the same view as FIG. 104, except the implant has now been fully inserted into the prepared space in the sacroiliac joint.

FIG. 105 is the same view as FIG. 104, except the implant 25 has now been fully inserted into the prepared space 1029 in the sacroiliac joint 1000. As illustrated in FIGS. 99J and 105, the implant 25 is fully received in the prepared sacroiliac space 1029 such that the wide planar members 50 are oriented generally parallel to, and aligned with, the sacroiliac joint line 2019 (i.e., the wide planar members 50 are generally located within the joint plane 1030), and the implant's narrow planar members 55 are generally transverse to the joint plane 1030 and, in some embodiments, have even entered the bone material forming the sacrum and ilium articular surfaces of the sacroiliac joint (see, e.g., FIGS. 102C and 102D). As can be understood from FIG. 99J, the longitudinal axis of the implant 25 and the longitudinal axis of the implant arm 110 may be coaxially aligned with each other and generally located in the sacroiliac joint plane 1030.

Figure 99L:
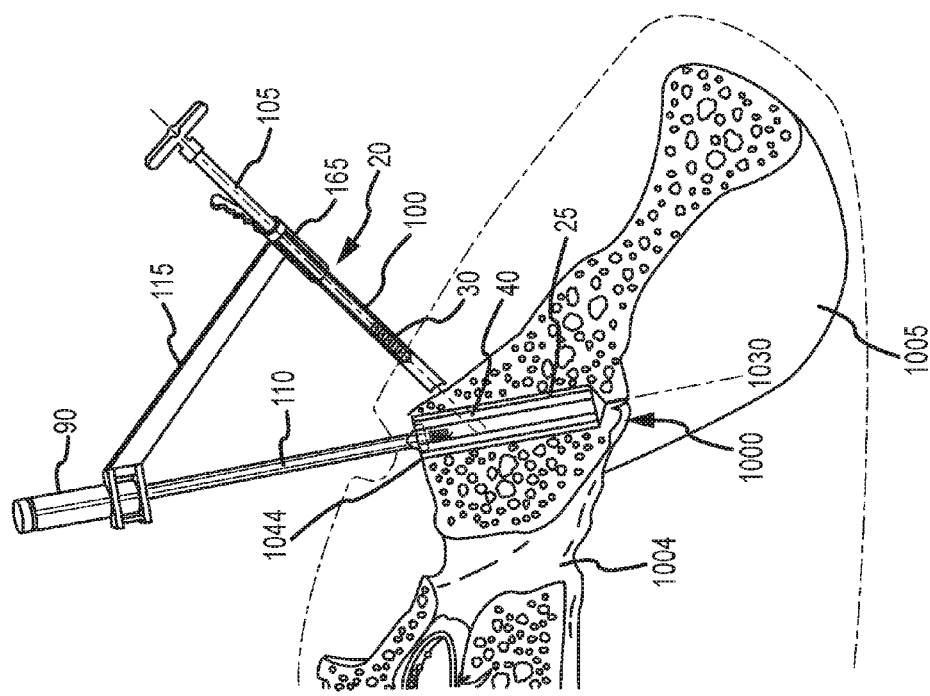
Figure 99K:
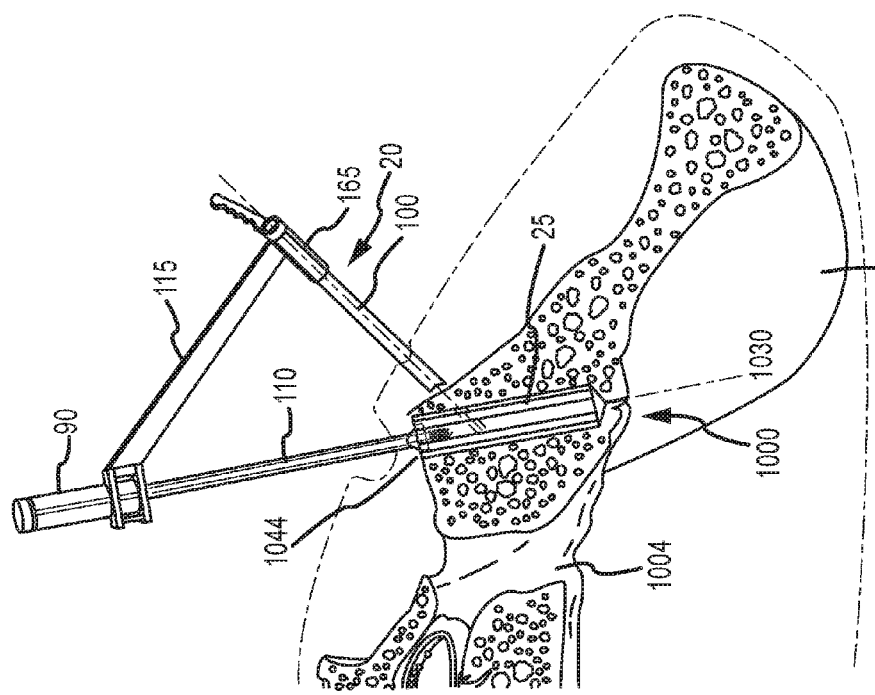
Figure 106A:
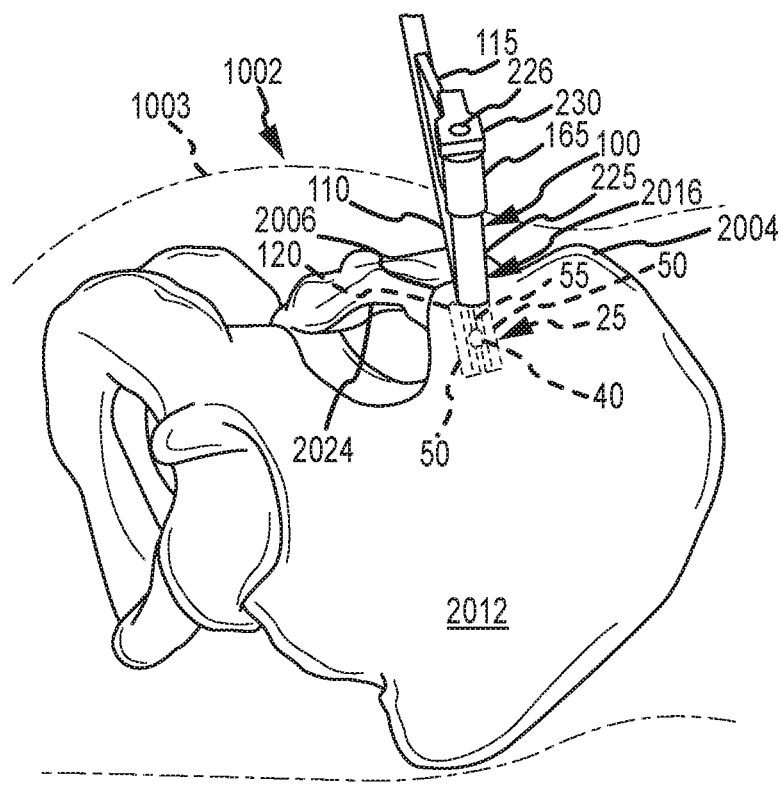
FIG. 106A is the same view as FIG. 104, except the sleeve is now received in the collar of the anchor arm.

FIG. 106A is the same view as FIG. 104, except the sleeve 100 is now received in the collar 165 of the anchor arm 115. As can be understood from FIGS. 99K and 106A, the distal end of the sleeve 100 may extend through an incision in the patient's soft tissue such that the distal end of the sleeve 100 is positioned generally against the lateral surface of the ilium 1005. The longitudinal axis of the sleeve and collar of the anchor arm can be understood to be generally coaxially aligned with the longitudinal axis of the bore 40 of the implant 25.

Figure 106B:
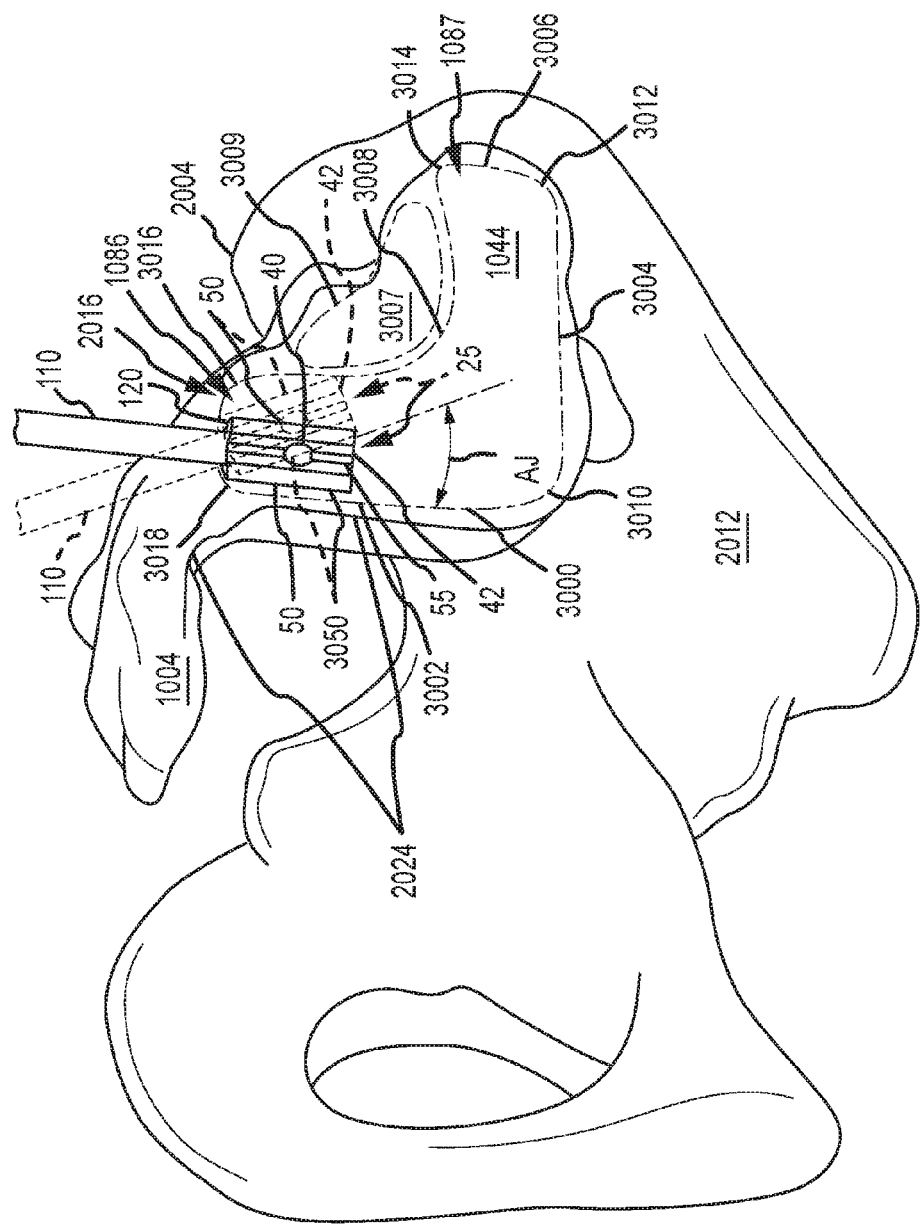
FIG. 106B is generally the same view as FIG. 106A, except the ilium is removed to show the sacroiliac joint space boundary defined along the sacrum and the implant positioned for implantation within the joint space.

FIG. 106B is generally the same view as FIG. 106A, except the ilium 1005 is removed to show the sacroiliac joint space boundary 3000 defined along the sacrum 1004 and outlining the sacroiliac joint articular region 1044, the implant 25 positioned for implantation within the sacroiliac joint articular region 1044. As shown in FIG. 106B, the sacroiliac joint space boundary includes an inferior boundary segment 3002, an anterior boundary segment 3004, a superior boundary segment 3006, and a posterior boundary segment 3008. The inferior boundary segment 3002 is immediately adjacent, and extends along, the sciatic notch 2024.

The inferior boundary segment 3002 and anterior boundary segment 3004 intersect to form an anterior-inferior corner 3010. The anterior boundary segment 3004 and superior boundary segment 3006 intersect to form an anterior-superior corner 3012. The superior boundary segment 3006 and posterior boundary segment 3008 intersect to form a superior-posterior corner 3014. The posterior boundary segment 3008 and posterior inferior access region 2016 intersect to form a superior-posterior corner 3016 of the posterior inferior access region 2016. The inferior boundary segment 3002 and posterior inferior access region 2016 intersect to form an inferior-posterior corner 3018 of the posterior inferior access region 2016.

The inferior boundary segment 3002 extends between corners 3010 and 3018. The anterior boundary segment 3004 extends between corners 3010 and 3012. The superior boundary segment 3006 extends between corners 3012 and 3014 and provides an access into the cranial portion 1087 of the sacroiliac joint. The posterior boundary segment 3008 extends between corners 3014 and 3016. The posterior inferior access region 2016 extends between corners 3016 and 3018 and provides an access into the caudal region 1086 of the sacroiliac joint. The posterior boundary segment 3008 separates articular region 1044 and extra-articular region 3007, which includes the sacral fossa on the sacrum 1004 and the corresponding iliac tuberosity on the ilium 1005 and defined by the extra-articular region boundary 3009.

As shown in FIG. 106B, the implant 25 is inserted via the implant arm 110 of the delivery tool 20 into the caudal region 1086 of the sacroiliac joint articular region 1044. As shown via the implant 25 and implant arm 110 shown in solid lines, in one embodiment, the implant 25 enters the posterior inferior access region 2016, and is further advanced into the caudal region 1086 of the sacroiliac joint articular region 1044, in an orientation such that the implant arm 110 and wide planar members 50 are in the joint plane 1030 (see, for example, FIGS. 99I-99J) and the longitudinally extending edge 3050 of the wide planar member 50 next to the inferior boundary segment 3002 is generally parallel to, and immediately adjacent to, the inferior boundary segment 3002. Thus, the distal end 42 of the implant is heading generally perpendicular to, and towards, the anterior boundary segment 3004.

As shown in FIG. 106B via the implant 25 and implant arm 110 shown in dashed lines, in one embodiment, the implant 25 enters the posterior inferior access region 2016, and is further advanced into the caudal region 1086 of the sacroiliac joint articular region 1044, in an orientation such that the implant arm 110 and wide planar members 50 are in the joint plane 1030 (see, for example, FIGS. 99I-99J) and the longitudinally extending edge 3050 of the wide planar member 50 next to the inferior boundary segment 3002 is somewhere between being generally parallel to the inferior boundary segment 3002 (as illustrated by the solid-lined implant 25 in FIG. 106B) or forming an angle AJ with the inferior boundary segment 3002 of up to approximately 50 degrees. Thus, the distal end 42 of the implant shown in dashed lines can be said to head anywhere from generally perpendicular to, and towards, the anterior boundary segment 3004 to heading generally towards the superior-anterior corner 3012, or points in between.

In one embodiment, the implant 25 may be first directed into the joint space as illustrated by the solid-lined implant 25 in FIG. 106B after which the implant 25 is rotated within the joint space to be positioned somewhere between, and including, angled position depicted by the dashed-lined implant 25. In other embodiments, the implant 25 may be first directed into the joint space as illustrated by the dashed-lined implant 25 in FIG. 106B after which the implant 25 is rotated within the joint space to be positioned somewhere between, and including, the parallel position depicted by the solid-lined implant 25.

Figure 99M:
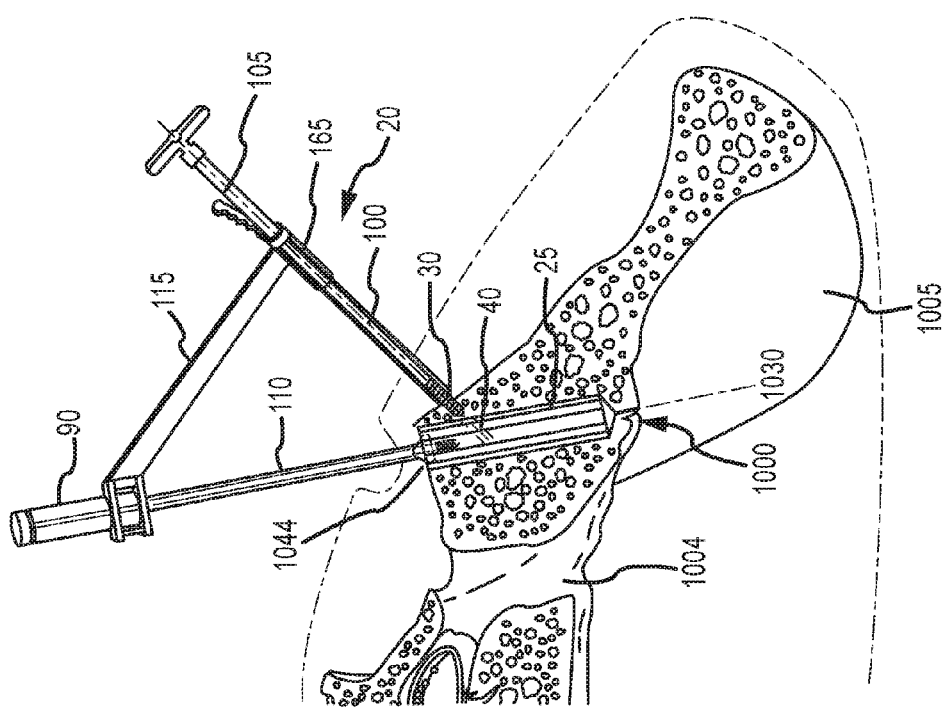
Figure 99N:
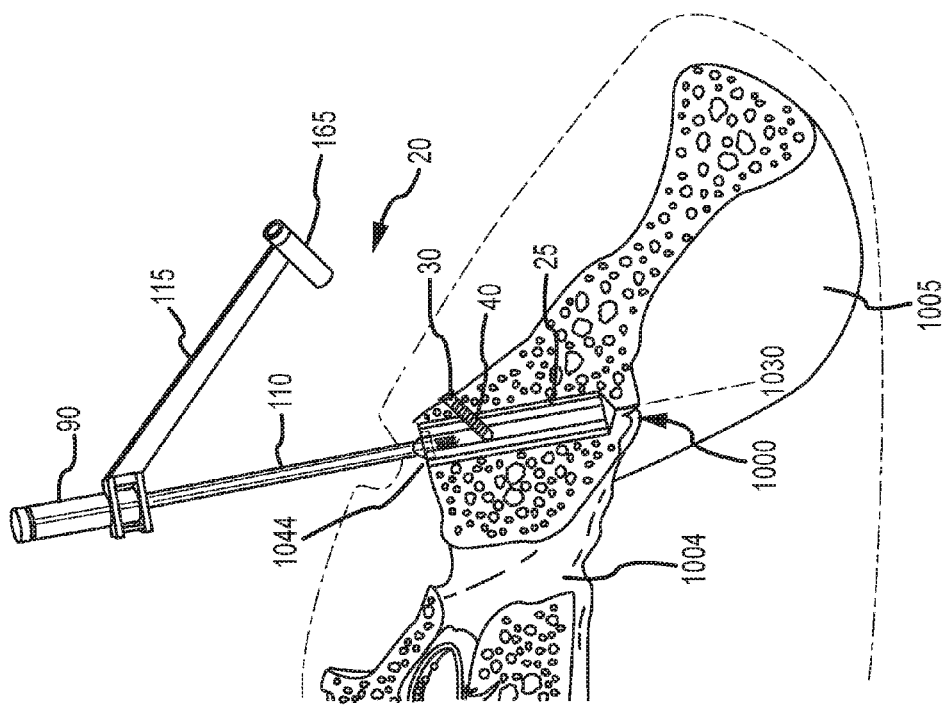
Figure 107A:
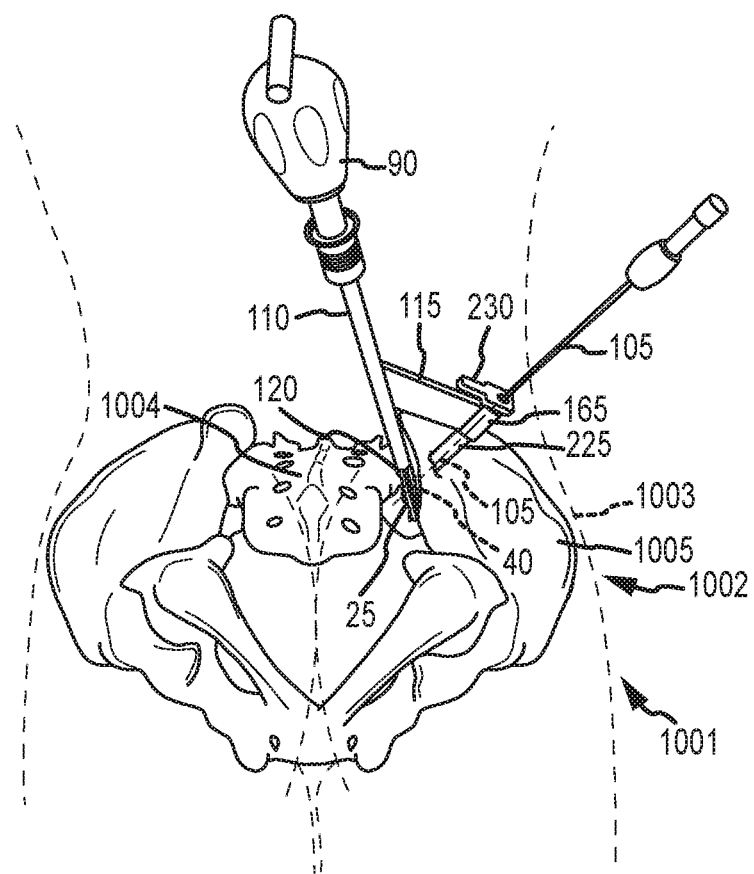
FIG. 107A is a posterior-inferior view of the hip region of the patient, wherein the soft tissue surrounding the skeletal hip bones is shown in dashed lines.
Figure 107B:
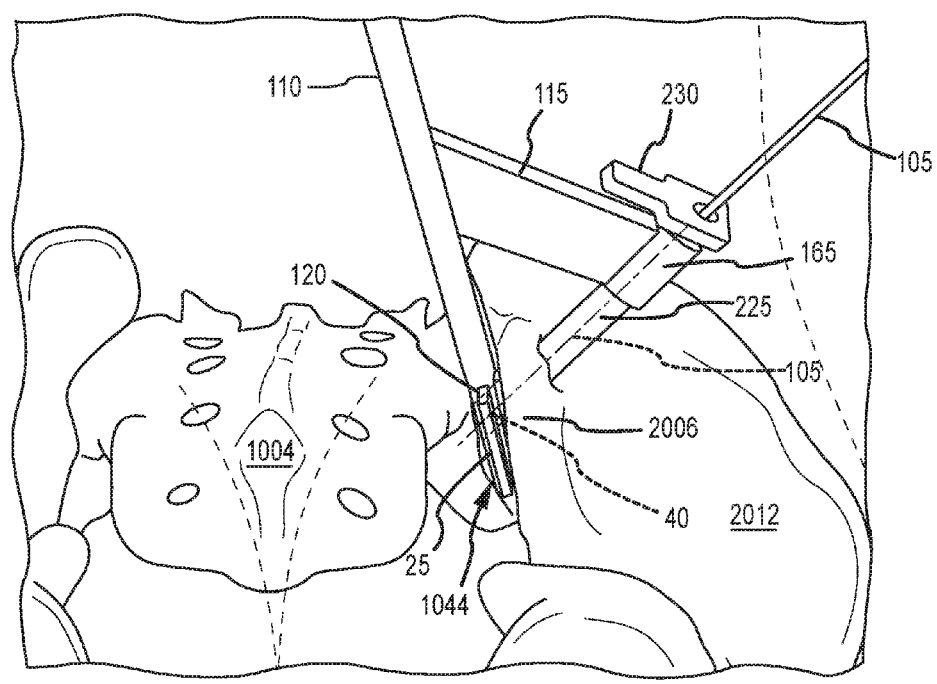
FIG. 107B is an enlarged view of the implant region of FIG. 107A.

FIG. 107A is a posterior-inferior view of the hip region 1002 of the patient 1001, wherein the soft tissue 1003 surrounding the skeletal hip bones is shown in dashed lines. FIG. 107B is an enlarged view of the implant region of FIG. 107A. As can be understood from FIGS. 99L, 107A and 107B, the anchor member 30 is positioned in the lumen of the sleeve 100. A driving tool 105 (e.g., screw driver) is extended through the lumen of the sleeve 100 so the distal end of the tool 105 is engaged with a proximal end of the anchor member 30 (e.g., screw). As shown in FIG. 99M, the tool 105 is used to drive the anchor member 30 distally through the bone of the ilium 1005 and into the bore 40 of the implant 25 generally transverse to the joint line plane 1030. As a result, as indicated in FIG. 99N, the implant assembly formed of the implant 25 and anchor member 30 is secured at the implantation site such that the implant 25 is located in the prepared space 1029 of the sacroiliac joint space, and the anchor member 30 extends through the bone of the ilium 1005 and into the implant bore 40 generally transverse to the joint space plane 1030. The tool 105 and sleeve 100 can be removed from the anchor arm collar 165, and the incision associated with the sleeve 100 can be closed. Additionally, tool 105 can be a cutting tool 105 (e.g., drill bit, hole punch, or etc) which can used in similar steps as above describe to remove bone or other tissues in the path where anchor member 30 is to be placed.

Figure 99Q:
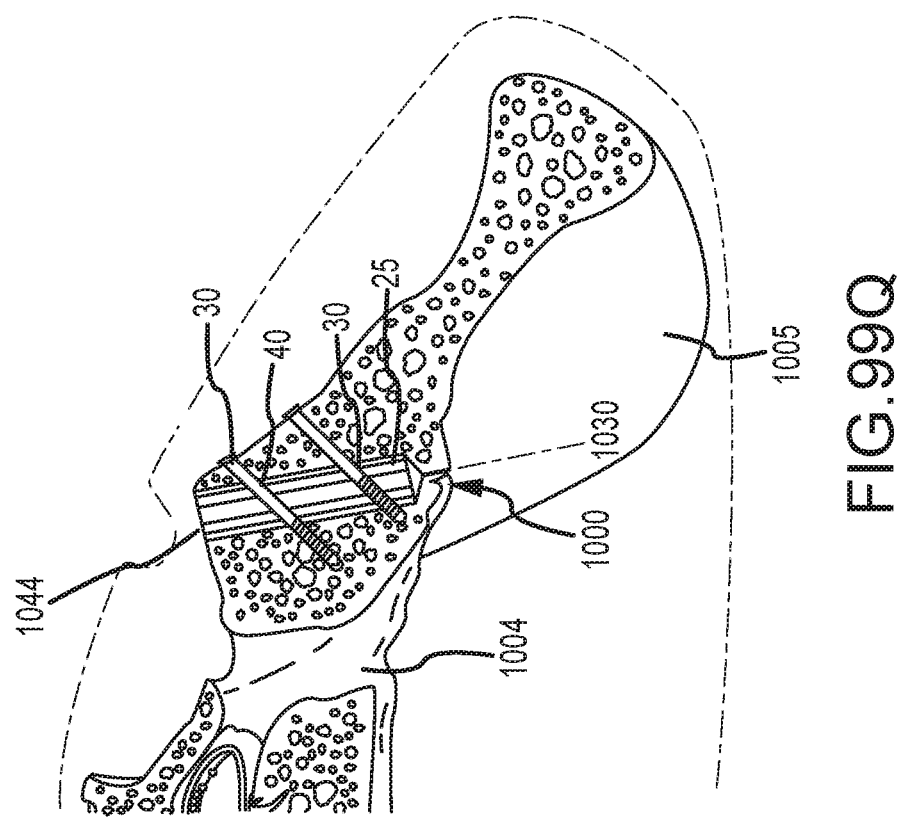

As indicated in FIG. 99O, the distal end of the implant arm is decoupled from the proximal end of the implant 25 and removed. The incision associated with the implant arm can be closed. In some embodiments, the anchor member 30 will only be long enough to span bone of the ilium 1005 and enter the implant bore 40. In other embodiments, as illustrated in FIG. 99P, the anchor member 30 will be sufficiently long to extend through the bone of the ilium, completely through the implant bore 40, and into the bone of the sacrum 1004. As illustrated in FIG. 99Q, in certain embodiments, implant 25 can be configured to have more than one implant bore 40 which can also receive an anchor member 30. The anchor member 30 prevents migration of the implant 25 within the joint space. The anchor member 30 also can draw the ilium and sacrum together about the implant 25, increasing the sturdiness of the fixation of the implant in the joint space. Where the anchor member extends through the implant bore and into the bone of both the sacrum and ilium, the anchor member 30 can be used to drawn the articular surfaces 1016 of the sacroiliac joint 1000 against the external surfaces of the sacroiliac joint implant 25. With the implant implanted in the sacroiliac joint, the body will cause the joint surfaces to fuse together about the implant 25.

Figure 108A:
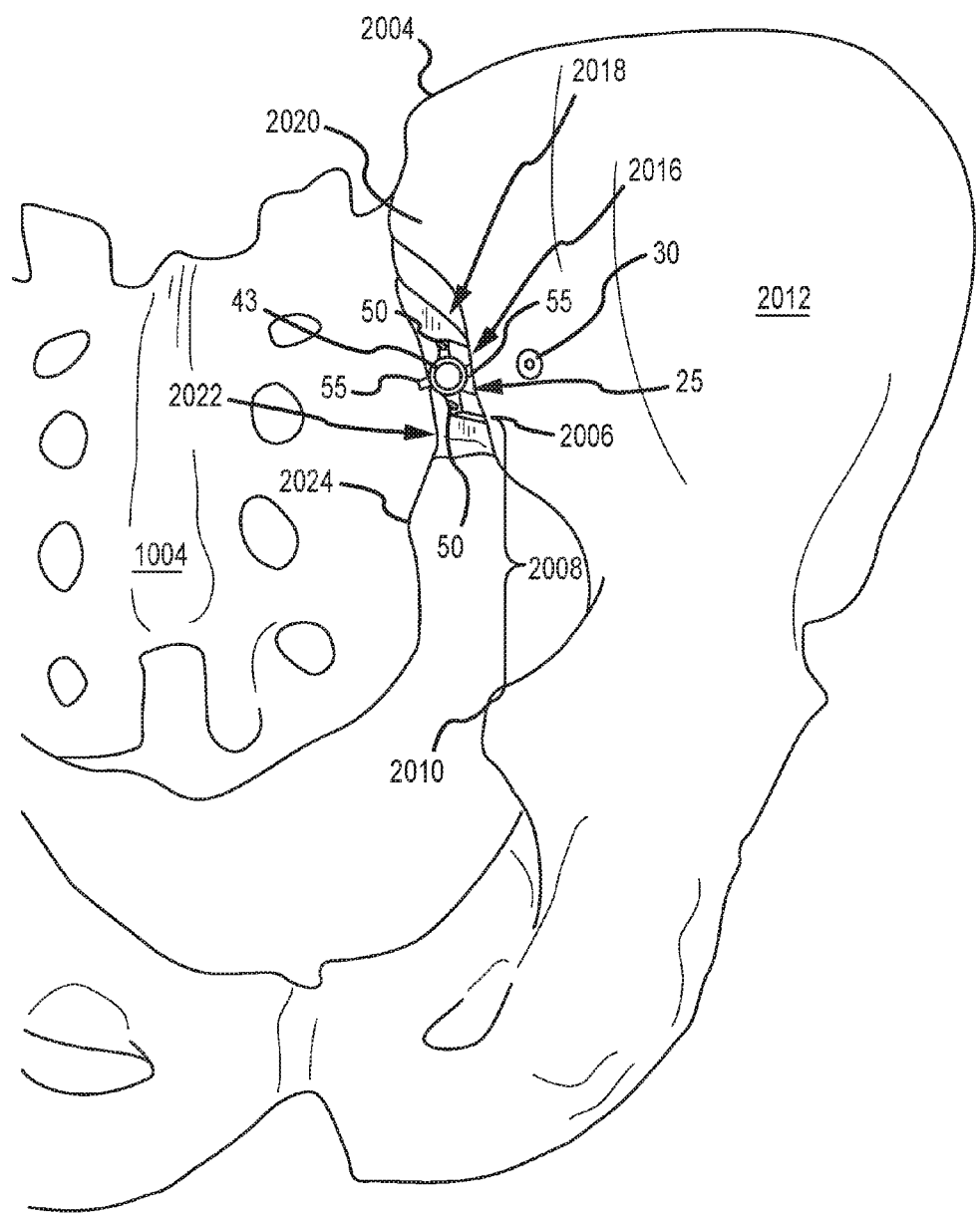
FIGS. 108A and 108B are, respectively, posterior and posterior-lateral views of the implantation area and the implant assembly implanted there.
Figure 108B:
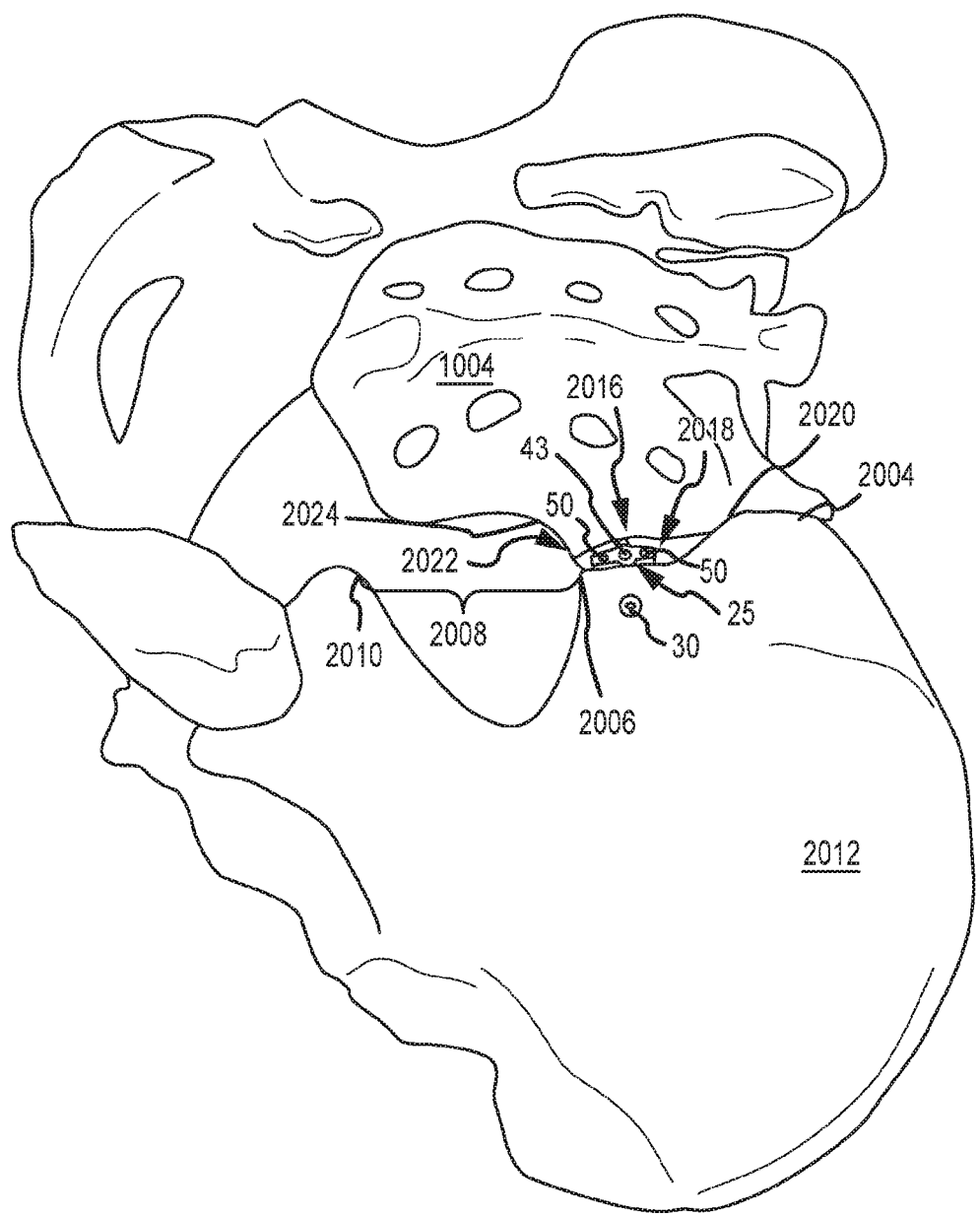

As can be understood from FIGS. 108A and 108B, which are, respectively, posterior and posterior-lateral views the implantation area and the implant assembly implanted there, proximal end 43 of the implant 25 can be seen positioned in the posterior inferior access region 2016, the implant being implanted in the caudal area of the sacroiliac joint space. The anchor member 30 can be understood to have been driven into the implant bore 40 transversely to the joint plane 1030 via a route in the ilium 1005 that avoids contact with vascular and neurological structures, thereby avoiding potentially life threatening injury to such structures. The ability to blindly, yet safely, drive the anchor member 30 into the implant bore 40 while the implant 25 is hidden in the joint space is made possible by the cooperating configurations of the implant 25 and the delivery tool 20. Specifically, the longitudinal axis $LCA_1$ of the anchor arm collar 165 being coaxially aligned with the longitudinal axis BA of the implant bore 40 when the proximal end 43 of the implant 25 is supported off of the implant arm 115 of the delivery tool 20 makes it possible to safely drive the anchor member 30 through the ilium 1005 bone and into the implant bore 40 when the implant is hidden in the joint space on account of being delivered to the joint space via the delivery tool 20.

Figure 111A:
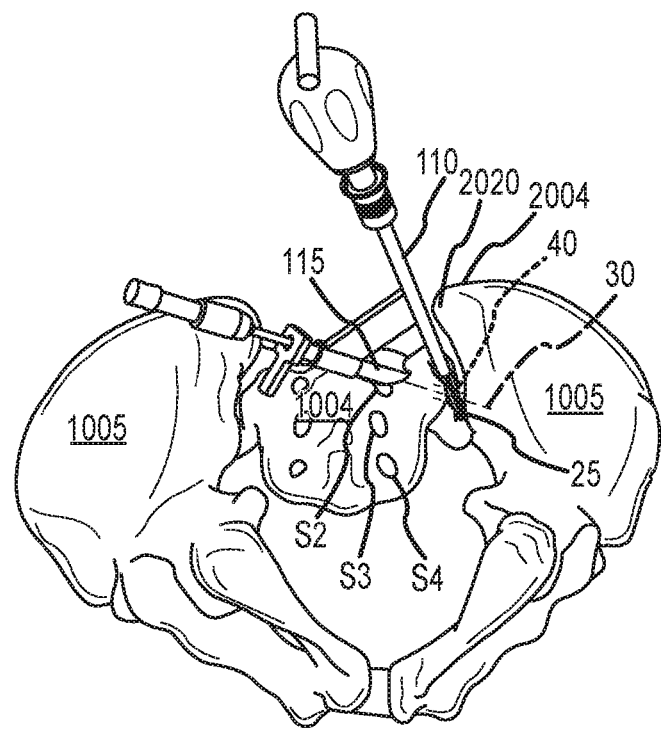
FIG. 111A is an inferior-posterior view of the patient's hip skeletal structure similar to the view depicted in FIG. 107A.
Figure 111B:
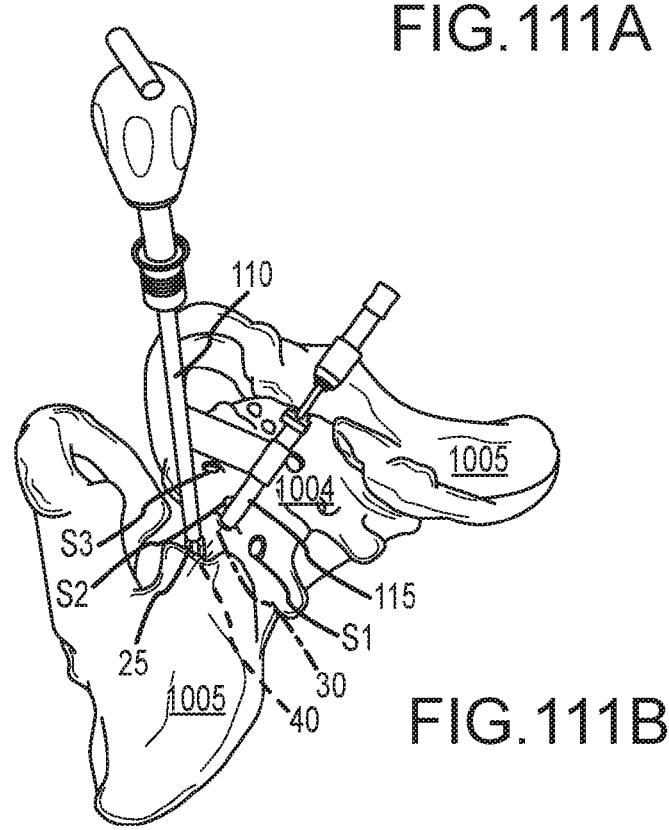
FIG. 111B is a lateral-superior-posterior view of the patient's hip skeletal structure.
Figure 111C:
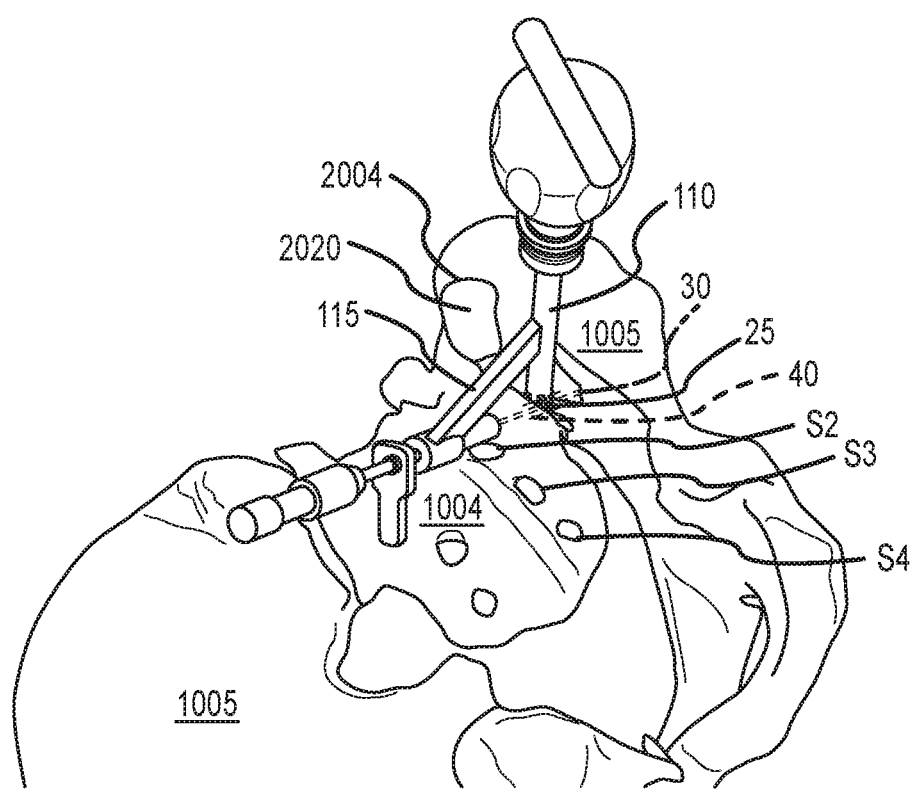
FIG. 111C is an inferior-posterior view of the patient's hip skeletal structure taken from a perspective laterally opposite the view depicted in FIG. 111B.

To begin a detailed discussion of another method of employing the system 10 to fuse the sacroiliac joint, reference is made to FIGS. 111A-111C. FIG. 111A is an inferior-posterior view of the patient's hip skeletal structure similar to the view depicted in FIG. 107A. FIG. 111B is a lateral-superior-posterior view of the patient's hip skeletal structure. FIG. 111C is an inferior-posterior view of the patient's hip skeletal structure taken from a perspective laterally opposite the view depicted in FIG. 111B. The S1 through S4 foramina can be seen at the respective indicators S1, S2, S3 and S4 in FIGS. 111A-111C.

As can be understood from a comparison of FIGS. 111A to 107A, the delivery tool 20 has been reversed such that the anchor collar 165 is oriented so as to deliver the anchor member 30 through the sacrum 1004 first and then into the bore 40 of the implant 25 and optionally further into the ilium 1005. In other words, unlike the method depicted in FIG. 107A, wherein the anchor member 30 is driven lateral to medial through the ilium 1005 first and then into the implant followed by the sacrum 1004 (optional), the method depicted in FIG. 111A shows the anchor member 30 being driven medial to lateral through the sacrum 1004 first and then into the implant followed by the ilium 1005 (optional). As can be understood from a comparison of FIGS. 111A to 107A, the implant 25 of FIG. 111A is located in the sacroiliac joint with its wide radial members 50, narrow radial members 55 and body 45 oriented as explained above with respect to FIGS. 102A-107B, the only difference being the direction the bore 40 is oriented and the way the anchor member 30 penetrates the surrounding bone structures.

In the embodiment of FIG. 111A, the anchor member 30 may be an S2 alar iliac (S2AI) screw. Such a screw may penetrate the sacrum 1004 just lateral the lateral edge of the S2 foramen and, in some instances, generally superiorly-inferiorly even with the superior edge of the S2 foramen so as to mimic an S2 alar iliac pelvic fixation.

Figure 112A:
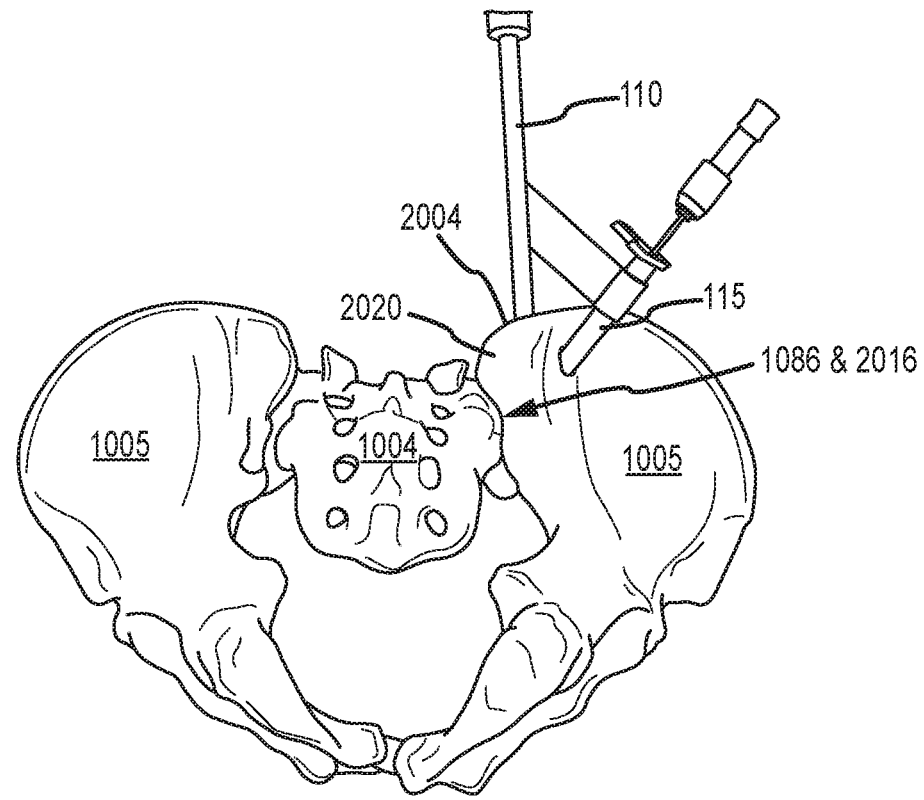
FIG. 112A is an inferior-posterior view of the patient's hip skeletal structure similar to the view depicted in FIG. 107A.
Figure 112B:
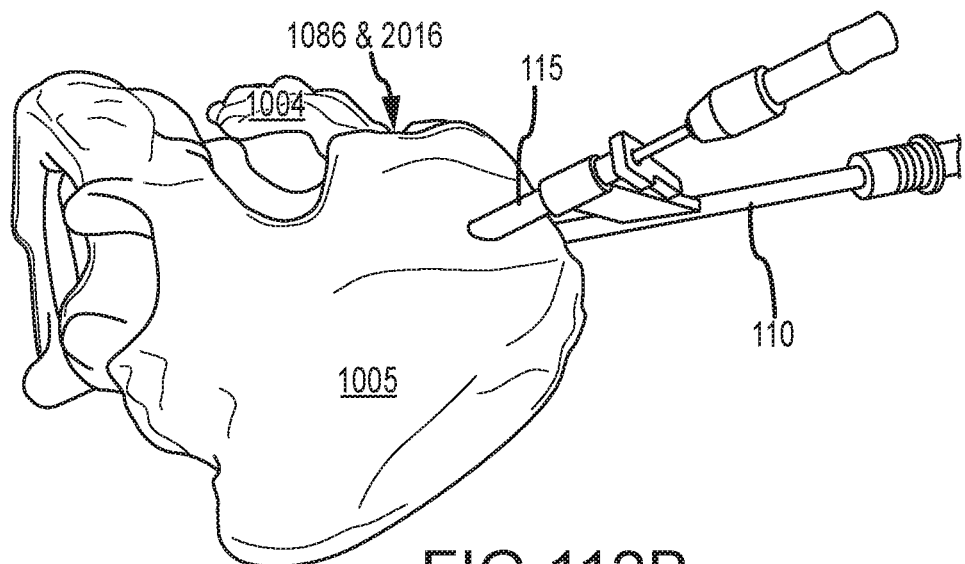
FIG. 112B is a side view of the patient's hip skeletal structure similar to the view depicted in FIG. 106A.
Figure 112C:
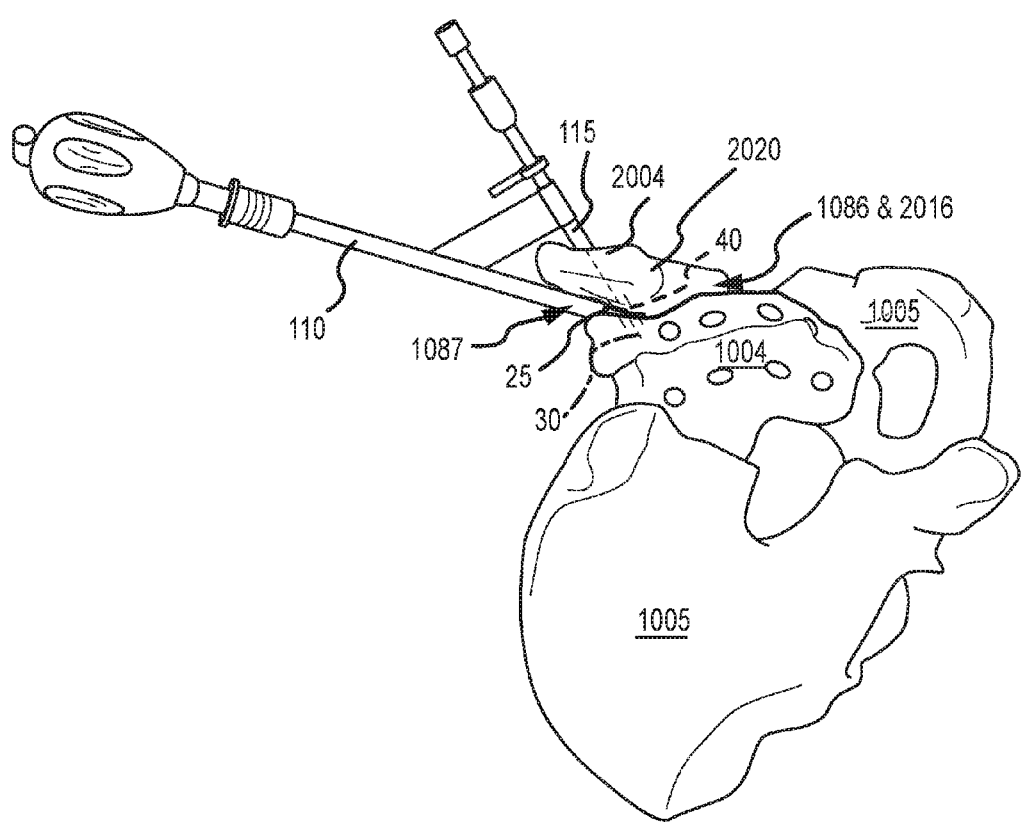
FIG. 112C is a view of the patient's hip skeletal structure similar to the view depicted in FIG. 103A, except from an opposite lateral perspective.
Figure 112D:
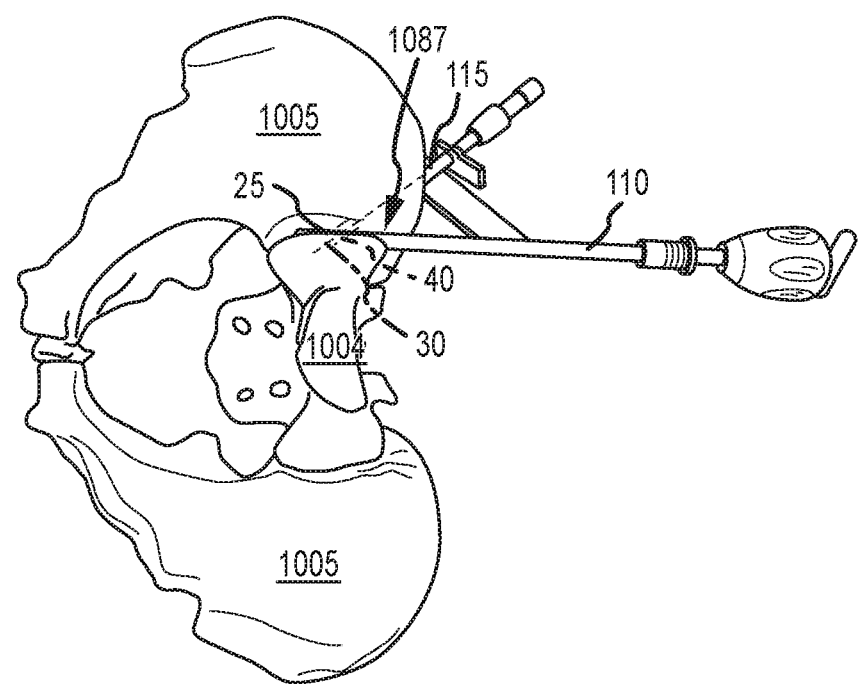
FIG. 112D is a superior view of the patient's hip skeletal structure.

To begin a detailed discussion of another method of employing the system 10 to fuse the sacroiliac joint, reference is made to FIGS. 112A-112D. FIG. 112A is an inferior-posterior view of the patient's hip skeletal structure similar to the view depicted in FIG. 107A. FIG. 112B is a side view of the patient's hip skeletal structure similar to the view depicted in FIG. 106A. FIG. 112C is a view of the patient's hip skeletal structure similar to the view depicted in FIG. 103A, except from an opposite lateral perspective. FIG. 112D is a superior view of the patient's hip skeletal structure.

As can be understood from a comparison of FIGS. 112A and 112B to FIGS. 107A and 106A, respectively, in the embodiment depicted in FIGS. 112A-112D, the delivery tool 20 has a trajectory that is generally superior-to-inferior as opposed to posterior-to-anterior. Further, unlike the embodiments described above wherein the implant 25 gains access to the sacroiliac joint space 1044 via the caudal access 2016 to be implanted in the caudal region 1086 of the sacroiliac joint space 1044 (see, for example, FIG. 106B and related figures and discussion), the embodiment of FIGS. 112A-112D gains access to gains access to the sacroiliac joint space 1044 via the cranial access 2017 (e.g., at the superior boarder 3006 shown in FIG. 106B) to be implanted in the cranial region 1087 of the sacroiliac joint space 1044 (see, for example, FIG. 112C-112D).

As indicated in FIGS. 112A-112D, the delivery tool 20 is oriented such that the anchor collar 165 is positioned so as to deliver the anchor member 30 through the ilium 1005 first and then into the bore 40 of the implant 25 and optionally further into the sacrum 1004. In other words, the method depicted in FIGS. 112A-112D shows the anchor member 30 being driven lateral to medial through the ilium 1005 first and then into the implant followed by the sacrum 1004 (optional). Other than being delivered via a different trajectory and access location and being implanted in a different region of the sacroiliac joint, the implant 25 of FIGS. 112C-112D is located in the sacroiliac joint with its wide radial members 50, narrow radial members 55 and body 45 oriented as explained above with respect to FIGS. 102A-102D, the only difference being the implant 25 being accessed via, and implanted in, the cranial region 1087 as opposed to the caudal region 1086.

Figure 117A:
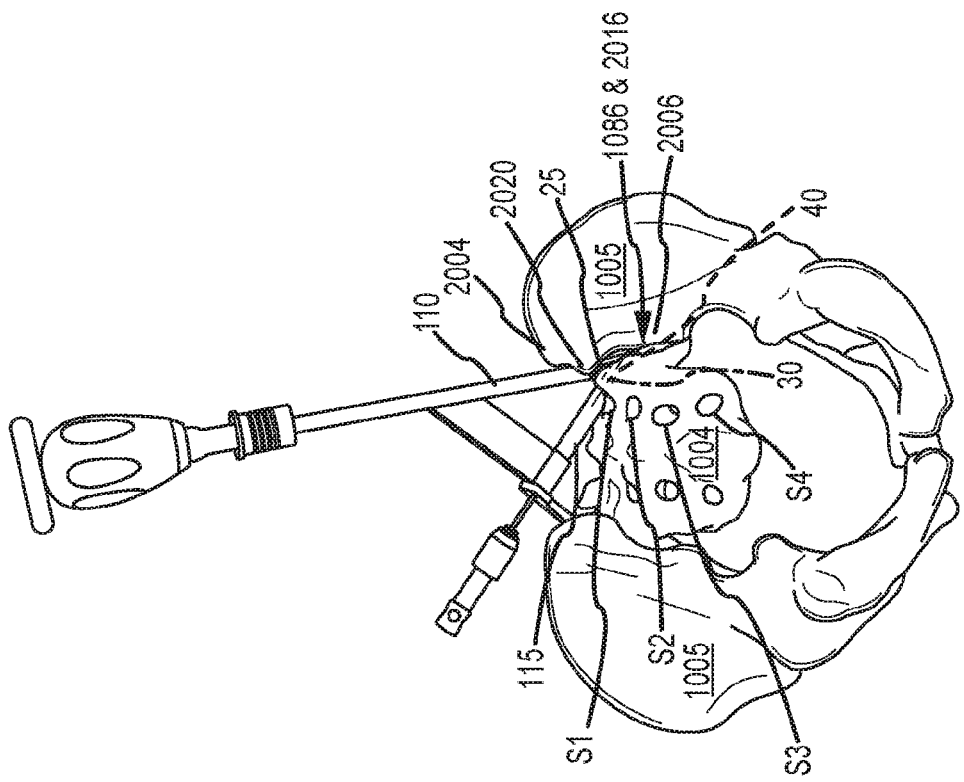
FIG. 117A is a lateral-inferior-posterior view of the patient's hip skeletal structure similar to the view depicted in FIG. 111C.
Figure 117B:
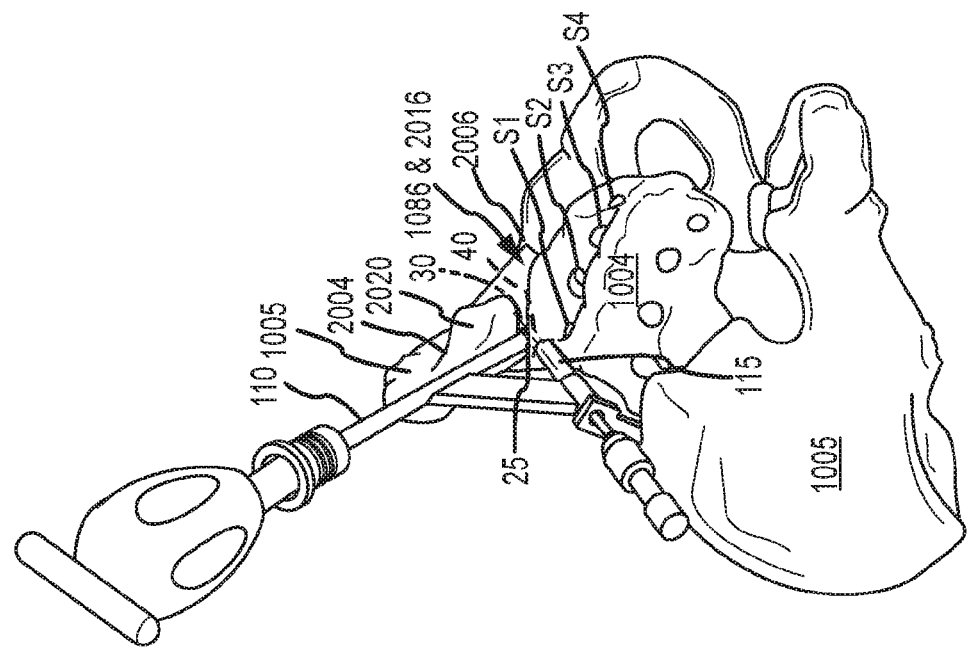
FIG. 117B is an inferior-posterior view of the patient's hip skeletal structure similar to the view depicted in FIG. 111A.
Figure 117C:
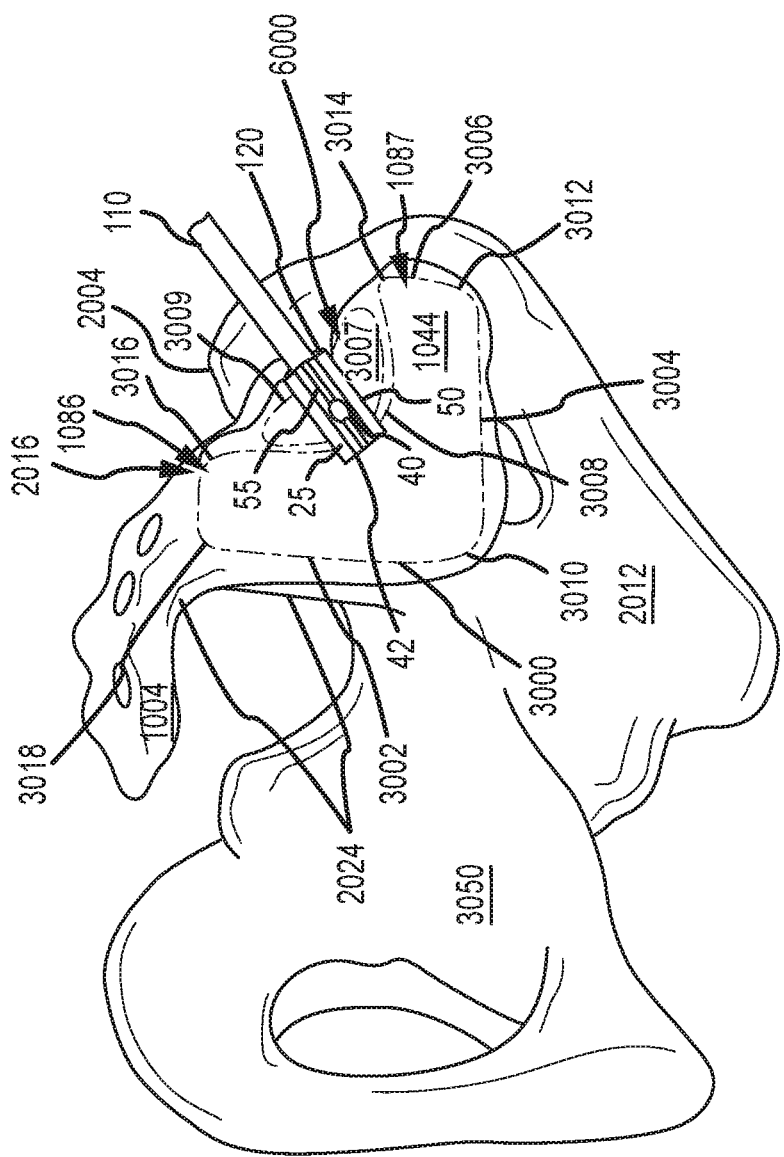
FIG. 117C is the same view as FIG. 106B, except showing the implant being implanted in the extra-articular space, as opposed to the sacroiliac joint articular region.

To begin a detailed discussion of another method of employing the system 10 to fuse the sacroiliac joint, reference is made to FIGS. 117A-117C. FIG. 117A is a lateral-inferior-posterior view of the patient's hip skeletal structure similar to the view depicted in FIG. 111C. FIG. 117B is an inferior-posterior view of the patient's hip skeletal structure similar to the view depicted in FIG. 111A. FIG. 117C is the same view as FIG. 106B, except showing the implant 25 being implanted in the extra-articular space 3007, as opposed to the sacroiliac joint articular region 1044, and accessing the extra-articular space 3007 via an extra-articular recess access region 6000. The S1 through S4 foramina can be seen at the respective indicators S1, S2, S3 and S4 in FIGS. 117A-117B.

As can be understood from a comparison of FIGS. 117A to 107A, the delivery tool 20 has been reversed such that the anchor collar 165 is oriented so as to deliver the anchor member 30 through the sacrum 1004 first and then into the bore 40 of the implant 25 and optionally further into the ilium 1005. In other words, unlike the method depicted in FIG. 107A, wherein the anchor member 30 is driven lateral to medial through the ilium 1005 first and then into the implant followed by the sacrum 1004 (optional), the method depicted in FIG. 117A shows the anchor member 30 being driven medial to lateral through the sacrum 1004 first and then into the implant followed by the ilium 1005 (optional). In the embodiment of FIG. 117A, the anchor member 30 may be a bone screw the same as or similar to an S2 alar iliac (S2AI) screw. Such a screw may penetrate the sacrum 1004 just lateral the lateral edge of the S1 foramen and just superior the superior edge of the S1 foramen. Thus, the anchor element 30 can enter the bone of sacrum near the first sacral foramen (S1AI trajectory) then into or through implant bore 40 and can further enter the bone of the ilium. The implant 25, as with any of the implantation locations and implants 25 discussed herein can optionally be employed to be configured to serve as an attachment point for structural components of a spinal support system with a spanning element as discussed below with respect to FIGS. 115 and 116 or with a coupling element as discussed below with respect to FIG. 114.

As can be understood from a comparison of FIGS. 117A to 107A, FIGS. 117B to 111C, and FIGS. 117C to 106B, the implant 25 of FIG. 117C is located in the extra-articular region 3007 as opposed to the sacroiliac joint articular region 1044. Further, the implant 25 of FIGS. 117A-C has entered the extra-articular region 3007 via an extra-articular recess access region 6000, which, is on the opposite side of the posterior inferior overhang 2020 of the posterior superior iliac spine 2004 from the caudal portion 1086 of the sacroiliac joint articular region 1014 and posterior inferior access region 2016 leading to the sacroiliac joint articular region 1044 employed to implant the implant 25 in the caudal portion 1086 of the sacroiliac joint articular region 1044, as discussed above with respect to FIGS. 103A-108B or FIGS. 111A-111C.

As can be understood from FIG. 117C, the implant 25 is oriented in the extra-articular region 3007 with its wide radial members 50 generally coplanar with the plane of the extra-articular region 3007 and the narrow radial members 55 extending into the sacrum and ilium bone defining each side of the extra-articular region 3007.

As illustrated in FIG. 117C, in some embodiments, the implant 25 is oriented within the extra-articular region 3007 such that the longitudinal axis of the body 45 is generally perpendicular to the posterior boundary segment 3008 of the boundary 3000 of the sacroiliac joint articular region 1014. Also, the distal end 42 of the implant 25, when implanted in the extra-articular region 3007, points towards the anterior-inferior corner 3010 of the boundary 3000 of the sacroiliac joint articular region 1014. The distal end 42 of the implant 25 may extend across the posterior boundary segment 3008 of the boundary 3000 of the sacroiliac joint articular region 1014 and into the sacroiliac joint articular region 1014. Thus, when implanting the implant 25 via the extra-articular recess access region 6000, the general direction of travel for the implant distal end 42 is towards the anterior-inferior corner 3010, and the implant 25 can be positioned substantially within the extra-articular region 3007 or, alternatively, the implant 25 can be further advanced to also occupy a portion of the sacroiliac joint articular region 1044.

As discussed above with respect to FIGS. 117A-117B, in implanting the implant 25 in the extra-articular region 3007, the delivery tool 20 is configured to drive the anchor element 30 medial to lateral through the sacrum 1004 into the implant bore 40 and, optionally, further into the ilium 1005. However, in some embodiments, the delivery tool 20 and implant bore 40 may have as-manufactured configurations that allow the anchor element 30 to be driven lateral to medial through the ilium 1005 into the implant bore 40 and, optionally, further into the sacrum 1004.

In some embodiments, the system 10 may be provided in the form of a kit 4999. Such a kit 4999 is shown in FIG. 113. The kit 4999 may include the system 10 enclosed in a sterile main package 5000. For example, the delivery tool 20, the implant 25 and anchor member 30 may be sealed within the sterile main package 5000. The delivery tool 20 may be any of the tool embodiments disclosed herein and may include all of its components. Also, the implant 25 may be any of the implant embodiments disclosed herein.

As illustrated in FIG. 113, in some embodiments, the kit 4999 may include multiple sizes of the implant 25 and/or multiple sizes of the anchor member 30. The multiple implants 25 may be contained in a sterile individual package 5002 within the sterile main package 5000, and the multiple anchor members 30 may be contained in another sterile individual package 5004 within the sterile main package 5000. By providing the multiple sizes of implants 25 and anchor members 30, the implants and anchor members can be used as trials during certain steps of the procedure to determine appropriate implant sizes and to allow a physician, who is presented with the kit 4999 containing the delivery system 20 and multiple sizes of the implant and anchor members, to evaluate particular embodiments of an implant and anchor member as described herein that would be best suited to a particular patient, application or implant receiving space. The kit 4999 may also or alternatively contain multiple implants 25 with different angles of bore 40 to provide various desirable trajectories for an anchor member 30 and multiple delivery systems 20 with as-manufactured angular relations corresponding to the different angles of the bore. The kit 4999 may also include color coded, numeric or other indicators corresponding between delivery systems 20 and the corresponding implants 25.

In some embodiments, the kit 4999 may include instructions 5006 that lay out the steps of using the system 10. The instructions 5006 may be contained within one of the sterile packages such as, for example, the sterile main package 5000. Alternatively, the instructions 5006 may be adhered or otherwise attached to an exterior surface of one of the sterile packages such as, for example, the sterile main package 5000. Alternatively, the instructions 5006 may be simply provided separately such as, for example, via simply shipped loose with the rest of the kit 4999, emailed, available for download at a manufacturer website, or provided via a manufacture offered training seminar program.

In some embodiments, the kit 4999 may have any one or more of the tool 20, implants 25 and anchor members 30 contained in individual sterile packages that are not held within a sterile main package. Alternatively, the tool 20, implants 25 and anchor members 30 may be contained in a single common package or in any combination of packages and combination of tool, implants and anchor members.

Figure 114:
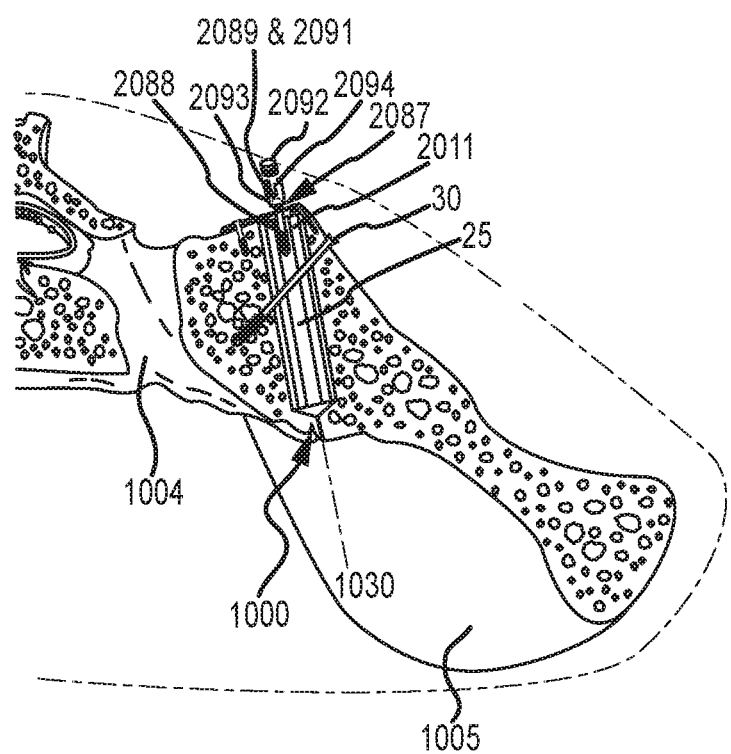
FIG. 114 is the same transverse cross sectional view of the patient's hip as shown in FIGS. 99A-99Q, except showing the implant having structure attached thereto that will allow the implant to serve as an attachment point for structural components of a spinal support system configured to support across the patient's hip structure and/or to support along the patient's spinal column.

As can be understood from FIG. 114, which is the same transverse cross sectional view of the patient's hip as shown in FIGS. 99A-99Q, once the implant 25 and anchor(s) 30 are secured at the sacroiliac joint 1000 in any of the manners depicted in FIGS. 99O-99Q, the implant 25 can be used as an attachment point for structural components of a spinal support system configured to support across the patient's hip structure and/or to support along the patient's spinal column. To serve as an attachment point for structural components of a spinal support system, a coupling element 2087 is connected to the proximal end 2011 of the sacroiliac joint implant 25. As a non-limiting example, the coupling element 2087 can be disposed in fixed relation to the proximal end 2011 of the sacroiliac joint implant 25 by threaded engagement of a fastener portion 2088; however, the invention is not so limited and the fastener portion 2088 can be connected to the first end 2011 of the sacroiliac joint implant 25 by any method such as welding, spin welding, adhesive, or the like. The coupling element 2087 can further provide a coupling portion 2089 configured to join with a numerous and wide variety of cross sectional geometries of spanning members 2090. As a non-limiting example, the coupling portion 2089 can be configured as cylindrical cup 2091 pivotally coupled to the fastener portion 2088. A spiral thread can be coupled to the internal surface of the cylindrical cup 2091 to rotationally receive a spirally threaded body 2092. The side wall 2093 of the cylindrical cup 2091 can include a pass through element 2094 in which part of a spanning member 2090 can be received. The part of the spanning member 2090 received within the pass through element 2094 can be placed in fixed relation to the cylindrical cup 2091 by rotational engagement of the spirally threaded body 2092.

Figure 115:
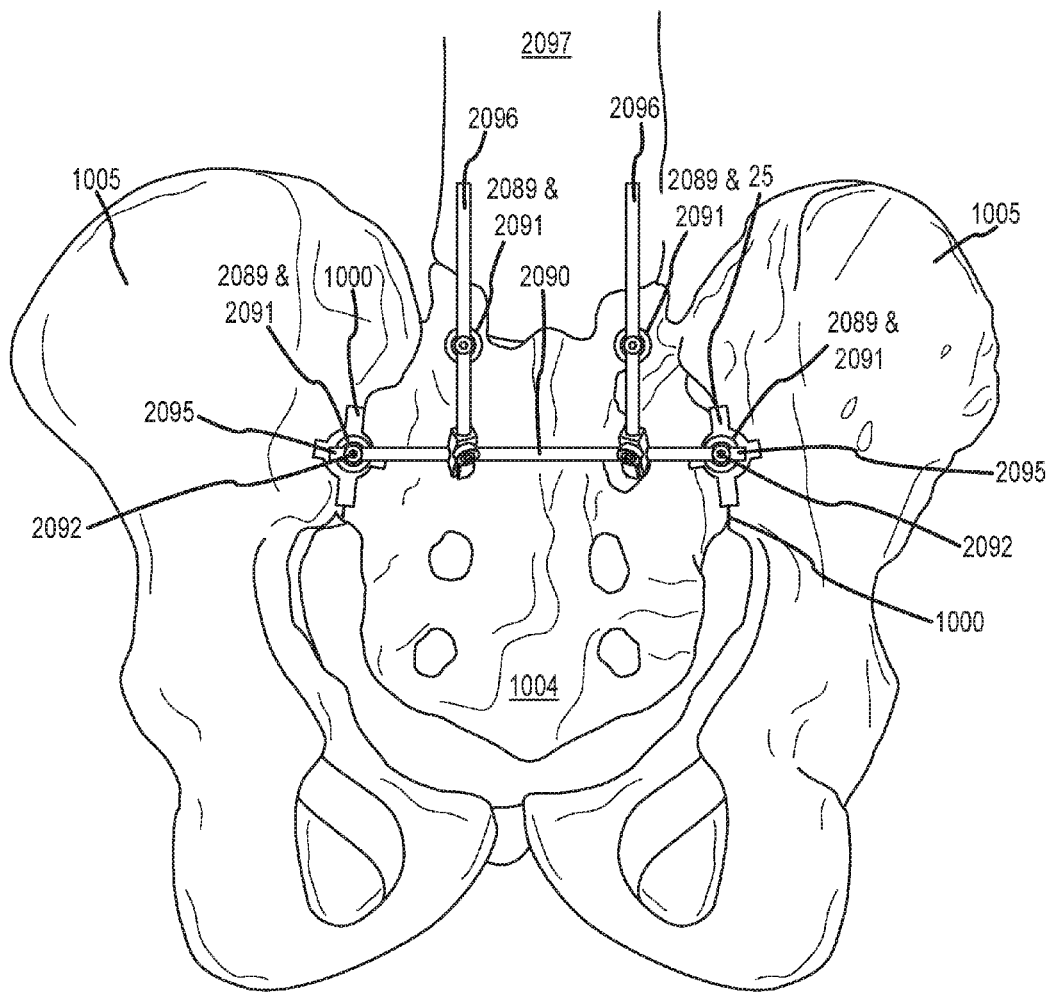
FIG. 115 is a posterior view of the patient's sacrum and illiums, wherein structural components of a spinal support system extend medial-lateral across the patient's hip structure and superiorly to support along the patient's spinal column.

FIG. 115 is a posterior view of the patient's sacrum 1004 and illiums 1005, wherein structural components of a spinal support system extend medial-lateral across the patient's hip structure and superiorly to support along the patient's spinal column. As shown in FIG. 115, in one embodiment, each of a pair of sacroiliac joints 1000 can receive an embodiment of the sacroiliac joint implants 25, above-described, each having a coupling element 2087 coupled to the first end 2011. Each of the coupling elements 2087 can receive the opposed ends 2095 of a spanning member 2090. Additionally, the spanning member 2090 in fixed relation to the sacroiliac joint implants 25 can be connected to a plurality of additional spanning members 2096 which can as a non-limiting example be placed in positional relation to the vertebral column 2097 to allow support of additional implants which can be anchored between vertebrae.

Figure 116:
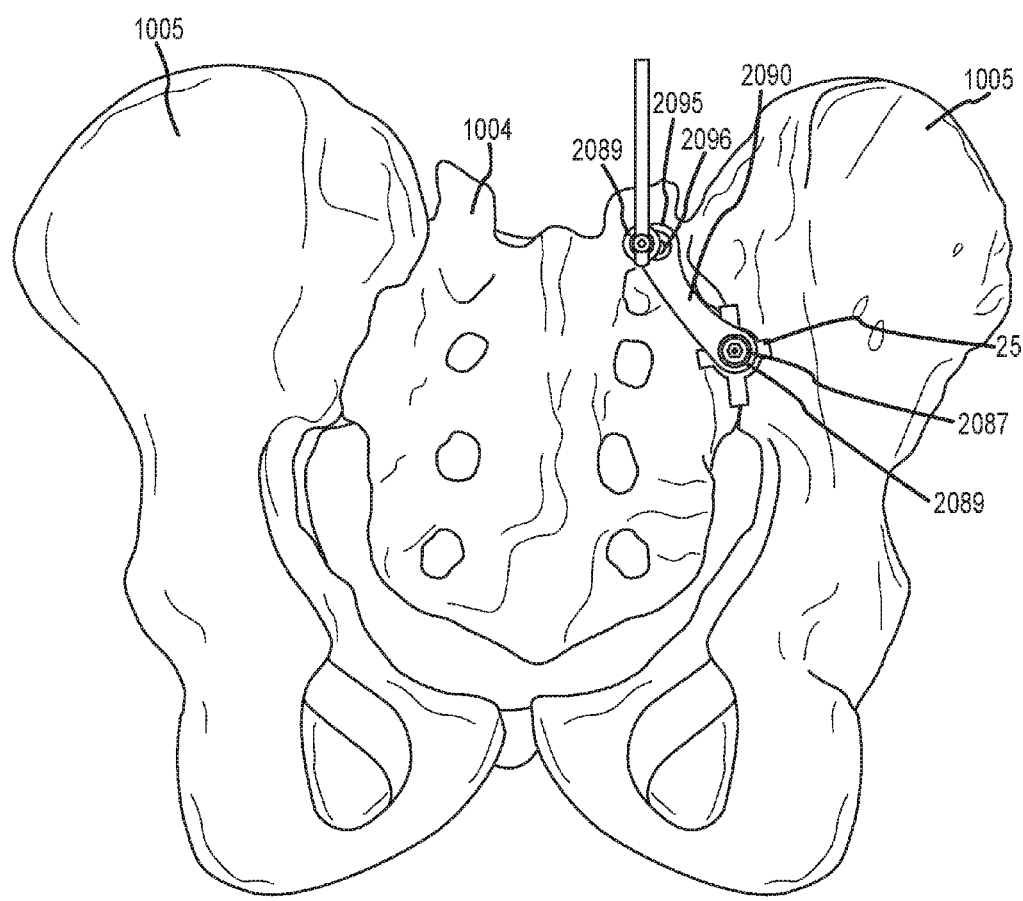
FIG. 116 is the same view as FIG. 117, except having a different spanning member structure.

FIG. 116 is the same view as FIG. 117, except having a different spanning member structure. As illustrated in FIG. 116, a first coupling element 2087 can be joined to the first end 2011 of an embodiment of a sacroiliac joint implant 25 as above described and the fastener portion 2088 of a second coupling element 2087 can be disposed directly into the bone of the sacrum 1004 or the ilium 1005, or both. The opposed ends 2095 of a spanning element 2090 in the form of a flat plate can be can provide apertures 2096 through which the fastener portion 2088 of the coupling element 2087 can pass. The corresponding parts of the external surface of the coupling portion 2089 and the spanning member 2090 can be engaged to fix the location of the spanning member 2090 allowing for coupling of the lumbar spine to the stabilized pelvis by a plurality of fixation elements to further increase stability.

As can be understood from FIG. 116 and with continuing reference to FIGS. 111A-C, according to particular embodiments, the spanning element 2090 can be configured to receive an S2AI screw positioned and directed in a trajectory as substantially shown in FIGS. 111A-C. As a non-limiting example, an S2AI screw or other elongate fixation body can pass through an aperture 2096, which can be located on an opposed end 2095 of the spanning element 2090 and can be disposed directly into the bone of the sacrum 1004, pass through or engage the bore 40 of an implant 25, and into the bone of the ilium 1005. According to certain embodiments, an engagement between an S2AI screw and the bore 40 can be configured, for example, as having a bore 40 which can have threads or other surface that are generally complementary to those of a fastener 2088. Said complementary surfaces can be configured to provide a virtual cold weld between components to further resist undesirable movement."

As can be understood from the foregoing, various embodiments of the delivery tools or system configurations as described herein can be similarly configured to operate with various embodiments of the sacroiliac joint implants disclosed in U.S. Provisional 61/520,956.

In summary and as can be understood from the preceding discussion, the sacroiliac joint fusion systems 10 disclosed herein include a joint implant 25, an anchor element 30 and a delivery tool 20. The joint implant 25 includes a longitudinal axis CA (e.g., see FIG. 10) and a bore 40 extending non-parallel to the longitudinal axis CA. The anchor element 30 is configured to be received in the bore 40.

The delivery tool 20 includes an implant arm 110 and an anchor arm 115. The implant arm 110 is configured to releasably couple to the joint implant 25. The anchor arm 115 is coupled to the implant arm and configured to deliver the anchor element 30 to the bore 40.

The final manufactured configuration of the tool 20 and final manufactured configuration of the joint implant 25 are such that, when the system 10 is assembled such that the implant arm 110 is releasably coupled to the joint implant 25 (e.g., as shown in FIGS. 2A, 21A, 21C, 32, 37 and 109), a delivery arrangement automatically exists such that the anchor arm 115 is correctly oriented to deliver the anchor element 30 to the bore 40. Thus, when the system 10 is shipped from the manufacturer to the medical facility where the sacroiliac joint fusion will take place, the components 20, 25, 30, 40, 110, 115 are each configured such that simply plugging them together such that the tool 20 is fully assembled and the implant 25 is supported off of the distal end of the tool 20 is all that is required to employ the tool 20 to both deliver the implant 25 into the sacroiliac joint 1000 and deliver the anchor element 30 into the bore 40 so as to anchor the implant 25 in the sacroiliac joint. In other words, once the components of the system 10 are coupled together, the cumulative result of the as-manufactured three dimensional configurations of each component of the system 10 is that the system 10 has a delivery arrangement such that the anchor arm 115 is correctly oriented to deliver the anchor element 30 to the bore 40 without having to adjust the as-manufactured three dimensional configurations of any of the components of the system 10. This automatically arrived-at delivery arrangement is even the case wherein the anchor arm 115 being employed is part of a plurality of anchor arms (as discussed with respect to FIG. 21B) or where the anchor arm 115 is pivotally coupled to the implant arm 110 and further equipped with an arcuate slider 105 at a free distal end of the anchor arm, the arcuate radius of the anchor arm 115 at the arcuate slider 105 being such that the radius extends through the bore 40 (as discussed with respect to FIG. 34).

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A method of fusing a sacroiliac joint comprising a sacrum, an ilium, and a sacroiliac joint space defined therebetween, the ilium comprising a posterior superior iliac spine and a posterior inferior iliac spine, the method comprising:
   a) approaching a posterior aspect of the sacroiliac joint space with a joint implant comprising a body extending a length between a distal end and a proximal end, the joint implant in an alignment relative to the sacroiliac joint space where the length of the joint implant is generally parallel with a plane defined by the sacroiliac joint space; and
   b) delivering the joint implant into the sacroiliac joint space in the alignment such that the joint implant passes through an access region defined between the posterior superior iliac spine and the posterior inferior iliac spine, the joint implant being oriented in the sacroiliac joint space such that a portion of the body of the joint implant is positioned within a joint plane of the sacroiliac joint space, and such that the distal end of the joint implant is positioned posteriorly of an anterior boundary of the sacroiliac joint space.

2. The method of claim 1, wherein the body defines a generally planar member having a generally rectangular configuration, the body comprises a sacral face extending along the length, an iliac face extending along the length that is opposite the sacral face, a width between the sacral face and the iliac face being about a width of an implant receiving space formed between the sacrum and the ilium, a top surface extending between the sacral face and iliac face and extending along the length, a bottom surface opposite the top surface and extending between the sacral face and iliac face and extending along the length, and a height between the top surface and bottom surface being substantially greater than the width and being about the height of an implant receiving space formed between the sacrum and the ilium, the height of the implant receiving space extending generally within the joint plane of the sacroiliac joint space and being generally perpendicular to the width of the implant receiving space, the length extending generally within the joint plane of the sacroiliac joint space when positioned within the joint plane of the sacroiliac joint space and being generally perpendicular to both the width and the height and being substantially greater than both the width and the height.

3. The method of claim 2, further comprising: c) inserting a guide wire into the sacroiliac joint space; and d) advancing a cannulated probe having a distal spatulate portion over the guide wire and into the sacroiliac joint space.

4. The method of claim 2, further comprising forming the implant receiving space prior to delivering the joint implant into the sacroiliac joint space.

5. The method of claim 4, wherein the step of forming the implant receiving space comprises: aligning a drill jig comprising a plurality of drill guide holes such that at least one of the plurality of drill guide holes is generally coplanar with the joint plane of the sacroiliac joint space; and drilling a plurality of bores into the sacroiliac joint so as to form the implant receiving space for the subsequent delivery of the joint implant.

6. The method of claim 4, wherein the step of forming the implant receiving space comprises: aligning a drill jig comprising a plurality of drill guide holes such that the plurality of drill guide holes is generally coplanar with the joint plane of the sacroiliac joint space; and drilling a plurality of bores within the sacroiliac joint space such that each of the plurality of bores removes an amount of cartilage from within the sacroiliac joint space so as to produce the implant receiving space.

7. The method of claim 4, wherein the step of forming the implant receiving space comprises: positioning a broach jig up to the sacroiliac joint space, the broach jig comprising a broach guide hole configured to guide a broach into the sacroiliac joint space; and advancing a distal end of a broach into the sacroiliac joint space to form the implant receiving space.

8. The method of claim 2, wherein the joint implant is implanted in a caudal region of the sacroiliac joint space.

9. The method of claim 8, wherein the caudal region is bounded on an inferior side by an inferior boundary segment and on a superior side by a laterally extending portion of a posterior boundary segment.

10. The method of claim 2, wherein, in delivering the joint implant into the sacroiliac joint space, the bottom surface of the body of the joint implant is generally parallel to an inferior sacroiliac joint space border.

11. The method of claim 2, wherein the distal end tapers to a terminal end.

12. The method of claim 2, wherein the body comprises a passageway extending between an opening on the sacral face and an opening on the iliac face.

13. The method of claim 12, further comprising inserting biocompatible material within the passageway.

14. The method of claim 1, wherein the body of the joint implant comprises an end cap having an end cap perimeter selected from at least one of a circle, oval, square or rectangle configuration.

15. The method of claim 1, wherein the body of the joint implant further comprises an anti-migration element coupled to the proximal end.

16. The method of claim 15, wherein the anti-migration element comprises an enlarged terminal portion.

17. The method of claim 1, wherein the joint implant further comprises a first planar member coupled to and extending generally perpendicularly with the body.

18. The method of claim 1, wherein the joint implant further comprises one or more planar members configured to extend into the sacrum and one or more planar members configured to extend into the ilium when the portion of the body of the joint implant is positioned within a joint plane of the sacroiliac joint space.

19. A method of fusing a sacroiliac joint comprising a sacrum, an ilium, and a sacroiliac joint space defined therebetween, the ilium comprising a posterior superior iliac spine and a posterior inferior iliac spine, the method comprising:
  a) approaching a posterior aspect of the sacroiliac joint space with a joint implant comprising a body extending a length between a distal end portion and a proximal end portion, a sacral bore defined within the proximal end portion on a sacral side of the joint implant, and an iliac bore defined within the proximal end portion on an iliac side of the joint implant; and
  b) delivering the joint implant into the sacroiliac joint space such that the joint implant passes through an access region defined between the posterior superior iliac spine and the posterior inferior iliac spine, the joint implant being oriented in the sacroiliac joint space such that: a portion of the body of the joint implant is positioned within a joint plane of the sacroiliac joint space; the distal end of the joint implant is positioned posteriorly of an anterior boundary of the sacroiliac joint space; and, the sacral bore is positioned proximate the sacrum and the iliac bore is positioned proximate the ilium.

20. The method of claim 19, wherein the sacral and iliac bore are coupled via a planar member.

21. The method of claim 20, wherein the planar member comprises an end cap having a perimeter defining an oval, square, or rectangle.

22. The method of claim 19, wherein the joint implant approaches the posterior aspect of the sacroiliac joint space in an alignment relative to the sacroiliac joint space where the length of the joint implant is generally parallel with a plane defined by the sacroiliac joint space, and wherein delivery of the joint implant into the sacroiliac joint space is in the alignment.

23. The method of claim 19, further comprising preparing an implant receiving space prior to delivery of the joint implant into the sacroiliac joint space.

24. A method of fusing a sacroiliac joint comprising a sacrum, an ilium, and a sacroiliac joint space defined therebetween, the ilium comprising a posterior superior iliac spine and a posterior inferior iliac spine, the method comprising:
  a) approaching a posterior aspect of the sacroiliac joint space with a joint implant comprising a body extending a length between a distal end and a proximal end, a first planar member extending the length, and a second planar member extending the length, the first and second planar members coupled to each other near a midsection thereof; and
  b) delivering the joint implant into the sacroiliac joint space such that the joint implant passes through an access region defined between the posterior superior iliac spine and the posterior inferior iliac spine, the joint implant being oriented in the sacroiliac joint space such that a portion of the body of the joint implant is positioned within a joint plane of the sacroiliac joint space, and such that the distal end of the joint implant is positioned posteriorly of an anterior boundary of the sacroiliac joint space.

25. The method of claim 24, wherein the joint implant approaches the posterior aspect of the sacroiliac joint space in an alignment relative to the sacroiliac joint space where the length of the joint implant is generally parallel with a plane defined by the sacroiliac joint space, and wherein delivery of the joint implant into the sacroiliac joint space is in the alignment.

26. The method of claim 24, wherein the first and second planar members are oriented generally perpendicular to each other.

27. The method of claim 24, wherein each of the first and second planar members comprises an aperture element comprising an aperture perimeter, the aperture elements extending through opposite faces of the first and second planar members, respectively.

28. The method of claim 24, further comprising preparing an implant receiving space prior to delivery of the joint implant into the sacroiliac joint space.

29. A method of fusing a sacroiliac joint comprising a sacrum, an ilium, and a sacroiliac joint space defined therebetween, the ilium comprising a posterior superior iliac spine and a posterior inferior iliac spine, the method comprising:
  a) approaching a posterior aspect of the sacroiliac joint space with a joint implant comprising a body extending a length between a distal end and a proximal end, the body comprising an end cap having an end cap perimeter selected from at least one of a circle, oval, square or rectangle configuration; and
  b) delivering the joint implant into the sacroiliac joint space such that the joint implant passes through an access region defined between the posterior superior iliac spine and the posterior inferior iliac spine, the joint implant being oriented in the sacroiliac joint space such that a portion of the body of the joint implant is positioned within a joint plane of the sacroiliac joint space, and such that the distal end of the joint implant is positioned posteriorly of an anterior boundary of the sacroiliac joint space.

30. The method of claim 29, wherein the joint implant approaches the posterior aspect of the sacroiliac joint space in an alignment relative to the sacroiliac joint space where the length of the joint implant is generally parallel with a plane defined by the sacroiliac joint space, and wherein delivery of the joint implant into the sacroiliac joint space is in the alignment.

31. A method of fusing a sacroiliac joint comprising a sacrum, an ilium, and a sacroiliac joint space defined therebetween, the ilium comprising a posterior superior iliac spine and a posterior inferior iliac spine, the method comprising:
  a) approaching a posterior aspect of the sacroiliac joint space with a joint implant comprising a body extending a length between a distal end and a proximal end, the body comprising an anti-migration element coupled to the proximal end; and
  b) delivering the joint implant into the sacroiliac joint space such that the joint implant passes through an access region defined between the posterior superior iliac spine and the posterior inferior iliac spine, the joint implant being oriented in the sacroiliac joint space such that a portion of the body of the joint implant is positioned within a joint plane of the sacroiliac joint space, and such that the distal end of the joint implant is positioned posteriorly of an anterior boundary of the sacroiliac joint space.

32. The method of claim 31, wherein the joint implant approaches the posterior aspect of the sacroiliac joint space in an alignment relative to the sacroiliac joint space where the length of the joint implant is generally parallel with a plane defined by the sacroiliac joint space, and wherein delivery of the joint implant into the sacroiliac joint space is in the alignment.

33. A method of fusing a sacroiliac joint comprising a sacrum, an ilium, and a sacroiliac joint space defined therebetween, the ilium comprising a posterior superior iliac spine and a posterior inferior iliac spine, the method comprising:
  a) approaching a posterior aspect of the sacroiliac joint space with a joint implant comprising a body extending a length between a distal end and a proximal end, and a first planar member coupled to and extending generally perpendicularly with the body; and
  b) delivering the joint implant into the sacroiliac joint space such that the joint implant passes through an access region defined between the posterior superior iliac spine and the posterior inferior iliac spine, the joint implant being oriented in the sacroiliac joint space such that a portion of the body of the joint implant is positioned within a joint plane of the sacroiliac joint space, and such that the distal end of the joint implant is positioned posteriorly of an anterior boundary of the sacroiliac joint space.

34. The method of claim 33, wherein the joint implant approaches the posterior aspect of the sacroiliac joint space in an alignment relative to the sacroiliac joint space where the length of the joint implant is generally parallel with a plane defined by the sacroiliac joint space, and wherein delivery of the joint implant into the sacroiliac joint space is in the alignment.

* * * * *